US012534763B2

(12) United States Patent
Kennedy et al.

(10) Patent No.: US 12,534,763 B2
(45) **Date of Patent: *Jan. 27, 2026**

(54) SYSTEMS AND METHODS OF DIAGNOSING IDIOPATHIC PULMONARY FIBROSIS

(71) Applicant: Veracyte, Inc., South San Francisco, CA (US)

(72) Inventors: Giulia C. Kennedy, San Francisco, CA (US); James Diggans, South San Francisco, CA (US); Jing Huang, South San Francisco, CA (US); Yoonha Choi, South San Francisco, CA (US); Su Yeon Kim, South San Francisco, CA (US); Daniel Pankratz, Los Gatos, CA (US); Moraima Pagan, San Francisco, CA (US)

(73) Assignee: Veracyte, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/181,535

(22) Filed: Mar. 9, 2023

(65) Prior Publication Data

US 2024/0110242 A1 Apr. 4, 2024

Related U.S. Application Data

(63) Continuation of application No. 17/218,125, filed on Mar. 30, 2021, now Pat. No. 11,639,527, which is a continuation of application No. 16/840,009, filed on Apr. 3, 2020, now abandoned, which is a continuation of application No. 16/551,645, filed on Aug. 26, 2019, now abandoned, which is a continuation of application No. 15/523,654, filed as application No. PCT/US2015/059309 on Nov. 5, 2015, now abandoned.

(60) Provisional application No. 62/130,800, filed on Mar. 10, 2015, provisional application No. 62/075,328, filed on Nov. 5, 2014.

(51) Int. Cl.

| | |
|---|---|
| ***C12Q 1/6883*** | (2018.01) |
| ***C12Q 1/6806*** | (2018.01) |
| ***C12Q 1/686*** | (2018.01) |
| ***C12Q 1/6874*** | (2018.01) |
| ***C12Q 1/6876*** | (2018.01) |

(52) U.S. Cl.

CPC ......... *C12Q 1/6883* (2013.01); *C12Q 1/6806* (2013.01); *C12Q 1/686* (2013.01); *C12Q 1/6874* (2013.01); *C12Q 1/6876* (2013.01); *C12Q 2600/112* (2013.01); *C12Q 2600/156* (2013.01); *C12Q 2600/158* (2013.01)

(58) Field of Classification Search

None

See application file for complete search history.

(56) References Cited

U.S. PATENT DOCUMENTS

| | | | |
|---|---|---|---|
| 3,640,268 | A | 2/1972 | Davis |
| 3,645,691 | A | 2/1972 | Knapp et al. |
| 3,687,808 | A | 8/1972 | Merigan, Jr. et al. |
| 4,641,662 | A | 2/1987 | Jaicks |
| 4,800,896 | A | 1/1989 | Jalowayski |
| 5,130,238 | A | 7/1992 | Malek et al. |
| 5,143,854 | A | 9/1992 | Pirrung et al. |
| 5,288,514 | A | 2/1994 | Ellman |
| 5,384,261 | A | 1/1995 | Winkler et al. |
| 5,399,491 | A | 3/1995 | Kacian et al. |
| 5,422,273 | A | 6/1995 | Garrison et al. |
| 5,440,942 | A | 8/1995 | Hubbard |
| 5,455,166 | A | 10/1995 | Walker |
| 5,477,863 | A | 12/1995 | Grant |
| 5,494,810 | A | 2/1996 | Barany et al. |
| 5,538,848 | A | 7/1996 | Livak et al. |
| 5,677,195 | A | 10/1997 | Winkler et al. |
| 5,705,365 | A | 1/1998 | Ryder et al. |
| 5,710,029 | A | 1/1998 | Ryder et al. |
| 5,726,060 | A | 3/1998 | Bridges |
| 5,795,782 | A | 8/1998 | Church et al. |
| 5,830,711 | A | 11/1998 | Barany et al. |
| 5,846,717 | A | 12/1998 | Brow et al. |
| 5,854,033 | A | 12/1998 | Lizardi |
| 5,876,978 | A | 3/1999 | Willey et al. |
| 5,888,779 | A | 3/1999 | Kacian et al. |
| 5,965,360 | A | 10/1999 | Zain et al. |
| 5,985,557 | A | 11/1999 | Prudent et al. |
| 5,989,815 | A | 11/1999 | Skolnick et al. |
| 5,994,069 | A | 11/1999 | Hall et al. |
| 6,001,567 | A | 12/1999 | Brow et al. |
| 6,013,431 | A | 1/2000 | Soederlund et al. |
| 6,015,714 | A | 1/2000 | Baldarelli et al. |

(Continued)

FOREIGN PATENT DOCUMENTS

| | | | |
|---|---|---|---|
| CA | 2712773 | A1 | 7/2009 |
| CN | 1620309 | A | 5/2005 |

(Continued)

OTHER PUBLICATIONS

Abrahamson et al. Cystatins. Biochem. Soc. Symp. 70: 179-199 (2003).

(Continued)

*Primary Examiner* — Samuel C Woolwine

*Assistant Examiner* — Carolyn L Greene

(74) *Attorney, Agent, or Firm* — WILSON SONSINI GOODRICH & ROSATI

(57) ABSTRACT

The present invention provides methods for sequencing and analysis of nucleic acids and determining that a subject is positive for a non-usual interstitial pneumonia subtype.

25 Claims, 11 Drawing Sheets

Specification includes a Sequence Listing.

(56) References Cited

U.S. PATENT DOCUMENTS 6,022,692 A 2/2000 Coulie et al.
6,027,887 A 2/2000 Zavada et al.
6,085,907 A 7/2000 Hochmeister et al.
6,090,543 A 7/2000 Prudent et al.
6,136,182 A 10/2000 Dolan et al.
6,225,051 B1 5/2001 Sugiyama et al.
6,251,639 B1 6/2001 Kurn
6,268,142 B1 7/2001 Duff et al.
6,410,278 B1 6/2002 Notomi et al.
6,436,642 B1 8/2002 Gould-Rothberg et al.
6,627,067 B1 9/2003 Branton et al.
6,667,154 B1 12/2003 Wang et al.
6,676,609 B1 1/2004 Rutenberg et al.
6,723,506 B2 4/2004 Fletcher et al.
6,746,846 B1 6/2004 Wang et al.
7,186,514 B2 3/2007 Zavada et al.
7,211,390 B2 5/2007 Rothberg et al.
7,238,485 B2 7/2007 Akeson et al.
7,244,559 B2 7/2007 Rothberg et al.
7,258,838 B2 8/2007 Li et al.
7,264,929 B2 9/2007 Rothberg et al.
7,280,922 B2 10/2007 Mei et al.
7,300,788 B2 11/2007 Matsuzaki et al.
7,319,011 B2 1/2008 Riggins et al.
7,323,305 B2 1/2008 Leamon et al.
7,335,762 B2 2/2008 Rothberg et al.
7,358,061 B2 4/2008 Yamamoto et al.
7,361,488 B2 4/2008 Fan et al.
7,378,233 B2 5/2008 Sidransky et al.
7,407,755 B2 8/2008 Lubinski et al.
7,541,169 B2 6/2009 Freimuth et al.
7,598,052 B2 10/2009 Giordano et al.
7,662,553 B2 2/2010 Lenz
7,767,391 B2 8/2010 Scott et al.
7,901,881 B2 3/2011 Libutti et al.
7,901,888 B2 3/2011 Kebebew
7,927,826 B2 4/2011 Riggins et al.
8,008,009 B2 8/2011 Choquet-Kastylevsky et al.
8,202,692 B2 6/2012 Giordano et al.
8,293,880 B2 10/2012 Cote et al.
8,354,228 B2 1/2013 Ron
8,465,914 B2 6/2013 Brown et al.
8,541,170 B2 9/2013 Kennedy et al.
8,568,971 B2 10/2013 Brown et al.
8,669,057 B2 3/2014 Kennedy et al.
8,802,599 B2 8/2014 Aharonov et al.
8,828,656 B2 9/2014 Bullerdiek et al.
8,877,445 B2 11/2014 Shackney
8,945,829 B2 2/2015 Keutgen et al.
9,040,286 B2 5/2015 Zon, I et al.
9,074,258 B2 7/2015 Davicioni et al.
9,096,906 B2 8/2015 Aharonov et al.
9,157,123 B2 10/2015 Xing
9,175,352 B2 11/2015 Keutgen et al.
9,206,482 B2 12/2015 Davicioni et al.
9,234,244 B2 1/2016 Zeiger et al.
9,495,515 B1 11/2016 Kennedy et al.
9,587,279 B2 3/2017 Fahey, III et al.
9,617,604 B2 4/2017 Davicioni et al.
9,708,667 B2 7/2017 Barnett-Itzhaki et al.
9,714,452 B2 7/2017 Davicioni et al.
9,856,537 B2 1/2018 Kennedy et al.
9,920,374 B2 3/2018 Brody et al.
9,994,907 B2 6/2018 Davicioni et al.
10,036,069 B2 7/2018 Noth et al.
10,114,924 B2 10/2018 Kennedy et al.
10,236,078 B2 3/2019 Kennedy et al.
10,422,009 B2 9/2019 Davicioni et al.
10,446,272 B2 10/2019 Wilde et al.
10,526,655 B2 1/2020 Whitney et al.
10,570,454 B2 2/2020 Brody et al.
10,672,504 B2 6/2020 Kennedy et al.
10,731,223 B2 8/2020 Kennedy et al.
10,808,285 B2 10/2020 Brody et al.
10,927,417 B2 2/2021 Beane-Ebel et al.
10,934,587 B2 3/2021 Kennedy et al.
10,961,582 B2 3/2021 Noth et al.
11,217,329 B1 1/2022 Choi et al.
11,639,527 B2 5/2023 Kennedy et al.
11,976,329 B2 5/2024 Kennedy et al.
2001/0051344 A1 12/2001 Shalon et al.
2002/0031496 A1 3/2002 Firestein et al.
2002/0076735 A1 6/2002 Williams et al.
2002/0081612 A1 6/2002 Katz et al.
2002/0094547 A1 7/2002 Burstein
2002/0160388 A1 10/2002 Macina et al.
2002/0169137 A1 11/2002 Reiner et al.
2003/0104499 A1 6/2003 Pressman et al.
2003/0116159 A1 6/2003 Orr et al.
2003/0186248 A1 10/2003 Erlander et al.
2003/0190602 A1 10/2003 Pressman et al.
2003/0194734 A1 10/2003 Jatkoe
2004/0005294 A1 1/2004 Lee
2004/0009489 A1 1/2004 Golub et al.
2004/0019466 A1 1/2004 Minor et al.
2004/0058378 A1 3/2004 Kong et al.
2004/0063120 A1 4/2004 Beer et al.
2004/0197785 A1 10/2004 Willey et al.
2004/0241725 A1 12/2004 Xiao et al.
2004/0241728 A1 12/2004 Liew
2005/0042222 A1 2/2005 Yamamoto et al.
2005/0048533 A1 3/2005 Sidransky et al.
2005/0065447 A1 3/2005 Lee et al.
2005/0137805 A1 6/2005 Lewin et al.
2005/0240357 A1 10/2005 Minor
2005/0250125 A1 11/2005 Novakoff
2005/0260586 A1 11/2005 Demuth et al.
2005/0266409 A1 12/2005 Brown et al.
2005/0266443 A1 12/2005 Croce et al.
2006/0003171 A1 1/2006 Igawa et al.
2006/0019256 A1 1/2006 Clarke et al.
2006/0019272 A1 1/2006 Geraci et al.
2006/0019615 A1 1/2006 Ditmer
2006/0035244 A1 2/2006 Riggins et al.
2006/0083744 A1 4/2006 Chen et al.
2006/0088851 A1 4/2006 Erlander et al.
2006/0094061 A1 5/2006 Brys et al.
2006/0105360 A1 5/2006 Croce et al.
2006/0127907 A1 6/2006 Matsubara et al.
2006/0127928 A1 6/2006 Bacus et al.
2006/0140960 A1 6/2006 Wang et al.
2006/0154278 A1 7/2006 Brody et al.
2006/0183144 A1 8/2006 Willey et al.
2006/0188909 A1 8/2006 Willey et al.
2006/0190192 A1 8/2006 Willey et al.
2006/0194216 A1 8/2006 Willey et al.
2006/0241869 A1 10/2006 Schadt et al.
2006/0252057 A1 11/2006 Raponi et al.
2006/0265138 A1 11/2006 Bowtell et al.
2007/0020657 A1 1/2007 Grebe et al.
2007/0031873 A1 2/2007 Wang et al.
2007/0037186 A1 2/2007 Jiang et al.
2007/0048738 A1 3/2007 Donkena et al.
2007/0065833 A1 3/2007 Gupta
2007/0092891 A1 4/2007 Willey et al.
2007/0092892 A1 4/2007 Willey et al.
2007/0092893 A1 4/2007 Willey et al.
2007/0099209 A1 5/2007 Clarke et al.
2007/0105133 A1 5/2007 Clarke et al.
2007/0148650 A1 6/2007 Brody et al.
2007/0148667 A1 6/2007 Williams et al.
2007/0148687 A1 6/2007 Bedingham et al.
2007/0161004 A1 7/2007 Brown et al.
2007/0172844 A1 7/2007 Lancaster et al.
2007/0220621 A1 9/2007 Clarke et al.
2007/0238119 A1 10/2007 Yu et al.
2008/0028302 A1 1/2008 Meschkat
2008/0044824 A1 2/2008 Giordano et al.
2008/0124344 A1 5/2008 Combs et al.
2008/0131892 A1 6/2008 Becker et al.
2008/0145841 A1 6/2008 Libutti et al.
2008/0254470 A1 10/2008 Berlin
2008/0274457 A1 11/2008 Eng et al.
2008/0280302 A1 11/2008 Kebebew

(56) References Cited

U.S. PATENT DOCUMENTS

| | | | |
|---|---|---|---|
| 2008/0281568 | A1 | 11/2008 | Kao et al. |
| 2009/0020433 | A1 | 1/2009 | Cohen et al. |
| 2009/0029477 | A1 | 1/2009 | Meller et al. |
| 2009/0042184 | A1 | 2/2009 | Mas et al. |
| 2009/0061454 | A1 | 3/2009 | Brody et al. |
| 2009/0186951 | A1 | 7/2009 | Brody et al. |
| 2009/0191535 | A1 | 7/2009 | Connelly et al. |
| 2009/0204333 | A1 | 8/2009 | Friend et al. |
| 2009/0246779 | A1 | 10/2009 | Rabinovitch et al. |
| 2009/0280490 | A1 | 11/2009 | Baker et al. |
| 2009/0291853 | A1 | 11/2009 | Kim et al. |
| 2009/0311692 | A1 | 12/2009 | Brody et al. |
| 2010/0035244 | A1 | 2/2010 | Brody et al. |
| 2010/0055689 | A1 | 3/2010 | Spira et al. |
| 2010/0055704 | A1 | 3/2010 | Giordano et al. |
| 2010/0075384 | A1 | 3/2010 | Kong et al. |
| 2010/0099093 | A1 | 4/2010 | Weaver et al. |
| 2010/0119474 | A1 | 5/2010 | Crystal et al. |
| 2010/0131286 | A1 | 5/2010 | Houlgatte et al. |
| 2010/0131432 | A1 | 5/2010 | Kennedy et al. |
| 2010/0143312 | A1 | 6/2010 | Hariri et al. |
| 2010/0178653 | A1 | 7/2010 | Aharonov et al. |
| 2010/0204058 | A1 | 8/2010 | Chang et al. |
| 2010/0255486 | A1 | 10/2010 | Showe et al. |
| 2010/0273674 | A1 | 10/2010 | Kamalakaran et al. |
| 2010/0285979 | A1 | 11/2010 | Zeiger et al. |
| 2010/0303813 | A1 | 12/2010 | Carulli et al. |
| 2011/0053158 | A1 | 3/2011 | Mambo et al. |
| 2011/0092375 | A1 | 4/2011 | Zamore et al. |
| 2011/0152110 | A1 | 6/2011 | Vierlinger et al. |
| 2011/0190150 | A1 | 8/2011 | Brody et al. |
| 2011/0190156 | A1 | 8/2011 | Whitfield et al. |
| 2011/0212855 | A1 | 9/2011 | Rafnar et al. |
| 2011/0217315 | A1 | 9/2011 | Schwartz et al. |
| 2011/0217717 | A1 | 9/2011 | Brody et al. |
| 2011/0224313 | A1 | 9/2011 | Tsao et al. |
| 2011/0229894 | A1 | 9/2011 | Levy et al. |
| 2011/0230372 | A1 | 9/2011 | Willman et al. |
| 2011/0269142 | A1 | 11/2011 | Zavras |
| 2011/0287946 | A1 | 11/2011 | Gudmundsson et al. |
| 2011/0294684 | A1 | 12/2011 | Baty et al. |
| 2011/0312520 | A1 | 12/2011 | Kennedy et al. |
| 2011/0312530 | A1 | 12/2011 | Aharonov et al. |
| 2012/0015839 | A1 | 1/2012 | Chinnaiyan |
| 2012/0015843 | A1 | 1/2012 | Von Hoff et al. |
| 2012/0041686 | A1 | 2/2012 | Brody et al. |
| 2012/0115735 | A1 | 5/2012 | Vogelstein et al. |
| 2012/0115743 | A1 | 5/2012 | Davicioni et al. |
| 2012/0122698 | A1 | 5/2012 | Stacey et al. |
| 2012/0122718 | A1 | 5/2012 | Reisman |
| 2012/0157334 | A1 | 6/2012 | Beaudenon-Huibregtse et al. |
| 2012/0172243 | A1 | 7/2012 | Davicioni et al. |
| 2012/0190567 | A1 | 7/2012 | Brody et al. |
| 2012/0208706 | A1 | 8/2012 | Downing et al. |
| 2012/0214165 | A1 | 8/2012 | Walfish et al. |
| 2012/0220474 | A1 | 8/2012 | Kennedy et al. |
| 2012/0264626 | A1 | 10/2012 | Nana-Sinkam et al. |
| 2012/0288860 | A1 | 11/2012 | Van Hoek et al. |
| 2012/0322673 | A1 | 12/2012 | Brody et al. |
| 2012/0329666 | A1 | 12/2012 | Steele et al. |
| 2013/0023434 | A1 | 1/2013 | Van Laar |
| 2013/0023437 | A1 | 1/2013 | Brody et al. |
| 2013/0029873 | A1 | 1/2013 | De Perrot et al. |
| 2013/0142728 | A1 | 6/2013 | Beaudenon-Huibregtse et al. |
| 2013/0150257 | A1 | 6/2013 | Abdueva et al. |
| 2013/0172203 | A1 | 7/2013 | Yeatman et al. |
| 2013/0184999 | A1 | 7/2013 | Ding |
| 2013/0196868 | A1 | 8/2013 | Lebowitz et al. |
| 2013/0225662 | A1 | 8/2013 | Kennedy et al. |
| 2013/0231258 | A1 | 9/2013 | Wilde et al. |
| 2013/0273543 | A1 | 10/2013 | Gudmundsson et al. |
| 2013/0287772 | A1 | 10/2013 | Halbert et al. |
| 2013/0302810 | A1 | 11/2013 | Latham et al. |
| 2013/0303826 | A1 | 11/2013 | Jurisica et al. |
| 2014/0030714 | A1 | 1/2014 | Paschke et al. |
| 2014/0080731 | A1 | 3/2014 | Davicioni et al. |
| 2014/0087961 | A1 | 3/2014 | Sulem et al. |
| 2014/0099261 | A1 | 4/2014 | Keutgen et al. |
| 2014/0121126 | A1 | 5/2014 | Bivona et al. |
| 2014/0143188 | A1 | 5/2014 | Mackey et al. |
| 2014/0179771 | A1 | 6/2014 | Bancel et al. |
| 2014/0220006 | A1 | 8/2014 | Aghvanyan et al. |
| 2014/0243240 | A1 | 8/2014 | Soldin et al. |
| 2014/0302042 | A1 | 10/2014 | Chin et al. |
| 2014/0315199 | A1 | 10/2014 | Rhodes et al. |
| 2014/0315739 | A1 | 10/2014 | Aharonov et al. |
| 2014/0329251 | A1 | 11/2014 | Moerman et al. |
| 2014/0349856 | A1 | 11/2014 | Schnabel et al. |
| 2014/0349864 | A1 | 11/2014 | Kennedy et al. |
| 2014/0371096 | A1 | 12/2014 | Umbricht et al. |
| 2014/0378425 | A1 | 12/2014 | Wilde et al. |
| 2015/0038376 | A1 | 2/2015 | Tian et al. |
| 2015/0080243 | A1 | 3/2015 | Whitney et al. |
| 2015/0088430 | A1 | 3/2015 | Whitney et al. |
| 2015/0099665 | A1 | 4/2015 | Rosenfeld et al. |
| 2015/0141470 | A1 | 5/2015 | Garraway et al. |
| 2015/0152474 | A1 | 6/2015 | Pawlowski et al. |
| 2015/0275306 | A1 | 10/2015 | Bernards et al. |
| 2015/0299808 | A1 | 10/2015 | Gonzalez et al. |
| 2015/0307947 | A1 | 10/2015 | Basu et al. |
| 2015/0329915 | A1 | 11/2015 | Davicioni et al. |
| 2015/0337385 | A1 | 11/2015 | Harris et al. |
| 2015/0354008 | A1 | 12/2015 | Brody et al. |
| 2015/0368724 | A1 | 12/2015 | Aharonov et al. |
| 2016/0024583 | A1 | 1/2016 | Whitney et al. |
| 2016/0024586 | A1 | 1/2016 | Delfour et al. |
| 2016/0032400 | A1 | 2/2016 | Gomis et al. |
| 2016/0068915 | A1 | 3/2016 | Kennedy et al. |
| 2016/0115546 | A1 | 4/2016 | Rosenfeld et al. |
| 2016/0120832 | A1 | 5/2016 | Rabinowitz et al. |
| 2016/0130656 | A1 | 5/2016 | Whitney et al. |
| 2016/0312305 | A1 | 10/2016 | Kennedy et al. |
| 2016/0312306 | A1 | 10/2016 | Kennedy et al. |
| 2016/0312307 | A1 | 10/2016 | Kennedy et al. |
| 2016/0312308 | A1 | 10/2016 | Kennedy et al. |
| 2017/0016076 | A1 | 1/2017 | Barnett-Itzhaki et al. |
| 2017/0127976 | A1 | 5/2017 | Phillips et al. |
| 2017/0145513 | A1 | 5/2017 | Kennedy et al. |
| 2017/0166980 | A1 | 6/2017 | Fahey, III et al. |
| 2017/0226591 | A1 | 8/2017 | Brody et al. |
| 2017/0247759 | A1 | 8/2017 | Wilde, I et al. |
| 2017/0328908 | A1 | 11/2017 | Brody et al. |
| 2017/0329894 | A1 | 11/2017 | Kennedy et al. |
| 2017/0335396 | A1 | 11/2017 | Kennedy et al. |
| 2018/0016642 | A1 | 1/2018 | Kennedy et al. |
| 2018/0030540 | A1 | 2/2018 | Davicioni et al. |
| 2018/0068058 | A1 | 3/2018 | Abdueva et al. |
| 2018/0112275 | A1 | 4/2018 | Davicioni et al. |
| 2018/0122508 | A1 | 5/2018 | Wilde et al. |
| 2018/0127832 | A1 | 5/2018 | Kennedy et al. |
| 2018/0349548 | A1 | 12/2018 | Walsh et al. |
| 2019/0080047 | A1 | 3/2019 | Kennedy et al. |
| 2019/0100805 | A1 | 4/2019 | Davicioni et al. |
| 2019/0100809 | A1 | 4/2019 | Kennedy et al. |
| 2019/0172551 | A1 | 6/2019 | Kennedy et al. |
| 2019/0292600 | A1 | 9/2019 | Spira et al. |
| 2019/0330680 | A1 | 10/2019 | Kennedy et al. |
| 2019/0376148 | A1 | 12/2019 | Brody et al. |
| 2020/0096513 | A1 | 3/2020 | Brody et al. |
| 2020/0115763 | A1 | 4/2020 | Brody et al. |
| 2020/0143944 | A1 | 5/2020 | Wilde et al. |
| 2020/0176078 | A1 | 6/2020 | Kennedy et al. |
| 2020/0202974 | A1 | 6/2020 | Kennedy et al. |
| 2020/0232045 | A1 | 7/2020 | Brody et al. |
| 2020/0232046 | A1 | 7/2020 | Kennedy |
| 2020/0248274 | A1 | 8/2020 | Brody et al. |
| 2020/0405225 | A1 | 12/2020 | Kennedy et al. |
| 2021/0040559 | A1 | 2/2021 | Wilde et al. |
| 2021/0040562 | A1 | 2/2021 | Whitney et al. |
| 2021/0079471 | A1 | 3/2021 | Kennedy et al. |
| 2021/0238686 | A1 | 8/2021 | Kennedy et al. |
| 2021/0324464 | A1 | 10/2021 | Kennedy et al. |
| 2021/0332431 | A1 | 10/2021 | Wilde et al. |
| 2021/0355524 | A1 | 11/2021 | Kennedy et al. |

(56) References Cited

U.S. PATENT DOCUMENTS

| | | | |
|---|---|---|---|
| 2021/0381062 A1 | 12/2021 | Spira et al. | |
| 2022/0112561 A1 | 4/2022 | Kennedy et al. | |
| 2022/0235417 A1 | 7/2022 | Noth et al. | |

FOREIGN PATENT DOCUMENTS

| | | | |
|---|---|---|---|
| CN | 1688582 | A | 10/2005 |
| CN | 101014720 | A | 8/2007 |
| CN | 101501214 | A | 8/2009 |
| CN | 102640001 | A | 8/2012 |
| CN | 102858991 | A | 1/2013 |
| CN | 103038635 | A | 4/2013 |
| CN | 104334744 | A | 2/2015 |
| CN | 104853802 | A | 8/2015 |
| CN | 105247075 | A | 1/2016 |
| CN | 105378104 | A | 3/2016 |
| DE | 10219117 | C1 | 10/2003 |
| EP | 0684315 | A1 | 11/1995 |
| EP | 1403638 | A1 | 3/2004 |
| EP | 1975245 | A1 | 10/2008 |
| EP | 1975252 | A1 | 10/2008 |
| EP | 2231874 | A2 | 9/2010 |
| EP | 2295599 | A1 | 3/2011 |
| EP | 2366800 | A1 | 9/2011 |
| EP | 2971128 | A2 | 1/2016 |
| EP | 3215170 | A1 | 9/2017 |
| EP | 3360978 | A2 | 8/2018 |
| EP | 3510173 | A1 | 7/2019 |
| EP | 3770274 | A1 | 1/2021 |
| EP | 4219761 | A1 | 8/2023 |
| JP | 2004526154 | A | 8/2004 |
| JP | 2005168432 | A | 6/2005 |
| JP | 2005304497 | A | 11/2005 |
| JP | 2007513635 | A | 5/2007 |
| JP | 2008545400 | A | 12/2008 |
| JP | 2008545431 | A | 12/2008 |
| JP | 2013532295 | A | 8/2013 |
| JP | 2013212052 | A | 10/2013 |
| JP | 2015519966 | A | 7/2015 |
| JP | 2018504138 | A | 2/2018 |
| KR | 20080020083 | A | 3/2008 |
| KR | 20130017525 | | 2/2013 |
| WO | WO-9015070 | A1 | 12/1990 |
| WO | WO-9210092 | A1 | 6/1992 |
| WO | WO-9309668 | A1 | 5/1993 |
| WO | WO-9322684 | A1 | 11/1993 |
| WO | WO-9515331 | A1 | 6/1995 |
| WO | WO-9857145 | A1 | 12/1998 |
| WO | WO-9960160 | A1 | 11/1999 |
| WO | WO-0006780 | A1 | 2/2000 |
| WO | WO-0120035 | A2 | 3/2001 |
| WO | WO-0128428 | A1 | 4/2001 |
| WO | WO-0206791 | A2 | 1/2002 |
| WO | WO-0244331 | A2 | 6/2002 |
| WO | WO-02072866 | A2 | 9/2002 |
| WO | WO-02086443 | A2 | 10/2002 |
| WO | WO-03015613 | A2 | 2/2003 |
| WO | WO-03029273 | A2 | 4/2003 |
| WO | WO-03040325 | A2 | 5/2003 |
| WO | WO-03062389 | A2 | 7/2003 |
| WO | WO-03097666 | A2 | 11/2003 |
| WO | WO-2004005891 | A2 | 1/2004 |
| WO | WO-2004029055 | A1 | 4/2004 |
| WO | WO-2004091383 | A2 | 10/2004 |
| WO | WO-2004091511 | A2 | 10/2004 |
| WO | WO-2004111197 | A2 | 12/2004 |
| WO | WO-2005000098 | A2 | 1/2005 |
| WO | WO-2005005601 | A2 | 1/2005 |
| WO | WO-2005047451 | A2 | 5/2005 |
| WO | WO-2005085471 | A2 | 9/2005 |
| WO | WO-2005100608 | A2 | 10/2005 |
| WO | WO-2005005601 | A3 | 4/2006 |
| WO | WO-2006047484 | A2 | 5/2006 |
| WO | WO-2006062118 | A1 | 6/2006 |
| WO | WO-2006105252 | A2 | 10/2006 |
| WO | WO-2006110593 | A2 | 10/2006 |
| WO | WO-2006113467 | A2 | 10/2006 |
| WO | WO-2006127537 | A2 | 11/2006 |
| WO | WO-2006113467 | A3 | 4/2007 |
| WO | WO-2007038792 | A2 | 4/2007 |
| WO | WO-2007103541 | A2 | 9/2007 |
| WO | WO-2007038792 | A3 | 11/2007 |
| WO | WO-2007126882 | A2 | 11/2007 |
| WO | WO-2008104380 | A2 | 9/2008 |
| WO | WO-2008119776 | A1 | 10/2008 |
| WO | WO-2008130887 | A1 | 10/2008 |
| WO | WO-2008104380 | A3 | 11/2008 |
| WO | WO-2008140774 | A2 | 11/2008 |
| WO | WO-2009006323 | A2 | 1/2009 |
| WO | WO-2009020905 | A2 | 2/2009 |
| WO | WO-2009026605 | A2 | 3/2009 |
| WO | WO-2009029266 | A2 | 3/2009 |
| WO | WO-2009037337 | A1 | 3/2009 |
| WO | WO-2009039457 | A1 | 3/2009 |
| WO | WO-2006127537 | A3 | 4/2009 |
| WO | WO-2009042728 | A1 | 4/2009 |
| WO | WO-2009068591 | A2 | 6/2009 |
| WO | WO-2009079450 | A2 | 6/2009 |
| WO | WO-2009087139 | A1 | 7/2009 |
| WO | WO-2009096903 | A1 | 8/2009 |
| WO | WO-2009111881 | A1 | 9/2009 |
| WO | WO-2009121070 | A1 | 10/2009 |
| WO | WO-2009126271 | A1 | 10/2009 |
| WO | WO-2009143603 | A1 | 12/2009 |
| WO | WO-2010000907 | A1 | 1/2010 |
| WO | WO-2010018600 | A1 | 2/2010 |
| WO | WO-2010018601 | A2 | 2/2010 |
| WO | WO-2010028274 | A1 | 3/2010 |
| WO | WO-2010054233 | A1 | 5/2010 |
| WO | WO-2010056374 | A2 | 5/2010 |
| WO | WO-2010073248 | A2 | 7/2010 |
| WO | WO-2010056374 | A3 | 9/2010 |
| WO | WO-2010073248 | A3 | 9/2010 |
| WO | WO-2010099598 | A1 | 9/2010 |
| WO | WO-2010123626 | A1 | 10/2010 |
| WO | WO-2010124372 | A1 | 11/2010 |
| WO | WO-2010127322 | A1 | 11/2010 |
| WO | WO-2010129934 | A2 | 11/2010 |
| WO | WO-2011044142 | A1 | 4/2011 |
| WO | WO-2011079846 | A2 | 7/2011 |
| WO | WO-2011086174 | A2 | 7/2011 |
| WO | WO-2011094345 | A1 | 8/2011 |
| WO | WO-2011137060 | A1 | 11/2011 |
| WO | WO-2011143361 | A2 | 11/2011 |
| WO | WO-2012006632 | A2 | 1/2012 |
| WO | WO-2012055565 | A1 | 5/2012 |
| WO | WO-2012129237 | A2 | 9/2012 |
| WO | WO-2012149550 | A1 | 11/2012 |
| WO | WO-2013033640 | A1 | 3/2013 |
| WO | WO-2013049152 | A2 | 4/2013 |
| WO | WO-2013063544 | A1 | 5/2013 |
| WO | WO-2013074938 | A2 | 5/2013 |
| WO | WO-2013086429 | A2 | 6/2013 |
| WO | WO-2013086522 | A1 | 6/2013 |
| WO | WO-2013088457 | A1 | 6/2013 |
| WO | WO-2013148232 | A1 | 10/2013 |
| WO | WO-2013163568 | A2 | 10/2013 |
| WO | WO-2013177060 | A2 | 11/2013 |
| WO | WO-2013190092 | A1 | 12/2013 |
| WO | WO-2014043803 | A1 | 3/2014 |
| WO | WO-2014144564 | A2 | 9/2014 |
| WO | WO-2014144821 | A1 | 9/2014 |
| WO | WO-2014151764 | A2 | 9/2014 |
| WO | WO-2014186036 | A1 | 11/2014 |
| WO | WO-2015068157 | A1 | 5/2015 |
| WO | WO-2015071876 | A2 | 5/2015 |
| WO | WO-2016011068 | A1 | 1/2016 |
| WO | WO-2016073768 | A1 | 5/2016 |
| WO | WO-2016094330 | A2 | 6/2016 |
| WO | WO-2016141127 | A1 | 9/2016 |
| WO | WO-2017065959 | A2 | 4/2017 |
| WO | WO-2017197335 | A1 | 11/2017 |
| WO | WO-2018009915 | A1 | 1/2018 |

(56) References Cited

FOREIGN PATENT DOCUMENTS

| | | | |
|---|---|---|---|
| WO | WO-2018048960 | A1 | 3/2018 |
| WO | WO-2018223066 | A1 | 12/2018 |
| WO | WO-2019023517 | A2 | 1/2019 |

OTHER PUBLICATIONS

Abratani, Hiroyuki. Characteristic Diagnosis of Cancer by Gene Expression Profiling. Personalized Diagnosis of Cancer by Gene Expression Profiling. English Translation. Journal of Clinical and Experimental Medicine (Igaku No Ayumi), Jun. 1, 2002, vol. 201, No. 9, p. 687-692.

Abrosimov et al. The cytoplasmic expression of MUC1 in papillary thyroid carcinoma of different histological variants and its correlation with cyclin D1 overexpression. Endocr Pathol. 2007;18(2):68-75.

Abubaker et al. Clinicopathological analysis of papillary thyroid cancer with PIK3CA alterations in a Middle Eastern population. J Clin Endocrinol Metab. 2008;93(2):611-8.

Accession N M_000441. 2008. *Homo sapiens* solute carrier family 26, member 4 (SLC26A4), mRNA (Year: 2008).

Adams, J.U., The Human Genome project set out to sequence all of the 3 billion nucleotides in the human genome. Exactly how was this daunting task done with such incredible speed and accuracy? DNA sequencing technologies. Nature Education, 2008; 1(1):193, pp. 1-6.

Adapt, The Peterson Institute for Cancer Research, probesets for ARSG, printed Jan. 10, 2013.

Adapt, The Peterson Institute for Cancer Research, probesets for FREM2, printed Jan. 10, 2013.

Adapt, The Peterson Institute for Cancer Research, probesets for GIMAP2, printed Jan. 10, 2013.

Adapt, The Peterson Institute for Cancer Research, probesets for HRASLS3, printed Jan. 10, 2013.

Adapt, The Peterson Institute for Cancer Research, probesets for PIGN, printed Jan. 10, 2013.

Adapt website. Paterson Institute for Cancer Research. Probesets for AUTS2. Printed Jul. 1, 2014. 2 pages.

Adapt website. Paterson Institute for Cancer Research. Probesets for FXYD6. Printed Jul. 1, 2014. 1 page.

Affymetrix CDKL2 ( https://www.affymetriix.com/analysis/netaffx/showresults.affx , Mar. 21, 2019).

Affymetrix: "Data Sheet Affymetrix(R) Genome-Wide Human SNP Array 6.0", 2007, pp. 1-4, XP002525407. Retrieved from the Internet: URL: http://www.affymetrix.com/support/technical/datasheets/genomewide_snp6_datasheet.pdf.

Affymetrix HG-U 133 Plus 2.0 Annotation File (filtered excerpt, obtained from http://www.affymetrix.com/Auth/analysis/downloads/na26/ivt/HG-U133_Pius_2.na26.annot.csv.zip on Mar. 18, 2013, 1 page) (Year: 2013).

Affymetrix HG-U 133A Annotation File (filtered excerpt, obtained from http://www.affymetrix.com/Auth/analysis/downloads/na35/ivt/HG-U 133A.na35.annot.csv.zip on Apr. 29, 2016, 1 page) (Year: 2016).

Affymetrix HLA-F ( https://www.affymetrix.com/analysis/netaffx/showresults.affz , Mar. 21, 2019).

Affymetrix Technical Note: GeneChip® Gene 1.0 ST Array Design (created Sep. 5, 2007; downloaded from http://media.affymetrix.com/support/technical/technotes/gene_1_0_st_technote.pdf).

Affymetrix website for HG-U133A probe set list version 2004, Archived NetAffx Annotation Files (http://www.affymetrix.com/estore/catalog/131537/AFFY/Human+Genome+U133A+2.0+Array#1_3) printed Mar. 2015.

Afink, et al. Molecular characterization of iodotyrosine dehalogenase deficiency in patients with hypothyroidism. J Clin Endocrinol Metab. Dec. 2008;93(12):4894-901.

Aggarwal et al. Thyroid carcinoma-associated genetic mutations also occur in thyroid lymphomas. Mod Pathol. vol. 25 No. 9. May 11, 2012. pp. 1203-1211.

Agrawal, et al. Cancer Genome Atlas Research Network. Integrated genomic characterization of papillary thyroid carcinoma. Cell. Oct. 23, 2014;159(3):676-90. doi: 10.1016/j.cell.2014.09.050.

Akashi et al. Histopathologic analysis of sixteen autopsy cases of chronic hypersensitivity pneumonitis and comparison with idiopathic pulmonary fibrosis/usual interstitial pneumonia. American Journal of Clinical Pathology (2009); 131.3: 405-415.

Akester et al. Cancer in the thyroid is not always thyroid cancer. Hormones-Athens—2 (2003): 250-255.

Akita, et al. Molecular Biology of Lung Cancer. The Journal of the Japanese Respiratory Society, 42(5): (2004).

Aldred et al. Caveolin-1 and caveolin-2, together with three bone morphogenetic protein-related genes, may encode novel tumor suppressors down-regulated in sporadic follicular thyroid carcinogenesis. Cancer Res. 2003;63(11):2864-71.

Aldred et al. Papillary and follicular thyroid carcinomas show distinctly different microarray expression profiles and can be distinguished by a minimum of five genes. J Clin Oncol. 2004;22(17):3531-9.

Alexander et al. Preoperative diagnosis of benign thyroid nodules with indeterminate cytology. N Engl J Med. Aug. 23, 2012;367(8):705-15.

Ali et al. Use of the Afirma® Gene Expression Classifier for Preoperative Identification of Benign Thyroid Nodules with Indeterminate Fine Needle Aspiration Cytopathology. PLoS Currents 5:pp. 1-7 (2013).

Ambion, Inc. GeneAssist Pathway Atlas for P13K Signaling. Accessed from < http://www5.appliedbiosystems.com/tools/pathway/pathway proteins.php?pathway=P13K> on May 3, 2011.

American Thoracic Society, American Thoracic Society/European Respiratory Society International Multidisciplinary Consensus Classification of the Idiopathic Interstitial Pneumonias. AM. J. Respir. Crit. Care Med. 165, 277-304, 2002.

American Thoracic Society. European Respiratory Society. Idiopathic pulmonary fibrosis: diagnosis and treatment. International consensus statement. Am J Respir Crit Care Med (2000); 161.2 pt 1: 646-664.

Anbazhagan et al. Classification of Small Cell Lung Cancer and Pulmonary Carcinoid by Gene Expression Profiles. Cancer Research, 59:5119-5122, (Oct. 15, 1999).

Anders et al. HTSeq-a Python framework to work with high-throughput sequencing data. Bioinformatics (2015); 31(2): 166-169.

Anderson et al. Deaths: Leading Causes for 2001. National Vital Statistics Report; 52(9): 1-88 (Nov. 7, 2003).

Anonymous: "Bronchogenic carcinoma / definition of bronchogenic carcinoma by Medicaldictionary," Feb. 13, 2019 (Feb. 13, 2019), retrieved from the internet: URL: https://medicaldictionary.thefreedictionary.com/bronchogenic+carcinoma [retrieved on Feb. 13, 2019].

Anonymous: "Bronchogenic carcinoma is a malignant neoplasm of the lung arising from theepithelium of the bronchus or bronchiole", Apr. 22, 2003 (Apr. 22, 2003), retrieved from theinternet: URL: http://www.meddean.luc.edu/lumen/meded/medicine/pulmonar/pathms/path19.htm [retrieved on Feb. 13, 2019].

Anthonisen et al. Effects of Smoking Intervention and the Use of an Inhaled Anticholinergic Bronchodilator on the Rate of Decline of FEV1. JAMA; 272(19):1497-1505 (Nov. 16, 1994).

Appleby et al. New technologies for ultra-high throughput genotyping in plants. Plant Genomics: Methods and Protocols (2009); 513: 19-39.

Arimura et al. Elevated Serum 6-Defensins Concentrations in Patients with Lung Cancer. Anticancer Res. Nov.-Dec. 2004;24(6):4051-7.

Arnesen et al. Expression of N-acetyl transferase human and human Arrest defective 1 proteins in thyroid neoplasms. Thyroid. 2005;15(10):1131-6.

Ashley. Towards precision medicine. Nature Reviews Genetics 17.9 (2016): 507.

Asseroshn et al. The feasibility of using fine needle aspiration from primary breast cancers for cDNA microarray analyses. Clinical Cancer Research 8.3 (2002): 794-801.

"Ausubel, et al. Current Protocols in Molecular Biology. Wiley & Sons, New York, 1995."

(56) References Cited

OTHER PUBLICATIONS

Auton et al. 1000 Genomes Project Consortium. A global reference for human genetic variation. Nature 526, 7571 (2015): 68.
Bach, et al. Benefits and harms of CT screening for lung cancer: a systematic review. Jama 307.22 (2012): 2418-2429.
Bai et al. Mutational analysis of thyroid transcription factor-1 gene (TTF-1) in lung carcinomas. In Vitro Cell Dev Biol Anim. 2008;44(1-2):17-25.
Baker et al., Screening for bronchogenic carcinoma: The Surgical experience, J. Thorac Cardiovasc Surg, 1979; 78:876-882.
Baker, Stuart. The Central Role of Receiver Operating Characteristic (ROC) Curves in Evaluating Tests for the Early Detection of Cancer. Journal of the National Cancer Institute, 95(7): 511-515 (Apr. 2003).
Baldi; et al., DNA microarrays and gene expression: from experiments to data analysis and modeling. Cambridge university press, 2002.
Baloch, et al. Our approach to follicular-patterned lesions of the thyroid. J Clin Pathol. Mar. 2007;60(3):244-50. Epub Jun. 23, 2006.
Banito et al. Aneuploidy and RAS mutations are mutually exclusive events in the development of well-differentiated thyroid follicular tumours. Clin Endocrinol (Oxf). 2007;67(5):706-11.
Barden et al. Classification of follicular thyroid tumors by molecular signature: results of gene profiling. Clin Cancer Res. 2003;9(5):1792-800.
Baris et al. Transcriptional profiling reveals coordinated up-regulation of oxidative metabolism genes in thyroid oncocytic tumors. J Clin Endocrinol Metab. 2004;89(2):994-1005.
Bauer et al. A novel genomic signature with translational significance for human idiopathic pulmonary fibrosis. American Journal of Respiratory Cell and Molecular Biology (2015); 52.2: 217-231.
Beane et al. A Prediction Model for Lung Cancer Diagnosis that Integrates Genomic and Clinical Features. Cancer Prevention Research, 1:56-64 (2008).
Beane et al. Reversible and permanent effects of tobacco smoke exposure on airway epithelial gene expression. Genome Biology 2007, 8:R201 (Sep. 25, 2007).
Beane, Jennifer, et al., Characterizing The Impact Of Smoking And Lung Cancer On The Airway Transcriptome Using RNA-Seq. Cancer Prevention Research (philadelphia, Pa.) 4(6):803-817 (2011).
Beane-Ebel. Single-Cell RNA Sequencing of the Bronchial Epithelium in Smokers With Lung Cancer. U.S. Army Medical Research and Material Command. Jul. 2015 version. [retrieved on Sep. 19, 2017]. Retrieved from the Internet at http://www.dtic.mil/dtic/tr/fulltext/u2/a624219.pdf.
Beaudenon-Huibregtse, et al. Centralized molecular testing for oncogenic gene mutations complements the local cytopathologic diagnosis of thyroid nodules. Thyroid. Oct. 2014;24(10):1479-87. Epub Jun. 18, 2014.
Beer et al. Gene-expression profiles predict survival of patients with lung adenocarcinoma. Nature Medicine, 8: 816-824 (2002).
Belinksky et al. Aberrant promoter methylation in bronchial epithelium and sputum from current and former smokers. Cancer Res., 62(8): 2370-7 (2002).
Belperio, et al., Critical role for CXCR2 and CXCR2 ligands during the pathogenesis of ventilator-induced lung injury. J Clin Invest. 2002; 110(11): 1703-1716.
Belyavsky et al. PCR-based cDNA library construction: general cDNA libraries at the level of a few cells. Nucleic Acids Research (1989); 17.8: 2919-2932.
Benner, et al. Evolution, language and analogy in functional genomics. Trends in Genetics, 17:414-418 (2001).
Berbescu et al. Transbronchial biopsy in usual interstitial pneumonia. CHEST Journal (May 2006); 129.5: 1126-1131.
Berman, Jeffrey S. Abstract Immunopathology of the nasal mucosa in sarcoidosis National Institutes of Health Grant No. 1 R21 HL077498-01 (Funding Start Date Sep. 15, 2004).
Bernard et al. Multiplex messenger assay: simultaneous, quantitative measurement of expression of many genes in the context of T cell activation. Nucleic Acids Research (1996); 24.8: 1435-1442.
Bessarabova, et al. Bimodal gene expression patterns in breast cancer. BMC Genomics. Feb. 10, 2010;11 Suppl 1:S8. doi: 10.1186/1471-2164-11-S1-S8.
Beum et al. Epidermal Growth Factor Downregulates Core 2 Enzymes in a Human Airway Adenocarcinoma Cell Line. Am. J. Respir. Cell Mol. Biol., 29:48-56 (Jan. 2003).
Bhattacharjee et al. Classification of human lung carcinoma by mRNA expression profiling reveals distinct adenocarcinoma subclasses. Proc Natl Acad Sci USA, 98(24): 13790-5 (Nov. 20, 2001).
Bild et al. Oncogenic Pathway Signatures in Human Cancers as a Guide to Targeted Therapies. Nature, 439: 353-357 (Jan. 2006).
Bjoraker et al. Prognostic significance of histopathologic subsets in idiopathic pulmonary fibrosis. American Journal of Respiratory and Critical Care Medicine (1998); 157.1: 199-203.
Blower et al. PLOS One. 2013. 8(10):e77700. (Year: 2013).
Bohula et al. The Efficacy of Small Interfering RNAs Targeted to the Type 1 Insulin-like Growth Factor Receptor (IGF1R) Is Influenced by Secondary Structure in the IGF1R Transcript. The Journal of Biological Chemistry 278(18): 15991-15997 (May 2003).
Bolstad, et al. A comparison of normalization methods for high density oligonucleotide array data based on variance and bias. Bioinformatics. Jan. 22, 2003;19(2):185-93.
Bonora et al. Novel germline variants identified in the inner mitochondrial membrane transporter TIMM44 and their role in predisposition to oncocytic thyroid carcinomas. Br J Cancer. 2006;95(11):1529-36.
Bosse et al. Molecular signature of smoking in human lung tissues. Cancer Research (2012); 72.15: 3753-3763.
Boulesteix, et al. Evaluating microarray-based classifiers: an overview. Cancer Inform. 2008;6:77-97. Epub Feb. 29, 2008.
Braakhuis et al. A Genetic Explanation of Slaughter's Concept of Field Cancerization Evidence and Clinical Implications. Cancer Research, 63: 1727-1730 (Apr. 2003).
Brambilla et al. p53 Mutant Immunophenotype and Deregulation of p53 Transcription Pathway (Bc12, Bax and Waf1) in Precursor Bronchial Lesions of Lunch Cancer. Clinical Cancer Research (4): 1609-1618 (1998).
Brasseur et al. Papillary thyroid carcinoma in a 9-year-old girl with ataxia-telangiectasia. Pediatr Blood Cancer. 2008;50(5):1058-60.
Brenner, et al. Gene expression analysis by massively parallel signature sequencing (MPSS) on microbead arrays. Nat Biotechnol. Jun. 2000;18(6):630-4.
British Thoracic society bronchoscopy committee, British Thoracic Society guidelines on diagnostic flexible bronchoscopy. Thorax, 2001, 56 (suppl I): i1-i21).
Brody, Jerome S. Abstract: Airway epithelial gene expression in COPD. National Institutes of Health. Grant No. 1RO1HL071771-01 (Funding Start Date Sep. 30, 2002).
Brozek et al. Thyroid cancer in two siblings with FAP syndrome and APC mutation. Int J Colorectal Dis. 2008;23(3):331-2.
Buckanovich et al. Nova, the paraneoplastic Ri antigen, is homologous to an RNA-binding protein and is specifically expressed in the developing motor system. Neuron (1993); 11.4: 657-672.
Bugalho et al. Mutation analysis of the RET proto-oncogene and early thyroidectomy: results of a Portuguese cancer centre. Surgery. 2007;141(1):90-5.
Byron et al. Translating RNA sequencing into clinical diagnostics: opportunities and challenges. Nature Reviews Genetics 17.5 (2016): 257.
Cameselle-Teijeiro et al. Follicular thyroid carcinoma with an unusual glomeruloid pattern of growth. Hum Pathol. 2008;39(10):1540-7.
Campbell, et al., Applying gene expression microarrays to pulmonary disease. Respirology, 16; 2011:407-418.
Camus et al. Interstitial lung disease induced by drugs and radiation. Respiration. Jul.-Aug. 2004;71(4):301-26.
Carda et al. Anaplastic carcinoma of the thyroid with rhabdomyosarcomatous differentiation: a report of two cases. Virchows Arch. 2005;446(1):46-51.
Carroll et al. Promising Molecular Techniques for Discriminating Among Follicular Thyroid Neoplasms. Surgical Oncology, Blackwell Scientific Publ., Oxford, GB, vol. 15, No. 2, Aug. 1, 2006, pp. 59-64.

(56) References Cited

OTHER PUBLICATIONS

Castro et al. Adenomas and follicular carcinomas of the thyroid display two major patterns of chromosomal changes. J Pathol. 2005;206(3):305-11.
Castro et al.PAX8-PPARgamma rearrangement is frequently detected in the follicular variant of papillary thyroid carcinoma. J Clin Endocrinol Metab. 2006;91(1):213-20.
Centeno et al. Classification of human tumors using gene expression profiles obtained after microarray analysis of fine-needle aspiration biopsy samples. Cancer Cytopathology: Interdisciplinary International Journal of the American Cancer Society 105.2 (2005): 101-109.
Cerutti et al. A preoperative diagnostic test that distinguishes benign from malignant thyroid carcinoma based on gene expression. J Clin Invest. 2004;113(8):1234-42.
Cerutti et al. Diagnosis of suspicious thyroid nodules using four protein biomarkers. Clin Cancer Res. 2006;12(11 Pt 1):3311-8.
Chan, et al. Integrating Transcriptomics and Proteomics. Drug Discovery and Development. Apr. 1, 2006. 4 pages. Published in G&P magazine 2006 vol. 6 No. 3 pp. 20-26.
Chan et al. Integrating Transcriptomics and Proteomics. Genomics & Proteomics Magazine, 6(3), text of article reprinted and accessed from www.dddmag.com Published Oct. 4, 2007. http://www.dddmag.com/article/2007/10/integrating-transcriptomics-and-proteomics.
Chari et al. Effect of active smoking on the human bronchial epithelium transcriptome. BMC Genomics, 8:297 (Aug. 29, 2007).
Chaudhuri et al. Low sputum MMP-9/TIMP ratio is associated with airway narrowing in smokers with asthma. European Respiratory Journal (Jul. 3, 2014); 44(4): 895-904.
Chen et al. Discordant Protein and mRNA Expression in Lung Adenocarcinomas. Molecular and Cellular Proteomics, 1: 304-313 (2001).
Chen et al. Enrichr: interactive and collaborative HTMLS gene list enrichment analysis tool. BMC Bioinformatics (2013); 14: 128.
Chen et al: "Expression of dihydrodiol dehydrogenase in theresected stage I non-small cell lung cancer", Oncologyreports, vol. 9, No. 3 May 1, 2002, pp. 515-519.
Chen et al. Restricted kappa/lambda light chain ratio by flow cytometry in germinal center B cells in Hashimoto thyroiditis. Am J Clin Pathol. 2006;125(1):42-8.
Chen et al. Up-regulations of Tumor Interleukin-8 Expression by Infiltrating Macrophages: Its Correlation with Tumor Angiogenesis and Patient Survival in Non-Small Cell Lung Cancer. Clinical Cancer Research: p. 729, (Feb. 1, 2003).
Cheng et al. A Multi-Cancer Mesenchymal Transition Gene Expression Signature Is Associated with Prolonged Time to Recurrence in Glioblastoma. Plos One 7(4):e34705 (2012).
Cheng et al. Reduced expression levels of nucleotide excision repair genes in lung cancer: a case-control analysis. Carcinogenesis. 21(8):1527-1530 (2000).
Cheung, et al. Immunohistochemical diagnosis of papillary thyroid carcinoma. Mod Pathol. Apr. 2001;14(4):338-42.
Cheung, et al. Natural Variation in Human Gene Expression Assessed in Lymphoblastoid Cells. Nature Genetics. vol. 33 (2003): pp. 422-425.
Chevillard et al. Gene expression profiling of differentiated thyroid neoplasms: diagnostic and clinical implications. Clin Cancer Res. 2004;10(19):6586-97.
Chiappetta et al. The antiapoptotic protein BAG3 is expressed in thyroid carcinomas and modulates apoptosis mediated by tumor necrosis factor-related apoptosis-inducing ligand. J Clin Endocrinol Metab. 2007;92(3):1159-63.
Cho et al. System biology of interstitial lung diseases: integration of mRNA and microRNA expression changes. 2011, BMC Medical Genomics, 4:8, p. 1-20.
Choi et al. Case-control association testing in the presence of unknown relationships. Genetic epidemiology 33.8 (2009): 668-678.
Choi etal. Model Assisted Statistics and Applications.2017. 12:265-273. (Year: 2017).
Chudova, et al. Molecular classification of thyroid nodules using high-dimensionality genomic data. J Clin Endocrinol Metab. Dec. 2010;95(12):5296-304. doi: 10.1210/jc.2010-1087. Epub Sep. 8, 2010.
Chung et al. Detection of BRAFV600E mutation on fine needle aspiration specimens of thyroid nodule refines cyto-pathology diagnosis, especially in BRAF600E mutation-prevalent area. Clin Endocrinol (Oxf). 2006;65(5):660-6.
Chung KW et al., Gene expression profiling of papillary thyroid carcinomasin Korean patients by oligonucleotide microarrays. Journal of the KoreanSurgical Society, Apr. 26, 2012, vol. 82, No. 5, pp. 271-280whole document.
Ciampi et al. BRAF copy number gains in thyroid tumors detected by fluorescence in situ hybridization. Endocr Pathol. 2005;16(2):99-105.
Cibas, et al. The Bethesda System for Reporting Thyroid Cytopathology. Am J Clin Pathol. Nov. 2009;132(5):658-65. doi: 10.1309/AJCPPHLWMI3JV4LA.
Cirulli Uncovering the roles of rare variants in common disease through whole-genome sequencing. Nature Reviews Genetics 11.6 (2010): 415.
Clark et al. Altered Protein Kinase C (Pkc) Isoforms in Non-Small Cell Lung Cancer Cells: PKCdelta Promotes Cellular Survival and Chemotherapeutic Resistance. Cancer Research, 63(4): 780-786 (2003).
Clark et al. Discovery of tissue-specific exons using comprehensive human exon microarrays. Genome Biol. 2007;8(4):R64.
Cogan, et al., Rare variants in RTEL1 Are associated with familial interstitial Pneumonia. American Journal of respiratory and critical care medicine, Mar. 15, 2015; 191(6):646-655.
Cohen et al. Mutational analysis of BRAF in fine needle aspiration biopsies of the thyroid: a potential application for the preoperative assessment of thyroid nodules. Clin Cancer Res. 2004;10(8):2761-2765.
Coleman, Of Mouse And Man—what Is The Value Of The Mouse In Predicting Gene Expression In Humans?. Drug Discovery Today. vol. No. 8, Issue No. 6 (2003): 233-235.
Collard et al. Changes in clinical and physiologic variables predict survival in idiopathic pulmonary fibrosis. American Journal of Respiratory and Critical Care Medicine (May 2003); 168.5: 538-542.
Cooper, et al. Management guidelines for patients with thyroid nodules and differentiated thyroid cancer. Thyroid. Feb. 2006;16(2):109-42.
Cooper. Gene Expression Studies in Lung Cancer. The Molecular Genetics of Lung Cancer, pp. 167-186, (2005).
Co-pending U.S. Appl. No. 15/096,739, inventors Giulia; C. Kennedy et al., filed Apr. 12, 2016.
Co-pending U.S. Appl. No. 16/279,252, inventors KennedyGiulia; C. et al., filed Feb. 19, 2019.
Co-pending U.S. Appl. No. 16/422,109, inventors KennedyGiulia; C. et al., filed May 24, 2019.
Co-pending U.S. Appl. No. 16/534,889, inventors KennedyGiulia; C. et al., filed Aug. 7, 2019.
Co-pending U.S. Appl. No. 16/541,041, inventors KennedyGiulia; C. et al., filed Sep. 5, 2019.
Co-pending U.S. Appl. No. 16/551,645, inventors KennedyGiulia; C. et al., filed Aug. 26, 2019.
Co-pending U.S. Appl. No. 16/557,278, inventors WildeJonathan; I. et al., filed Aug. 30, 2019.
Co-pending U.S. Appl. No. 16/593,918, inventors WhitneyDuncan; H. et al., filed Oct. 4, 2019.
Co-pending U.S. Appl. No. 16/594,586, inventors KennedyGiulia; C. et al., filed Oct. 7, 2019.
Co-pending U.S. Appl. No. 16/693,194, inventors WhitneyDuncan; H. et al., filed Nov. 22, 2019.
Co-pending U.S. Appl. No. 16/721,783, inventors KennedyGiulia; C. et al., filed Dec. 19, 2019.
Co-pending U.S. Appl. No. 16/820,537, inventors KennedyGiulia; C. et al., filed Mar. 16, 2020.
Co-pending U.S. Appl. No. 16/820,599, inventors Kennedy; Giulia C. et al., filed Mar. 16, 2020.

(56) References Cited

OTHER PUBLICATIONS

Co-pending U.S. Appl. No. 16/886,477, inventors Kennedy; Giulia C. et al., filed May 28, 2020.
Co-pending U.S. Appl. No. 16/910,039, inventors Kennedy; Giulia C. et al., filed Jun. 23, 2020.
Co-pending U.S. Appl. No. 16/945,119, inventors WhitneyDuncan; H. et al., filed Jul. 31, 2020.
Co-pending U.S. Appl. No. 17/003,228, inventors KennedyGiulia; C. et al., filed Aug. 26, 2020.
Co-pending U.S. Appl. No. 17/084,593, inventors KennedyGiulia; C. et al., filed Oct. 29, 2020.
Co-pending U.S. Appl. No. 17/084,622, inventors KennedyGiulia; C. et al., filed Oct. 29, 2020.
Co-pending U.S. Appl. No. 17/145,563, inventors KennedyGiulia; C. et al., filed Jan. 11, 2021.
Co-pending U.S. Appl. No. 17/169,082, inventors KennedyGiulia; C. et al., filed Feb. 5, 2021.
Co-pending U.S. Appl. No. 17/169,397, inventors Davicionielai et al., filed Feb. 5, 2021.
Co-pending U.S. Appl. No. 17/190,408, inventors WhitneyDuncan; H. et al., filed Mar. 3, 2021.
Co-pending U.S. Appl. No. 17/322,681, inventors KennedyGiulia; C. et al., filed May 17, 2021.
Co-pending U.S. Appl. No. 17/338,585, inventors KennedyGiulia; C. et al., filed Jun. 3, 2021.
Co-pending U.S. Appl. No. 17/338,587, inventors KennedyGiulia; C. et al., filed Jun. 3, 2021.
Co-pending U.S. Appl. No. 17/409,670, inventors KennedyGiulia; C. et al., filed Aug. 23, 2021.
Co-pending U.S. Appl. No. 17/476,284, inventors KennedyGiulia; C. et al., filed Sep. 15, 2021.
Co-pending U.S. Appl. No. 17/501,856, inventors WhitneyDuncan; H. et al., filed Oct. 14, 2021.
Cortes et al. Support-vector networks. Machine Learning. 1995; 20:273-297.
Costa et al. New somatic mutations and WNK1-B4GALNT3 gene fusion in papillary thyroid carcinoma. Oncotarget 6:11242-11251 (2015).
Cottin et al. Neglected evidence in idiopathic pulmonary fibrosis and the importance of early diagnosis and treatment. European Respiratory Review (Mar. 1, 2014); 23.131: 106-110.
Covey et al. Factors associated with pneumothorax and pneumothorax requiring treatment after percutaneous lung biopsy in 443 consecutive patients. Journal of Vascular and Interventional Radiology (2004); 15.5: 479-483.
Crawford et al. Normal Bronchial Epithelial Cell Expression of Glutathione Transferase P1, Glutathione Transferase M3, and Glutathione Peroxidase is Low in Subjects with Bronchogenic Carcinoma. Cancer Research, 60: 1609-1618 (Mar. 15, 2000).
Crescioli et al. Methimazole inhibits CXC chemokine ligand 10 secretion in human thyrocytes. J Endocrinol. 2007;195(1):145-55.
Cross et al. The promise of molecular profiling for cancer identification and treatment. Clinical medicine & research 2.3 (2004): 147-150.
Cummings, SR. et al. Estimating the probability of malignancy in solitary pulmonary nodules. A Bayesian approach, Am Rev Respir Dis 1986;134:449-52 (1986).
Dai et al. Evolving gene/transcript definitions significantly alter the interpretation of GeneChip data. Nucleic Acids Research 33.20 (2005): e175-e175.
Danel et al. Quantitative Assessment of the Epithelial and Inflammatory Cell Populations in Large Airways of Normals and Individuals with Cystic Fibrosis. Am. Journal of Resp. And Critical Care Medicine 153:362-368 (1996).
Dauletbaev et al. Expression of Human Beta Defensin (HBD-1 and HBD-2) mRNA in Nasal Epithelia of Adult Cystic Fibrosis Patients, Healthy Individuals, and Individuals with Acute Cold. Respiration, 69:46-51 (2002).
De Figueiredo-Pontes, Idenification and characterization of ALK kinase splicing isoforms on non-small-cell lung cancer, J Thorac Oncol, 9(2): 248-253, Feb. 2014. (Year: 2014).
De Lellis et al. The pathobiology of the human calcitonin (C)-cell: a review. Pathol Annu. 1981;16(Pt 2):25-52.
Del Senno et al. c-myc oncogene alterations in human thyroid carcinomas. Cancer Detect Prev. 1987;10(3-4):159-66.
Delehaye, et al., Elevated levels of calcitonin mRNA: A marker for the spontaneous development of medullary thyroid carcinoma in rats. Biochemical and biophysical research communications, Mar. 15, 1989; 159(2): 528-535.
Delellis et al. C-cell hyperplasia. An ultrastructural analysis. Lab Invest. 1977;36(3):237-48.
Delibasis, et al., "Computer-Aided Diagnosis of Thyroid Malignancy Using an Artificial Immune System Classification Algorithm," IEEE Transactions on Information Technology in Biomedicine, vol. 13, No. 5, pp. 680-686, Sep. 2009.
DeLong et al. Comparing the areas under two or more correlated receiver operating characteristic curves: a nonparametric approach. Biometrics (1988); 44(3): 837-845.
DeLuca et al. RNA-SeQC: RNA-seq metrics for quality control and process optimization. Bioinformatics (2012); 28.11: 1530-1532.
DeMeo et al. The SERPINE2 gene is associated with chronic obstructive pulmonary disease. Am J Hum Genet., 78(2): 253-264 (Feb. 2006).
Demoly et al. c-fos Proto-oncogene Expression in Bronchial Biopsies of Asthmatics. American Journal of Respiratory Cell and Molecular Biology 7:128-133 (1992).
Dempsey, et al. Lung disease and PKCs. Pharmacol Res., 55 6 : 545-59 2007.
DeMuth et al. The Gene Expression of Index c-myc X E2F-1/p21 Is Highly Predictive of Malignant Phenotype in Human Bronchial Epithelial Cells. Am. J. Cell Mol. Bio. (19): 18-24 (1998).
Deng et al. Ubiquitous Induction of Resistance to Platinum Drugs in Human Ovarian, Cervical, Germ-Cell and Lung Carcinoma Tumor Cells Overexpressing Isoforms 1 and 2 of Dihydrodiol Dehydrogenase. Cancer Chemother. PharmacoL, 54:301-307, (2004).
Denis et al. RING3 Kinase Transactivates Promoters of Cell Cycle Regulatory Genes through E2F1 Cell. Growth Differ; 11: 417-424 (Aug. 2000).
Depeursinge et al. Automated classification of usual interstitial pneumonia using regional volumetric texture analysis in high-resolution computed tomography. Invest Radiol. Apr. 2015;50(4):261-7.
DePianto et al. Heterogeneous gene expression signatures correspond to distinct lung pathologies and biomarkers of disease severity in idiopathic pulmonary fibrosis. Thorax (2015); 70.1: 48¬56.
Derringer, et al. Malignant lymphoma of the thyroid gland: a clinicopathologic study of 108 cases. Am J Surg Pathol. May 2000;24(5):623-39.
Details for HG-U133A:217291 _AT (Ceacams) (https://www.affymetrix.com/analysis/netaffx/fullrecord.affx?pk=HG-U133A:217291_AT, downloaded Apr. 22, 2016).
DetailsforHG-U112A:823_AT (http://www.affymetrix.com/analysis/netaffx/fultrecord.affx?pk=HG-U133A:823 AT, downloaded Dec. 10, 2012).
DetailsforHG-U133A:202831_AT (https://www.affymetrix.com/analysis/netaffx/fullrecord.affx?pk=HG-U133A:202831AT, downloaded Dec. 10, 2012).
DetailsforHG-U133a-207469_S_AT (https://www.affymetrix.com/analysis/netaffx/fullrecod.affx?pk=HG-U133A:207469 S AT, downloaded Dec. 10, 2012).
DetailsforHG-U133A:210519_S_AT (https://www.affvmetrix.com/analysis/netaffx/fullrecord.affx?pk=HG-U133A:210519 S AT downloaded Dec. 10, 2012).
Detterbeck et al. Screening for lung cancer: diagnosis and management of lung cancer: American College of Chest Physicians evidence-based clinical practice guidelines. Chest Journal (2013); 143.5_suppl: e78S-e92S.
Dettori et al. Aneuploidy in oncocytic lesions of the thyroid gland: diffuse accumulation of mitochondria within the cell is associated with trisomy 7 and progressive numerical chromosomal alterations. Genes Chromosomes Cancer. 2003;38(1):22-31.

(56) References Cited

OTHER PUBLICATIONS

Diaz-Uriarte et al. Gene selection and classification of microarray data using random forest. BMC Bioinformatics. 2006;7:3.
Ding et al. A high-throughput gene expression analysis technique using competitive PCR and matrix-assisted laser desorption ionization time-of-flight MS. Proceedings of the National Academy of Sciences USA (2003); 100.6: 3059-3064.
Dobin et al.: Star: Ultrafast Universal RNA-Seq Aligner. Bioinformatics 29:15-21 (2012).
Doll et al. Mortality in relation to smoking: 40 years' observations on male British doctors. BMJ; 309:901-911 (Oct. 8, 1994).
Doris et al. Quantitative analysis of gene expression by ion-pair high-performance liquid chromatography. Journal of Chromatography A (1998); 806.1: 47-60.
Dou et al. PLOS Genetics. 2017. 13(9):e1007021. (Year:2017).
Dougherty. The fundamental role of pattern recognition for gene-expression/microarray data in bioinformatics. Pattern recognition. 2005; 38:2226-2228.
Druckenthaner et al. Evidence for Somatostatin receptor 2 in thyroid tissue. Regul Pept. 2007;138(1):32-9.
Du Bois et al. Ascertainment of individual risk of mortality for patients with idiopathic pulmonary fibrosis. American Journal of Respiratory and Critical Care Medicine (2011); 184.4: 459-466.
Du Bois, R. M. Strategies for treating idiopathic pulmonary fibrosis. Nature reviews Drug Discovery (2010); 9.2: 129-140.
Durand et al. Evaluation of gene expression profiles in thyroid nodule biopsy material to diagnose thyroid cancer. J Clin Endocrinol Metab. 2008;93(4):1195-202.
Durante, et al. BRAF mutations in papillary thyroid carcinomas inhibit genes involved in iodine metabolism. J Clin Endocrinol Metab. Jul. 2007;92(7):2840-3. Epub May 8, 2007.
Durham et al. The Relationship Between COPD and Lung Cancer. Lung Cancer, 90:121-127, (2015).
Ebbert, et al. Lung Cancer Risk Reduction After Smoking Cessation: Observations From a Prospective Cohort of Women. J Clin Oncol; 21(5):921-926 (Mar. 1, 2003).
Elisabeth Brambilla, et al., "Advances in Brief p53 Mutant Immunophenotype and Deregulationof p53 Transcription Pathway (Bc12, Bax, and Waft) in Precursor Bronchial Lesions of LungCancer", Clinical Cancer Research 4.7 (1998): 1609-1618.
Elisei et al. RET genetic screening in patients with medullary thyroid cancer and their relatives: experience with 807 individuals at one center. J Clin Endocrinol Metab. 2007;92(12):4725-9.
Elliot, et al., Transcriptome analysis of peripheral blood mononuclear cells in human subjects following a 36 h fast provides evidence of effects on genes regulating inflammation, apoptosis and energy metabolism. Genes & Nutrition; studying the relationship between genetics and nutrition in the improvement of human health, Berlin; Heidelberg: Springer, DE. Sep. 2014; 9(6): 1-11.
Ellis, et al., Rare variants in MYD88, IRAK4 and IKBKG and susceptibility to invasive Pneumococcal disease: A population-based case-control study. PLoS One, Apr. 2015; 10(4): 1-9.
EMBL database (Gene: CXCL2 ENSG00000081041. https://useast.ensembl.org/Homo_sapiens/Gene/Summary?g=ENSG00000081041;r=4:740 . . . , downloaded Jul. 20, 2020.
EMBL database (Gene: ZNF671 ENSG00000083814. https://useast.ensembl.org/Homo_sapiens/Gene/Summary?g=ENSG00000083814;r=19:57719751-57727624, downloaded Jul. 20, 2020.
Enard, et al. Intra- and interspecific variation in primate gene expression patterns. Science. Apr. 12, 2002;296(5566):340-343. doi: 10.1126/science.1068996.
Endocrine website. http://www.endocrineweb.com/noduleus.html (Accessed Dec. 9, 2011) (last update Oct. 12, 2010).
Englisch, et al. Chemically Modified Oligonucleotides as Probes and Inhibitors. Angew. Chem. Int. Ed. Eng. 1991; 30:613-629.
Engstrom et al. Systematic evaluation of spliced alignment programs for RNA-seq data. Nature methods 10.12 (2013): 1185.
Erdogan et al. The prevalence of RET/PTC mutations in papillary thyroid cancers in Turkish population and its relation between tumor histopathology and prognostic factors. Exp Clin Endocrinol Diabetes. 2008;116(4):225-30.
Erkkila et al. Probabilistic analysis of gene expression measurements from heterogeneous tissues. Bioinformatics 26(20):2571-2577 (2010).
Ernst et al. Interventional pulmonary procedures: guidelines from the American College of Chest Physicians. Chest Journal (May 2003); 123.5: 1693-1717.
Esperante, et al. Identification and characterization of four PAX8 rare sequence variants (p.T225M, p.L233L, p.G336S and p.A439A) in patients with congenital hypothyroidism and dysgenetic thyroid glands. Clin Endocrinol (Oxf). May 2008;68(5):828-35.
Eszlinger et al. Gene expression analysis reveals evidence for inactivation of the TGF-beta signaling cascade in autonomously functioning thyroid nodules. Oncogene. 2004;23(3):795-804.
Eszlinger et al. Meta- and reanalysis of gene expression profiles of hot and cold thyroid nodules and papillary thyroid carcinoma for gene groups. J Clin Endocrinol Metab. 2006;91(5):1934-42.
Eszlinger et al. Perspectives and limitations of microarray-based gene expression profiling of thyroid tumors. Endocr Rev. 2007;28(3):322-38.
Eszlinger, et al. Perspectives for Improved and More Accurate Classification of Thyroid Epithelial Tumors. J Clin Endocrinol Metab. Sep. 2008;93(9):3286-94. Epub Jul. 1, 2008.
Fahy, JV. Remodeling of the Airway Epithelium in Asthma. Am. J. Respir. Crit. Care Med. 164:S46-S51 (2001).
Ferrari, et al. An approach to estimate between- and within-group correlation coefficients in multicenter studies: plasma carotenoids as biomarkers of intake of fruits and vegetables. Am J Epidemiol. Sep. 15, 2005;162(6):591-8. Epub Aug. 10, 2005.
Fielding et al. Heterogeneous Nuclear Ribonucleoprotein A2B1 Up-Regulation in Bronchial Lavage Specimens: A Clinical Marker of Early Lung Cancer Detection. Clinical Cancer Research. 5:4048-4052 (1999).
Filicori, et al. Risk stratification of indeterminate thyroid fine-needle aspiration biopsy specimens based on mutation analysis. Surgery. Dec. 2011;150(6):1085-91.
Finley et al. Advancing the molecular diagnosis of thyroid nodules: defining benign lesions by molecular profiling. Thyroid. 2005;15(6):562-8.
Finley et al. Discrimination of benign and malignant thyroid nodules by molecular profiling. Ann Surg. 2004;240(3):425-36; discussion 436-7.
Finley et al. Molecular analysis of Hurthle cell neoplasms by gene profiling. Surgery. 2004;136(6):1160-8.
Finley et al. Molecular profiling distinguishes papillary carcinoma from benign thyroid nodules. J Clin Endocrinol Metab. 2004;89(7):3214-23.
Finn, et al. Expression microarray analysis of papillary thyroid carcinoma and benign thyroid tissue: emphasis on the follicular variant and potential markers of malignancy. Virchows Arch. Mar. 2007;450(3):249-60.
Fishel, et al. Meta-analysis of gene expression data: a predictor-based approach. Bioinformatics. Jul. 1, 2007;23(13):1599-606. Epub Apr. 26, 2007.
Flaherty et al. Clinical significance of histological classification of idiopathic interstitial pneumonia. European Respiratory Journal (2002); 19.2: 275-283.
Flaherty et al. Histopathologic variability in usual and nonspecific interstitial pneumonias. American Journal of Respiratory and Critical Care Medicine (2001); 164.9: 1722-1727.
Flaherty et al. Idiopathic interstitial pneumonia: what is the effect of a multidisciplinary approach to diagnosis?. American Journal of Respiratory and Critical Care Medicine (2004); 170.8: 904¬910.
Flaherty et al. Radiological versus histological diagnosis in UIP and NSIP: survival implications. Thorax (Feb. 2003); 58.2: 143-148.
Fodor, et al. Light-directed, spatially addressable parallel chemical synthesis. Science. Feb. 15, 1991;251(4995):767-73.
Fontaine, et al. Increasing the number of thyroid lesions classes in microarray analysis improves the relevance of diagnostic markers. PLoS One. Oct. 29, 2009;4(10):e7632.

(56) References Cited

OTHER PUBLICATIONS

Fontaine et al. Microarray analysis refines classification of non-medullary thyroid tumours of uncertain malignancy. Oncogene. 2008;27(15):2228-36.
Fontaine-Delaruelle et al. Is transthoracic core needle biopsy under CT scan a good deal for benign diseases' diagnosis? European Respiratory Journal (2014); 44.Suppl 58: P679.
Foppiani et al. Uncommon association of germline mutations of RET proto-oncogene and CDKN2A gene. Eur J Endocrinol. 2008;158(3):417-22.
Fox et al. Applications of ultra-high-throughput sequencing. Methods in molecular biology. vol. No. 553 (2009): pp. 79-108.
Frampton, et al. Development and validation of a clinical cancer genomic profiling test based on massively parallel DNA sequencing. Nat Biotechnol. Nov. 2013;31(11):1023-31. Epub Oct. 20, 2013.
Franklin, et al. Widely Dispersed p53 Mutation in Respiratory Epithelium. The Journal of Clinical Investigation, 100(8): 2133-2137 (1997).
Frattini, et al. Alternative mutations of BRAF, RET and NTRK1 are associated with similar but distinct gene expression patterns in papillary thyroid cancer. Oncogene. Sep. 23, 2004;23(44):7436-40.
Freeman et al. DNA from Buccal Swabs Recruited by Mail: Evaluation of Storage Effects on Long-term Stability and Suitability for Multiplex Polymerase Chain Reaction Genotyping, Behavior Genetics, 33: 67 (2003).
Friedman et al. Regularization Paths for Generalized Linear Models via Coordinate Descent. J Stat Softw 33:1-22 (2010).
Fritz et al. Nasal mucosal gene expression in patients with allergic rhinitis with and without nasal polyps. Journal of Allergy Clin. Immunol, 112(6): 1057-1063 (Dec. 2003).
Frohman et al. Rapid production of full-length cDNAs from rare transcripts: amplification using a single gene-specific oligonucleotide primer. Proc Natl Acad Sci U S A. Dec. 1988;85(23):8998-9002.
Frohman On Beyond Classic RACE (Rapid Amplification of eDNA Ends) PCR Methods and Applications vol. 4, pp. S40-S58 (Year: 1994).
Fryknas et al. Molecular markers for discrimination of benign and malignant follicular thyroid tumors. Tumour Biol. 2006;27(4):211-20.
Fujarewicz, et al. A multi-gene approach to differentiate papillary thyroid carcinoma from benign lesions: gene selection using support vector machines with bootstrapping. Endocr Relat Cancer. Sep. 2007;14(3):809-26.
Fukumoto et al. Overexpression of the Aldo-Keto Reductase Family Protein AKR1B10 is Highly Correlated with Smokers' Non-Small Cell Lung Carcinomas. Clinical Cancer Research 11:1776-1785 (2005).
Furneaux et al. Selective expression of Purkinje-cell antigens in tumor tissue from patients with paraneoplastic cerebellar degeneration. New England Journal of Medicine (1990); 322.26: 1844-1851.
Gait. Chapter 16: Oligoribonucleotides. Antisense Research and Applications, Crookeand Lebleu Eds., CRC Press (pp. 289-302) (1993).
Garber et al. Diversity of gene expression in adenocarcinoma of the lung. PNAS, 98(24): 13784-13789 (Nov. 20, 2001).
Garcia-Alvarez et al. Tissue inhibitor of metalloproteinase-3 is up-regulated by transforming growth factor-131 in vitro and expressed in fibroblastic foci in vivo in idiopathic pulmonary fibrosis. Experimental Lung Research (Apr. 2006); 32(5): 201-214.
Garcia-Closas et al. Collection of Genomic DNA from Adults in Epidemiological Studies by Buccal Cytobrush and Mouthwash. Cancer Epidemiology, Biomarkers and Prevention, 10(6): 687-696 (2001).
Garcia-Lopez et al. Thyrocytes from autoimmune thyroid disorders produce the chemokines IP-10 and Mig and attract CXCR3+ lymphocytes. J Clin Endocrinol Metab. 2001;86(10):5008-16.
Gardina et al. Alternative splicing and differential gene expression in colon cancer detected by a whole genome exon array. BMC Genomics. 2006;7:325.
Gasparre et al. Disruptive mitochondrial DNA mutations in complex I subunits are markers of oncocytic phenotype in thyroid tumors. Proc Natl Acad Sci USA. 2007;104(21):9001-6.
Gebel, et al. Gene expression profiling in respiratory tissues from rats exposed to mainstream cigarette smoke. Carcinogenesis. Feb. 2004;25(2):169-78.
Gene Annot Website. Array Probesets for HOMER2, printed Jan. 2016.
Gene Annot website. Probesets for ALDH1B1. Printed Feb. 2018.
Gene Annot website. Probesets for AUTS2. Printed Feb. 2018.
Gene Annot website. Probesets for CFHR1. Printed Feb. 2018.
Gene Annot website. Probesets for CPE. Printed Feb. 2018.
Gene Annot website. Probesets for FN1. Printed Feb. 2018.
Gene Annot website. Probesets for GABRB2. Printed Feb. 2018.
Gene Annot website. Probesets for PLCB1. Printed Feb. 2018.
Gene Annot website. Probesets for PYGL. Printed Feb. 2018.
Gene Annot website. Probesets for ROS1. Printed Feb. 2018.
GeneAnnot Search for Affymetrix HG-U 133A microarray pro besets for TIMP1, printed Dec. 2018.
GeneAnnot Search for Affymetrix HG-U 133A microarray probesets for SLCA4, printed Dec. 2018.
GeneAnnot website. Probesets for AKT1. Printed Aug. 30, 2016. 1 page.
GeneAnnot website. Probesets for ALK. Printed Aug. 30, 2016. 1 page.
GeneAnnot website. Probesets for BRAF. Printed Aug. 30, 2016. 1 page.
GeneAnnot website. Probesets for CALCA. Printed Aug. 30, 2016. 1 page.
GeneAnnot website. Probesets for CTNNB1. Printed Aug. 30, 2016. 1 page.
GeneAnnot website. Probesets for EIF1AY. Printed Aug. 30, 2016. 1 page.
GeneAnnot website. Probesets for IGF2BP2. Printed Aug. 30, 2016. 1 page.
GeneAnnot website. Probesets for KRAS. Printed Feb. 7, 2017. 2 pages.
GeneAnnot website. Probesets for KRT7. Printed Aug. 30, 2016. 1 page.
GeneAnnot website. Probesets for MET. Printed Aug. 30, 2016. 1 page.
GeneAnnot website. Probesets for NTRK2. Printed Aug. 30, 2016. 1 page.
GeneAnnot website. Probesets for NTRK3. Printed Aug. 30, 2016. 2 pages.
GeneAnnot website. Probesets for PIK3CA. Printed Aug. 30, 2016. 1 page.
GeneAnnot website. Probesets for PPARGC1A. Printed Aug. 30, 2016. 1 page.
GeneAnnot website. Probesets for PROS1. Printed Nov. 8, 2016. 1 page.
GeneAnnot website. Probesets for PTEN. Printed Aug. 30, 2016. 2 pages.
GeneAnnot website. Probesets for PTH. Printed Aug. 30, 2016. 1 page.
GeneAnnot website. Probesets for RASA1. Printed Aug. 30, 2016. 1 page.
GeneAnnot website. Probesets for RET. Printed Aug. 30, 2016. 1 page.
GeneAnnot website. Probesets for RXRG. Printed Nov. 8, 2016. 1 page.
GeneAnnot website. Probesets for TP53. Printed Aug. 30, 2016. 1 page.
GeneAnnot website. Probesets for TSHR. Printed Aug. 30, 2016. 1 page.
GeneAnnot website. Probesets for TTF1. Printed Aug. 30, 2016. 1 page.

(56) References Cited

OTHER PUBLICATIONS

Geneloc CYP4F11. Geneloc Integrated Map for Chromosome 19: Exon structure for CYP4F11, https://genecards.weizmann.ac.il/ geneloc-bin/exon_struct.pl?disp_name=CYP4F11&chr_nr=19, accessed Dec. 13, 2019, pp. 1-2 (Year: 2019).
Geraghty et al. CT-guided transthoracic needle aspiration biopsy of pulmonary nodules: Needle size and pneumothorax rate 1. Radiology. Nov. 2003;229(2):475-81.
Gereben et al. Pretranslational regulation of type 2 deiodinase. Thyroid. 2005;15(8):855-64.
Gerstung, et al. Combining gene mutation with gene expression data improves outcome prediction in myelodysplastic syndromes. Nat Commun. Jan. 9, 2015;6:5901.
Gildea et al. Electromagnetic navigation diagnostic bronchoscopy: a prospective study. American Journal of Respiratory and Critical Care Medicine. Nov. 2006; 174(9):982-989.
Gill, et al. Nucleic acid isothermal amplification technologies: a review. Nucleosides Nucleotides Nucleic Acids. Mar. 2008;27(3):224-43.
Giordano et al. Delineation, functional validation, and bioinformatic evaluation of gene expression in thyroid follicular carcinomas with the PAX8-PPARG translocation. Clin Cancer Res. 2006;12(7 Pt 1):1983-93.
Giordano et al. Distinct transcriptional profiles of adrenocortical tumors uncovered by DNA microarray analysis. Am J Pathol. 2003;162(2):521-31.
Giordano et al. Molecular Classification of Papillary Thyroid Carcinoma; distinct Braf, Ras and RET/PTC mutation-specific gene expression profiles discovered by DNA microarray Analysis Oncogene. Oncogene 24:6646-6656 (2005).
Giordano et al. Organ-specific molecular classification of primary lung, colon, and ovarian adenocarcinomas using gene expression profiles. Am J Pathol. 2001;159(4):1231-8.
Giordano. Genome-wide studies in thyroid neoplasia. Endocrinol Metab Clin North Am. 2008;37(2):311-31, vii-viii.
Golub, et al. Molecular classification of cancer: Discovery and class prediction by gene expression monitoring. Science, 286, 531-537, 1999.
Gombos, et al. Characterization of microarray gene expression profiles of early stage thyroid tumours. Cancer Genomics Proteomics. Nov.-Dec. 2007;4(6):403-9.
Gonzalez-Campora et al. Blood group antigens in differentiated thyroid neoplasms. Arch Pathol Lab Med. 1998;122(11):957-65.
Gorringe, et al., Loss of Heterozygosity. eLS, 2016; 1-8.
Gould et al. (1987). Synaptophysin expression in neuroendocrine neoplasms as determined by immunocytochemistry. Am J Pathol. 126(2):243-57.
Gould et al. A clinical model to estimate the pretest probability of lung cancer in patients with solitary pulmonary nodules. Chest Journal (2007); 131.2: 383-388.
Gould et al. Evaluation of individuals with pulmonary nodules: When is it lung cancer?: Diagnosis and management of lung cancer: American College of Chest Physicians evidence-based clinical practice guidelines. Chest Journal (2013); 143.5_suppl: e93S-e120S.
Gould et al. Recent trends in the identification of incidental pulmonary nodules. Am J Respir Crit Care Med. Nov. 15, 2015;192(10):1208-14.
Gower A C et al: “Transcriptomic studies of the airway field of injury associated with smoking-related lung disease”, Proceedings of the American Thoracic Society May 1, 2011 American Thoracic Society USA, val. 8, No. 2, May 1, 2011 (May 1, 2011 ), pp. 173-179.
Goy, A. et al., ’The feasibility of gene expression profiling generated in fine-needle aspiration specimensfrom patients with follicular lymphoma and diffuse large B-cell lymphoma’, Cancer. 2006 vol. 108 pp. 10-20.
Greenbaum, et al. Comparing protein abundance and mRNA expression levels on a genomic scale. Genome Biol. 2003;4(9):117. Epub Aug. 29, 2003.
Greenbaum, et al. Interrelating different types of genomic data, from proteome to secretome: ’oming in on function. Genome Res. Sep. 2001;11(9):1463-8.
Greenlee et al. Cancer Statistics, 2001. CA Cancer J Clin; 51(1):15-36 (2001).
Grepmeier et al. Deletions at chromosome 2q and 12p are early frequent molecular alterations in bronchial epithelium and NSCLC of long-term smokers. Int J Oncol., 27(2):481-8(2005).
Griffith, et al. Biomarker panel diagnosis of thyroid cancer: a critical review. Expert Rev Anticancer Ther. Sep. 2008;8(9):1399-413.
Griffith et al. Meta-analysis and meta-review of thyroid cancer gene expression profiling studies identifies important diagnostic biomarkers. J Clin Oncol. 2006;24(31):5043-51.
Grogan et al. Thoracic operations for pulmonary nodules are frequently not futile in patients with benign disease. Journal of Thoracic Oncology (2011); 6.10: 1720-1725.
Guajardo et al. Altered gene expression profiles in nasal respiratory epithelium reflect stable versus actue childhood asthma. J. Allergy Clin Immunol; 115(2): 243-251 (2005).
Guatelli, J C, et al., Isothermal, In Vitro Amplification Of Nucleic Acids By A Multienzyme Reaction Modeled After Retroviral Replication. Proceedings of the National Academy of Sciences of the United States of America 87(5):1874-1878 (1990).
Gulati, Mridu. Diagnostic assessment of patients with interstitial lung disease. Prim Care Respir J. Jun. 2011;20(2):120-7.
Gurney, JW. Determining the likelihood of malignancy in solitary pulmonary nodules with Bayesian analysis Part 1 Theory. Radiology 1993; 186:405-13 (2005).
Gustafson, Adam M, et al., Airway PI3K Pathway Activation Is An Early And Reversible Event In Lung Cancer Development. Science Translational Medicine 2(26): 25 Pages (2010).
Ha et al. Localized non-Hodgkin lymphoma involving the thyroid gland. Cancer91.4 (2001): 629-635.
Hackett, et al., The Human Airway epithelial basal cell transcriptome, Plos One, 2011; 6(5): e18378 pp. 1-22.
Hackett et al. Variability of antioxidant-related gene expression in the airway epithelium of cigarette smokers. Am J Respir Cell Mol Biol., 29: 331-43 (Apr. 2003).
Hadd, et al. Targeted, high-depth, next-generation sequencing of cancer genes in formalin- fixed, paraffin-embedded and fine-needle aspiration tumor specimens. J Mol Diagn. Mar. 2013;15(2):234-47. doi: 10.1016/j.jmoldx.2012.11.006. Epub Jan. 13, 2013.
Hamada, et al. Diagnostic usefulness of PCR profiling of the differentially expressed marker genes in thyroid papillary carcinomas. Cancer Lett. Jun. 28, 2005;224(2):289-301. Epub Nov. 18, 2004.
Hamilton et al. Diagnosis of lung cancer in primary care: a structured review. Fam Pract. Dec. 2004;21(6):605-11.
Hanley et al. The meaning and use of the area under a receiver operating characteristic (ROC) curve. Radiology. Apr. 1982;143(1):29-36.
Harach et al. Histology of familial thyroid tumours linked to a gene mapping to chromosome 19p13.2. J Pathol. 1999;189(3):387-93.
Hartigan, et al. The dip test of unimodality. Annals of Statistics. 1985; 13(1):70-84.
Haugen, et al. Development of a novel molecular classifier to accurately identify benign thyroid nodules in patients with indeterminate FNA cytology. Abstract presented at 14th International Thyroid Congress. Sep. 15, 2010.
Haugen et al. Increased expression of genes encoding mitochondrial proteins in papillary thyroid carcinomas. Thyroid. 2003;13(7):613-20.
Hawthorn, et al. TIMP1 and SERPIN-A overexpression and TFF3 and CRABP1 underexpression as biomarkers for papillary thyroid carcinoma. Head Neck. Dec. 2004;26(12):1069-83.
He, et al. A susceptibility locus for papillary thyroid carcinoma on chromosome 8q24. Cancer Res. Jan. 15, 2009;69(2):625-31.
He et al. The role of microRNA genes in papillary thyroid carcinoma. Proc Natl Acad Sci USA. 2005;102(52):19075-80.
Hecht, SS. Tobacco carcinogens, their biomarkers and tobacco-induced cancer. Nature Review Cancer; 3:733-744 (Oct. 2003).

(56) References Cited

OTHER PUBLICATIONS

Hellmann et al. Gene Expression Profiling of Cultured Human Bronchia Epithelial and Lung Cacinoma Cells. Toxicological Sciences, 61: 154-163 (2001).
Hellwig, et al. Comparison of scores for bimodality of gene expression distributions and genome-wide evaluation of the prognostic relevance of high-scoring genes. BMC Bioinformatics. May 25, 2010;11:276. doi: 10.1186/1471-2105-11-276.
Hemmer et al. Comparison of benign and malignant follicular thyroid tumours by comparative genomic hybridization. Br J Cancer. 1998;78(8):1012-7.
Hemmer, et al. DNA copy number changes in thyroid carcinoma. Am J Pathol. May 1999;154(5):1539-47.
Hennessy et al. Exploiting the PI3KAKT Pathway for Cancer Drug Discovery Nature vol. 4:988-1004 (2005).
Heuer et al. Different cytokine mRNA profiles in Graves' disease, Hashimoto's thyroiditis, and nonautoimmune thyroid disorders determined by quantitative reverse transcriptase polymerase chain reaction (RT-PCR). Thyroid. 1996;6(2):97-106.
Hindiyeh et al. Evaluation of a Multiplex Real-Time Reverse Transcriptase PCR Assay for Detection and Differentiation of Influenza Viruses A and B during the 2001-2002 Influenza Season in Israel. Journal of Clinical Microbiology, 2005, 43(2):589-595. doi: 10.1128/JCM.43.2.589-595.2005.
Hirsch et al. Early Detection of Lung Cancer: Clinical Perspectives of Recent Advances in Biology and Radiology. Clinical Cancer Research (7): 5-22 (2001).
Hodnett et al. Fibrosing interstitial lung disease: a practical HRCT based approach to diagnosis and management and review of the literature. Am J Respir Crit Care Med (2013); 188.2: 141-149.
Holden et al. Tyrosine kinase activating mutations in human malignancies: implications for diagnostic pathology. Exp Mol Pathol. 2008; 85(1):68-75.
Holland et al. Detection of specific polymerase chain reaction product by utilizing the 5'----3' exonuclease activity of Thermus aquaticus DNA polymerase. PNAS USA 88(16):7276-7280 (1991).
Hoshikawa, et al. Hypoxia Induces Different Genes in the Lungs of Rats Compared With Mice. Physiological Genomics. vol. 12, Issue. 3 (2003): pp. 209-219.
Hou et al. Genetic alterations and their relationship in the phosphatidylinositol 3-kinase/Akt pathway in thyroid cancer. Clin Cancer Res. 2007;13(4):1161-70.
Howlader et al. SEER stat fact sheets: lung and bronchus cancer. Bethesda: National Cancer Institute (2011). http://seer.cancer.gov/statfacts/html/lungb.html [Downloaded Oct. 18, 2016], 9 pages.
Hsu et al. Characterization of a novel tripartite nuclear localization sequence in the EGFR family. J Biol Chem. 2007;282(14):10432-40.
Hsu et al. Overexpression of dihydrodiol dehydrogenase as a prognostic marker of non-small cell lung cancer. Cancer research, Mar. 2001; 61(6): 2727-2731.
Hu et al. Nature Protocols. 2006. 1 (4): 17 43. (Year: 2006).
Huang et al. A genome-wide approach to identify genetic variants that contribute to etoposide-induced cytotoxicity. Proc Natl Acad Sci USA. 2007;104(23):9758-63.
Huang et al. A tool for RNA sequencing sample identity check. Bioinformatics 29.11 (2013): 1463-1464.
Huang et al. Gene expression in papillary thyroid carcinoma reveals highly consistent profiles. Proc Natl Acad Sci USA. 2001;98(26):15044-9.
Huang et al. Systematic and integrative analysis of large gene lists using DAVID bioinformatics resources. Nature protocols 4:44-57 (2009).
Human hg 19 chr5 (Human hg 19 chr5: 136368834-136368864 UCSC Genome Browser v410, 2009) (Year: 2009).
Human hg19 chr11 (Human hg19 chr11 :30509671-30509898 UCSC Genome Browser v410, 2009) (Year: 2009).
Hummert et al. Creation and Comparison of Different Chip Definition Files for Affymetrix Microarrays. Proceedings of the International Conference on Bioinformatics and Computational Biology. BioComp'11, Jul. 18-21, 2011, Las Vegas, USA, 1(1): 16-22.
Hunt, et al. A microdissection and molecular genotyping assay to confirm the identity of tissue floaters in paraffin-embedded tissue blocks Arch Pathol Lab Med. 2003; 127(2):213-217.
Hviid et al. HLA-G polymorphisms and HLA-G expression in sarcoidosis. Sarcoidosis, vasculitis, and diffuse lung diseases: official journal of WASOG/World Association of Sarcoidosis and Other Granulomatous Disorders (Mar. 23, 2006); 23.1: 30-37.
Ikeda et al. Malignancy associated changes in bronchial epithelial cells and clinical application as a biomarker. Lung Cancer, 19(3): 161-166 (1998).
Imelfort et al. De novo sequencing of plant genomes using second-generation technologies. Briefings in Bioinformatics (2009); 10.6: 609-618.
Inaji et al. Demonstration and diagnostic significance of pro-gastrin-releasing peptide in medullary thyroid carcinoma. Oncology. 2000;59(2):122-5.
Irizarry, et al. Exploration, normalization, and summaries of high density oligonucleotide array probe level data. Biostatistics. Apr. 2003;4(2):249-64.
Irizarry et al. Summaries of Affymetrix GeneChip probe level data. Nucleic Acids Res 31(4):e15 (Feb. 2003).
Ito, et al. Distant and lymph node metastases of thyroid nodules with No. pathological evidence of malignancy: a limitation of pathological examination. Endocr J. Oct. 2008;55(5):889-94. Epub Jun. 14, 2008.
Ito et al. Simultaneous expression of keratan sulphate epitope (a sulphated poly-N-acetyllactosamine) and blood group ABH antigens in papillary carcinomas of the human thyroid gland. Histochem J. 1996;28(9):613-23.
Ivana et al. Expression of cilium-associated genes defines novel molecular subtypes of idiopathic pulmonary fibrosis. Thorax(2013): thoraxjnl-2012.
Ivana et al. Gene expression profiling of familial and sporadic interstitial pneumonia. American journal of respiratory and critical care medicine 175.1 (2007): 45-54.
Jacques et al. Two-step differential expression analysis reveals a new set of genes involved in thyroid oncocytic tumors. J Clin Endocrinol Metab. 2005;90(4):2314-20.
Jang et al. Activation of melanoma antigen tumor antigens occurs early in lung carcinogenesis. Cancer Research 61: 7959-7963 (2001).
Jarzab et al. Gene Expression Profile of Papillary Thyroid Cancer: Sources of Variability and Diagnostic Implications. Cancer Res. 2005;65(4):1587-1597.
Jazdzewski et al. Common SNP in pre-miR-146a decreases mature miR expression and predisposes to papillary thyroid carcinoma. Proc Natl Acad Sci USA. 2008;105(20):7269-74.
Ji et al., Long-term impact of initial surgical and medical therapy on young patients with papillary thyroid cancer and bilateral cervical metastases. Chinese Medical Journal, 2008; 121(1) :63-66.
Jin et al. The Cystic fibrosis transmembrane conductance regulator as a biomarker in non-small cell lung cancer. International Journal of Oncology, 2015; 46: 2107-2115.
Jo, et al. Influence of the BRAF V600E mutation on expression of vascular endothelial growth factor in papillary thyroid cancer. J Clin Endocrinol Metab. Sep. 2006;91(9):3667-70. Epub Jun. 13, 2006.
Johansson, et al. Confirmation of a BRAF mutation-associated gene expression signature in melanoma. Pigment Cell Res. Jun. 2007;20(3):216-21.
Johnson et al. Adjusting batch effects in microarray expression data using empirical Bayes methods. Biostatistics (2007); 8.1: 118-127.
Jones et al., Value and accuracy of cytology in addition to histology in the diagnosis of lung cancer at flexible bronchoscopy. Respiratory Medicine, 2001; 95: 374-378.
Jonigk et al. Molecular profiling in lung biopsies of human pulmonary allografts to predict chronic lung allograft dysfunction. The American Journal of Pathology (2015); 185.12: 3178-3188.
Joseph et al. Lack of mutations in the thyroid hormone receptor (TR) alpha and beta genes but frequent hypermethylation of the TRbeta gene in differentiated thyroid tumors. J Clin Endocrinol Metab. 2007;92(12):4766-70.

(56) References Cited

OTHER PUBLICATIONS

Joshua D Campbell et al: "A gene expression signature of emphysema-related lung destruction and its reversal by the tripeptide GHK", Genome Med, Biomed Central L TO, London, UK, vol. 4, No. 8, Aug. 31, 2012 (Aug. 31, 2012 ), p. 67.
Jovanovic et al. Most multifocal papillary thyroid carcinomas acquire genetic and morphotype diversity through subclonal evolution following the intra-glandular spread of the initial neoplastic clone. J Pathol. 2008;215(2):145-54.
Jun et al. Detecting and estimating contamination of human DNA samples in sequencing and array-based genotype data. The American Journal of Human Genetics 91.5 (2012): 839-848.
Jung et al., Expression of MAGE and GAGE genes in the bronchogenic cancer tissues obtained by bronchoscopy. Korean journal of medicine, 2002, 62(1): 58-68.
Kadara et al. Transcriptomic architecture of the adjacent airway field cancerization in non-small cell lung cancer. Journal of the National Cancer Institute (2014); 106.3: dju004.
Kakudo et al. Immunohistochemical study of substance P-like immunoreactivity in human thyroid and medullary carcinoma of the thyroid. J Submicrosc Cytol. 1983;15(2):563-8.
Kanehisa. Use of statistical criteria for screening potential homologies in nucleic acid sequences. Nucleic Acids Res. Jan. 11, 1984;12(1 Pt 1):203-13.
Kang et al. High prevalence of RET, RAS, and ERK expression in Hashimoto's thyroiditis and in papillary thyroid carcinoma in the Korean population. Thyroid. 2007;17(11):1031-8.
Kannengiesser, et al. Gene expression signature associated with BRAF mutations in human primary cutaneous melanomas. Mol Oncol. Apr. 2008;1(4):425-30. doi: 10.1016/j.molonc.2008.01.002. Epub Jan. 12, 2008.
Kanner et al. Effects of randomized assignment to a smoking cessation intervention and changes in smoking habits on respiratory symptoms in smokers with early chronic obstructive pulmonary disease: the lung health study. American Journal of Medicine; 106:410-416 (1999).
Kao, et al. Tumor-associated Antigen L6 and the Invasion of Human Lung Cancer Cells. Clin Cancer Res. 9:2807-2816 (Jul. 2003).
Kapadia, et al. Malignant lymphoma of the thyroid gland: a clinicopathologic study. Head Neck Surg. Mar.-Apr. 1982;4(4):270-80.
Kasraeian, et al. A comparison of fine-needle aspiration, core biopsy, and surgical biopsy in the diagnosis of extremity soft tissue masses. Clin Orthop Relat Res. Nov. 2010;468(11):2992-3002. doi: 10.1007/s11999-010-1401-x.
Katoh et al. Thyroid transcription factor-1 in normal, hyperplastic, and neoplastic follicular thyroid cells examined by immunohistochemistry and nonradioactive in situ hybridization. Mod Pathol. 2000;13(5):570-6.
Katz et al. Automated detection of genetic abnormalities combined with cytology in sputum is a sensitive predictor of lung cancer. Modern Pathology;21:950-960 (2008).
Katzenstein, Anna-Luise A. Smoking-related interstitial fibrosis (SRIF), pathogenesis and treatment of usual interstitial pneumonia (UIP), and transbronchial biopsy in UIP. Modern Pathology (2012); 25: S68-S78.
Katzenstein et al. Diagnosis of usual interstitial pneumonia and distinction from other fibrosing interstitial lung diseases. Erratum to Diagnosis of usual interstitial pneumonia and distinction from other fibrosing interstitial lung diseases. [Hum Pathol (2008); 39: 1275-1294]. Human Pathology (2008); 39.11: 1562-1581.
Katzenstein et al. Idiopathic Pulmonary Fibrosis. Am J Respir Crit Care Med (1998); 157: 1301-1315.
Katzenstein et al. Usual interstitial pneumonia: histologic study of biopsy and explant specimens. The American Journal of Surgical Pathology (2002); 26.12: 1567-1577.
Kauffmann et al. arrayQualityMetrics—a bioconductor package for quality assessment of microarray data. Bioinformatics (2009); 25.3: 415-416.
Kawai, et al. Recent Advances of DNA chip application. Latest Situation in DNA Chip Applications. English Translation. Protein Nucleic Acid and Enzyme, Aug. 1, 2000, vol. 45, No. 11, p. 47-53.
Kazemi-Noureini et al. Differential gene expression between squamous cell carcinoma of esophageus and its normal epithelium; altered pattern of mal, akrlc2, and rab11a expression. World J Gastroenterol. Jun. 15, 2004; 10(12): 1716-1721.
Kebebew et al. Diagnostic and extent of disease multigene assay for malignant thyroid neoplasms. Cancer. 2006;106(12):2592-7.
Kebebew et al. Diagnostic and prognostic value of angiogenesis-modulating genes in malignant thyroid neoplasms. Surgery. Dec. 2005;138(6):1102-9; discussion 1109-10.
Kebebew, et al. The prevalence and prognostic value of BRAF mutation in thyroid cancer. Ann Surg. Sep. 2007;246(3):466-70; discussion 470-1.
Kelmemi et al. BMC Medical Genetics. 2015. 16:50.(Year: 2015).
Key, Objective cough frequency in Idiopathic Pulomnary Fibrosis, Cough, 6:4, pp. 1-7, 2010. (Year: 2010).
Khan et al. Classification and Diagnostic Prediction of Cancers Using Gene Expression Profiling and Artificial Neural Networks. Nature Medicine, 7(6):673-679, (Jun. 2001).
Kim, et al., Classification of usual interstitial pneumonia in patients with interstitial lung disease: Assessment of a machine learning approach using high-dimensional transcriptional data. The Lancet respiratory medicine, elsevier oxford, Jun. 2015; 3(6): 473-482.
Kim et al. Diagnostic use of molecular markers in the evaluation of thyroid nodules. Endocrine Practice Sep./Oct. 2012, vol. 18, No. 5, pp. 796-802 (Year: 2012).
Kim et al. Identification of bronchioalveolar stem cells in normal lung and lung cancer. Cell (2005); 121.6: 823-835.
King et al. Idiopathic pulmonary fibrosis. The Lancet (2011); 378.9807: 1949-1961.
King Jr. et al. A phase 3 trial of pirfenidone in patients with idiopathic pulmonary fibrosis. N Engl J Med. May 29, 2014;370(22):2083-92.
King, T.E., Clinical advances in the diagnosis and therapy of the interstitial lung diseases. Am J Resp. Crit care med. vol. 172; 2005: 268-279.
Kiss, et al. Anatomisk Atlas over Manniskokroppen, band II. Natur och Kultur Stockholm, Stockholm, Sweden ISBN: 91-27-67278-6; 1973.
Kitahara et al. Alternations of Gene Expression during Colorectal Carcinogenesis Revealed by cDNA Microarrays after Laser-Capture Microdissection of Tumor Tissues and Normal Epithelia. Cancer Research, 61: 3544-3549 (May 1, 2001).
Knudsen et al. Ri antibodies in patients with breast, ovarian or small cell lung cancer determined by a sensitive immunoprecipitation technique. Cancer Immunology Immunotherapy 55.10 (Jan. 2006): 1280-1284.
Kocarnik et al. Replication of Associations Between GWAS SNPs and Melanoma Risk in the Population Architecture Using Genomics and Epidemiology (PAGE) Study. Journal of Investigative Dermatology, 134:2049-2052, (Feb. 27, 2014).
Konishi, Gene Expression Profiles of Acute Exacerbations of Idiopathic Pulmonary Fibrosis, Am J Respir Crit Care Med, 180, 167-175, 2009. (Year: 2009).
Korn et al., Glucocorticoid receptor mRNA levels in bronchial epithelial cells of patients with COPD: influence of glucocorticoids. Respiratory Medicine, 1998; 92: 1102-1109.
Koshkin et al. LNA (locked nucleic acids): An RNA mimic forming exceedingly stable LNA: LNA duplexes. J Am Chem Soc 120:13252-13253 (1998).
Koshkin et al. LNA (locked nucleic acids): synthesis of the adenine, cytosine, guanine 5-methylcytosine, thymine and uracil bicyclonucleoside monomers, oligomerisation, and unprecedented nucleic acid recognition. Tetrahedron 54(14):3607-3630 (1998).
Kraft et al. Expression of epithelial markers in nocturnal asthma. Journal of Allergy and Clinical Immunology, 102(3): 376-381 (1998).
Krause, et al. Characterisation of DEHAL1 expression in thyroid pathologies. Eur J Endocrinol. Mar. 2007;156(3):295-301.

(56) References Cited

OTHER PUBLICATIONS

Krawczak, et al. The mutational spectrum of single base-pair substitutions in mRNA splice junctions of human genes: causes and consequences. Hum Genet. Sep.-Oct. 1992;90(1-2):41-54.
Kreula, et al. Sample size in fine needle aspiration biopsy. Br J Surg. Dec. 1989;76(12):1270-2.
Kristensen, et al. Genetic variation in putative regulatory loci controlling gene expression in breast cancer. Proc Natl Acad Sci U S A. May 16, 2006;103(20):7735-40. Epub May 9, 2006.
Kroese et al. Genetic tests and their evaluation: Can we answer the key questions? Genetics in Medicine 6:475-480 (2004).
Kroschwitz. The Concise Encyclopedia Of Polymer Science And Engineering. (pp. 858-859) (1990).
Kumar, et al. The first analogues of LNA (locked nucleic acids): phosphorothioate-LNA and 2'-thio-LNA. Bioorg Med Chem Lett. Aug. 18, 1998;8(16):2219-22.
Kuriakose et al. Selection and validation of differentially expressed genes in head and neck cancer. Cellular and Molecular Life Sciences CMLS 61. (11):1372-83, Jul. 2004.
Kwan, et al. Heritability of alternative splicing in the human genome. Genome Res. Aug. 2007;17(8):1210-8.
Kwoh, D Y, et al., Transcription-based Amplification System And Detection Of Amplified Human Immunodeficiency Virus Type 1 With A Bead-based Sandwich Hybridization Format. Proceedings of the National Academy of Sciences of the United States of America 86(4):1173-1177 (1989).
Lacobuzio-Donahue et al., Highly Expressed Genes in Pancreatic Ductal Adenocarcinomas: A Comprehensive Characterization and Comparison of the Transcription Profiles Obtained from Three Major Technologies. Cancer Research, Dec. 2003; 63: 8614-8622.
Lacroix, et al. PAX8 and peroxisome proliferator-activated receptor gamma 1 gene expression status in benign and malignant thyroid tissues. Eur J Endocrinol. Sep. 2004;151(3):367-74.
Lacroix et al. Sensitive Detection of Rare Cancer Cell in Sputum and Peripheral Blood Samples of Patients with Lunch Cancer by Preprogrp-Specific TR-PCR. Int. J. Cancer, vol. 92: 1-8 (2001).
Lam et al. A Phase I Study of myo-Inositol for Lung Cancer Chemoprevention. Cancer Epidemiology, Biomarkers & Prevention 15(8): 1526-1531 (Aug. 2006).
Lampe et al. Signatures of environmental exposures using peripheral leukocyte gene expression: tobacco smoke. Cancer Epidemiology Biomarkers & Prevention (2004); 13.3: 445-453.
Landegren, et al., A ligase-mediated gene detection technique. Science. Aug. 26, 1988;241(4869):1077-80.
Lander, et al. Initial sequencing and analysis of the human genome. Nature 409:860-921 (Feb. 15, 2001).
Langford et al. Is the Property of Being Positively Correlated Transitive. The American Statistician. 55(4):322-325 (2001).
Lau et al. Thyroid transcription factor-1: a review. Appl Immunohistochem Mol Morphol. 2002;10(2):97-102.
Lauter et al. Mutational analysis of CDKN1B, a candidate tumor-suppressor gene, in refractory secondary/tertiary hyperparathyroidism. Kidney Int. 2008;73(10):1137-40.
Lee, et al., Expression of mRNA of Trefoil Factor Peptides in Human Nasal Mucosa. Acta Oto-Laryngologica. 2001;121(7):849-853.
Lee et al. NGSCheckMate: software for validating sample identity in next-generation sequencing studies within and across data types. Nucleic acids research 45.11 (2017).
Lewis et al. Cotinine levels and self-reported smoking status in patients attending a bronchoscopy clinic. Biomarkers (2003); 8.3-4: 218-228.
Li et al. Gene expression profiling in human lung fibroblast following cadmium exposure. Food and Chemical Toxicology (2008); 46.3: 1131-1137.
Li, Lexin. Survival prediction of diffuse large-B-cell lymphoma based on both clinical and gene expression information. Bioinformatics 2006; 22:466-71, (Feb. 2006).
Li, X et al. American Journal of Respiratory and Critical Care Medicine 183(1 Supp.): abstract A6176 (May 1, 2011) (3 pages).
Liao et al. Expression and significance of PTEN/PI3K signal transduction-related proteins in nonsmall cell lung cancer. Ai Zheng 25: 10, p. 1238-42. Abstract (Oct. 2006).
Lima et al. Thyroid Peroxidase and Thyroglobulin Expression in Normal Human Thyroid Glands. Endocr Pathol. 1998;9(1):333-338.
Lin et al. Effects of Dexamethasone on Acute Lung Injury Rat Cells Signal Transduction Systems ERK and P13-K. Medical Journal of Chinese People's Liberation Army 6(31): 592-594 (Sep. 2006).
Lin et al. Expression of sodium iodide symporter in benign and malignant human thyroid tissues. Endocr Pathol. 2001;12(1):15-21.
Lin, et al. Thyroid ultrasonography with fine-needle aspiration cytology for the diagnosis of thyroid cancer. J Clin Ultrasound. Mar.-Apr. 1997;25(3):111-8.
Liu et al. An oligonucleotide microchip for genome-wide microRNA profiling in human and mouse tissues. Proc Natl Acad Sci USA, 2004, 101(26):9740-9744.
Liu et al. Effects of physiological versus pharmacological g-carotene supplementation on cell proliferation and histopathological changes in the lungs of cigarette smoke-exposed ferrets. Carcinogenesis, 21: 2245-2253 (2000).
Liu et al. Highly prevalent genetic alterations in receptor tyrosine kinases and phosphatidylinositol 3-kinase/akt and mitogen-activated protein kinase pathways in anaplastic and follicular thyroid cancers. J Clin Endocrinol Metab. 2008;93(8):3106-16.
Liu, et al. Quantitative Proteome Analysis Reveals Annexin A3 as a Novel Biomarker in Lung Adenocarcinoma. Journal of Pathology, 217: 54-64 (2009).
Liu, Y. 'Active learning with support vector machine applied to gene expression data for cancer classification', J Chem Inf Comput Sci. 2004, vol. 44, pp. 1936-1941.
Lockstone et al. Gene set analysis of lung samples provides insight into pathogenesis of progressive, fibrotic pulmonary sarcoidosis. American Journal of Respiratory and Critical Care Medicine (2010); 181.12: 1367-1375.
Love, et al. Moderated Estimation of Fold Change and Dispersion for RNA-seq data with DESeq2. Genome Biology. vol. 15, Issue 12:550 (2014).
Lubitz et al. 2006; Microarray analysis of thyroid nodule fine-needle aspirates accurately classifies benign and malignant lesions. J Mol Diagn. 8(4):490-8; quiz 528.
Lubitz et al. Molecular analysis of minimally invasive follicular carcinomas by gene profiling. Surgery. 2005;138(6):1042-8; discussion 1048-9.
Lubitz, et al., The differentiation of Benign and malignant thyroid nodules. Advances in sur. Jan. 1, 2005; 39(1): 355-377.
Lucentini, J. Gene Association Studies Typically Wrong. The Scientist, 18(24):20 (2004).
Lui et al. 2008;CREB3L2-PPARgamma fusion mutation identifies a thyroid signaling pathway regulated by intramembrane proteolysis. Cancer Res. 68(17):7156-64.
Machens et al. Genotype-phenotype based surgical concept of hereditary medullary thyroid carcinoma. World J Surg. 2007;31(5):957-68.
Mackay, et al. Targeting the protein kinase C family: are we there yet? Nature Reviews Cancer. 7(7):554-62 (Jul. 1, 2007).
Macmahon et al. Guidelines for management of small pulmonary nodules detected on CT scans: a statement from the Fleischner Society 1. Radiology (2005); 237.2: 395-400.
Majewski, K. et al., Serum concentrations of antimicrobial peptide cathelicidin LL-37 in patients with bacterial lung infections. Cent Eur J Immunol. 2018; 43(4): 453-457.
Mak (Thesis: "Expression of CFTR mRNA Epithelium and Vas Deferens", 1997, Univ of Toronto).
Manichaikul, et al. Robust relationship inference in genome-wide association studies. Bioinformatics. Nov. 15, 2010;26(22):2867-73. Epub Oct. 5, 2010.
Mannino et al. Low lung function and incident lung cancer in the United States: data From the First National Health and Nutrition Examination Survey follow-up. Arch Intern Med. 163(12):1475-80 (Jun. 23, 2003).
Margulies, et al. Genome sequencing in microfabricated high-density picolitre reactors. Nature. 437(7057) (2005):376-380.

(56) References Cited

OTHER PUBLICATIONS

Mariani Thomas J et al: "Molecular markers for quantitative and discrete COPD phenotypes", The Faseb Journal, Federation of American Societies for Experimental Biology, US, vol. 21, No. 5, Apr. 1, 2007 (Apr. 1, 2007 ), p. A8.
Marinov et al. Targeting mTOR signaling in lung cancer. Critical Reviews in Oncology/Hematology 63: 172-182 (Aug. 2007).
Marsh, et al. Genome-wide copy number imbalances identified in familial and sporadic medullary thyroid carcinoma. J Clin Endocrinol Metab. Apr. 2003;88(4):1866-72.
Martin. A New Access to 2'-O-Alkylated Ribonucleosides and Properties of 2'-O-Alkylated Oligoribonucleotides. Helv. Chim. Acta. 1995; 78:486-504. (in German with English abstract).
Masini-Repiso et al. Ultrastructural localization of thyroid peroxidase, hydrogen peroxide- generating sites, and monoamine oxidase in benign and malignant thyroid diseases. Hum Pathol. 2004; 35(4):436-46.
Mason, et al. Bimodal distribution of RNA expression levels in human skeletal muscle tissue. BMC Genomics. Feb. 7, 2011;12:98. doi: 10.1186/1471-2164-12-98.
Matsubayashi et al. Gastrin-releasing peptide immunoreactivity in medullary thyroid carcinoma. Cancer. 1984;53(11):2472-7.
Maximo et al. Somatic and germline mutation in GRIM-19, a dual function gene involved in mitochondrial metabolism and cell death, is linked to mitochondrion-rich (Hurthle cell) tumours of the thyroid. Br J Cancer. 2005;92(10):1892-8.
May et al. How Many Species are there on Earth? Science 241:1441-1449 (1988).
Mazzanti, et al. Using gene expression profiling to differentiate benign versus malignant thyroid tumors. Cancer Res. Apr. 15, 2004;64(8):2898-903.
McCarroll, et al. Integrated detection and population-genetic analysis of SNPs and copy No. variation. Nature Genetics 40, 1166-1174 (2008).
McWilliams et al. Probability of cancer in pulmonary nodules detected on first screening CT. New England Journal of Medicine (2013); 369.10: 910-919.
Medical News: Targeted, Oral Agent Enzastaurin Shows Favorable Results in Late-Stage Lung Cancer. (Jun. 11, 2007), Retrieved from the Internet URL: https://www.medicalnewstoday.com/releases/73761.php.
Memoli et al. Meta-analysis of guided bronchoscopy for the evaluation of the pulmonary nodule. Chest Journal (2012); 142.2: 385-393.
Merrium-Webster.com ( http://www.merriam-webstercom/dictionary/questionnaire), downloaded Oct. 26, 2013.
Meyer et al. Support vector machines. The Interface to libsvm in package e1071. FH Technikum Wien, Austria (2015); pp. 1-8.
Mi, et al., The PANTHER database of protein families, subfamilies, functions and pathways, Neucleic acids research, 2005, 3: D284-88.
Michalczyk et al. Fresh and cultured buccal cells as a source of mRNA and protein for molecular analysis. Biotechniques. Aug. 2004;37(2):262-4, 266-9.
Miklos, et al. Microarray reality checks in the context of a complex disease. Nature Biotechnology, 22:5 (May 2005).
Mineva, et al. Differential expression of alphaB-crystallin and Hsp27-1 in anaplastic thyroid carcinomas because of tumor-specific alphaB-crystallin gene (CRYAB) silencing. Cell Stress Chaperones. 2005 Autumn; 10(3):171-84.
Minhyeok; Lee et al., Mol Biol Rep, 2011, 38, 5211-5217.
Mitomo et al. Downregulation of miR-138 is associated with overexpression of human telomerase reverse transcriptase protein in human anaplastic thyroid carcinoma cell lines. Cancer Sci. 2008;99(2):280-6.
Miura et al. Laser capture microdissection and microarray expression analysis of lung adenocarcinoma reveals tobacco smoking- and prognosis-related molecular profiles. Cancer Res., 62(11): 3244-50 (Jun. 1, 2002).
Miyamoto et al. Potential Marker of Oral Squamous Cell Carcinoma Aggressiveness Detected by Fluorescence in Situ Hybridization in Fine-Needle Aspiration Biopsies. Cancer American Cancer Society 95(10):2152-2159 (Jun. 6, 2002).
Mizukami, et al. Late bone metastasis from an encapsulated follicular carcinoma of the thyroid without capsular and vascular invasion. Pathol Int. Jun. 1996;46(6):457-61.
Modrek et al. Genome-wide detection of alternative splicing in expressed sequences of human genes. Nucleic Acids Research, 29(13): 2850-2859 (2001).
Moller et al. Altered Ratio of Endothelin ETA- and ETB Receptor mRNA in Bronchial Biopsies from Patients with Asthma and Chronic Airway Obstruction. (European Journal of Pharmacology, 1999, 365: R1-R3).
Mollerup et al. Sex Differences in Lung CYP1A1 Expression and DNA Adduct Levels among Lung Cancer Patients. Cancer Research, 1999, 59: 3317-3320 (1999).
Mongiat et al. Fibroblast Growth Factor-binding Protein Is a Novel Partner for Perlecan Protein Core. The Journal of Biological Chemistry; 276(13):10263-10271 (Mar. 30, 2001).
Montero-Conde et al. Molecular profiling related to poor prognosis in thyroid carcinoma. Combining gene expression data and biological information. Oncogene. 2008;27(11):1554-61.
Monti et al. Consensus Clustering: A Resampling-Based Method for Class Discovery and Visualization of Gene Expression Microarray Data. Machine Learning (Jul. 2003); 52(1): 91-118.
Morales et al. Accuracy of self-reported tobacco use in newly diagnosed cancer patients. Cancer Causes & Control (2013); 24.6: 1223-1230.
Moreno, et al. Mutations in the iodotyrosine deiodinase gene and hypothyroidism. N Engl J Med. Apr. 24, 2008;358(17):1811-8. doi: 10.1056/NEJMoa0706819.
Morin et al.: Profiling the HeLa S3 transcriptome using randomly primed cDNA and massively parallel short-read sequencing. Biotechniques. 45:81-94 (2008).
Morozova et al. Applications of next-generation sequencing technologies in functional genomics. Genomics (2008); 92.5: 255-264.
Murphy et al. Identification of immunohistochemical biomarkers for papillary thyroid carcinoma using gene expression profiling. Hum Pathol. 2008;39(3):420-6.
Nakano et al. Apoptosis-induced decrease of intrathyroidal CD4(+)CD25(+) regulatory T cells in autoimmune thyroid diseases. Thyroid. 2007;17(1):25-31.
Nakashima et al. Foci formation of P53-binding protein 1 in thyroid tumors: activation of genomic instability during thyroid carcinogenesis. Int J Cancer. 2008;122(5):1082-8.
Nakashima et al. RET oncogene amplification in thyroid cancer: correlations with radiation-associated and high-grade malignancy. Hum Pathol. 2007;38(4):621-8.
Nakayama et al. High molecular weight caldesmon positive stromal cells in the capsule of thyroid follicular tumours and tumour-like lesions. J Clin Pathol. 2002;55(12):917-20.
Nam, et al. BRAF V600E mutation analysis of thyroid nodules needle aspirates in relation to their ultrasongraphic classification: a potential guide for selection of samples for molecular analysis. Thyroid. Mar. 2010;20(3):273-9. doi: 10.1089/thy.2009.0226.
National Cancer Institute web page: "Common Cancer Types", captured by WayBack machine on Dec. 4, 2011, http://www.cancer.gov/cancertopics/types/commoncancers.
National Lung Screening Trial Research Team et al. Reduced lung-cancer mortality with low-dose computed tomographic screening. N Engl J Med 365:395-409 (2011).
NCBI gene report for LOC100131599. Printed Feb. 2018.
Neonakis et al. Expression of calcitonin and somatostatin peptide and mRNA in medullary thyroid carcinoma. World J Surg. 1994;18(4):588-93.
Neubauer et al. Cure of Helicobacter pylori Infection and Duration of Remission of Low-Grade Gastric Mucosa-Associated Lymphoid Tissue Lymphoma. J. Natl. Cancer Inst., 89(18):1350-1355 (Sep. 17, 1997).
Newton et al. On Differential Variability of Expression Ratios: Improving Statistical Inference about Gene Expression Changes from Microarray Data. Journal of Computational Biology, 8: 37-52 (2001).

(56) References Cited

OTHER PUBLICATIONS

Nicholson et al. Inter-observer variation between pathologists in diffuse parenchymal lung disease. Thorax (2004); 59.6: 500-505.
Nicholson et al. The relationship between individual histologic features and disease progression in idiopathic pulmonary fibrosis. American Journal of Respiratory and Critical Care Medicine (2002); 166.2: 173-177.
Nielsen et al. Aquaporins in complex tissues. II. Subcellular distribution in respiratory and glandular tissues of rat. American Journal of Physiology—Cell Physiology (1997); 273.5: C1549-C1561.
Nielsen et al. Sequence-selective recognition of DNA by strand displacement with a thymine-substituted polyamide. Science 254:1497-1500 (1991).
Nikiforov et al. Impact of Mutational Testing on the Diagnosis and Management of Patients with Cytologically Indeterminate Thyroid Nodules: A Prospective Analysis of 1056 FNA Samples Journal of Clinical Endocrinology and Metabolism vol. 96, pp. 3390-3397 (Year: 2011).
Nikiforova, et al. Highly accurate diagnosis of cancer in thyroid nodules with follicular neoplasm/suspicious for a follicular neoplasm cytology by ThyroSeq v2 next-generation sequencing assay. Cancer. Dec. 1, 2014;120(23):3627-34. Epub Sep. 10, 2014.
Nikiforova et al. MicroRNA expression profiling of thyroid tumors: biological significance and diagnostic utility. J Clin Endocrinol Metab. 2008;93(5):1600-8.
Nikiforova, et al. Molecular diagnostics and predictors in thyroid cancer. Thyroid. Dec. 2009;19(12):1351-61.
Nikiforova, et al. Targeted Next-Generation Sequencing Panel (ThyroSeq) for Detection of Mutations in Thyroid Cancer. J Clin Endocrinol Metab. Nov. 2013; 98(11): E1852-E1860.
Nikolova et al. Genome-wide gene expression profiles of thyroid carcinoma: Identification of molecular targets for treatment of thyroid carcinoma. 2008;Oncol Rep. 20(1):105-21.
Noble et al. Pirfenidone in patients with idiopathic pulmonary fibrosis (Capacity): two randomised trials. 2011, Lancet, 377, 1760-69.
Notterman et al. Tumor Biology and Microarray Analysis of Solid Tumors: Colorectal Cancer as a Model System. Microarrays and Cancer Research, Warrington et al (eds.), Eaton Publishing, Westborough, MA, pp. xi-xvi, (2002).
Nucera, et al. BRAF(V600E) mutation and the biology of papillary thyroid cancer. Endocr Relat Cancer. Mar. 2008; 15(1):191-205. doi: 10.1677/ERC-07-0212.
Oerntoft, et al. Genome-wide study of gene copy numbers, transcripts, and protein levels in pairs of non-invasive and invasive human transitional cell carcinomas. Mol Cell Proteomics. Jan. 2002;1(1):37-45.
Ohtsuka et al. ADAM28 is overexpressed in human non-small cell lung carcinomas and correlates with cell proliferation and lymph node metastasis. International Journal of Cancer, 118 2 : 263-273, Jan. 2006.
Okudela et al. K-ras Gene Mutation Enhances Motility of Immortalized Airway Cells and Lung Adenocarcinoma Cells Via Akt Activation: Possible Contribution to Non-Invasive Expansion of Lung Adenocarcinoma. Am J Pathol. Jan. 2004; 164(1): 91-100.
Oler, et al. Gene expression profiling of papillary thyroid carcinoma identifies transcripts correlated with BRAF mutational status and lymph node metastasis. Clin Cancer Res. Aug. 1, 2008;14(15):4735-42. doi: 10.1158/1078-0432.CCR-07-4372.
Ooi et al. Molecular Profiling of Premalignant Lesions in Lung Squamous Cell Carcinomas Identifies Mechanisms Involved in Stepwise Carcinogenesis. Cancer Prevention Research, 7(5):487-495, (Mar. 11, 2014).
Oshlack et al. FRom RNA-seq reads to differential expression results Genome Biology vol. 11, article 220 (Year: 201 0).
Ost et al. The solitary pulmonary nodule. New England Journal of Medicine (Jun. 19, 2003); 348.25: 2535-2542.
Oster et al. Identification and validation of highly frequent CpG island hypermethylation in colorectal adenomas and carcinomas. International Journal of Cancer (2011); 129.12: 2855-2866.
Otsubo et al. TSPAN2 is involved in cell invasion and motility during lung cancer progression. Cell Reports (2014); 7.2: 527-538.
Owens, et al. Metastatic breast carcinoma involving the thyroid gland diagnosed by fine-needle aspiration: a case report. Diagn Cytopathol. Aug. 2005;33(2):110-5.
Pallante et al. MicroRNA deregulation in human thyroid papillary carcinomas. Endocr Relat Cancer. 2006;13(2):497-508.
Panicker et al. A common variation in deiodinase 1 gene DIO1 is associated with the relative levels of free thyroxine and triiodothyronine. J Clin Endocrinol Metab. 2008;93(8):3075-81.
Pankratz et al. Usual interstitial pneumonia can be detected in transbronchial biopsies using machine learning. Annals of the American Thoracic Society 14.11 (2017): 1646-1654.
Pardo et al. Up-regulation and profibrotic role of osteopontin in human idiopathic pulmonary fibrosis. PLoS Med (2005); 2.9: e251.
Paull, D.E. et al., 'Gene expression profiles from needle biopsies provide useful signatures of non-smallcell lung carcinomas', Biomark Insights. 2007, vol. 2, pp. 253-259.
Pavelic, et al. Molecular genetic alterations of FHIT and p53 genes in benign and malignant thyroid gland lesions. Mutat Res. Jul. 25, 2006;599(1-2):45-57. Epub May 15, 2006.
Pavey, et al. Microarray expression profiling in melanoma reveals a BRAF mutation signature. Oncogene. May 20, 2004;23(23):4060-7.
Peluso et al. Comparison of DNA adduct levels in nasal mucosa, lymphocytes and bronchial mucosa of cigarette smokers and interaction with metabolic gene polymorphisms. Carcinogenesis 25(12): 2459-2465 (2004).
Penland, et al. RNA expression analysis of formalin-fixed paraffin-embedded tumors. Lab Invest. Apr. 2007;87(4):383-91.
Penning et al. Genomics of smoking exposure and cessation: lessons for cancer prevention and treatment. Cancer Prevention Research (2008); 1.2: 80-83.
Perez et al. Incidence, prevalence, and clinical course of idiopathic pulmonary fibrosis: a population-based study. Chest Journal (2010); 137.1: 129-137.
Phenekos et al. Th1 and Th2 serum cytokine profiles characterize patients with Hashimoto's thyroiditis (Th1) and Graves' disease (Th2). Neuroimmunomodulation. 2004;11(4):209-13.
Pinto et al. mRNA expression of tachykinins and tachykinin receptors in different human tissues. Eur J Pharmacol. 2004;494(2-3):233-9.
Piotrowski et al. The selected genetic polymorphisms of metalloproteinases MMP2, 7, 9 and MMP inhibitor TIMP2 in sarcoidosis. Medical Science Monitor (2011); 17.10: CR598-CR607.
Pita et al. Gene expression profiling associated with the progression to poorly differentiated thyroid carcinomas. Br J Cancer. 2009; 101(10):1782-1791.
Pittman et al. Integrated modeling of clinical and gene expression information for personalized prediction of disease outcomes. Proc Natl Acad Sci U S A. Jun. 1, 2004;101(22):8431-6.
Platform GPL6244 https://www.ncbi.nlm.nih.gov/geo/query/acc.cgi?acc=gp16244 , Submission Date Dec. 5, 2007 [Downloaded Oct. 18, 2016], 3 pages.
Poletti et al. Invasive diagnostic techniques in idiopathic interstitial pneumonias. Respirology (2016); 21.1: 44-50.
Potti et al. A Genomic Strategy to Refine Prognosis in Early-Stage Non Small-Cell Lung Cancer. The New England Journal of Medicine 2006; 335(6):570-580 (Aug. 2006).
Potti et al. Genomic Signatures to Guide the Use of Chemotherapeutics. Nature Medicine, 12(11): 1294-1300 (Oct. 2006).
Powell et al. Gene expression in lung adenocarcinomas of smokers and nonsmokers. American Journal of Respiratory Cell and Molecular Biology, 29: 157-162 (Aug. 2003).
Powell et al. Patterns of allelic loss differ in lung adenocarcinomas of smokers and nonsmokers. Lung Cancer, 39 1 : 23-29 (2003).
Powell, et al., Loss of Heterozygosity in epithelial cells obtained by bronchial brushing: clinical utility in lung cancer. Clinical cancer research, Aug. 1999, 5: 2025-2034.
Prasad et al. Identification of genes differentially expressed in benign versus malignant thyroid tumors. Clin Cancer Res. 2008;14(11):3327-37.
Printout from database NCBIGEO accession No. GSE4115 [Online] NCB dated Feb. 27, 2006.

(56) References Cited

OTHER PUBLICATIONS

Proctor, RN. Tobacco and the global lung cancer epidemic. Nature Reviews Cancer, 1: 82-86 (Oct. 2001).
Puissegur et al. miR-210 is overexpressed in late stages of lung cancer and mediates mitochondrial alterations associated with modulation of HIF-1 activity. Cell Death Differ. 18(3):465-478 (2011).
Puskas, et al. Gene profiling identifies genes specific for well-differentiated epithelial thyroid tumors. Cell Mol Biol (Noisy-le-grand). Sep. 5, 2005;51(2):177-86.
Pusztai, L. et al., 'Gene expression profiles obtained from fine-needle aspirations of breast cancer reliablyidentify routine prognostic markers and reveal large-scale molecular differences between estrogen-negative andestrogen-positive tumors', Clin Cancer Res. 2003, vol. 9, pp. 2406-2415.
Qian, et al. Renal cell carcinoma metastatic to Hurthle cell adenoma of thyroid. Ann Diagn Pathol. Oct. 2004;8(5):305-8.
Quackenbush, et al. Microarray data normalization and transformation. Nature Genetics Supplement. Dec. 2002. vol. 32, p. 496-501.
R Core Team (2021). R: A language and environment for statistical computing. R Foundation for Statistical Computing, Vienna, Austria. URL: https://www.R-project.org/. homepage provided (3 pages); obtained online on Sep. 11, 2023.
Raghu et al. An official ATS/ERS/JRS/ALAT statement: idiopathic pulmonary fibrosis: evidence-based guidelines for diagnosis and management. American Journal of Respiratory and Critical Care Medicine (2011); 183.6: 788-824.
Ramaswamy, et al. "Multiclass cancer diagnosisusing tumor gene expression signatures" Proceedings of the National Academyof Sciences Dec. 2001, 98 (26) 15149-15154.
Ramzy et al., Clinical Cytopathology and Aspiration Biopsy: Fundamental principles and practice. McGraw Hill Professional, 2001.
Rekha Vij et al: "Peripheral blood biomarkers in IDP", Translational Research, vol. 159, No. 4, (Apr. 1, 2012), pp. 218-227, XP055240430,ISSN: 1931-5244, DOI: 10.1016/j.trsl.2012.01.012.
Reyes, et al. Identification of kallikrein 7, kallikrein 10 and secreted frizzled-related protein 2 as candidate molecular markers for papillary thyroid carcinoma using microarray analysis. Proc Amer Assoc Cancer Res. 2005, vol. 46, Abstract #38.
Reynolds et al. Pre-protachykinin-A mRNA is increased in the airway epithelium of smokers with chronic bronchitis. Respiratory, 6:187-197 (2001).
Richeldi et al. Efficacy and safety of nintedanib in idiopathic pulmonary fibrosis. N Engl J Med. May 29, 2014;370(22):2071-82.
Riise et al. Bronchial Brush Biopsies for Studies of Epithelial Inflammation in Stable Asthma and Nonobstructive Chronic Bronchitis. European Respiratory Journal, 9: 1665-1671 (1996).
Riley, et al., Ectopic synthesis of high-Mr calcitonin by the BEN lung carcinoma cell line reflects aberrant proteolytic processing. FEBS lettes, Mar. 17, 1986; 198(1): 71-79.
Ringel et al. Expression of the sodium iodide symporter and thyroglobulin genes are reduced in papillary thyroid cancer. Mod Pathol. 2001;14(4):289-96.
Rivera et al. Establishing the diagnosis of lung cancer: Diagnosis and management of lung cancer: American College of Chest Physicians evidence-based clinical practice guidelines. Chest Journal 143.5_suppl (2013): e142S-e165S.
Robin et al. pROC: an open-source package for R and S+ to analyze and compare ROC curves. BMC Bioinformatics 12:77 (2011).
Robinson, et al. A comparison of Affymetrix gene expression arrays. BMC Bioinformatics. Nov. 15, 2007;8:449.
Robinson et al. A dynamic programming approach for the alignment of signal peaks in multiple gas chromatography-mass spectrometry experiments. BMC bioinformatics 8.1 (2007): 419.
Rodrigues-Serpa, et al. Loss of heterozygosity in follicular and papillary thyroid carcinomas. Cancer Genet Cytogenet. Feb. 2003;141(1):26-31.
Ronaghi et al. Real-time DNA sequencing using detection of pyrophosphate release. Anal Biochem. 1996; 242(1):84-89.
Roque, et al. Chromosome imbalances in thyroid follicular neoplasms: a comparison between follicular adenomas and carcinomas. Genes Chromosomes Cancer. Mar. 2003;36(3):292-302.
Ros et al. Thyroid-specific Gene Expression in the Multi-Step Process of Thyroid Carcinogenesis, Biochimie, Masson, Paris, FR, vol. 81, No. 4, Apr. 1, 1999, pp. 389-396.
Rosai et al. Pitfalls in the diagnosis of thyroid neoplasms. Pathol Res Pract. 1987;182(2):169-79.
Rosen et al. A six-gene model for differentiating benign from malignant thyroid tumors on the basis of gene expression. Surgery. 2005;138(6):1050-6; discussion 1056-7.
Roura-Mir et al. Single-cell analysis of intrathyroidal lymphocytes shows differential cytokine expression in Hashimoto's and Graves' disease. Eur J Immunol. 1997;27(12):3290-302.
Rouskin et al. Genome-wide probing of RNA structure reveals active unfolding of mRNA structures in vivo. Nature. Jan. 30, 2014;505(7485):701-5.
Rowe et al. Utility of BRAF V600E Mutation Detection in Cytologically Indeterminate Thyroid Nodules. CytoJoural 3(10):1-10 (Apr. 2006).
Rusznak et al. Effect of Cigarette Smoke on the Permeability and IL-1B and sICAM-1 Release from Cultured Human Bronchial Epithelial Cells of Never-Smokers, Smokers, and Patients with Chronic Obstructive Pulmonary Disease. Am. J. Respir. Cell Mol. Biol., 23:530-536 (2000).
Saal et al. Poor Prognosis in Carcinoma is Associated with A Gene Expression Signature of Aberrant PTEN Tumor Suppressor Pathway Activitiy. PNAS 104(18):7564-7569 (2007).
Sabo-Attwood, et al. Gene Expression Profiles Reveal Increased mClca3 (Gob5) Expression and Mucin Production in a Murine Model of Asbestos-Induced Fibrogenesis. American Journal of Pathology. vol. 167 No. 5; Nov. 2005: pp. 1243-1256.
Saeys, et al. A review of feature selection techniques in bioinformatics. Bioinformatics. Oct. 1, 2007;23(19):2507-17. Epub Aug. 24, 2007.
Saheki et al. Pathogenesis and pathophysiology of citrin (a mitochondrial aspartate glutamate carrier) deficiency. Metabolic Brain Disease; 17(4):335-346 (Dec. 2002).
Saito-Hisaminato et al. Genome-Wide Profiling of Gene Expression in 29 Normal Human Tissues with a cNDA Microarray. DNA Research, 2002, 9:35-45.
Saiz et al. Immunohistochemical expression of cyclin D1, E2F-1, and Ki-67 in benign and malignant thyroid lesions. J Pathol. 2002; 198(2):157-62.
Salemi et al. Cerebellar degeneration-related autoantigen 1 (CDR1) gene expression in prostate cancer cell lines. Int J Biol Markers (2014); 29.3: e288-290.
Salvatore et al. A cell proliferation and chromosomal instability signature in anaplastic thyroid carcinoma. Cancer Res. 2007;67(21):10148-58.
Sambrook; et al., "Molecular Cloning: A Laboratory Manual. Second edition, Cold Spring Harbor Laboratory Press, 1989.".
Sanghvi. Heterocyclic base modifications in nucleic acids and their applications in antisense oligonucleotides. in Antisense Research and Applications. Crooke, S. T. and Lebleu, B., ed., CRC Press. 1993; Ch 15 274-285.
Santarpia et al. Phosphatidylinositol 3-kinase/akt and ras/raf-mitogen-activated protein kinase pathway mutations in anaplastic thyroid cancer. J Clin Endocrinol Metab. 2008;93(1):278-84.
Santiyagu M. Savarimuthu Francis et al: "Genes and Gene Ontologies Common to Airflow Obstruction and Emphysema in the Lungs of Patients with COPD", Plos One, vol. 6, No. 3, 2011, p. e17442.
Sapio, et al., Detection of RETIPTC, TRK and BRAF mutations in preoperative diagnosis of thyroid nodules with indeterminate cytological findings, C]Jnica1 Endocrinology, 2007, 66: 678-683.
Satake et al. Overview of the primary structure, tissue-distribution, and functions of tachykinins and their receptors. Curr Drug Targets. 2006;7(8):963-74.
Savagner et al. Defective mitochondrial ATP synthesis in oxyphilic thyroid tumors. J Clin Endocrinol Metab. 2001;86(10):4920-5.
Savagner et al. PGC-1-related coactivator and targets are upregulated in thyroid oncocytoma. Biochem Biophys Res Commun. 2003;310(3):779-84.

(56) References Cited

OTHER PUBLICATIONS

Schembri et al. MicroRNAs as modulators of smoking-induced gene expression changes in human airway epithelium. Proc Natl Acad Sci U S A, 106(7), 2319-24 (Feb. 2009).
Schiff, et al. Epidermal growth factor receptor (EGFR) is overexpressed in anaplastic thyroid cancer, and the EGFR inhibitor gefitinib inhibits the growth of anaplastic thyroid cancer. Clin Cancer Res. Dec. 15, 2004;10(24):8594-602.
Schraufangel. "Interstitial Lung Disease," Chapter 10, pp. 99-107, in Breathing in America: Diseases, Progress and Hope, American Thoracic Society (2010).
Schraufnagel, Dean. Breathing in America: Diseases, Progress, and Hope. The American Thoracic Society. Published 2010. 282 pages.
Schroeder, et al. The RIN: an RNA integrity number for assigning integrity values to RNA measurements. BMC Mol Biol. Jan. 31, 2006;7:3.
Schulz et al. Activation of bronchial epithelial cells in smokers without airway obstruction and patients with COPD. Chest. May 2004;125(5):1706-13.
Schulz et al. Upregulation of MCAM in primary bronchial epithelial cells from patients with COPD. European Respiratory Journal (Sep. 2003); 22.3: 450-456.
Selman et al. Gene expression profiles distinguish idiopathic pulmonary fibrosis from hypersensitivity pneumonitis. American Journal of Respiratory and Critical Care Medicine (2006); 173.2: 188-198.
Selman et al. Idiopathic pulmonary fibrosis: aberrant recapitulation of developmental programs?. PLoS medicine 5.3 (2008): e62.
Selman et al. Revealing the pathogenic and aging-related mechanisms of the enigmatic idiopathic pulmonary fibrosis. An integral model. Am J Respir Crit Care Med. May 15, 2014;189(10):1161-72.
Selman, M. et al., Accelerated variant of idiopathic pulmonary fibrosis: Clinical behavior and gene expression pattern. Plos One, May 2007, Issue 5, e482, 11 Pages.
Shah et al. SIEGE: Smoking Induced Pithelial Gene Expression Database. Nucleic Acids Research, 33: D573-D579 (2005).
Shalon, D. et al. A DNA microarray system for analyzing complex DNA samples using two-color fluorescent probe hybridization. Genome research, 6(7): 639-645 (1996).
Shendure et al, Accurate multiplex polony sequencing of an evolved bacterial genome . Science 309(5741) (2005):1728-1732 with supplemental materials.
Sheu et al. The C allele of the GNB3 C825T polymorphism of the G protein beta3-subunit is associated with an increased risk for the development of oncocytic thyroid tumours. J Pathol. 2007;211(1):60-6.
Shi, et al. Combined analysis of gene expression, DNA copy number, and mutation profiling data to display biological process anomalies in individual breast cancers. Breast Cancer Res Treat. Apr. 2014;144(3):561-8. Epub Mar. 12, 2014.
Shibru, et al. Does the 3-gene diagnostic assay accurately distinguish benign from malignant thyroid neoplasms? Cancer. Sep. 1, 2008;113(5):930-5.
Shibuya et al., Increased telomerase activity and elevated hTERT mRNA expression during multistage carcinogenesis of squamous cell carcinoma of the lung. Cancer, Aug. 2001; 92(4):849-855.
Shields, PG. Molecular epidemiology of lung cancer. Annals of Oncology, 10(5):S7-S11 (1999).
Shih et al. A new Mel-CAM (CD146)-specific monoclonal antibody, MN-4, on paraffin- embedded tissue. Modern Pathology: an Official Journal of the United States and Canadian Academy of Pathology, Inc (1998); 11.11: 1098-1106.
Shim et al. Histopathologic findings of transbronchial biopsy in usual interstitial pneumonia. Pathology International (2010); 60.5: 373-377.
Shipp, et al. Diffuse large B-cell lymphoma outcome prediction by gene-expression profiling and supervised machine learning. Nat Med. Jan. 2002;8(1):68-74.
Shirasawa, S. Susceptibility genes for the development of autoimmune thyroid disease. Nippon Rinsho. Dec. 2006;64(12):2208-14. (Abstract only).
Shriver et al. Sex-Specific Expression of Gastrin-Releasing Peptide Receptor: Relationship to Smoking History and Risk of Lung Cancer. J. Natl. Cancer Inst., 92: 24-33 (2000).
Shvero et al. Immunohistochemical profile and treatment of uncommon types of thyroid carcinomas. Oncol Rep. 2003;10(6):2075-8.
Silvestri et al. A bronchial genomic classifier for the diagnostic evaluation of lung cancer. N Engl J Med. Jul. 16, 2015;373(3):243-51.
Silvestri et al. Latest advances in advanced diagnostic and therapeutic pulmonary procedures. Chest Journal (2012); 142.6: 1636-1644.
Simon et al. Up-regulation of MUC18 in airway epithelial cells by IL-13: implications in bacterial adherence. American Journal of Respiratory Cell and Molecular Biology (2011); 44.5: 606-613.
Singh et al. LNA (locked nucleic acids): synthesis and high-affinity nucleic acid recognition. Chem Commun 4:455-456 (1998).
Singh et al. Screening for genetic aberrations in papillary thyroid cancer by using comparative genomic hybridization. Surgery. 2000;128(6):888-93;discussion 893-4.
Singh et al. Synthesis of 2'-amino-LNA: A novel conformationally restricted high-affinity oligonucleotide analogues with a handle. J Bio Chem 63:10035-10039 (1998).
Singhal et al. Alterations in cell cycle genes in early stage lung adenocarcinoma identified by expression profiling. Cancer Biol Ther. May-Jun. 2003;2(3):291-8.
Singhal S et al: "Gene expression profiling of Non-small cell lung cancer", Lung Cancer, val. 60, No. 3, Jun. 1, 2008 (Jun. 1, 2008 ), pp. 313-324, XP022690999.
Siragusa et al. MUC1 oncoprotein promotes refractoriness to chemotherapy in thyroid cancer cells. Cancer Res. 2007;67(11):5522-30.
Siraj, et al., Genome-wide expression analysis of middle eastern papillary thyroid cancer reveals c-MET as a novel target for cancer therapy. The journal of pathology. Oct. 1, 2007; 213(2): 190-199.
Slonim, Donna. From Patterns to Pathways: Gene Expression Data Analysis Comes of Age. Nature Genetics Supplement, 32: 502-508, 2002.
Smirnov et al. Global gene expression profiling of circulating endothelial cells in patients with metastatic carcinomas. Cancer Res. Mar. 15, 2006;66(6):2918-22.
Smith et al. Methylation status of genes in papillary thyroid carcinoma. Arch Otolaryngol Head Neck Surg. 2007;133(10):1006-11.
Smith et al. Prevalence of benign disease in patients undergoing resection for suspected lung cancer. The Annals of Thoracic Surgery (May 2006); 81.5: 1824-1829.
Smyth. Limma: Linear Models for Microarray Data. In: Bioinformatics and Computational Biology Solutions using R and Bioconductor, R. Gentleman, V. Carey, S. Dudoit, R. Irizarry, W. Huber (eds.), Springer, New York. 2005; pp. 397-420.
Smyth. Linear models and empirical bayes methods for assessing differential expression in microarray experiments. Stat Appl Genet Mol Biol. 2004;3:Article3. Epub Feb. 12, 2004.
Song Kim, et al., Phase II clinical and exploratory biomarker study of dacomitinib in recurrent and/or metastatic esophageal squamous cell carcinoma. Oncotarget, Oct. 9, 2015, vol. 6, No. 42, pp. 44971-44984.
Soni et al. Progress toward ultrafast DNA sequencing using solid-state nanopores. Clinical Chemistry. vol. No. 53, Issue No. 11 (2007):1996-2001.
Sotos, et al. The Transitivity Misconception of Pearson's Correlation Coefficient. Statistics Education Research Journal. 8(2):33-55 (2009).
Soumyaroop Bhattacharya1 et al: "Molecular biomarkers for quantitative and discrete COPD phenotypes", American Journal of Respiratory Cell and Molecular Biology, American Lung Association, val. 40, No. 3, (Oct. 10, 2008), pp. 359-367.
Spargo, et al. Detection of M. tuberculosis DNA using thermophilic strand displacement amplification. Mol Cell Probes. Aug. 1996;10(4):247-56.
Speed et al. Nature Reviews. 2015. 16:33. (Year: 2015).

(56) References Cited

OTHER PUBLICATIONS

Spira, Avrum E. Abstract: Airway gene expression in smokers: an early diagnostic biomarker for lung cancer. National Institutes of Health Grant No. 1 RO1 CA124640-01 (Funding Start Date May 1, 2007).
Spira, Avrum E. Abstract: The airway transcriptome as a biomarker for lung cancer. National Institutes of Health Grant No. 1 R21 CA106506-01A2 (Funding Start Date Aug. 9, 2005).
Spira, et al. Airway epithelial gene expression in the diagnostic evaluation of smokers with suspect lung cancer. Nature Medicine 13: 361-366 (2007).
Spira, et al. Effects of cigarette smoke on the human airway epithelial cell transcriptome. PNAS, 101: 27, p. 10143-10148 (Jul. 6, 2004).
Spira et al. Gene Expression Profiling of Human Lung Tissue from Smokers with Severe Emphysema. Am J Respir Cell Mol Biol. Dec. 2004;31(6):601-10.
Spira, et al. Impact of cigarette smoke on the normal airway transcriptome. Chest. 125 (5 Suppl):115S (May 2004).
Spira et al. Noninvasive method for obtaining RNA from buccal mucosa epithelial cells for gene expression profiling. Biotechniques, 36(3): 484-7 (Apr. 2004).
Spivack, et al. Gene-environment interaction signatures by quantitative mRNA profiling in exfoliated buccal mucosal cells. Cancer Res. Sep. 15, 2004;64(18):6805-13.
Sridhar et al. Smoking-induced gene expression changes in the bronchial airway are reflected in nasal and buccal epithelium. BMC Genomics, 9: 259 (May 2008).
St. Croix et al. Genes Expressed in Human Tumor Endothelium. Science, 289:1197-1202, (Aug. 18, 2000).
Stanta et al. The biochemical and immunohistochemical profile of thyroid neoplasia. Pathol Annu. 1988;23 Pt 1: 129-57.
Steiling et al: "A Dynamic Bronchial AirwayGene Expression Signature of Chronic Obstructive Pulmonary Disease and LungFunction impairment", American Journal of Respiratory and Critical Caremedicine, vol. 187, No. 9, (Mar. 7, 2013), pp. 933-942.
Steiling et al. The field of tissue injury in the lung and airway. Cancer Prevention Research (2008); 1.6: 396-403.
Steiling K et al: "Airway gene expression in chronic obstructive pulmonary disease", Proceedings of the American Thoracic Society Dec. 15, 2009 American Thoracic Society USA, vol. 6, No. 8, Dec. 15, 2009 (Dec. 15, 2009), pp. 697-700,ISSN: 1546-3222.
Stephenson et al. Integration of gene expression profiling and clinical variables to predict prostate carcinoma recurrence after radical prostatectomy, Cancer 2005; 104:290-8, 2005.
Stewart, JH. Lung Carcinoma in African Americans, A Review of the Current Literature. Cancer; 91(12): 2476-2482 (Jun. 15, 2001).
Strausberg et al. Reading the Molecular Signatures of Cancer. Microarrays and Cancer Research, Warrington et al. (eds.), Eaton Publishing, Westborough, MA, pp. 81-111, (2002).
Su et al. Molecular Classification of Human Carcinomas by Use of Gene Expression Signatures. Cancer Research, 61:7388-7393, (Oct. 15, 2001).
Subramaniam et al. Clonal characterization of sporadic cribriform-morular variant of papillary thyroid carcinoma by laser microdissection-based APC mutation analysis. Am J Clin Pathol. 2007;128(6):994-1001.
Subramanian et al. Gene Set Enrichment Analysis: a Knowledge-based Approach for Interpreting Genome-wide Expression Profiles. Proceedings of the National Academy of Sciences of the United States of America. vol. 102, Issue 43 (2005): pp. 15545-15550.
Sugita et al. Combined Use of Oligonucleotide and Tissue Microarrays Identifies Cancer/Testis Antigens as Biomarkers in Lung Carcinoma. Cancer Research. Jul. 2002. vol. 62, Issue 14, pp. 3971-3979.
Sumikawa et al. Computed tomography findings in pathological usual interstitial pneumonia: relationship to survival. American Journal of Respiratory and Critical Care Medicine (2008); 177.4: 433-439.
Suomalainen et al. Quantitative analysis of human DNA sequences by PCR and solid-phase minisequencing. Molecular Biotechnology (2000); 15.2: 123-131.
Suykens et al. Least squares support vector machine classifiers. Neural Processing Letters (1999); 9.3: 293-300.
Suzanne A Eccles et al: "Metastasis: recent discoveries and novel treatment strategies", The Lancet, val. 369, No. 9574, May 1, 2007 (May 1, 2007 ), pp. 1742-1757, XP055231616.
Swensen et al. Solitary pulmonary nodules: clinical prediction model versus physicians. Mayo Clinic Proc 1999; 74:319-29 (1999).
Swensen et al. The probability of malignancy in solitary pulmonary nodules. Application to small radiologically indeterminate nodules. Arch Intern Med 1997; 157:849-55, 1997.
Symmans, et al. Total RNA Yield and Microarray Gene Expression Profiles from Fine-Needle Aspiration Biopsy and Core-Needle Biopsy Samples of Breast Carcinoma. 2003; Cancer 97(12):2960-2971.
Takakura et al. Oncogenic role of miR-17-92 cluster in anaplastic thyroid cancer cells. Cancer Sci. 2008;99(6):1147-54.
Takano et al. Expression of oncofetal fibronectin messenger ribonucleic acid in fibroblasts in the thyroid: a possible cause of false positive results in molecular-based diagnosis of thyroid carcinomas. J Clin Endocrinol Metab. 2000;85(2):765-8.
Takano et al. Preoperative diagnosis of thyroid papillary and anaplastic carcinomas by real- time quantitative reverse transcription-polymerase chain reaction of oncofetal fibronectin messenger RNA. Cancer Res. 1999;59(18):4542-5.
Takizawa et al. Increased expression of transforming growth factor-betal in small airway epithelium from tobacco smokers and patients with chronic obstructive pulmonary disease (COPD). American Journal of Respiratory and Critical Care Medicine, 163:1476-1483 (2001).
Tamir et al. Expression and development of a functional plasmalemmal 5-hydroxytryptamine transporter by thyroid follicular cells. Endocrinology. 1996; 137(10):4475-86.
Tanaka et al. Trial to establish an animal model of paraneoplastic cerebellar degeneration with anti-Yo antibody: 1. Mouse strains bearing different MHC molecules produce antibodies on immunization with recombinant Yo protein, but do not cause Purkinje cell loss. Clinical Neurology and Neurosurgery (1995); 97.1: 95-100.
Taniguchi et al. Differentiation of follicular thyroid adenoma from carcinoma by means of gene expression profiling with adapter-tagged competitive polymerase chain reaction. Oncology. 2005;69(5):428-35.
Tanoue et al. Lung cancer screening. American Journal of Respiratory and Critical Care Medicine (2015); 191.1: 19-33.
Tarca et al. Analysis of microarray experiments of gene expression profiling. Am J Obstet Gynecol 195(2): 373-388 (Aug. 2006).
Terada. Brain metastasis from thyroid adenomatous nodules or an encapsulated thyroid follicular tumor without capsular and vascular invasion: a case report. Cases J. Jul. 17, 2009;2:7180. doi: 10.4076/1757-1626-2-7180.
Tetzlaff et al. Differential expression of miRNAs in papillary thyroid carcinoma compared to multinodular goiter using formalin fixed paraffin embedded tissues. Endocr Pathol. 2007;18(3):163-73.
Theocharis et al. Metallothionein: a multifunctional protein from toxicity to cancer. Int Biol Markers, 18(3):162-169 (2003).
Thisteda. What is a P-value. Departments of Statistics and Health Studies. The University of Chicago. (May 25, 1988).
Thompson et al. Primary smooth muscle tumors of the thyroid gland. Cancer. 1997;79(3):579-87.
Thornton et al. Estimating kinship in admixed populations. The American Journal of Human Genetics 91.1 (2012): 122-138.
Thurston et al. Modeling lung cancer risk in case-control studies using a new dose metric of smoking. Cancer Epidemiol Biomarkers Prey 2005; 14(10): 2296-302 (2005).
Tian, et al. A combined oncogenic pathway signature of Braf, Kras and PI3KCA mutation improves colorectal cancer classification and cetuximab treatment prediction. Gut. Apr. 2013;62(4):540-9. doi: 10.1136/gutjnl-2012-302423. Epub Jul. 14, 2012.
Tian, et al. Effects of Gender on Gene Expression in the Blood of Ischemic Stroke Patients. Journal of Cerebral Blood Flow & Metabo-

(56) References Cited

OTHER PUBLICATIONS lism. J Cereb Blood Flow Metab. May 2012;32(5):780-91. doi: 10.1038/jcbfm.2011.179. Epub Dec. 14, 2011.
Tibshirani. Regression shrinkage and selection via the lasso. Journal of the Royal Statistical Society Series B (Methodological) 58:267-288 (1996).
Tichelaar et al. Increased staining for phospho-Akt, p65/RELA and cIAP-2 in pre-neoplastic human bronchial biopsies. BMC Cancer 5(155):1-13 (2005).
Tjarda Van Heek et al., Gene expression profiling identifies markers of ampullary adenocarcinoma. (Cancer biology & Therapy, 2004, 3(7):651-656.).
Tockman, et al., Considerations in Bringing a Cancer Biomarker to Clinical Application. Cancer Res May 1, 1992; (52): 2711s-2718s.
Todaro et al. Autocrine production of interleukin-4 and interleukin-10 is required for survival and growth of thyroid cancer cells. Cancer Res. 2006;66(3):1491-9.
Tokunaga et al., Enhanced expression of a Glyceraldehyde-3-phosphate Dehydrogenase Gene in human lung cancers. (Cancer Research, 1987, 47: 5616-5619).
Tomassetti et al. Bronchoscopic lung cryobiopsy increases diagnostic confidence in the multidisciplinary diagnosis of idiopathic pulmonary fibrosis. American Journal of Respiratory and Critical Care Medicine (2016); 193.7: 745-752.
Tomassetti et al. Transbronchial biopsy is useful in predicting UIP pattern. Respiratory Research (2012); 13.1: 96.
Trahan et al. Role of surgical lung biopsy in separating chronic hypersensitivity pneumonia from usual interstitial pneumonia/idiopathic pulmonary fibrosis: analysis of 31 biopsies from 15 patients. Chest Journal (2008); 134.1: 126-132.
Trapnell, et al. TopHat: discovering splice junctions with RNA-Seq. Bioinformatics. May 1, 2009;25(9):1105-11. doi: 10.1093/bioinformatics/btp120. Epub Mar. 16, 2009.
Travis et al. An official American Thoracic Society/European Respiratory Society statement: Update of the international multidisciplinary classification of the idiopathic interstitial pneumonias. Am J Respir Crit Care Med (2013); 188.6: 733-748.
Treutlein et al. Reconstructing lineage hierarchies of the distal lung epithelium using single-cell RNA-seq. Nature. May 15, 2014;509(7500):371-5. doi: 10.1038/nature13173. Epub Apr. 13, 2014.
Trovato, et al., Expression of the hepatocyte growth factor and c-met in normal thyroid, non-neoplastic, and neoplastic nodules. Thyroid, Jan. 1, 1998; 8(2): 125-131.
Trovisco et al. Molecular Genetics of Papillary Thyroid Carcinoma—Great Expectations . . . Arq Bras Endocrinol Metab, Jul. 1, 2007, pp. 643-653.
Trunk et al. The management and evaluation of the solitary pulmonary nodule. Chest 1974; 66:236-9 (1974).
Tsao et al. Increased Phospho-AKT (Ser4(3) Expression in Bronchial Dysplasia: Implications for Lunch Cancer Prevention Studies. Cancer Epidemiology Biomarkers & Prevention. 12:660-664 (2003).
Tsukamoto et al. Involvement of gicerin, a cell adhesion molecule, in tracheal development and regeneration. Cell Growth and Differentiation-Publication Cell Growth & Differentiation (1996); 7.12: 1761-1768.
Tsukamoto et al. The role of gicerin, a novel cell adhesion molecule, in development, regeneration and neoplasia. Histology and Histopathology (2001); 16.2: 563-571.
Tukey et al. Population-based estimates of transbronchial lung biopsy utilization and complications. Respiratory Medicine (2012); 106.11: 1559-1565.
Tukey. Exploratory Data Analysis: Past, Present, and Future. Technical Report No. 302. Department of Statistics, Princeton University. 1971-1977. 1993.
Tzen, et al. Is atypical follicular adenoma of the thyroid a preinvasive malignancy? Hum Pathol. Jul. 2003;34(7):666-9.
Ueda, et al. Analysis of PAX8 Gene in Congenital Hypothyroidism Mass Screening Positive Subjects. Folia Endocrinologica Japonica. Mar. 30, 2007, vol. 82, No. 4, p. 859. (in Japanese with English translation).
Ullmannová, et al. The use of housekeeping genes (HKG) as an internal control for the detection of gene expression by quantitative real-time RT-PCR. Folia Biol (Praha). 2003;49(6):211-6.
Ung et al. 18Fluorodeoxyglucose positron emission tomography in the diagnosis and staging of lung cancer: a systematic review. J Nat'l Cancer Institute, 99(23): 1753-67 (2007).
Unger et al. Array CGH demonstrates characteristic aberration signatures in human papillary thyroid carcinomas governed by RET/PTC. Oncogene. 2008;27(33):4592-602.
Van Allen et al. Whole-exome sequencing and clinical interpretation of formalin-fixed, paraffin-embedded tumor samples to guide precision cancer medicine. Nature medicine 20.6 (2014): 682.
Van Der Laan, et al. A new algorithm for hybrid hierarchical clustering with visualization and the bootstrap. Journal of Statistical Planning and Inference. Dec. 2003. 117(2):275-303.
Van Dyck, E. et al., Bronchial airway gene expression in smokers with lung or head and neck cancer. Cancer Medicine, Apr. 2014; 3(2): 322-336.
Vasko, et al. Gene expression and functional evidence of epithelial-to-mesenchymal transition in papillary thyroid carcinoma invasion. Proc Natl Acad Sci U S A. Feb. 20, 2007;104(8):2803-8. Epub Feb. 12, 2007.
Viale et al. Coexpression of cytokeratins and vimentin in normal and diseased thyroid glands. Lack of diagnostic utility of vimentin immunostaining. Am J Surg Pathol. 1989;13(12):1034-40.
Viney et al. Regulation of the cell-specific calcitonin/calcitonin gene-related peptide enhancer by USF and the Foxa2 forkhead protein. J Biol Chem. 2004;279(48):49948-55.
Visone et al. MicroRNAs (miR)-221 and miR-222, both overexpressed in human thyroid papillary carcinomas, regulate p27Kip1 protein levels and cell cycle. Endocr Relat Cancer. 2007;14(3):791-8.
Visone et al. Specific microRNAs are downregulated in human thyroid anaplastic carcinomas. Oncogene. 2007;26(54):7590-5.
Volm et al. Prognostic significance of the expression of c-fos, c-jun and c-erbB-1 oncogene products in human squamous cell lung carcinomas. J Cancer Res Clin Oncol, 119: 507-510 (1993).
Voynow et al. UC2, and MUC5/5AC in Nasal Epithelial Cells of Cystic Fibrosis, Allergic Rhinitis, and Normal Individuals. Lung 176: 345-354 (1998).
Wahidi, et al. Evidence for the treatment of patients with pulmonary nodules: when is it lung cancer? ACCP evidence-based clinical practice guidelines 2nd Edition. Chest 2007; 132:94-1075 (2007).
Wang et al. Association of the T1799A BRAF mutation with tumor extrathyroidal invasion, higher peripheral platelet counts, and over-expression of platelet-derived growth factor-B in papillary thyroid cancer. Endocr Relat Cancer. 2008;15(1):183-90.
Wang et al. RNA-seq: a revolutionary tool for transcriptomics. Nature Reviews Genetics 10:57-63 (2009).
Wang et al. The expression analysis of ICOS-L on activated T cells and immature dendritic cells as well as malignant B cells and Grave's-disease-derived thyroid tissues by two novel mAbs against human ICOS-L. Tissue Antigens. 2007;69(1):62-72.
Wardlaw et al. Effect of cigarette smoke on CYP1A1, CYP1A2 and CYP2B1/2 of nasal mucosae in F344 rats. Carcinogenesis 19(4): 655-662 (1998).
Watanabe et al. Decrease of intrathyroidal CD161+Valpha24+Vbeta11+ NKT cells in Graves' disease. Endocr J. 2008; 55(1):199-203.
Wattel, et al. Gene expression in thyroid autonomous adenomas provides insight into their physiopathology. Oncogene. Oct. 20, 2005;24(46):6902-16.
Watters et al. Developing Gene Expression Signatures of Pathway Deregulation in Tumors. Molecular Cancer Therapeutics, 5: 2444-2449, Oct. 2006.
Weber et al. A limited set of human MicroRNA is deregulated in follicular thyroid carcinoma. J Clin Endocrinol Metab. 2006;91(9):3584-91. Epub Jul. 5, 2006.

(56) References Cited

OTHER PUBLICATIONS

Weber et al. Genetic classification of benign and malignant thyroid follicular neoplasia based on a three-gene combination. J Clin Endocrinol Metab. 2005;90(5):2512-21.
Weber et al. Silencing of the maternally imprinted tumor suppressor ARHI contributes to follicular thyroid carcinogenesis. J Clin Endocrinol Metab. 2005;90(2):1149-55.
Wells, Athol U. Managing diagnostic procedures in idiopathic pulmonary fibrosis. European Respiratory Review (2013); 22.128: 158-162.
Wells, Athol U. The revised ATS/ERS/JRS/ALAT diagnostic criteria for idiopathic pulmonary fibrosis (IPF)-practical implications. Respiratory Research (2013); 14(Suppl 1):S2.
Weng et al., Association between the risk of lung cancer and influenza: a population-based nested case-control study. International Journal of infectious diseases, 2019, 88: 8-13.
Wessagowit, et al. Normal and abnormal mechanisms of gene splicing and relevance to inherited skin diseases. J Dermatol Sci. Nov. 2005;40(2):73-84. Epub Jul. 27, 2005.
Wessels, et al., A protocol for building and evaluating predictors of disease state based on microarray data, Bioinformatics, 2005, 21:3755-3762).
West et al. Embracing the complexity of genomic data for personalized medicine. Genome Res 2006; 16:559-66, May 2006.
West et al. Rapid Akt Activation by Nicotine and Tobacco Carcinogen Modulates the Phenotype of Normal Human Airway Epithelial Cells. The Journal of Clinical Investigation. 111(1):81-90 (Jan. 2003).
Wharam, et al. Specific detection of DNA and RNA targets using a novel isothermal nucleic acid amplification assay based on the formation of a three-way junction structure. Nucleic Acids Res. Jun. 1, 2001;29(11):E54-4.
Whitehead, et al. Variation in Tissue-specific Gene Expression Among Natural Populations. Genome Biology. vol. 6, Issue. 2 (2005): pp. R13- R13.14.
Whitney et al. Derivation of a bronchial genomic classifier for lung cancer in a prospective study of patients undergoing diagnostic bronchoscopy. BMC Med Genomics. May 6, 2015;8:18.
Wiener et al. An official American Thoracic Society/American College of Chest Physicians policy statement: implementation of low-dose computed tomography lung cancer screening programs in clinical practice. Am J Respir Crit Care Med. Oct. 1, 2015;192(7):881-91.
Wiener et al. Population-based risk for complications after transthoracic needle lung biopsy of a pulmonary nodule: an analysis of discharge records. Annals of Internal Medicine (2011); 155.3: 137-144.
Wiener et al. Risks of transthoracic needle biopsy: how high? Clinical Pulmonary Medicine (2013); 20.1: 29-35.
Wilkerson et al. ConsensusClusterPlus: a class discovery tool with confidence assessments and item tracking. Bioinformatics (2010); 26.12: 1572-1573.
Willey et al. Quantitative RT-PCR Measurement of Cytochromes p450 1A1, 161, and 2B7, Microsomal Epoxide Hydrolase, and NADPH Oxidoreductase Expression in Lung Cells of Smokers and Nonsmokers. Am. J. Respir. Cell Mol. Biol., 1997, 17:114-124.
Wiseman et al. Molecular phenotyping of thyroid tumors identifies a Marker panel for differentiated thyroid cancer diagnosis. Ann Surg Oncol. 2008; 15(10):2811-26.
Wistuba et al. High resolution chromosome 3p allelotyping of human lung cancer and preneoplastic/preinvasive bronchial epithelium reveals multiple, discontinuous sites of 3p allele loss and three regions of frequent breakpoints. Cancer Res., 60(7): 1949-60 (Apr. 1, 2000).
Wistuba et al. Molecular damage in the bronchial epithelium of current and former smokers. J Natl Cancer Inst., 89(18): 1366-73 (Sep. 17, 1997).
Woenckhaus et al. Expression Profiling of Non-Small Cell Lung Cancers and Bronchi of Smokers and Non Smokers. Study Group: Molecular Pathology/Pathology—Research and Practice, 200:p. 255, (2004).
Woenckhaus et al. Smoking and cancer-related gene expression in bronchial epithelium and non-small-cell lung cancers. Journal of Pathology, 210: 192-204 (Oct. 2006).
Wojnarowski et al. Cytokine Expression in Bronchial Biopsies of Cystic Fibrosis Patients With and Without Acute Exacerbation. (Eur Respir, 1999, 14: 1136-114).
Wong et al. Development of a quantitative assay for SARS coronavirus and correlation of GAPDH mRNA with SARS coronavirus in clinical specimens. J Clin Pathol, 2005, 58: 276-280, doi: 10.1136/jcp.2004016592.
Woodcock et al. The treatment of idiopathic pulmonary fibrosis. F1000Prime Rep. Mar. 3, 2014;6:16.
Wreesmann et al. Genome-wide profiling of papillary thyroid cancer identifies MUC1 as an independent prognostic marker. Cancer Res. 2004;64(11):3780-9.
Wu, et al. A comparative study of 200 fine needle aspiration biopsies performed by clinicians and cytopathologists. Laryngoscope. Jul. 2006;116(7):1212-5.
Wu et al. Uncommon mutation, but common amplifications, of the PIK3CA gene in thyroid tumors. J Clin Endocrinol Metab. 2005;90(8):4688-93.
Wu, Thomas D. Analysing gene expression data from DNA microarrays to identify candidate genes. Journal of Pathology, 195:53-65 (2001).
Wuenschell et al. Embryonic mouse lung epithelial progenitor cells co-express immunohistochemical markers of diverse mature cell lineages. Journal of Histochemistry and Cytochemistry (1996); 44.2: 113-123.
Xing et al. Braf V600E and TERT Promoter Mutations Cooperatively Identify the Most Aggressive Papillary Thyroid Cancer With Highest Recurrence Journal of Clinical Oncology vol. 32, pp. 2718-2726 (Year: 2014).
Xu et al. Differential expression of galectin-1 and galectin-3 in thyroid tumors. Potential diagnostic implications. Am J Pathol. 1995;147(3):815-22.
Yan, et al. Isothermal amplified detection of DNA and RNA. Mol Biosyst. May 2014; 10(5):970-1003.
Yang et al. C-myc, N-myc, N-ras, and c-erb-B: lack of amplification or rearrangement in human medullary thyroid carcinoma and a derivative cell line. Anticancer Res. 1990;10(1):189-92.
Yang et al. Expression of cilium-associated genes defines novel molecular subtypes of idiopathic pulmonary fibrosis. Thorax (2013): 68(12):1114-11121.
Yang et al. Gene expression profiling of familial and sporadic interstitial pneumonia. American Journal of Respiratory and Critical Care Medicine (2007); 175.1: 45-54.
Yang et al. Reduction of Dihydrodiol Dehydrogenase Expression in Resected Hepatocellular Carcinoma. OncoL Rep., 10(2):271-276, (2003).
Yang, I.V., et al., Epigenetics of Idiopathic Pulmonary Fibrosis. Transl Res. Jan. 2015; 165(1): 48-60.
Yang Ivana V. et al: "The Peripheral Blood Transcriptome Identifies the Presence and Extent of Disease in Idiopathic Pulmonary Fibrosis", Plos One, vol. 7, No. 6, Sep. 30, 2011 (Sep. 30, 2011), p. e37708, XP055819869,DOI: 10.1371 /journal.pone.0037708.
Yano et al. Gene expression profiling identifies platelet-derived growth factor as a diagnostic molecular marker for papillary thyroid carcinoma. Clin Cancer Res. 2004;10(6):2035-43.
Yatabe et al. Epidermal growth factor receptor gene amplification is acquired in association with tumor progression of EGFR-mutated lung cancer. Cancer Res. 2008;68(7):2106-11.
Yeh et al. Differentiated thyroid cancer cell invasion is regulated through epidermal growth factor receptor-dependent activation of matrix metalloproteinase (MMP)-2/gelatinase A. Endocr Relat Cancer. 2006;13(4):1173-83.
Yeh et al. Somatic mitochondrial DNA (mtDNA) mutations in papillary thyroid carcinomas and differential mtDNA sequence variants in cases with thyroid tumours. Oncogene. 2000;19(16):2060-6.
Yen-Tsung; Huang et al, Journal of Clinical Oncology, Jun. 1, 2009, 27 (16), 2660-2667.
Yoneda et al. Development of High-Density DNA Microarray Membrane for Profiling Smoke- and Hydrogen Peroxide-Induced

(56) References Cited

OTHER PUBLICATIONS

Genes in a Human Bronchial Epithelial Cell Line. American Journal of Respiratory and Critical Care Medicine, 164:S86-S89, (2001).
Yoon et al. Identification of a novel noncoding RNA gene, NAMA, that is downregulated in papillary thyroid carcinoma with BRAF mutation and associated with growth arrest. Int J Cancer. 2007;121(4):767-75.
Yousefi et al. A SNP panel for identification of DNA and RNA specimens. BMC genomics 19.1 (2018): 90.
Yukinawa, et al. A multi-class predictor based on a probabilistic model: application to gene expression profiling-based diagnosis of thyroid tumors. BMC Genomics. Jul. 27, 2006;7:190.
Yu-Rong, et al. Tumor-associated antisen L6 and the invasion of human lung cancer cells. Clinical Cancer Research, Jul. 2003; vol. 9: 2807-2816.
Zabel et al. S-100 protein and neuron-specific enolase in parathyroid glands and C-cells of the thyroid. Histochemistry. 1987;86(4):389-92.
Zabner et al. Comparison of DNA-Lipid Complexes and DNA Alone for Gene Transfer to Cystic Fibrosis Airway Epithelia in vivo. (J Clin Invest, 1997, 100(6): 1529-1537.).
Zanna et al. Trop-1 are conserved growth stimulatory molecules that mark early stages of tumor progression. Cancer. 2007;110(2):452-64.
Zeeberg et al. GoMiner: a resource for biological interpretation of genomic and proteomic data. Genome Biology, 4(4):R28.1-R28.8 (Mar. 2003).
Zemke et al. Molecular staging of epithelial maturation using secretory cell-specific genes as markers. American Journal of Respiratory Cell and Molecular Biology (2009); 40.3: 340-348.
Zeng et al. The contributions of oestrogen receptor isoforms to the development of papillary and anaplastic thyroid carcinomas. J Pathol. 2008;214(4):425-33.
Zeskind Julie E et al: "Translating the COPD transcriptome: insights into pathogenesis and tools for clinical anagement.",Proceedings of the American Thoracic Society Dec. 1, 2008, vol. 5, No. 8, Dec. 1, 2008 (Dec. 1, 2008), pp. 834-841.
Zhang, et al. Association between single-nucleotide polymorphisms of BRAF and papillary thyroid carcinoma in a Chinese population. Thyroid. Jan. 2013;23(1):38-44. doi: 10.1089/thy.2012.0228.
Zhang, et al., Biomarkers in idiopathic pulmonary fibrosis, Current opinion in pulmonary medicine, vol. 18, No. 5, Sep. 1, 2012, 441-446.
Zhang, et al. CDC23 Regulates Cancer Cell Phenotype and is Overexpressed in Papillary Thyroid Cancer. Endocr Relat Cancer. Endocr Relat Cancer. Nov. 28, 2011;18(6):731-42. doi: 10.1530/ERC-11-0181. Print 2011.
Zhang et al. Comparison of smoking-induced gene expression on Affymetrix Exon and 3'-based expression arrays. Genome Inform. 18: 247-57 (2007).
Zhang, et al., Identifying driver mutations from sequencing data of heterogeneous tumors in the era of personalized genome sequencing. Briefings in bioinformatics 15.2 (2014): 244-255.
Zhang et al. Regulation of tumor necrosis factor-related apoptosis-inducing ligand-induced apoptosis by DJ-1 in thyroid cancer cells. Endocr Relat Cancer. 2008;15(2):535-44.
Zhang, Xiaoling, et al., Similarities And Differences Between Smoking-related Gene Expression In Nasal And Bronchial Epithelium. Physiological Genomics 41(1):1-8 (2010).
Zhou et al. RET proto-oncogene mutations are restricted to codons 634 and 918 in mainland Chinese families with MEN2A and MEN2B. Clin Endocrinol (Oxf). 2007;67(4):570-6.
Zhu et al. U1 snRNP-dependent function of TIAR in the regulation of alternative RNA processing of the human calcitonin/CGRP pre-mRNA. Mol Cell Biol. 2003;23(17):5959-71.
Zochbauer-Muller et al. 5' CpG Island Methylation of the FHIT Gene is Correlated with Loss of Gene Expression in Lung and Breast. Cancer Research, 61:3581-3585, (May 2, 2001).
Achiron, Anat, et al., Blood Transcriptional Signatures of Multiple Sclerosis: Unique Gene Expression of Disease Activity. Annals of Neurology 55(3):410-417 (2004).
Baine, Michael J, et al., Transcriptional Profiling of Peripheral Blood Mononuclear Cells in Pancreatic Cancer Patients Identifies Novel Genes With Potential Diagnostic Utility. PLoS One 6(2):e17014, 10 Pages (2011).
Bluth, Martin, et al., Use of Gene Expression Profiles in Cells of Peripheral Blood to Identify New Molecular Markers of Acute Pancreatitis. Archery of Surgery 143(3):227-233 (2008).
Bull, Todd M, et al., Microarray Analysis of Peripheral Blood Cells in Pulmonary Arterial Hypertension, Surrogate to Biopsy. Chest 128(6 Suppl):584S (2005).
De Hoon, Michael., Cluster 3.0 for Windows, Mac OS X, Linux, Unix, Retrieved from Internet URL[ http://bonsai.hgc.jp/~mdehoon/software/cluster/manual/] accessed Apr. 26, 2024, 34 pages.
Du Bois, Roland M, et al., Forced Vital Capacity in Patients With Idiopathic Pulmonary Fibrosis: Test Properties and Minimal Clinically Important Difference. American Journal of Respiratory and Critical Care Medicine 184(12):1382-1389 (2011).
Efron, Bradley, et al., On Testing the Significance of Set of Genes. The Annals of Applied Statistics 1(1):107-129 (2007).
Egan, TM, et al., Development of the New Lung Allocation System in the United States. American Journal of Transplantation 6(5 Pt 2):1212-1227 (2006).
Feghali-Bostwick, Carol A, et al., Cellular and Humoral Autoreactivity in Idiopathic Pulmonary Fibrosis. Journal of Immunology 179(4):2592-2599 (2007).
Gilani, Syed R, et al., CD28 Down-regulation on Circulating CD4 T-cells is Associated With Poor Prognoses of Patients With Idiopathic Pulmonary Fibrosis. PLoS One 5(1): E8959, 11pages (2010).
Herazo et al., Peripheral blood monuclear cells gene expression patterns predict mortality in patients with Idiopathic Pulmonary Fibrosis. Am J Respir Crit Care Med 183;A5306 (2011) (Abstract).
Herazo-Maya, Jose D, et al., Personalized Medicine: Applying 'omics' to Lung Fibrosis. Biomarkers in Medicine 6(4): 529-540 (2012).
Ihaka, Ross, et al., A Language for Data Analysis and Graphics. Journal of Computational and Graphical Statistics 5(3):299-314 (1996).
Karampitsakos, Theodoros, et al. Precision medicine advances in idiopathic pulmonary fibrosis. eBioMedicine 95:104766, 12 pages, (2023).
Kinder, Brent W, et al., Serum Surfactant Protein-A is a Strong Predictor of Early Mortality in Idiopathic Pulmonary Fibrosis. Chest 135(6):1557-1563(2009).
King, Talmadge E, et al., Predicting Survival in Idiopathic Pulmonary Fibrosis: Scoring System and Survival Model. American Journal of Respiratory and Critical Care Medicine 164(7): 1171-1181 (2011).
Ley, Brett, et al., Clinical Course and Prediction of Survival in Idiopathic Pulmonary Fibrosis. American Journal of Respiratory and Critical Care Medicine 183(4):431-440(2011).
Moeller, Antje, et al., Circulating Fibrocytes Are an Indicator of Poor Prognosis in Idiopathic Pulmonary Fibrosis. American Journal of Respiratory and Critical Care Medicine 179(7): 588-594(2009).
Moore, David, et al., Using Peripheral Blood Mononuclear Cells to Determine a Gene Expression Profile of Acute Ischemic Stroke: a Pilot Investigation. Circulation 111(2):212-221 (2005).
Murphy, S A, et al., On Profile Likelihood. Journal of the American Statistical Association 95(450):449-465 (2000).
Ottoboni, Linda, et al., An RNA Profile Identifies Two Subsets of Multiple Sclerosis Patients Differing in Disease Activity. Science Translational Medicine 4(153): 153ra131, 8 Pages (2012).
Pham, Michael X, et al., Gene-expression Profiling for Rejection Surveillance After Cardiac Transplantation. New England Journal of Medicine 362(20):1890-900 (2010).
Prasse, Antje, et al., Serum CC-chemokine Ligand 18 Concentration Predicts Outcome in Idiopathic Pulmonary Fibrosis. American Journal of Respiratory and Critical Care Medicine 179(8):717-723 (2009).

(56) References Cited

OTHER PUBLICATIONS

Richards, Thomas J, et al., Peripheral Blood Proteins Predict Mortality in Idiopathic Pulmonary Fibrosis. American Journal of Respiratory and Critical Care Medicine 185(1):67-76 (2012).
Risbano, Michael G, et al., Altered Immune Phenotype in Peripheral Blood Cells of Patients With Scleroderma-associated Pulmonary Hypertension. Clinical and Translational Science 3(5):210-218 (2010).
Rosas, et al. MMP1 and MMP7 as potential peripheral blood biomarkers in idiopathic pulmonary fibrosis. PLoS medicine 5.4 (2008): e93.
Schwartz, D A, et al., Determinants of Survival in Idiopathic Pulmonary Fibrosis. American Journal of Respiratory and Critical Care Medicine 149(2 Pt 1):450-454 (1994).
Segman, R H, et al., Peripheral Blood Mononuclear Cell Gene Expression Profiles Identify Emergent Post-traumatic Stress Disorder Among Trauma Survivors. Molecular Psychiatry 10(5):500-513 (2005).
Showe, Michael K, et al., Gene Expression Profiles in Peripheral Blood Mononuclear Cells Can Distinguish Patients With Non-small Cell Lung Cancer From Patients With Nonmalignant Lung Disease. Cancer Research 69(24):9202-9210 (2009).
Therneau, Terry M, et al., Modeling Survival Data: extending the Cox model. Springer : 10 Pages (2000).
Trulock, Elbert P, et al., Registry of the International Society for Heart and Lung Transplantation: Twenty-Second Official Adult Lung and Heart-Lung Transplant Report—2005. The Journal of Heart and Lung Transplantation 24(8):956-967 (2005).
Tusher et al. Significance analysis of microarrays applied to the ionizing radiation response. PNAS USA 98:5116-5121 (2001).
Venables, W N, et al., Modern Applied Statistics with S. Springer :504 Pages (2002).
Wu, Wei, et al., Comparison of Normalization Methods for Codelink Bioarray Data. BMC Bioinformatics 6:309, 14 Pages (2005).
Xue, Jianmin, et al., The HLA Class II Allele DRB1*1501 is Over-Represented in Patients with Idiopathic Pulmonary Fibrosis. PloS One 6(2):e14715, 7 Pages (2011).
Yokoyama, Akihito, et al., Prognostic Value of Circulating KL-6 in Idiopathic Pulmonary Fibrosis. Respirology 11(2):164-168 (2006).
Zahurak, Marianna, et al., Pre-Processing Agilent Microarray Data. BMC Bioinformatics 8:142, 13 Pages (2007).
Zappala, C J, et al., Marginal Decline in Forced Vital Capacity is Associated With a Poor Outcome in Idiopathic Pulmonary Fibrosis. The European Respiratory Journal 35(4):830-835 (2010).

| DE Genes | All Combined UIP vs. Non UIP | Smokers Only UIP vs. Non UIP | Non Smokers Only UIP vs. Non UIP |
|---|---|---|---|
| FDR p value <0.01 | 26 | 64 | 671 |

SYSTEMS AND METHODS OF DIAGNOSING IDIOPATHIC PULMONARY FIBROSIS

RELATED PATENT APPLICATIONS

This application is a continuation of U.S. patent application Ser. No. 17/218,125, filed Mar. 30, 2021 (now U.S. Pat. No. 11,639,527, issued May 2, 2023), which is a continuation of U.S. patent application Ser. No. 16/840,009, filed Apr. 3, 2020, which is a continuation of U.S. patent application Ser. No. 16/551,645, filed Aug. 26, 2019, which is a continuation of U.S. patent application Ser. No. 15/523,654, filed May 1, 2017, which is a U.S. National Stage Application pursuant to 35 U.S.C. § 371 of International Application No. PCT/US2015/059309, filed Nov. 5, 2015, which claims benefit of U.S. Provisional Application No. 62/130,800, filed Mar. 10, 2015 and claims benefit of U.S. Provisional Application No. 62/075,328, filed on Nov. 5, 2014, each of which is incorporated in its entirety by reference herein.

SEQUENCE LISTING

The instant application contains a Sequence Listing which has been submitted electronically in XML format and is hereby incorporated by reference in its entirety. Said XML copy, created on Mar. 9, 2023, is named 36024-739.304 SL.xml and is 67,863 bytes in size.

INTRODUCTION

Interstitial lung diseases (ILD) are a heterogeneous group of acute and chronic bilateral parenchymal pulmonary disorders with similar clinical manifestations, but a wide spectrum of severity and outcome[1,2]. Among these, idiopathic pulmonary fibrosis (IPF) is one of the most common and severe ILD, characterized by progressive fibrosis, worsening lung function and death[3-6]. Most patients diagnosed with IPF die within five years of their initial diagnosis[7,8]. However, the recent availability of two new drugs and other therapeutics in development may change this picture[9-11], and accurate diagnosis is critical for appropriate therapeutic intervention[5,12].

IPF can be challenging to diagnose. The diagnostic approach to IPF requires exclusion of other interstitial pneumonias, as well as connective tissue disease and environmental and occupational exposures[3-6]. Patients suspected of having IPF usually undergo high-resolution computed tomography (HRCT), which confirms the disease with high specificity only if the pattern of usual interstitial pneumonia (UIP) is clearly evident[5,13]. Yet, for a large number of patients, diagnosis necessitates an invasive surgical lung biopsy (SLB) to clarify the histopathologic features of interstitial pneumonia and/or UIP pattern[5,14] and the typical length of time to diagnose IPF from the onset of symptoms may be 1-2 years[15]. Discordance between pathologists occurs, and a correct diagnosis can be dependent on individual experience[16]. Despite histopathologic evaluation, a definitive diagnosis may remain elusive. Diagnostic accuracy has been shown to increase when multidisciplinary teams (MDT) of pulmonologists, radiologists, and pathologists confer[17]; unfortunately not all patients and their physicians have access to this level of expert review by an experienced MDT. Such reviews are time consuming and require patients to be seen at regional centers of recognized expertise.

Accordingly, more effective methods of diagnosing IPF are required. In addition, methods of differentiating UIP from non-UIP are required.

SUMMARY OF THE INVENTION

Disclosed herein is a method for nucleic acid sequencing comprising (a) obtaining a nucleic acid sample, wherein said nucleic acid sample comprises a plurality of messenger ribonucleic acid molecules; (b) subjecting said plurality of messenger ribonucleic acid molecules to reverse transcription to yield a plurality of complementary deoxyribonucleic acid molecules; and (c) subjecting the plurality of messenger ribonucleic acid molecules or derivatives thereof to sequencing. The messenger ribonucleic acid molecules can be derived from a tissue sample of the subject. Sequencing can comprise PCR. Subjecting can comprise hybridizing a plurality of probes to said plurality of messenger ribonucleic acid molecules. The plurality of probes can be labeled with a molecular marker.

Herein we describe methods of and systems used for differentiating between samples as usual interstitial pneumonia (UIP) or non-UIP using classifiers whose accuracy was confirmed using expert pathology diagnoses as truth labels. While gene expression profiling studies in the scientific literature have reported differential expression between IPF and other ILD subtypes[18,19], none have attempted to classify UIP in datasets containing other subtypes frequently present as part of the clinician's differential diagnosis.

In some embodiments, the present invention provides a method and/or system for detecting whether a lung tissue sample is positive for usual interstitial pneumonia (UIP) or non-usual interstitial pneumonia (non-UIP). In some embodiments a method is provided for: assaying the expression level of each of a first group of transcripts and a second group of transcripts in a test sample of a subject, wherein the first group of transcripts includes any one or more of the genes overexpressed in UIP and listed in any of Tables 5, 7, 9, 10, 11, and 12 and the second group of transcripts includes any one or more of the genes under-expressed in UIP and listed in any of Tables 5, 8, 9, 10, 11 or 12. In some embodiment, the method further provides for comparing the expression level of each of the first group of transcripts and the second group of transcripts with reference expression levels of the corresponding transcripts to (1) classify said lung tissue as usual interstitial pneumonia (UIP) if there is (a) an increase in an expression level corresponding to the first group or (b) a decrease in an expression level corresponding to the second group as compared to the reference expression levels, or (2) classify the lung tissue as non-usual interstitial pneumonia (non-UIP) if there is (c) an increase in the expression level corresponding to the second group or (d) a decrease in the expression level corresponding to the first group as compared to the reference expression levels. In some embodiments, the method further provides for determining and/or comparing sequence variants for any of the one or more genes listed in tables 5, 8, 9, 11, and/or 12.

In some embodiments, the present invention provides a method and/or system for detecting whether a lung tissue sample is positive for usual interstitial pneumonia (UIP) or non-usual interstitial pneumonia (non-UIP). In some embodiments, the method and/or system is used to assay by sequencing, array hybridization, or nucleic acid amplification the expression level of each of a first group of transcripts and a second group of transcripts in a test sample from a lung tissue of a subject, wherein the first group of transcripts includes any one or more of the genes overexpressed in UIP and listed in Tables 5, 7, 9, 10, 11 or 12 and the second group of transcripts includes any one or more of the genes under-expressed in UIP and listed in Tables 5, 8, 9, 10, 11 or 12. In certain embodiments, the method and/or system further compares the expression level of each of the first group of transcripts and the second group of transcripts with reference expression levels of the corresponding transcripts to (1) classify said lung tissue as usual interstitial pneumonia (UIP) if there is (a) an increase in an expression level corresponding to the first group or (b) a decrease in an expression level corresponding to the second group as compared to the reference expression levels, or (2) classify the lung tissue as non-usual interstitial pneumonia (non-UIP) if there is (c) an increase in the expression level corresponding to the second group or (d) a decrease in the expression level corresponding to the first group as compared to the reference expression levels.

In some embodiments, the present invention provides a method and/or system for detecting whether a test sample is positive for UIP or non-UIP by

- measuring the expression level of two or more transcripts expressed and/or determining sequence variants for one or more transcripts expressed in the sample;
- using a computer generated classifier to distinguish between UIP and non-UIP;
- wherein the classifier is built using a spectrum of Non-UIP pathology subtypes comprising HP, NSIP, sarcoidosis, RB, bronchiolitis, and organizing pneumonia (OP).

In some embodiments, the test sample is a biopsy sample or a bronchoalveolar lavage sample. In some embodiments, the test sample is fresh-frozen or fixed.

In some embodiments, the transcript expression levels are determined by RT-PCR, DNA microarray hybridization, RNASeq, or a combination thereof. In some embodiments, one or more of the transcripts is labeled.

In some embodiments, the method comprises detecting cDNA produced from RNA expressed in the test sample, wherein, optionally, the cDNA is amplified from a plurality of cDNA transcripts prior to the detecting step.

In some embodiments, the methods of the present invention further comprise measuring the expression level of at least one control nucleic acid in the test sample.

In some embodiments, the methods of the present invention classify the lung tissue as any one of interstitial lung diseases (ILD), a particular type of ILD, a non-ILD, or non-diagnostic. In particular embodiments, methods of the present invention classify the lung tissue as either idiopathic pulmonary fibrosis (IPF) or Nonspecific interstitial pneumonia (NSIP).

In some embodiments, the method and/or system of the present invention comprises assaying the test sample for the expression level of one or more transcripts of any one of SEQ ID NOS: 1-22. In some embodiments, the method further comprises assaying the test sample for the expression level of from 1 to 20 other genes. In some embodiments, the other genes comprise one or more, or optionally all of HMCN2, ADAMTSL1, CD79B, KEL, KLHL14, MPP2, NMNAT2, PLXDC1, CAPN9, TALDO1, PLK4, IGHV3-72, IGKV1-9, and CNTN4.

In some embodiments, the method and/or systems of the present invention further comprise using smoking status as a covariate during training of a UIP vs. non-UIP classifier disclosed herein, wherein, optionally, the smoking status is determined by detecting an expression profile indicative of the subject's smoker status. In some embodiments, such a classifier is used to determine whether a test sample is UIP or non-UIP.

In some embodiments, the method and/or systems of the present invention comprises training a UIP vs. non-UIP classifier, wherein genes that are susceptible to smoker-status bias are excluded or weighed differently than genes that are not susceptible to smoker-status bias during the classifier training.

In some embodiments, the present invention provides a method and/or system for detecting whether a lung tissue sample is positive for usual interstitial pneumonia (UIP) or non-usual interstitial pneumonia (non-UIP), as described herein, wherein the method comprises a first classification of a test sample as smoker or non-smoker using a first classifier trained to recognize gene signatures that distinguish smokers from non-smokers; and wherein the method further comprises a second classification of the test sample a UIP or non-UIP, wherein the second classification step uses a second or third classifier, which second and third classifiers are trained to distinguish UIP vs. non-UIP in smokers (smoker-specific classifier) and non-smokers (non-smoker-specific classifier), respectively, and wherein the second classification uses either (i) the smoker-specific classifier if the test sample is classified as smoker in the first classification or (ii) the non-smoker-specific classifier if the test sample is classified as non-smoker in the first classification.

In some embodiments, the present invention provides a method and/or system for detecting whether a lung tissue sample is positive for usual interstitial pneumonia (UIP) or non-usual interstitial pneumonia (non-UIP), wherein the methods comprise implementing a classifier trained using one or more feature selected from gene expression, variants, mutations, fusions, loss of heterozygoxity (LOH), and biological pathway effect. In some embodiments, the classifier is trained using features comprising gene expression, sequence variants, mutations, fusions, loss of heterozygoxity (LOH), and biological pathway effect.

In some embodiments, the present invention provides for assaying 2 or more different transcripts, or 3 or more, 4 or more, 5 or more, 10 or more, 15 or more, 20 or more, or more than 20 different transcripts in the first group and/or 2 or more different transcripts, or 3 or more, 4 or more, 5 or more, 10 or more, 15 or more, 20 or more, or more than 20 different transcripts in the second group.

In some embodiments, the method provides for detecting 2 or more different transcripts of any one of SEQ ID NOS:1-22, or 3 or more, 4 or more, 5 or more, 10 or more, 15 or more, 20 or more, or more than 20 different transcripts of any one of SEQ ID NOS:1-22. In particular embodiments, the current methods provide for assaying the test sample for the expression level of all of the transcripts of SEQ ID NOS: 1-22. In some embodiments, the method further comprises assaying the test sample for the expression level of from 1 to 20 other genes. In some embodiments, the method provides for assaying one or more of HMCN2, ADAMTSL1, CD79B, KEL, KLHL14, MPP2, NMNAT2, PLXDC1, CAPN9, TALDO1, PLK4, IGHV3-72, IGKV1-9, and CNTN4.

Disclosed herein is a method for determining that a subject is at risk for a non-usual interstitial pneumonia (non-UIP) subtype of a plurality of non-UIP subtypes, comprising: (a) obtaining a biological sample of said subject; (b) assaying nucleic acid molecules derived from said biological sample to identify a level of expression of at least one gene associated with said non-UIP subtype; and (c) processing said level of expression to generate a classification of said biological sample as being at risk for said non-UIP subtype. The non-UIP subtype can be hypersensitivity pneumonitis (HP), non-specific interstitial pneumonia (NSIP), sarcoidosis, respiratory bronchiolitis (RB), bronchiolitis, diffuse alveolar damage (DAD) or organizing pneumonia (OP). The biological sample can be a transbronchial biopsy sample or a bronchoalveolar lavage sample. Step (b) can comprise sequencing. Assaying can further comprise identifying a level of expression of at least one control nucleic acid molecule in said biological sample. The plurality of non-UIP subtypes can comprise hypersensitivity pneumonitis (HP), non-specific interstitial pneumonia (NSIP), sarcoidosis, respiratory bronchiolitis (RB), bronchiolitis, diffuse alveolar damage (DAD) or organizing pneumonia (OP). Step (c) can be performed using a machine learning algorithm that is trained to identify said non-UIP subtype of said plurality of non-UIP subtypes. The machine learning algorithm can be trained using features comprising gene expression variants, gene fusions, loss of heterozygosity, or biological pathway effect. The gene expression variants can be alternative splice variants. The machine learning algorithm can be trained with a training set that is independent of said biological sample. The biological sample can be fresh-frozen or fixed. The nucleic acid molecules can be ribonucleic acids (RNA) molecules, and said assaying can comprise generating complementary deoxyribonucleic acid (cDNA) molecules from said RNA molecules. The subject can be suspected of having an interstitial lung disease based at least in part on one or more clinical signs or one or more symptoms. The one or more symptoms can comprise shortness of breath or dry cough. The one or more clinical signs can comprise a result of an imaging test, a pulmonary function test, or a lung tissue analysis. The imaging test can be chest X-ray or computerized tomography. The computerized tomography can be high-resolution computerized tomography. The pulmonary function test can be spirometry, oximetry, or an exercise stress test. The lung tissue analysis can comprise histological or cytological analysis of a lung tissue sample of said subject. The method can further comprise providing a therapeutic intervention to said subject based at least in part on said classification generated in (c).

BRIEF DESCRIPTION OF THE FIGURES

FIG. 10A: differential expression of IGHV3-72 in UIP vs Non-UIP smokers vs. non-smokers. FIG. 10B: differential expression of CPXM1 in UIP vs Non-UIP smokers vs. non-smokers. FIG. 10C: differential expression of BPIFA1 in UIP vs Non-UIP smokers vs. non-smokers. FIG. 10D: differential expression of HLA-U in UIP vs Non-UIP smokers vs. non-smokers.

DEFINITIONS

Figure 1:
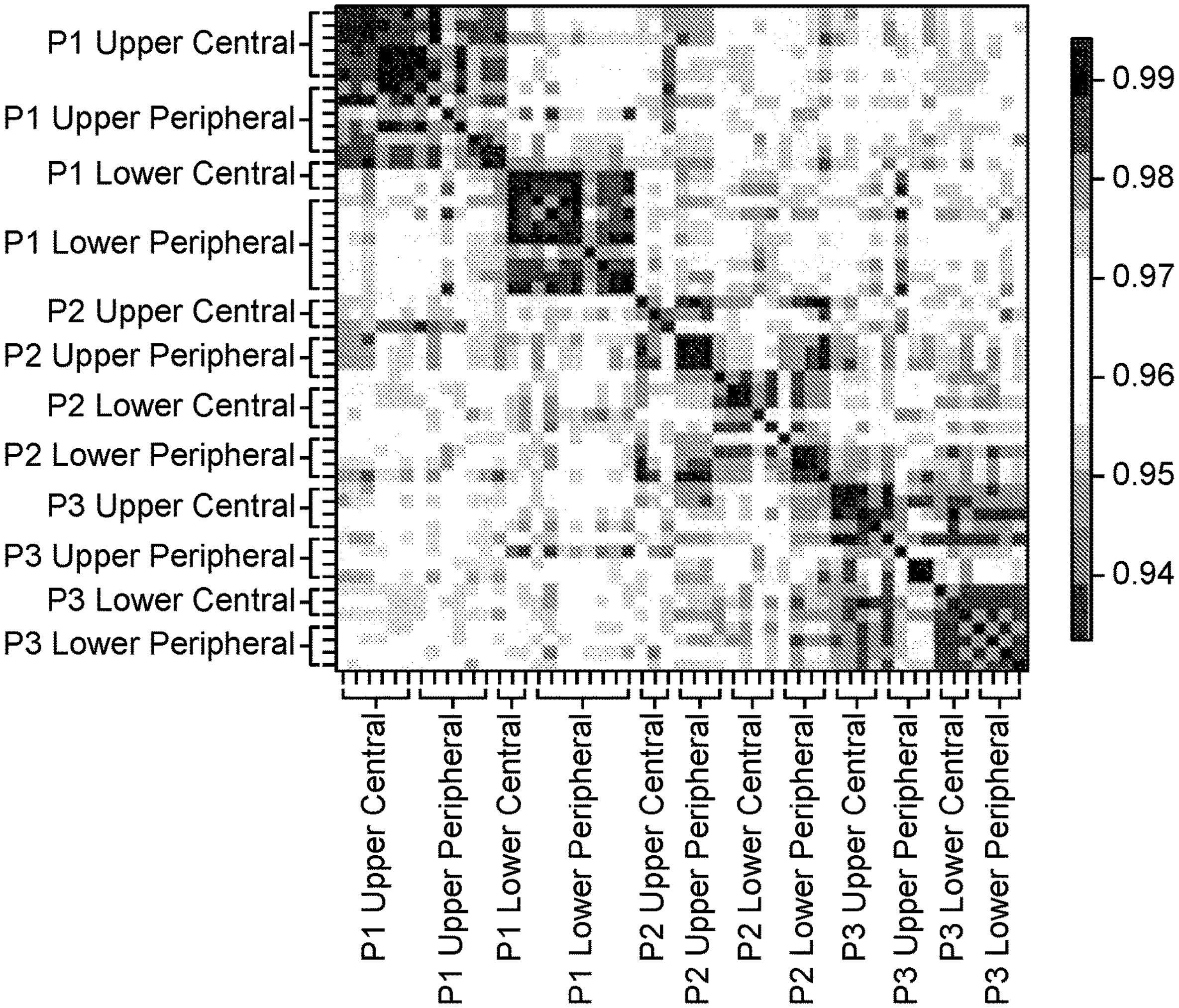
FIG. 1. Pairwise correlation on explant samples obtained from three patients diagnosed with IPF (Patients P1, P2, and P3). Locations (upper or lower, central or peripheral) are indicated for each sample. The top 200 differentially expressed genes separating IPF samples from normal lung samples were used to compute pairwise Pearson correlation coefficients and plotted as a heatmap with higher correlation represented in magenta color, and lower correlation represented in green color. Correlation between and with normal lung samples are in the 0.7 range (not shown).

"Interstitial lung disease" or "ILD" (also known as diffuse parenchymal lung disease (DPLD)) as used herein refers to a group of lung diseases affecting the interstitium (the tissue and space around the air sacs of the lungs). ILD can be classified according to a suspected or known cause, or can be idiopathic. For example, ILD can be classified as caused by inhaled substances (inorganic or organic), drug induced (e.g., antibiotics, chemotherapeutic drugs, antiarrhythmic agents, statins), associated with connective tissue disease (e.g., systemic sclerosis, polymyositis, dermatomyositis, systemic lupus erythematous, rheumatoid arthritis), associated with pulmonary infection (e.g., atypical pneumonia, *Pneumocystis* pneumonia (PCP), tuberculosis, *Chlamydia trachomatis*, Respiratory Syncytial Virus), associated with a malignancy (e.g., Lymphangitic carcinomatosis), or can be idiopathic (e.g., sarcoidosis, idiopathic pulmonary fibrosis, Hamman-Rich syndrome, antisynthetase syndrome).

"ILD Inflammation" as used herein refers to an analytical grouping of inflammatory ILD subtypes characterized by underlying inflammation. These subtypes can be used collectively as a comparator against IPF and/or any other non-inflammation lung disease subtype. "ILD inflammation" can include HP, NSIP, sarcoidosis, and/or organizing pneumonia.

"Idiopathic interstitial pneumonia" or "IIP" (also referred to as noninfectious pneumonia" refers to a class of ILDs which includes, for example, desquamative interstitial pneumonia, nonspecific interstitial pneumonia, lymphoid interstitial pneumonia, cryptogenic organizing pneumonia, and idiopathic pulmonary fibrosis.

"Idiopathic pulmonary fibrosis" or "IPF" as used herein refers to a chronic, progressive form of lung disease characterized by fibrosis of the supporting framework (interstitium) of the lungs. By definition, the term is used when the cause of the pulmonary fibrosis is unknown ("idiopathic"). Microscopically, lung tissue from patients having IPF shows a characteristic set of histologic/pathologic features known as usual interstitial pneumonia (UIP), which is a pathologic counterpart of IPF.

"Nonspecific interstitial pneumonia" or "NSIP" is a form of idiopathic interstitial pneumonia generally characterized by a cellular pattern defined by chronic inflammatory cells with collagen deposition that is consistent or patchy, and a fibrosing pattern defined by a diffuse patchy fibrosis. In contrast to UIP, there is no honeycomb appearance nor fibroblast foci that characterize usual interstitial pneumonia.

"Hypersensitivity pneumonitis" or "HP" refers to also called extrinsic allergic alveolitis, (EAA) refers to an inflammation of the alveoli within the lung caused by an exaggerated immune response and hypersensitivity to as a result of an inhaled antigen (e.g., organic dust).

"Pulmonary sarcoidosis" or "PS" refers to a syndrome involving abnormal collections of chronic inflammatory cells (granulomas) that can form as nodules. The inflammatory process for HP generally involves the alveoli, small bronchi, and small blood vessels. In acute and subacute cases of HP, physical examination usually reveals dry rales.

The term "microarray" refers to an ordered arrangement of hybridizable array elements, preferably polynucleotide probes, on a substrate.

The term "polynucleotide," when used in singular or plural, generally refers to any polyribonucleotide or polydeoxribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" can also include DNAs (e.g., cDNAs) and RNAs that contain one or more modified bases (e.g., to provide a detectable signal, such as a fluorophore). Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide (e.g., 100, 50, 20 or fewer nucleotides) including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The terms "gene product" or "expression product" are used herein interchangeably to refer to the RNA transcription products (RNA transcript) of a gene, including mRNA, and the polypeptide translation product of such RNA transcripts. A gene product can be, for example, a polynucleotide gene expression product (e.g., an unspliced RNA, an mRNA, a splice variant mRNA, a microRNA, a fragmented RNA, and the like) or a protein expression product (e.g., a mature polypeptide, a post-translationally modified polypeptide, a splice variant polypeptide, and the like). In some embodiments the gene expression product may be a sequence variant including mutations, fusions, loss of heterozygoxity (LOH), and/or biological pathway effects.

The term "normalized expression level" as applied to a gene expression product refers to a level of the gene product normalized relative to one or more reference (or control) gene expression products.

A "reference expression level" as applied to a gene expression product refers to an expression level for one or more reference (or control) gene expression products. A "reference normalized expression level" as applied to a gene expression product refers to a normalized expression level value for one or more reference (or control) gene expression products (i.e., a normalized reference expression level). In some embodiments, a reference expression level is an expression level for one or more gene product in normal sample, as described herein. In some embodiments, a reference expression level is determined experimentally. In some embodiments, a reference expression level is a historical expression level, e.g., a database value of a reference expression level in a normal sample, which sample indicates a single reference expression level, or a summary of a plurality of reference expression levels (such as, e.g., (i) an average of two or more, preferably three or more reference expression levels from replicate analysis of the reference expression level from a single sample; (ii) an average of two or more, preferably three or more reference expression levels from analysis of the reference expression level from a plurality of different samples (e.g., normal samples); (iii) and a combination of the above mentioned steps (i) and (ii) (i.e., average of reference expression levels analyzed from a plurality of samples, wherein at least one of the reference expression levels are analyzed in replicate). In some embodiments, the "reference expression level" is an expression level of sequence variants, for example, in a sample that has been definitively determined to be UIP or non-UIP by other means (i.e. confirmed pathological diagnosis).

A "reference expression level value" as applied to a gene expression product refers to an expression level value for one or more reference (or control) gene expression products. A "reference normalized expression level value" as applied to a gene expression product refers to a normalized expression level value for one or more reference (or control) gene expression products.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to re-anneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, (Wiley Interscience, 1995).

"Stringent conditions" or "high stringency conditions", as defined herein, typically: (1) employ low ionic strength solutions and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., Molecular Cloning: A Laboratory Manual (Cold Spring Harbor Press, 1989), and include the use of washing solution and hybridization conditions (e.g., temperature, ionic strength and % SDS) less stringent that those described above. An example of moderately stringent condition is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

"Sensitivity" as used herein refers to the proportion of true positives of the total number tested that actually have the target disorder (i.e., the proportion of patients with the target disorder who have a positive test result). "Specificity" as used herein refers to the proportion of true negatives of all the patients tested who actually do not have the target disorder (i.e., the proportion of patients without the target disorder who have a negative test result).

In the context of the present invention, reference to "at least one," "at least two," "at least five," etc. of the genes listed in any particular gene set means any one or any and all combinations of the genes listed.

The terms "splicing" and "RNA splicing" are used interchangeably and refer to RNA processing that removes introns and joins exons to produce mature mRNA with continuous coding sequence that moves into the cytoplasm of a eukaryotic cell.

The term "exon" refers to any segment of an interrupted gene that is represented in a mature RNA product (B. Lewin, Genes 7V(Cell Press, 1990)). In theory the term "intron" refers to any segment of DNA that is transcribed but removed from within the transcript by splicing together the exons on either side of it. Operationally, exon sequences occur in the mRNA sequence of a gene as defined by Ref. SEQ ID numbers. Operationally, intron sequences are the intervening sequences within the genomic DNA of a gene, bracketed by exon sequences and usually having GT and AG splice consensus sequences at their 5' and 3' boundaries.

A "computer-based system" refers to a system of hardware, software, and data storage medium used to analyze information. Hardware of a patient computer-based system can include a central processing unit (CPU), and hardware for data input, data output (e.g., display), and data storage. The data storage medium can include any manufacture comprising a recording of the present information as described above, or a memory access device that can access such a manufacture.

As used herein the term "module" refers to any assembly and/or set of operatively-coupled electrical components that can include, for example, a memory, a processor, electrical traces, optical connectors, software (executing in hardware), and/or the like. For example, a module executed in the processor can be any combination of hardware-based module (e.g., a field-programmable gate array (FPGA), an application specific integrated circuit (ASIC), a digital signal processor (DSP)) and/or software-based module (e.g., a module of computer code stored in memory and/or executed at the processor) capable of performing one or more specific functions associated with that module.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" or "computing means" references any hardware and/or software combination that will perform the functions required of it. For example, a suitable processor may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

A "test sample" is a sample of one or more cells, preferable a tissue sample (e.g., a lung tissue sample such as a transbronchial biopsy (TBB) sample) obtained from a subject. In some embodiments, a test sample is a biopsy sample obtained by any means known in the art. In particular embodiments, the test sample is a sample obtained by a video-assisted thoracoscopic surgery (VATS); a bronchoalveolar lavage (BAL); a transbronchial biopsy (TBB); or a cryo-transbronchial biopsy. In some embodiments the test sample is obtained from a patient suspected of having a lung disease, e.g., an ILD, based on clinical signs and symptoms with which the patient presents (e.g., shortness of breath (generally aggravated by exertion), dry cough), and, optionally the results of one or more of an imaging test (e.g., chest X-ray, computerized tomography (CT)), a pulmonary function test (e.g., spirometry, oximetry, exercise stress test), lung tissue analysis (e.g., histological and/or cytological analysis of samples obtained by bronchoscopy, bronchoalveolar lavage, surgical biopsy).

A "gene signature" is a gene expression pattern (i.e., expression level of one or more gene, or fragments thereof), which is indicative of some characteristic or phenotype. In some embodiments, gene signature refers to the expression (and/or lack of expression) of a gene, a plurality of genes, a fragment of a gene or a plurality fragments of one or more genes, which expression and/or lack of expression is indicative of UIP, Non-UIP, smoker-status, or Non-smoker-status.

As used herein, "is a smoker" is meant to refer to a subject who currently smokes cigarettes or a person who has smoked cigarettes in the past or a person who has the gene signature of a person who currently smokes cigarettes or has smoked cigarettes in the past.

As used herein, "variant", when used to describe a feature used during training of a classifier of the present invention, refers to an alternative splice variant.

As used herein, "mutation", when used to describe a feature used during training of a classifier of the present invention, refers to a sequence deviation from a known normal reference sequence. In some embodiments, the deviation is a deviation from an accepted native gene sequence according to a publically accessible database such as the UniGene database (Pontius J U, Wagner L, Schuler G D. UniGene: a unified view of the transcriptome. In: The NCBI Handbook. Bethesda (MD): National Center for Biotechnology Information; 2003, incorporated herein), RefSeq (The NCBI handbook [Internet]. Bethesda (MD): National Library of Medicine (US), National Center for Biotechnology Information; 2002 October. Chapter 18, The Reference Sequence (RefSeq) Project, available at the world wide web address: ncbi.nlm.nih.gov/refseq/), Ensembl (EMBL, available at the world wide web address: ensembl.org/index.html), and the like. In some embodiments, the mutation includes an addition, deletion, or substitution of a sequence residue present in the reference sequence.

Abbreviations include: HRCT, high-resolution computed tomography; VATS, video-assisted thorascopic surgery; SLB, surgical lung biopsy; TBB, transbronchial biopsy; RB, respiratory bronchiolitis; OP, organizing pneumonia, DAD, diffuse alveolar damage, CIF/NOC, chronic interstitial fibrosis not otherwise classified; MDT, multidisciplinary team; CV, cross-validation; LOPO, leave-one-patient-out; ROC, receiver operator characteristic; AUC, area under the curve; RNASeq, RNA sequencing by next-generation sequencing technology; NGS, next-generation sequencing technology; H&E, hematoxylin and eosin; FDR, false discovery rate; IRB, Institutional Review Board; ATS, American Thoracic Society; COPD, chronic obstructive pulmonary disease; KEGG, Kyoto Encyclopedia of Genes and Genomes; CI, confidence interval Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. As used herein, "about" means plus or minus 10% of the indicated value.

DETAILED DESCRIPTION OF THE INVENTION

Disclosed herein are methods of and/or systems for using a molecular signature to differentiate UIP from other ILD subtypes. The accurate diagnosis of UIP from samples where expert pathology is not available stands to benefit ILD patients by accelerating diagnosis, thus facilitating treatment decisions and reducing surgical risk to patients and costs to the healthcare system.

Also disclosed herein are methods of and/or systems for using the smoker or non-smoker status of a subject to improve differentiation of UIP from other ILD subtypes using a molecular signature.

Thus, the methods and/or systems disclosed herein provide classifiers which can differentiate UIP from non-UIP patterns based on high-dimensional transcriptional data without prior knowledge of clinical or demographic information.

In some embodiments, the present invention provides methods for differentiating UIP from non-UIP using a classifier that comprises or consists of one or more sequences or fragments thereof presented in any of Tables 5, 7, 8, 9, 10, 11, or 12 or at least one sequence or fragment thereof from each of Tables 5, 7, 8, 9, 10, 11 and 12. In some embodiments, the present invention provides such methods that use a classifier comprising or consisting of at least 1, 2, 3, 4, 5, 6, 7, 8, 9, 10 or more of the sequences provided in any one or more or all of Tables 5, 7, 8, 9, 10, 11 and 12. For example, in some embodiments, the present invention provides such methods that use classifiers comprising or consisting of at least 11, 12, 13, 14, 15, 20, 30, 50, 100, 150, 200, 250, 300, or more sequences provided in any one or more or all of Tables 5, 7, 8, 9, 10, 11 and 12, including all integers (e.g., 16, 17, 18, 19, 21, 22, 23, 24, 25 sequences, etc.) and ranges (e.g., from about 1-10 sequences from any one or more or all of Tables 5, 7, 8, 9, 10, 11, and 12, from about 10-15 sequences, 10-20 sequences, 5-30 sequences, 5-50 sequences, 10-100 sequences, 50-200 sequences, etc.) between.

In some particular embodiments, the present invention provides methods and/or systems for differentiating UIP from non-UIP using a classifier that comprises or consists of one or more of the following sequences or fragments thereof: 1) HLA-F (SEQ ID NO.:1), 2) CDKL2 (SEQ ID NO.:2), 3) GPR98 (SEQ ID NO.:3) 4) PRKCQ (SEQ ID NO.:4) 5) HLA-G (SEQ ID NO.:5), 6) PFKFB3 (SEQ ID NO.:6), 7) CEACAM1 (SEQ ID NO.:7), 8) RABGAP1L (SEQ ID NO.:8), 9) CD274 (SEQ ID NO.:9), 10) PRUNE2 (SEQ ID NO.:10), 11) ARAP2 (SEQ ID NO.:11), 12) DZIP1 (SEQ ID NO.:12), 13) MXRA7 (SEQ ID NO.:13), 14) PTCHD4 (SEQ ID NO.:14), 15) PDLIM3 (SEQ ID NO.:15), 16) CNN1 (SEQ ID NO.:16), 17) NIPSNAP3B (SEQ ID NO.:17), 18) PAQR7 (SEQ ID NO.:18), 19) ACTG2 (SEQ ID NO.:19), 20) NA (SEQ ID NO.:20), 21) TIMP2 (SEQ ID NO.:21), and 22) DES (SEQ ID NO.:22). In particular aspects, the classifier may contain 1, 2, 3, 4, 5, 6, 7, 8, or more additional genes. In other aspects, the classifier may omit 1, 2, 3, 4, 5, 6, 7, 8, or more, of these genes, while optionally including other genes.

In some embodiments, the present invention provides a method and/or system for differentiating UIP from non-UIP using a classifier that comprises or consists of 2; 3; 4; 5; 6; 7; 8; 9; 10; 11; 12; 13; 14; 15; 16; 17; 18; 19; 20; or 21 of the following sequences: 1) HLA-F (SEQ ID NO.:1), 2) CDKL2 (SEQ ID NO.:2), 3) GPR98 (SEQ ID NO.:3), 4) PRKCQ (SEQ ID NO.:4), 5) HLA-G (SEQ ID NO.:5), 6) PFKFB3 (SEQ ID NO.:6), 7) CEACAM1 (SEQ ID NO.:7), 8) RABGAP1L (SEQ ID NO.:8), 9) CD274 (SEQ ID NO.:9), 10) PRUNE2 (SEQ ID NO.:10), 11) ARAP2 (SEQ ID NO.:11), 12) DZIP1 (SEQ ID NO.:12), 13) MXRA7 (SEQ ID NO.:13), 14) PTCHD4 (SEQ ID NO.:14), 15) PDLIM3 (SEQ ID NO.:15), 16) CNN1 (SEQ ID NO.:16), 17) NIPSNAP3B (SEQ ID NO.:17), 18) PAQR7 (SEQ ID NO.:18), 19) ACTG2 (SEQ ID NO.:19), 20) NA (SEQ ID NO.:20), 21) TIMP2 (SEQ ID NO.:21), and 22) DES (SEQ ID NO.:22) in any combination. In particular aspects, such a classifier contains 1, 2, 3, 4, 5, 6, 7, 8, or more additional genes. In other aspects, the classifier may omit 1, 2, 3, 4, 5, 6, 7, 8, or more, of these genes, while optionally including other genes.

In some embodiments, the present invention provides a method and/or system for differentiating UIP from non-UIP using a classifier that comprises or consists of all of the following sequences: 1) HLA-F (SEQ ID NO.:1), 2) CDKL2 (SEQ ID NO.:2), 3) GPR98 (SEQ ID NO.:3), 4) PRKCQ (SEQ ID NO.:4), 5) HLA-G (SEQ ID NO.:5), 6) PFKFB3 (SEQ ID NO.:6), 7) CEACAM1 (SEQ ID NO.:7), 8) RABGAP1L (SEQ ID NO.:8), 9) CD274 (SEQ ID NO.:9), 10) PRUNE2 (SEQ ID NO.:10), 11) ARAP2 (SEQ ID NO.:11), 12) DZIP1 (SEQ ID NO.:12), 13) MXRA7 (SEQ ID NO.:13), 14) PTCHD4 (SEQ ID NO.:14), 15) PDLIM3 (SEQ ID NO.:15), 16) CNN1 (SEQ ID NO.:16), 17) NIPSNAP3B (SEQ ID NO.:17), 18) PAQR7 (SEQ ID NO.:18), 19) ACTG2 (SEQ ID NO.:19), 20) NA (SEQ ID NO.:20), 21) TIMP2 (SEQ ID NO.:21), and 22) DES (SEQ ID NO.:22). In particular aspects, the classifier contains 1, 2, 3, 4, 5, 6, 7, 8, or more additional genes.

In some particular embodiments, the present invention provides methods and/or systems for differentiating UIP from non-UIP using a classifier that comprises or consists of one or more of the following sequences or fragments thereof: 1) HLA-F (SEQ ID NO.:1), 2) HMCN2, 3) ADAMTSL1, 4) CD79B, 5) KEL, 6) KLHL14, 7) MPP2, 8) NMNAT2, 9) PLXDC1, 10) CAPN9, 11) TALDO1, 12) PLK4, 13) IGHV3-72, 14) IGKV1-9, and 15) CNTN4. In particular aspects, the classifier may contain 1, 2, 3, 4, 5, 6, 7, 8, or more additional genes. In other aspects, the classifier may omit 1, 2, 3, 4, 5, 6, 7, 8, or more, of these genes, while optionally including other genes.

In some embodiments, the present invention provides a method and/or system for differentiating UIP from non-UIP using a classifier that comprises or consists of 2; 3; 4; 5; 6; 7; 8; 9; 10; 11; 12; 13; or 14 of the following sequences: 1) HLA-F (SEQ ID NO.:1), 2) HMCN2, 3) ADAMTSL1, 4) CD79B, 5) KEL, 6) KLHL14, 7) MPP2, 8) NMNAT2, 9) PLXDC1, 10) CAPN9, 11) TALDO1, 12) PLK4, 13) IGHV3-72, 14) IGKV1-9, and 15) CNTN4. In particular aspects, the classifier may contain 1, 2, 3, 4, 5, 6, 7, 8, or more additional genes. In other aspects, the classifier may omit 1, 2, 3, 4, 5, 6, 7, 8, or more, of these genes, while optionally including other genes.

In some embodiments, the present invention provides a method and/or system for differentiating UIP from non-UIP using a classifier that comprises or consists of the following sequences: 1) HLA-F (SEQ ID NO.:1), 2) HMCN2, 3) ADAMTSL1, 4) CD79B, 5) KEL, 6) KLHL14, 7) MPP2, 8) NMNAT2, 9) PLXDC1, 10) CAPN9, 11) TALDO1, 12) PLK4, 13) IGHV3-72, 14) IGKV1-9, and 15) CNTN4. In particular aspects, the classifier may contain 1, 2, 3, 4, 5, 6, 7, 8, or more additional genes. In other aspects, the classifier may omit 1, 2, 3, 4, 5, 6, 7, 8, or more, of these genes, while optionally including other genes.

In some particular embodiments, the present invention provides methods and/or systems for differentiating UIP from non-UIP using a classifier that comprises or consists of HLA-F (SEQ ID NO.:1) or fragments thereof. In one such embodiment, the method uses a classifier comprising 1) HLA-F (SEQ ID NO.:1) and at least one of 2) CDKL2 (SEQ ID NO.:2), 3) GPR98 (SEQ ID NO.:3), 4) PRKCQ (SEQ ID NO.:4), 5) HLA-G (SEQ ID NO.:5), 6) PFKFB3 (SEQ ID NO.:6), 7) CEACAM1 (SEQ ID NO.:7), 8) RABGAP1L (SEQ ID NO.:8), 9) CD274 (SEQ ID NO.:9), 10) PRUNE2 (SEQ ID NO.:10), 11) ARAP2 (SEQ ID NO.:11), 12) DZIP1 (SEQ ID NO.:12), 13) MXRA7 (SEQ ID NO.:13), 14) PTCHD4 (SEQ ID NO.:14), 15) PDLIM3 (SEQ ID NO.:15), 16) CNN1 (SEQ ID NO.:16), 17) NIPSNAP3B (SEQ ID NO.:17), 18) PAQR7 (SEQ ID NO.:18), 19) ACTG2 (SEQ ID NO.:19), 20) NA (SEQ ID NO.:20), 21) TIMP2 (SEQ ID NO.:21), and 22) DES (SEQ ID NO.:22). In particular aspects, the classifier contains 1, 2, 3, 4, 5, 6, 7, 8, or more additional genes.

In some particular embodiments, the present invention provides methods and/or systems for differentiating UIP from non-UIP using a classifier that comprises or consists of HMCN2 or fragments thereof. In one such embodiment, the method uses a classifier comprising HMCN2 and at least one of 1) HLA-F (SEQ ID NO.:1) 2) CDKL2 (SEQ ID NO.:2), 3) GPR98 (SEQ ID NO.:3), 4) PRKCQ (SEQ ID NO.:4), 5) HLA-G (SEQ ID NO.:5), 6) PFKFB3 (SEQ ID NO.:6), 7) CEACAM1 (SEQ ID NO.:7), 8) RABGAP1L (SEQ ID NO.:8), 9) CD274 (SEQ ID NO.:9), 10) PRUNE2 (SEQ ID NO.:10), 11) ARAP2 (SEQ ID NO.:11), 12) DZIP1 (SEQ ID NO.:12), 13) MXRA7 (SEQ ID NO.:13), 14) PTCHD4 (SEQ ID NO.:14), 15) PDLIM3 (SEQ ID NO.:15), 16) CNN1 (SEQ ID NO.:16), 17) NIPSNAP3B (SEQ ID NO.:17), 18) PAQR7 (SEQ ID NO.:18), 19) ACTG2 (SEQ ID NO.:19), 20) NA (SEQ ID NO.:20), 21) TIMP2 (SEQ ID NO.:21), and 22) DES (SEQ ID NO.:22). In particular aspects, the classifier contains 1, 2, 3, 4, 5, 6, 7, 8, or more additional genes.

In some particular embodiments, the present invention provides methods and/or systems for differentiating UIP from non-UIP using a classifier that comprises or consists of ADAMTSL1 or fragments thereof. In one such embodiment, the method uses a classifier comprising ADAMTSL1 and at least one of 1) HLA-F (SEQ ID NO.:1) 2) CDKL2 (SEQ ID NO.:2), 3) GPR98 (SEQ ID NO.:3), 4) PRKCQ (SEQ ID NO.:4), 5) HLA-G (SEQ ID NO.:5), 6) PFKFB3 (SEQ ID NO.:6), 7) CEACAM1 (SEQ ID NO.:7), 8) RABGAP1L (SEQ ID NO.:8), 9) CD274 (SEQ ID NO.:9), 10) PRUNE2 (SEQ ID NO.:10), 11) ARAP2 (SEQ ID NO.:11), 12) DZIP1 (SEQ ID NO.:12), 13) MXRA7 (SEQ ID NO.:13), 14) PTCHD4 (SEQ ID NO.:14), 15) PDLIM3 (SEQ ID NO.:15), 16) CNN1 (SEQ ID NO.:16), 17) NIPSNAP3B (SEQ ID NO.:17), 18) PAQR7 (SEQ ID NO.:18), 19) ACTG2 (SEQ ID NO.:19), 20) NA (SEQ ID NO.:20), 21) TIMP2 (SEQ ID NO.:21), and 22) DES (SEQ ID NO.:22). In particular aspects, the classifier contains 1, 2, 3, 4, 5, 6, 7, 8, or more additional genes.

In some particular embodiments, the present invention provides methods and/or systems for differentiating UIP from non-UIP using a classifier that comprises or consists of CD79B or fragments thereof. In one such embodiment, the method uses a classifier comprising CD79B and at least one of 1) HLA-F (SEQ ID NO.:1) 2) CDKL2 (SEQ ID NO.:2), 3) GPR98 (SEQ ID NO.:3), 4) PRKCQ (SEQ ID NO.:4), 5) HLA-G (SEQ ID NO.:5), 6) PFKFB3 (SEQ ID NO.:6), 7) CEACAM1 (SEQ ID NO.:7), 8) RABGAP1L (SEQ ID NO.:8), 9) CD274 (SEQ ID NO.:9), 10) PRUNE2 (SEQ ID NO.:10), 11) ARAP2 (SEQ ID NO.:11), 12) DZIP1 (SEQ ID NO.:12), 13) MXRA7 (SEQ ID NO.:13), 14) PTCHD4 (SEQ ID NO.:14), 15) PDLIM3 (SEQ ID NO.:15), 16) CNN1 (SEQ ID NO.:16), 17) NIPSNAP3B (SEQ ID NO.:17), 18) PAQR7 (SEQ ID NO.:18), 19) ACTG2 (SEQ ID NO.:19), 20) NA (SEQ ID NO.:20), 21) TIMP2 (SEQ ID NO.:21), and 22) DES (SEQ ID NO.:22). In particular aspects, the classifier contains 1, 2, 3, 4, 5, 6, 7, 8, or more additional genes.

In some particular embodiments, the present invention provides methods and/or systems for differentiating UIP from non-UIP using a classifier that comprises or consists of KEL or fragments thereof. In one such embodiment, the method uses a classifier comprising KEL and at least one of 1) HLA-F (SEQ ID NO.:1) 2) CDKL2 (SEQ ID NO.:2), 3) GPR98 (SEQ ID NO.:3), 4) PRKCQ (SEQ ID NO.:4), 5) HLA-G (SEQ ID NO.:5), 6) PFKFB3 (SEQ ID NO.:6), 7) CEACAM1 (SEQ ID NO.:7), 8) RABGAP1L (SEQ ID NO.:8), 9) CD274 (SEQ ID NO.:9), 10) PRUNE2 (SEQ ID NO.:10), 11) ARAP2 (SEQ ID NO.:11), 12) DZIP1 (SEQ ID NO.:12), 13) MXRA7 (SEQ ID NO.:13), 14) PTCHD4 (SEQ ID NO.:14), 15) PDLIM3 (SEQ ID NO.:15), 16) CNN1 (SEQ ID NO.:16), 17) NIPSNAP3B (SEQ ID NO.:17), 18) PAQR7 (SEQ ID NO.:18), 19) ACTG2 (SEQ ID NO.:19), 20) NA (SEQ ID NO.:20), 21) TIMP2 (SEQ ID NO.:21), and 22) DES (SEQ ID NO.:22). In particular aspects, the classifier contains 1, 2, 3, 4, 5, 6, 7, 8, or more additional genes.

In some particular embodiments, the present invention provides methods and/or systems for differentiating UIP from non-UIP using a classifier that comprises or consists of KLHL14 or fragments thereof. In one such embodiment, the method uses a classifier comprising KLHL14 and at least one of 1) HLA-F (SEQ ID NO.:1) 2) CDKL2 (SEQ ID NO.:2), 3) GPR98 (SEQ ID NO.:3), 4) PRKCQ (SEQ ID NO.:4), 5) HLA-G (SEQ ID NO.:5), 6) PFKFB3 (SEQ ID NO.:6), 7) CEACAM1 (SEQ ID NO.:7), 8) RABGAP1L (SEQ ID NO.:8), 9) CD274 (SEQ ID NO.:9), 10) PRUNE2 (SEQ ID NO.:10), 11) ARAP2 (SEQ ID NO.:11), 12) DZIP1 (SEQ ID NO.:12), 13) MXRA7 (SEQ ID NO.:13), 14) PTCHD4 (SEQ ID NO.:14), 15) PDLIM3 (SEQ ID NO.:15), 16) CNN1 (SEQ ID NO.:16), 17) NIPSNAP3B (SEQ ID NO.:17), 18) PAQR7 (SEQ ID NO.:18), 19) ACTG2 (SEQ ID NO.:19), 20) NA (SEQ ID NO.:20), 21) TIMP2 (SEQ ID NO.:21), and 22) DES (SEQ ID NO.:22). In particular aspects, the classifier contains 1, 2, 3, 4, 5, 6, 7, 8, or more additional genes.

In some particular embodiments, the present invention provides methods and/or systems for differentiating UIP from non-UIP using a classifier that comprises or consists of MPP2 or fragments thereof. In one such embodiment, the method uses a classifier comprising MPP2 and at least one of 1) HLA-F (SEQ ID NO.:1) 2) CDKL2 (SEQ ID NO.:2), 3) GPR98 (SEQ ID NO.:3), 4) PRKCQ (SEQ ID NO.:4), 5) HLA-G (SEQ ID NO.:5), 6) PFKFB3 (SEQ ID NO.:6), 7) CEACAM1 (SEQ ID NO.:7), 8) RABGAP1L (SEQ ID NO.:8), 9) CD274 (SEQ ID NO.:9), 10) PRUNE2 (SEQ ID NO.:10), 11) ARAP2 (SEQ ID NO.:11), 12) DZIP1 (SEQ ID NO.:12), 13) MXRA7 (SEQ ID NO.:13), 14) PTCHD4 (SEQ ID NO.:14), 15) PDLIM3 (SEQ ID NO.:15), 16) CNN1 (SEQ ID NO.:16), 17) NIPSNAP3B (SEQ ID NO.:17), 18) PAQR7 (SEQ ID NO.:18), 19) ACTG2 (SEQ ID NO.:19), 20) NA (SEQ ID NO.:20), 21) TIMP2 (SEQ ID NO.:21), and 22) DES (SEQ ID NO.:22). In particular aspects, the classifier contains 1, 2, 3, 4, 5, 6, 7, 8, or more additional genes.

In some particular embodiments, the present invention provides methods and/or systems for differentiating UIP from non-UIP using a classifier that comprises or consists of NMNAT2 or fragments thereof. In one such embodiment, the method uses a classifier comprising NMNAT2 and at least one of 1) HLA-F (SEQ ID NO.:1) 2) CDKL2 (SEQ ID NO.:2), 3) GPR98 (SEQ ID NO.:3), 4) PRKCQ (SEQ ID NO.:4), 5) HLA-G (SEQ ID NO.:5), 6) PFKFB3 (SEQ ID NO.:6), 7) CEACAM1 (SEQ ID NO.:7), 8) RABGAP1L (SEQ ID NO.:8), 9) CD274 (SEQ ID NO.:9), 10) PRUNE2 (SEQ ID NO.:10), 11) ARAP2 (SEQ ID NO.:11), 12) DZIP1 (SEQ ID NO.:12), 13) MXRA7 (SEQ ID NO.:13), 14) PTCHD4 (SEQ ID NO.:14), 15) PDLIM3 (SEQ ID NO.:15), 16) CNN1 (SEQ ID NO.:16), 17) NIPSNAP3B (SEQ ID NO.:17), 18) PAQR7 (SEQ ID NO.:18), 19) ACTG2 (SEQ ID NO.:19), 20) NA (SEQ ID NO.:20), 21) TIMP2 (SEQ ID NO.:21), and 22) DES (SEQ ID NO.:22). In particular aspects, the classifier contains 1, 2, 3, 4, 5, 6, 7, 8, or more additional genes.

In some particular embodiments, the present invention provides methods and/or systems for differentiating UIP from non-UIP using a classifier that comprises or consists of PLXDC1 or fragments thereof. In one such embodiment, the method uses a classifier comprising PLXDC1 and at least one of 1) HLA-F (SEQ ID NO.:1) 2) CDKL2 (SEQ ID NO.:2), 3) GPR98 (SEQ ID NO.:3), 4) PRKCQ (SEQ ID NO.:4), 5) HLA-G (SEQ ID NO.:5), 6) PFKFB3 (SEQ ID NO.:6), 7) CEACAM1 (SEQ ID NO.:7), 8) RABGAP1L (SEQ ID NO.:8), 9) CD274 (SEQ ID NO.:9), 10) PRUNE2 (SEQ ID NO.:10), 11) ARAP2 (SEQ ID NO.:11), 12) DZIP1 (SEQ ID NO.:12), 13) MXRA7 (SEQ ID NO.:13), 14) PTCHD4 (SEQ ID NO.:14), 15) PDLIM3 (SEQ ID NO.:15), 16) CNN1 (SEQ ID NO.:16), 17) NIPSNAP3B (SEQ ID NO.:17), 18) PAQR7 (SEQ ID NO.:18), 19) ACTG2 (SEQ ID NO.:19), 20) NA (SEQ ID NO.:20) 21) TIMP2 (SEQ ID NO.:21), and 22) DES (SEQ ID NO.:22). In particular aspects, the classifier contains 1, 2, 3, 4, 5, 6, 7, 8, or more additional genes.

In some particular embodiments, the present invention provides methods and/or systems for differentiating UIP from non-UIP using a classifier that comprises or consists of CAPN9 or fragments thereof. In one such embodiment, the method uses a classifier comprising CAPN9 and at least one of 1) HLA-F (SEQ ID NO.:1) 2) CDKL2 (SEQ ID NO.:2), 3) GPR98 (SEQ ID NO.:3), 4) PRKCQ (SEQ ID NO.:4), 5) HLA-G (SEQ ID NO.:5), 6) PFKFB3 (SEQ ID NO.:6), 7) CEACAM1 (SEQ ID NO.:7), 8) RABGAP1L (SEQ ID NO.:8), 9) CD274 (SEQ ID NO.:9), 10) PRUNE2 (SEQ ID NO.:10), 11) ARAP2 (SEQ ID NO.:11), 12) DZIP1 (SEQ ID NO.:12), 13) MXRA7 (SEQ ID NO.:13), 14) PTCHD4 (SEQ ID NO.:14), 15) PDLIM3 (SEQ ID NO.:15), 16) CNN1 (SEQ ID NO.:16), 17) NIPSNAP3B (SEQ ID NO.: 17), 18) PAQR7 (SEQ ID NO.:18), 19) ACTG2 (SEQ ID NO.:19), 20) NA (SEQ ID NO.:20), 21) TIMP2 (SEQ ID NO.:21), and 22) DES (SEQ ID NO.:22). In particular aspects, the classifier contains 1, 2, 3, 4, 5, 6, 7, 8, or more additional genes.

In some particular embodiments, the present invention provides methods and/or systems for differentiating UIP from non-UIP using a classifier that comprises or consists of TALDO1 or fragments thereof. In one such embodiment, the method uses a classifier comprising TALDO1 and at least one of 1) HLA-F (SEQ ID NO.:1) 2) CDKL2 (SEQ ID NO.:2), 3) GPR98 (SEQ ID NO.:3), 4) PRKCQ (SEQ ID NO.:4), 5) HLA-G (SEQ ID NO.:5), 6) PFKFB3 (SEQ ID NO.:6), 7) CEACAM1 (SEQ ID NO.:7), 8) RABGAP1L (SEQ ID NO.:8), 9) CD274 (SEQ ID NO.:9), 10) PRUNE2 (SEQ ID NO.:10), 11) ARAP2 (SEQ ID NO.:11), 12) DZIP1 (SEQ ID NO.:12), 13) MXRA7 (SEQ ID NO.:13), 14) PTCHD4 (SEQ ID NO.:14), 15) PDLIM3 (SEQ ID NO.:15), 16) CNN1 (SEQ ID NO.:16), 17) NIPSNAP3B (SEQ ID NO.:17), 18) PAQR7 (SEQ ID NO.:18), 19) ACTG2 (SEQ ID NO.:19), 20) NA (SEQ ID NO.:20), 21) TIMP2 (SEQ ID NO.:21), and 22) DES (SEQ ID NO.:22). In particular aspects, the classifier contains 1, 2, 3, 4, 5, 6, 7, 8, or more additional genes.

In some particular embodiments, the present invention provides methods and/or systems for differentiating UIP from non-UIP using a classifier that comprises or consists of PLK4 or fragments thereof. In one such embodiment, the method uses a classifier comprising PLK4 and at least one of 1) HLA-F (SEQ ID NO.:1) 2) CDKL2 (SEQ ID NO.:2), 3) GPR98 (SEQ ID NO.:3), 4) PRKCQ (SEQ ID NO.:4), 5) HLA-G (SEQ ID NO.:5), 6) PFKFB3 (SEQ ID NO.:6), 7) CEACAM1 (SEQ ID NO.:7), 8) RABGAP1L (SEQ ID NO.:8), 9) CD274 (SEQ ID NO.:9), 10) PRUNE2 (SEQ ID NO.:10), 11) ARAP2 (SEQ ID NO.:11), 12) DZIP1 (SEQ ID NO.:12), 13) MXRA7 (SEQ ID NO.:13), 14) PTCHD4 (SEQ ID NO.:14), 15) PDLIM3 (SEQ ID NO.:15), 16) CNN1 (SEQ ID NO.:16), 17) NIPSNAP3B (SEQ ID NO.: 17), 18) PAQR7 (SEQ ID NO.:18), 19) ACTG2 (SEQ ID NO.:19), 20) NA (SEQ ID NO.:20), 21) TIMP2 (SEQ ID NO.:21), and 22) DES (SEQ ID NO.:22). In particular aspects, the classifier contains 1, 2, 3, 4, 5, 6, 7, 8, or more additional genes.

In some particular embodiments, the present invention provides methods and/or systems for differentiating UIP from non-UIP using a classifier that comprises or consists of IGHV3-72 or fragments thereof. In one such embodiment, the method uses a classifier comprising IGHV3-72 and at least one of 1) HLA-F (SEQ ID NO.:1) 2) CDKL2 (SEQ ID NO.:2), 3) GPR98 (SEQ ID NO.:3), 4) PRKCQ (SEQ ID NO.:4), 5) HLA-G (SEQ ID NO.:5), 6) PFKFB3 (SEQ ID NO.:6), 7) CEACAM1 (SEQ ID NO.:7), 8) RABGAP1L (SEQ ID NO.:8), 9) CD274 (SEQ ID NO.:9), 10) PRUNE2 (SEQ ID NO.:10), 11) ARAP2 (SEQ ID NO.:11), 12) DZIP1 (SEQ ID NO.:12), 13) MXRA7 (SEQ ID NO.:13), 14) PTCHD4 (SEQ ID NO.:14), 15) PDLIM3 (SEQ ID NO.:15), 16) CNN1 (SEQ ID NO.:16), 17) NIPSNAP3B (SEQ ID NO.:17), 18) PAQR7 (SEQ ID NO.:18), 19) ACTG2 (SEQ ID NO.:19), 20) NA (SEQ ID NO.:20), 21) TIMP2 (SEQ ID NO.:21), and 22) DES (SEQ ID NO.:22). In particular aspects, the classifier contains 1, 2, 3, 4, 5, 6, 7, 8, or more additional genes.

In some particular embodiments, the present invention provides methods and/or systems for differentiating UIP from non-UIP using a classifier that comprises or consists of IGKV1-9 or fragments thereof. In one such embodiment, the method uses a classifier comprising IGKV1-9 and at least one of 1) HLA-F (SEQ ID NO.:1) 2) CDKL2 (SEQ ID NO.:2), 3) GPR98 (SEQ ID NO.:3), 4) PRKCQ (SEQ ID NO.:4), 5) HLA-G (SEQ ID NO.:5), 6) PFKFB3 (SEQ ID NO.:6), 7) CEACAM1 (SEQ ID NO.:7), 8) RABGAP1L (SEQ ID NO.:8), 9) CD274 (SEQ ID NO.:9), 10) PRUNE2 (SEQ ID NO.:10), 11) ARAP2 (SEQ ID NO.:11), 12) DZIP1 (SEQ ID NO.:12), 13) MXRA7 (SEQ ID NO.:13), 14) PTCHD4 (SEQ ID NO.:14), 15) PDLIM3 (SEQ ID NO.:15), 16) CNN1 (SEQ ID NO.:16), 17) NIPSNAP3B (SEQ ID NO.:17), 18) PAQR7 (SEQ ID NO.:18), 19) ACTG2 (SEQ ID NO.:19), 20) NA (SEQ ID NO.:20), 21) TIMP2 (SEQ ID NO.:21), and 22) DES (SEQ ID NO.:22). In particular aspects, the classifier contains 1, 2, 3, 4, 5, 6, 7, 8, or more additional genes.

In some particular embodiments, the present invention provides methods and/or systems for differentiating UIP from non-UIP using a classifier that comprises or consists of CNTN4 or fragments thereof. In one such embodiment, the method uses a classifier comprising CNTN4 and at least one of 1) HLA-F (SEQ ID NO.:1) 2) CDKL2 (SEQ ID NO.:2), 3) GPR98 (SEQ ID NO.:3), 4) PRKCQ (SEQ ID NO.:4), 5) HLA-G (SEQ ID NO.:5), 6) PFKFB3 (SEQ ID NO.:6), 7) CEACAM1 (SEQ ID NO.:7), 8) RABGAP1L (SEQ ID NO.:8), 9) CD274 (SEQ ID NO.:9), 10) PRUNE2 (SEQ ID NO.:10), 11) ARAP2 (SEQ ID NO.:11), 12) DZIP1 (SEQ ID NO.:12), 13) MXRA7 (SEQ ID NO.:13), 14) PTCHD4 (SEQ ID NO.:14), 15) PDLIM3 (SEQ ID NO.:15), 16) CNN1 (SEQ ID NO.:16), 17) NIPSNAP3B (SEQ ID NO.: 17), 18) PAQR7 (SEQ ID NO.:18), 19) ACTG2 (SEQ ID NO.:19), 20) NA (SEQ ID NO.:20), 21) TIMP2 (SEQ ID NO.:21), and 22) DES (SEQ ID NO.:22). In particular aspects, the classifier contains 1, 2, 3, 4, 5, 6, 7, 8, or more additional genes.

In some embodiments, the present invention provides a method and/or system for differentiating UIP from non-UIP using a classifier that comprises or consists of 2; 3; 4; 5; 6; 7; 8; 9; 10; 11; 12; 13; 14; 15, 16, 17, 18, 19, 20, 21, 22, 23, 24, 25, 26, 27, 28, 29, 30, 31, 32, 33, 34, or 35 of the following sequences: 1) HLA-F (SEQ ID NO.:1), 2) CDKL2

(SEQ ID NO.:2), 3) GPR98 (SEQ ID NO.:3), 4) PRKCQ (SEQ ID NO.:4), 5) HLA-G (SEQ ID NO.:5), 6) PFKFB3 (SEQ ID NO.:6), 7) CEACAM1 (SEQ ID NO.:7), 8) RABGAP1L (SEQ ID NO.:8), 9) CD274 (SEQ ID NO.:9), 10) PRUNE2 (SEQ ID NO.:10), 11) ARAP2 (SEQ ID NO.:11), 12) DZIP1 (SEQ ID NO.:12), 13) MXRA7 (SEQ ID NO.:13), 14) PTCHD4 (SEQ ID NO.:14), 15) PDLIM3 (SEQ ID NO.:15), 16) CNN1 (SEQ ID NO.:16), 17) NIPSNAP3B (SEQ ID NO.:17), 18) PAQR7 (SEQ ID NO.:18), 19) ACTG2 (SEQ ID NO.:19), 20) NA (SEQ ID NO.:20), 21) TIMP2 (SEQ ID NO.:21), 22) DES (SEQ ID NO.:22), 23) HMCN2, 24) ADAMTSL1, 25) CD79B, 26) KEL, 27) KLHL14, 28) MPP2, 29) NMNAT2, 30) PLXDC1, 31) CAPN9, 32) TALDO1, 33) PLK4, 34) IGHV3-72, 35) IGKV1-9, and 36) CNTN4. In particular aspects, the classifier may contain 1, 2, 3, 4, 5, 6, 7, 8, or more additional genes. In other aspects, the classifier may omit 1, 2, 3, 4, 5, 6, 7, 8, or more, of these genes, while optionally including other genes.

In some embodiments, the present invention provides a method and/or system for differentiating UIP from non-UIP using a classifier that comprises or consists of all of the following sequences: 1) HLA-F (SEQ ID NO.:1), 2) CDKL2 (SEQ ID NO.:2), 3) GPR98 (SEQ ID NO.:3), 4) PRKCQ (SEQ ID NO.:4), 5) HLA-G (SEQ ID NO.:5), 6) PFKFB3 (SEQ ID NO.:6), 7) CEACAM1 (SEQ ID NO.:7), 8) RABGAP1L (SEQ ID NO.:8), 9) CD274 (SEQ ID NO.:9), 10) PRUNE2 (SEQ ID NO.:10), 11) ARAP2 (SEQ ID NO.:11), 12) DZIP1 (SEQ ID NO.:12), 13) MXRA7 (SEQ ID NO.:13), 14) PTCHD4 (SEQ ID NO.:14), 15) PDLIM3 (SEQ ID NO.:15), 16) CNN1 (SEQ ID NO.:16), 17) NIPSNAP3B (SEQ ID NO.:17), 18) PAQR7 (SEQ ID NO.:18), 19) ACTG2 (SEQ ID NO.:19), 20) NA (SEQ ID NO.:20), 21) TIMP2 (SEQ ID NO.:21), 22) DES (SEQ ID NO.:22), 23) HMCN2, 24) ADAMTSL1, 25) CD79B, 26) KEL, 27) KLHL14, 28) MPP2, 29) NMNAT2, 30) PLXDC1, 31) CAPN9, 32) TALDO1, 33) PLK4, 34) IGHV3-72, 35) IGKV1-9, and 36) CNTN4. In particular aspects, the classifier may contain 1, 2, 3, 4, 5, 6, 7, 8, or more additional genes. In other aspects, the classifier may omit 1, 2, 3, 4, 5, 6, 7, 8, or more, of these genes, while optionally including other genes. In some embodiments, the present invention provides a method and/or system for differentiating UIP from non-UIP using a classifier described herein, wherein the method further comprises implementing a classifier that classifies the subject as a smoker or non-smoker. Such a smoker status classification can optionally be implemented prior to implementing a UIP vs. Non-UIP classifier, or a smoker status classification step can be built in as a covariate used during the training (e.g., using a classifier training module) of a UIP vs. Non-UIP classifier of the present invention.

In some embodiments, alternatively, or additionally, the method of and/or system for differentiating UIP from non-UIP using a classifier described herein further comprises a step of excluding or assigning differential weight to certain genes or variants thereof that are susceptible to smoker-status bias during the training (e.g., using a classifier training module) or implementation of the UIP vs. Non-UIP classifier. As used herein, "smoker status bias" refers to genes or variants thereof, which in non-smoker patients are differentially expressed in UIP vs. non-UIP patients, but which are not detectably differentially expressed in UIP vs. non-UIP patients that are (or have been) smokers.

In some embodiments, the method of and/or system for the present invention comprises a tiered classifier comprising at least a first and a second classifier, wherein the first classifier is trained (e.g., using a classifier training module) to recognize gene signatures that distinguish smokers from non-smokers, and a second classifier is trained (e.g., using a classifier training module) to distinguish UIP vs. Non UIP in smokers or non-smokers, respectively.

In some embodiments, the method and/or systems of the present invention comprises:

- extracting nucleic acids (e.g., RNA, such as, e.g., total RNA) from a test sample (e.g. lung tissue);
- amplifying the nucleic acid to produce an expressed nucleic acid library (e.g., via polymerase chain reaction-mediated amplification of cDNAs (optionally labeled cDNAs), which cDNAs may be produced from one or more RNA sample by reverse transcription (RT-PCR));
- detecting expression of one or more nucleic acid present in the nucleic acid library (e.g., detecting RNA expression profiles by measuring cDNA species produced via RT-PCR) via an array (e.g., a microarray) or via direct sequencing (e.g., RNAseq); and determining whether the test sample is UIP or non-UIP using a trained classifier described herein.

In some embodiments, the method and/or system of the present invention further comprises incorporating smoker status into the training exercise. In certain embodiments, smoker status is optionally incorporated in one of the following ways:

(i) by using smoking status as a covariate in a UIP or Non-UIP classifier during training (e.g., using a classifier training module).

(ii) by identifying a plurality of genes that are susceptible to smoker-status bias and excluding, or optionally weighing such genes differently than genes that are not susceptible to such bias, during UIP or Non-UIP classifier training (e.g., using a classifier training module).

(iii) by constructing a tiered classification in which an initial classifier that is trained (e.g., using a classifier training module) to recognize gene signatures that distinguish smokers from non-smokers is used to pre-classify a test sample as "smoker" or "non-smoker" based upon the gene signature of the test sample; and then, subsequent to pre-classification, a distinct classifier that was trained (e.g., using a classifier training module) to distinguish UIP vs. Non UIP in either smokers or non-smokers is implemented. For example, if the pre-classifier determines that the test sample is from a smoker, a UIP vs. Non-UIP classification is performed using a classifier trained (e.g., using a classifier training module) with UIP and Non-UIP samples from smokers. Conversely, if the pre-classifier determines that the test sample is from a non-smoker, a UIP vs. Non-UIP classification is performed using a classifier trained (e.g., using a classifier training module) with UIP and Non-UIP samples from non-smokers. In some embodiments, such smoker- or non-smoker-specific classifiers provide improved diagnostic performance due, at least in part, to a reduction in background noise caused by the inclusion of genes susceptible to smoker-status bias in the classifier training.

Accordingly, the present invention also provides suitable classifiers for use in methods of differentiating UIP from non-UIP, as disclosed herein. In various embodiments, the present invention provides a classifier suitable for differentiating UIP from non-UIP, wherein the classifier is trained (e.g., using a classifier training module) using microarray or sequencing data from a sample corresponding to one or more histopathology label determined by an expert pathologist. In some embodiments, the sample is labelled UIP or Non-UIP.

In some embodiments, the present invention presents a classifier comprising or consisting of one or more sequences or fragments thereof presented in any of Tables 5, 7, 8, 9, 10, 11, or 12, or at least one sequence or fragment thereof from each of Tables 5, 7, 8, 9, 10, 11, or 12. In some embodiments, the present invention provides a classifier comprising or consisting of at least 1, 2, 3, 4, 5, 6, 7, 8, 9, 10 or more of the sequences provided in any one or more or all of Tables 5, 7, 8, 9, 10, 11 and 12. For example, in some embodiments, the present invention provides a classifier comprising or consisting of at least 11, 12, 13, 14, 15, 20, 30, 50, 100, 150, 200, 250, 300, or more sequences provided in any one or more or all of Tables 5, 7, 8, 9, 10, 11, or 12, including all integers (e.g., 16, 17, 18, 19, 21, 22, 23, 24, 25 sequences, etc.) and ranges (e.g., from about 1-10 sequences from any one or more or all of Tables 5, 7, 8, 9, 10, 11, or 12, from about 10-15 sequences, 10-20 sequences, 5-30 sequences, 5-50 sequences, 10-100 sequences, 50-200 sequences from any one or more or all of Tables 5, 7, 8, 9, 10, 11, or 12, etc.) between. In one embodiment, the present invention provides a classifier that comprises or consists of all sequences provided in Table 5, all sequences provided in Table 7, all sequences provided in Table 8, all sequences provided in Table 9, all sequences provided in table 10, all sequences provided in Table 11, or all sequences provided in Table 12. In one embodiment, the present invention provides a classifier that comprises or consists of all sequences provided in each of Tables 5, 7, 8, 9, 10, 11, or 12.

In some particular embodiments, the present invention provides a classifier for differentiating UIP from non-UIP, wherein the classifier comprises or consists of one or more of the following sequences or fragments thereof: 1) HLA-F (SEQ ID NO.:1), 2) CDKL2 (SEQ ID NO.:2), 3) GPR98 (SEQ ID NO.:3), 4) PRKCQ (SEQ ID NO.:4), 5) HLA-G (SEQ ID NO.:5), 6) PFKFB3 (SEQ ID NO.:6), 7) CEACAM1 (SEQ ID NO.:7), 8) RABGAP1L (SEQ ID NO.:8), 9) CD274 (SEQ ID NO.:9), 10) PRUNE2 (SEQ ID NO.:10), 11) ARAP2 (SEQ ID NO.:11), 12) DZIP1 (SEQ ID NO.:12), 13) MXRA7 (SEQ ID NO.:13), 14) PTCHD4 (SEQ ID NO.:14), 15) PDLIM3 (SEQ ID NO.:15), 16) CNN1 (SEQ ID NO.:16), 17) NIPSNAP3B (SEQ ID NO.: 17), 18) PAQR7 (SEQ ID NO.:18), 19) ACTG2 (SEQ ID NO.:19), 20) NA (SEQ ID NO.:20) 21) TIMP2 (SEQ ID NO.:21), and 22) DES (SEQ ID NO.:22). In one embodiment, the classifier comprises or consists of all 22 of the above mentioned sequences. In some embodiments, the present invention provides a classifier for differentiating UIP from non-UIP, wherein the classifier comprises or consists of 2; 3; 4; 5; 6; 7; 8; 9; 10; 11; 12; 13; 14; 15; 16; 17; 18; 19; 20; or 21 of the abovementioned 22 sequences. In particular aspects, the classifier contains 1, 2, 3, 4, 5, 6, 7, 8, or more additional genes or fragments thereof. In other aspects, the classifier omits 1, 2, 3, 4, 5, 6, 7, 8, or more, of the abovementioned 22 sequences, while optionally including other genes. In other aspects, each of the 22 genes may be used in combination with any 1 or more, up to 20 more, of the other genes.

Tissue Samples

A lung tissue sample for use in a subject analytical or diagnostic method can be a biopsy sample (e.g., a biopsy sample obtained by video-assisted thoracoscopic surgery; VATS); a bronchoalveolar lavage (BAL) sample; a transbronchial biopsy; a cryo-transbronchial biopsy; and the like." Lung tissue samples for analysis can be provided in a suitable preservation solution.

Tissue samples can be obtained from a patient suspected of having a lung disease, e.g., an ILD, based on clinical signs and symptoms with which the patient presents (e.g., shortness of breath (generally aggravated by exertion), dry cough), and, optionally the results of one or more of an imaging test (e.g., chest X-ray, computerized tomography (CT)), a pulmonary function test (e.g., spirometry, oximetry, exercise stress test), lung tissue analysis (e.g., histological and/or cytological analysis of samples obtained by bronchoscopy, bronchoalveolar lavage, surgical biopsy).

The lung tissue sample can be processed in any of a variety of ways. For example, the lung tissue sample can be subjected to cell lysis. The lung tissue sample can be preserved in RNAprotect solution (a solution that inhibits RNA degradation, e.g., that inhibits nuclease digestion of RNA) and subsequently subjected to cell lysis. Components such as nucleic acids and/or proteins can be enriched or isolated from the lung tissue sample, and the enriched or isolated component can be used in a subject method. Methods of enriching for and isolating components such nucleic acids and proteins are known in the art; and any known method can be used. Methods of isolating RNA for expression analysis have been described in the art.

In Vitro Methods of Determining Expression Product Levels

Additional approaches to assess expression of the panel further demonstrated the genomic signal observed in UIP vs. non-UIP classification is robust across diverse biochemical assays and detection methods. Specifically we generated RNASeq data for a subset of the cohort and evaluated performance under CV. Performance comparisons with matched array data demonstrated that classification using RNASeq data achieves similar performance to data generated from the microarray platform.

The general methods for determining gene expression product levels are known to the art and may include but are not limited to one or more of the following: additional cytological assays, assays for specific proteins or enzyme activities, assays for specific expression products including protein or RNA or specific RNA splice variants, in situ hybridization, whole or partial genome expression analysis, microarray hybridization assays, serial analysis of gene expression (SAGE), enzyme linked immunoabsorbance assays, mass-spectrometry, immunohistochemistry, blotting, sequencing, RNA sequencing, DNA sequencing (e.g., sequencing of cDNA obtained from RNA); Next-Gen sequencing, nanopore sequencing, pyrosequencing, or Nanostring sequencing. For example, gene expression product levels can be determined according to the methods described in Kim, et. al. (Lancet Respir Med. 2015 June; 3(6):473-82, incorporated herein in its entirety, including all supplements). As used herein, the terms "assaying" or "detecting" or "determining" are used interchangeably in reference to determining gene expression product levels, and in each case, it is contemplated that the above-mentioned methods of determining gene expression product levels are suitable for detecting or assaying gene expression product levels. Gene expression product levels may be normalized to an internal standard such as total mRNA or the expression level of a particular gene including but not limited to glyceraldehyde 3 phosphate dehydrogenase, or tubulin.

In various embodiments, a sample comprises cells harvested from a tissue sample (e.g., a lung tissue sample such as a TBB sample). Cells can be harvested from a sample using standard techniques known in the art or disclosed herein. For example, in one embodiment, cells are harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract nucleic acid, e.g., messenger RNA. All samples obtained from a subject, including those subjected to any sort of further processing, are considered to be obtained from the subject.

The sample, in one embodiment, is further processed before detection of the gene expression products is performed as described herein. For example, mRNA in a cell or tissue sample can be separated from other components of the sample. The sample can be concentrated and/or purified to isolate mRNA in its non-natural state, as the mRNA is not in its natural environment. For example, studies have indicated that the higher order structure of mRNA in vivo differs from the in vitro structure of the same sequence (see, e.g., Rouskin et al. (2014). Nature 505, pp. 701-705, incorporated herein in its entirety for all purposes).

mRNA from the sample in one embodiment, is hybridized to a synthetic DNA probe, which in some embodiments, includes a detection moiety (e.g., detectable label, capture sequence, barcode reporting sequence). Accordingly, in these embodiments, a non-natural mRNA-cDNA complex is ultimately made and used for detection of the gene expression product. In another embodiment, mRNA from the sample is directly labeled with a detectable label, e.g., a fluorophore. In a further embodiment, the non-natural labeled-mRNA molecule is hybridized to a cDNA probe and the complex is detected.

In one embodiment, once the mRNA is obtained from a sample, it is converted to complementary DNA (cDNA) in a hybridization reaction or is used in a hybridization reaction together with one or more cDNA probes. cDNA does not exist in vivo and therefore is a non-natural molecule. Furthermore, cDNA-mRNA hybrids are synthetic and do not exist in vivo. Besides cDNA not existing in vivo, cDNA is necessarily different than mRNA, as it includes deoxyribonucleic acid and not ribonucleic acid. The cDNA is then amplified, for example, by the polymerase chain reaction (PCR) or other amplification method known to those of ordinary skill in the art. For example, other amplification methods that may be employed include the ligase chain reaction (LCR) (Wu and Wallace, Genomics, 4:560 (1989), Landegren et al., Science, 241:1077 (1988), incorporated by reference in its entirety for all purposes, transcription amplification (Kwoh et al., *Proc. Natl. Acad. Sci. USA,* 86:1173 (1989), incorporated by reference in its entirety for all purposes), self-sustained sequence replication (Guatelli et al., *Proc. Nat. Acad. Sci. USA,* 87:1874 (1990), incorporated by reference in its entirety for all purposes), incorporated by reference in its entirety for all purposes, and nucleic acid based sequence amplification (NASBA). Guidelines for selecting primers for PCR amplification are known to those of ordinary skill in the art. See, e.g., McPherson et al., PCR Basics: From Background to Bench, Springer-Verlag, 2000, incorporated by reference in its entirety for all purposes. The product of this amplification reaction, i.e., amplified cDNA is also necessarily a non-natural product. First, as mentioned above, cDNA is a non-natural molecule. Second, in the case of PCR, the amplification process serves to create hundreds of millions of cDNA copies for every individual cDNA molecule of starting material. The number of copies generated are far removed from the number of copies of mRNA that are present in vivo.

In one embodiment, cDNA is amplified with primers that introduce an additional DNA sequence (e.g., adapter, reporter, capture sequence or moiety, barcode) onto the fragments (e.g., with the use of adapter-specific primers), or mRNA or cDNA gene expression product sequences are hybridized directly to a cDNA probe comprising the additional sequence (e.g., adapter, reporter, capture sequence or moiety, barcode). Amplification and/or hybridization of mRNA to a cDNA probe therefore serves to create non-natural double stranded molecules from the non-natural single stranded cDNA, or the mRNA, by introducing additional sequences and forming non-natural hybrids. Further, as known to those of ordinary skill in the art, amplification procedures have error rates associated with them. Therefore, amplification introduces further modifications into the cDNA molecules. In one embodiment, during amplification with the adapter-specific primers, a detectable label, e.g., a fluorophore, is added to single strand cDNA molecules. Amplification therefore also serves to create DNA complexes that do not occur in nature, at least because (i) cDNA does not exist in vivo, (i) adapter sequences are added to the ends of cDNA molecules to make DNA sequences that do not exist in vivo, (ii) the error rate associated with amplification further creates DNA sequences that do not exist in vivo, (iii) the disparate structure of the cDNA molecules as compared to what exists in nature and (iv) the chemical addition of a detectable label to the cDNA molecules.

In some embodiments, the expression of a gene expression product of interest is detected at the nucleic acid level via detection of non-natural cDNA molecules.

The gene expression products described herein include RNA comprising the entire or partial sequence of any of the nucleic acid sequences of interest, or their non-natural cDNA product, obtained synthetically in vitro in a reverse transcription reaction. The term "fragment" is intended to refer to a portion of the polynucleotide that generally comprise at least 10, 15, 20, 50, 75, 100, 150, 200, 250, 300, 350, 400, 450, 500, 550, 600, 650, 700, 800, 900, 1,000, 1,200, or 1,500 contiguous nucleotides, or up to the number of nucleotides present in a full length gene expression product polynucleotide disclosed herein. A fragment of a gene expression product polynucleotide will generally encode at least 15, 25, 30, 50, 100, 150, 200, or 250 contiguous amino acids, or up to the total number of amino acids present in a full-length gene expression product protein of the invention.

In certain embodiments, a gene expression profile may be obtained by whole transcriptome shotgun sequencing ("WTSS" or "RNAseq"; see, e.g., Ryan et al BioTechniques 45: 81-94), which makes the use of high-throughput sequencing technologies to sequence cDNA in order to about information about a sample's RNA content. In general terms, cDNA is made from RNA, the cDNA is amplified, and the amplification products are sequenced.

After amplification, the cDNA may be sequenced using any convenient method. For example, the fragments may be sequenced using Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513: 19-39) and Morozova (Genomics. 2008 92:255-64), which are incorporated by reference for the general descriptions of the methods and the particular steps of the methods, including all starting products, reagents, and final products for each of the steps. As would be apparent, forward and reverse sequencing primer sites that compatible with a selected next generation sequencing platform can be added to the ends of the fragments during the amplification step.

In other embodiments, the products may be sequenced using nanopore sequencing (e.g. as described in Soni et al Clin Chem 53: 1996-2001 2007, or as described by Oxford Nanopore Technologies). Nanopore sequencing is a single-molecule sequencing technology whereby a single molecule of DNA is sequenced directly as it passes through a nanopore. A nanopore is a small hole, of the order of 1 nanometer in diameter. Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence. Nanopore sequencing technology as disclosed in U.S. Pat. Nos. 5,795,782, 6,015,714, 6,627,067, 7,238,485 and 7,258,838 and U.S. patent application publications US2006003171 and US20090029477.

In some embodiments, the gene expression product of the subject methods is a protein, and the amount of protein in a particular biological sample is analyzed using a classifier derived from protein data obtained from cohorts of samples. The amount of protein can be determined by one or more of the following: enzyme-linked immunosorbent assay (ELISA), mass spectrometry, blotting, or immunohistochemistry.

In some embodiments, gene expression product markers and alternative splicing markers may be determined by microarray analysis using, for example, Affymetrix arrays, cDNA microarrays, oligonucleotide microarrays, spotted microarrays, or other microarray products from Biorad, Agilent, or Eppendorf. Microarrays provide particular advantages because they may contain a large number of genes or alternative splice variants that may be assayed in a single experiment. In some cases, the microarray device may contain the entire human genome or transcriptome or a substantial fraction thereof allowing a comprehensive evaluation of gene expression patterns, genomic sequence, or alternative splicing. Markers may be found using standard molecular biology and microarray analysis techniques as described in Sambrook Molecular Cloning a Laboratory Manual 2001 and Baldi, P., and Hatfield, W. G., DNA Microarrays and Gene Expression 2002.

Microarray analysis generally begins with extracting and purifying nucleic acid from a biological sample, (e.g. a biopsy or fine needle aspirate) using methods known to the art. For expression and alternative splicing analysis it may be advantageous to extract and/or purify RNA from DNA. It may further be advantageous to extract and/or purify niRNA from other forms of RNA such as tRNA and rRNA.

Purified nucleic acid may further be labeled with a fluorescent label, radionuclide, or chemical label such as biotin, digoxigenin, or digoxin for example by reverse transcription, polymerase chain reaction (PCR), ligation, chemical reaction or other techniques. The labeling can be direct or indirect which may further require a coupling stage. The coupling stage can occur before hybridization, for example, using aminoallyl-UTP and NHS amino-reactive dyes (like cyanine dyes) or after, for example, using biotin and labelled streptavidin. In one example, modified nucleotides (e.g. at a 1 aaUTP: 4 TTP ratio) are added enzymatically at a lower rate compared to normal nucleotides, typically resulting in 1 every 60 bases (measured with a spectrophotometer). The aaDNA may then be purified with, for example, a column or a diafiltration device. The aminoallyl group is an amine group on a long linker attached to the nucleobase, which reacts with a reactive label (e.g. a fluorescent dye).

The labeled samples may then be mixed with a hybridization solution which may contain sodium dodecyl sulfate (SDS), SSC, dextran sulfate, a blocking agent (such as COT1 DNA, salmon sperm DNA, calf thymus DNA, PolyA or PolyT), Denhardt's solution, formamine, or a combination thereof A hybridization probe is a fragment of DNA or RNA of variable length, which is used to detect in DNA or RNA samples the presence of nucleotide sequences (the DNA target) that are complementary to the sequence in the probe. The probe thereby hybridizes to single-stranded nucleic acid (DNA or RNA) whose base sequence allows probe-target base pairing due to complementarity between the probe and target. The labeled probe is first denatured (by heating or under alkaline conditions) into single DNA strands and then hybridized to the target DNA.

To detect hybridization of the probe to its target sequence, the probe is tagged (or labeled) with a molecular marker; commonly used markers are 32P or Digoxigenin, which is nonradioactive antibody-based marker. DNA sequences or RNA transcripts that have moderate to high sequence complementarity (e.g. at least 70%, 80%, 90%, 95%, 96%, 97%, 98%, 99%, or more complementarity) to the probe are then detected by visualizing the hybridized probe via autoradiography or other imaging techniques. Detection of sequences with moderate or high complementarity depends on how stringent the hybridization conditions were applied; high stringency, such as high hybridization temperature and low salt in hybridization buffers, permits only hybridization between nucleic acid sequences that are highly similar, whereas low stringency, such as lower temperature and high salt, allows hybridization when the sequences are less similar. Hybridization probes used in DNA microarrays refer to DNA covalently attached to an inert surface, such as coated glass slides or gene chips, and to which a mobile cDNA target is hybridized.

A mix comprising target nucleic acid to be hybridized to probes on an array may be denatured by heat or chemical means and added to a port in a microarray. The holes may then be sealed and the microarray hybridized, for example, in a hybridization oven, where the microarray is mixed by rotation, or in a mixer. After an overnight hybridization, non-specific binding may be washed off (e.g. with SDS and SSC). The microarray may then be dried and scanned in a machine comprising a laser that excites the dye and a detector that measures emission by the dye. The image may be overlaid with a template grid and the intensities of the features (e.g. a feature comprising several pixels) may be quantified.

Various kits can be used for the amplification of nucleic acid and probe generation of the subject methods. Examples of kit that can be used in the present invention include but are not limited to Nugen WT-Ovation FFPE kit, cDNA amplification kit with Nugen Exon Module and Frag/Label module. The NuGEN WT-Ovation™. FFPE System V2 is a whole transcriptome amplification system that enables conducting global gene expression analysis on the vast archives of small and degraded RNA derived from FFPE samples.

The system is comprised of reagents and a protocol required for amplification of as little as 50 ng of total FFPE RNA. The protocol can be used for qPCR, sample archiving, fragmentation, and labeling. The amplified cDNA can be fragmented and labeled in less than two hours for GeneChip™. 3' expression array analysis using NuGEN's FL-Ovation™. cDNA Biotin Module V2. For analysis using Affymetrix GeneChip™. Exon and Gene ST arrays, the amplified cDNA can be used with the WT-Ovation Exon Module, then fragmented and labeled using the FL-Ovation™. cDNA Biotin Module V2. For analysis on Agilent arrays, the amplified cDNA can be fragmented and labeled using NuGEN's FL-Ovation™. cDNA Fluorescent Module.

In some embodiments, Ambion WT-expression kit can be used. Ambion WT-expression kit allows amplification of total RNA directly without a separate ribosomal RNA (rRNA) depletion step. With the Ambion™ WT Expression Kit, samples as small as 50 ng of total RNA can be analyzed on Affymetrix™. GeneChip™ Human, Mouse, and Rat Exon and Gene 1.0 ST Arrays. In addition to the lower input RNA requirement and high concordance between the Affymetrix™ method and TaqMan™ real-time PCR data, the Ambion™. WT Expression Kit provides a significant increase in sensitivity. For example, a greater number of probe sets detected above background can be obtained at the exon level with the Ambion™ WT Expression Kit as a result of an increased signal-to-noise ratio. Ambion™-expression kit may be used in combination with additional Affymetrix labeling kit. In some embodiments, AmpTec Trinucleotide Nano mRNA Amplification kit (6299-A15) can be used in the subject methods. The ExpressArt™ TRinucleotide mRNA amplification Nano kit is suitable for a wide range, from 1 ng to 700 ng of input total RNA. According to the amount of input total RNA and the required yields of aRNA, it can be used for 1-round (input >300 ng total RNA) or 2-rounds (minimal input amount 1 ng total RNA), with aRNA yields in the range of >10 μg. AmpTec's proprietary TRinucleotide priming technology results in preferential amplification of mRNAs (independent of the universal eukaryotic 3'-poly(A)-sequence), combined with selection against rRNAs. More information on AmpTec Trinucleotide Nano mRNA Amplification kit can be obtained at www.amp-tec.com/products.htm. This kit can be used in combination with cDNA conversion kit and Affymetrix labeling kit.

The raw data may then be normalized, for example, by subtracting the background intensity and then dividing the intensities making either the total intensity of the features on each channel equal or the intensities of a reference gene and then the t-value for all the intensities may be calculated. More sophisticated methods, include z-ratio, loess and lowess regression and RMA (robust multichip analysis), such as for Affymetrix chips.

In some embodiments, the above described methods may be used for determining transcript expression levels for training (e.g., using a classifier training module) a classifier to differentiate whether a subject is a smoker or non-smoker. In some embodiments, the above described methods may be used for determining transcript expression levels for training (e.g., using a classifier training module) a classifier to differentiate whether a subject has UIP or non-UIP.

Data Analysis (i) Comparison of Sample to Normal

In some embodiments, results of molecular profiling performed on a sample from a subject ("test sample") may be compared to a biological sample that is known or suspected to be normal ("normal sample"). In some embodiments, a normal sample is a sample that does not comprise or is expected to not comprise an ILD, or conditions under evaluation, or would test negative in the molecular profiling assay for the one or more ILDs under evaluation. In some embodiments, a normal sample is that which is or is expected to be free of any ILD, or a sample that would test negative for any ILD in the molecular profiling assay. The normal sample may be from a different subject from the subject being tested, or from the same subject. In some cases, the normal sample is a lung tissue sample obtained from a subject such as the subject being tested for example. The normal sample may be assayed at the same time, or at a different time from the test sample. In some embodiments, a normal sample is a sample that is known or suspected to be from a non-smoker. In particular embodiments, the normal sample is a sample that has been confirmed by at least two expert pathologists to be Non-UIP. In particular embodiments, the normal sample is a sample that has been confirmed by at least two expert pathologists to be Non-IPF.

The results of an assay on the test sample may be compared to the results of the same assay on a sample having a known disease state (e.g., normal, affected by a selected ILD (e.g., IPF, NSIP, etc.), smoker, non-smoker). In some cases the results of the assay on the normal sample are from a database, or a reference. In some cases, the results of the assay on the normal sample are a known or generally accepted value or range of values by those skilled in the art. In some cases the comparison is qualitative. In other cases the comparison is quantitative. In some cases, qualitative or quantitative comparisons may involve but are not limited to one or more of the following: comparing fluorescence values, spot intensities, absorbance values, chemiluminescent signals, histograms, critical threshold values, statistical significance values, gene product expression levels, gene product expression level changes, alternative exon usage, changes in alternative exon usage, protein levels, DNA polymorphisms, copy number variations, indications of the presence or absence of one or more DNA markers or regions, or nucleic acid sequences.

(ii) Evaluation of Results

In some embodiments, the molecular profiling results are evaluated using methods known to the art for correlating gene product expression levels or alternative exon usage with specific phenotypes such as a particular ILD, or normalcy (e.g. disease or condition free). In some cases, a specified statistical confidence level may be determined in order to provide a diagnostic confidence level. For example, it may be determined that a confidence level of greater than 90% may be a useful predictor of the presence of an ILD or of a smoker or non-smoker status. In other embodiments, more or less stringent confidence levels may be chosen. For example, a confidence level of about or at least about 50%, 60%, 70%, 75%, 80%, 85%, 90%, 95%, 97.5%, 99%, 99.5%, or 99.9% may be chosen as a useful phenotypic predictor. The confidence level provided may in some cases be related to the quality of the sample, the quality of the data, the quality of the analysis, the specific methods used, and/or the number of gene expression products analyzed. The specified confidence level for providing a diagnosis may be chosen on the basis of the expected number of false positives or false negatives and/or cost. Methods for choosing parameters for achieving a specified confidence level or for identifying markers with diagnostic power include but are not limited to Receiver Operating Characteristic (ROC) curve analysis, binormal ROC, principal component analysis, partial least squares analysis, singular value decomposition, least absolute shrinkage and selection operator analysis, least angle regression, and the threshold gradient directed regularization method.

(iii) Data Analysis

Raw gene expression level and alternative splicing data may in some cases be improved through the application of methods and/or processes designed to normalize and or improve the reliability of the data. In some embodiments of the present disclosure the data analysis requires a computer or other device, machine or apparatus for application of the various methods and/or processes described herein due to the large number of individual data points that are processed. A "machine learning classifier" refers to a computational-based prediction data structure or method, employed for characterizing a gene expression profile. The signals corresponding to certain expression levels, which are obtained by, e.g., microarray-based hybridization assays, are typically subjected to the classifier to classify the expression profile. Supervised learning generally involves "training" a classifier to recognize the distinctions among classes and then "testing" the accuracy of the classifier on an independent test set. For new, unknown samples the classifier can be used to predict the class in which the samples belong. In various embodiments, such training is be achieved, e.g., using a classifier training module.

In some cases, the robust multi-array average (RMA) method may be used to normalize raw data. The RMA method begins by computing background-corrected intensities for each matched cell on a number of microarrays. The background corrected values are restricted to positive values as described by Irizarry et al. Biostatistics 2003 Apr. 4 (2): 249-64. After background correction, the base-2 logarithm of each background corrected matched-cell intensity is then obtained. The back-ground corrected, log-transformed, matched intensity on each microarray is then normalized using the quantile normalization method in which for each input array and each probe expression value, the array percentile probe value is replaced with the average of all array percentile points, this method is more completely described by Bolstad et al. Bioinformatics 2003. Following quantile normalization, the normalized data may then be fit to a linear model to obtain an expression measure for each probe on each microarray. Tukey's median polish algorithm (Tukey, J. W., Exploratory Data Analysis. 1977) may then be used to determine the log-scale expression level for the normalized probe set data.

Various other software and/or hardware modules or processes may be implemented. In certain methods, feature selection and model estimation may be performed by logistic regression with lasso penalty using glmnet (Friedman J, Hastie T, Tibshirani R. Regularization Paths for Generalized Linear Models via Coordinate Descent. *Journal of statistical software* 2010; 33(1): 1-22). Raw reads may be aligned using TopHat (Trapnell C, Pachter L, Salzberg SL. TopHat: discovering splice junctions with RNA-Seq. *Bioinformatics* 2009; 25(9): 1105-11). Gene counts may be obtained using HTS eq (Anders S, Pyl PT, Huber W. HTSeq-a Python framework to work with high-throughput sequencing data. Bioinformatics 2014) and normalized using DESeq (Love M I, Huber W, Anders S. Moderated estimation of fold change and dispersion for RNA-Seq data with DESeq2; 2014). In methods, top features (N ranging from 10 to 200) were used to train a linear support vector machine (SVM) (Suykens JAK, Vandewalle J. Least Squares Support Vector Machine Classifiers. *Neural Processing Letters* 1999; 9(3): 293-300) using the e1071 library (Meyer D. Support vector machines: the interface to libsvm in package e1071. 2014). Confidence intervals may be computed using the pROC package (Robin X, Turck N, Hainard A, et al. pROC: an open-source package for R and S+ to analyze and compare ROC curves. *BMC bioinformatics* 2011; 12: 77)

In addition, data may be filtered to remove data that may be considered suspect. In some embodiments, data deriving from microarray probes that have fewer than about 4, 5, 6, 7 or 8 guanosine+cytosine nucleotides may be considered to be unreliable due to their aberrant hybridization propensity or secondary structure issues. Similarly, data deriving from microarray probes that have more than about 12, 13, 14, 15, 16, 17, 18, 19, 20, 21, or 22 guanosine+cytosine nucleotides may be considered unreliable due to their aberrant hybridization propensity or secondary structure issues.

In some cases, unreliable probe sets may be selected for exclusion from data analysis by ranking probe-set reliability against a series of reference datasets. For example, RefSeq or Ensembl (EMBL) are considered very high quality reference datasets. Data from probe sets matching RefSeq or Ensembl sequences may in some cases be specifically included in microarray analysis experiments due to their expected high reliability. Similarly data from probe-sets matching less reliable reference datasets may be excluded from further analysis, or considered on a case by case basis for inclusion. In some cases, the Ensembl high throughput cDNA (HTC) and/or mRNA reference datasets may be used to determine the probe-set reliability separately or together. In other cases, probe-set reliability may be ranked. For example, probes and/or probe-sets that match perfectly to all reference datasets such as for example RefSeq, HTC, HTSeq, and mRNA, may be ranked as most reliable (1). Furthermore, probes and/or probe-sets that match two out of three reference datasets may be ranked as next most reliable (2), probes and/or probe-sets that match one out of three reference datasets may be ranked next (3) and probes and/or probe sets that match no reference datasets may be ranked last (4). Probes and or probe-sets may then be included or excluded from analysis based on their ranking. For example, one may choose to include data from category 1, 2, 3, and 4 probe-sets; category 1, 2, and 3 probe-sets; category 1 and 2 probe-sets; or category 1 probe-sets for further analysis. In another example, probe-sets may be ranked by the number of base pair mismatches to reference dataset entries. It is understood that there are many methods understood in the art for assessing the reliability of a given probe and/or probe-set for molecular profiling and the methods of the present disclosure encompass any of these methods and combinations thereof.

In some embodiments of the present invention, data from probe-sets may be excluded from analysis if they are not expressed or expressed at an undetectable level (not above background). A probe-set is judged to be expressed above background if for any group:

Integral from TO to Infinity of the standard normal distribution<Significance (0.01)

Where: TO=Sqr(GroupSize) (T-P)/Sqr(Pvar); GroupSize=Number of CEL files in the group, T=Average of probe scores in probe-set, P=Average of Background probes averages of GC content, and Pvar=Sum of Background probe variances/(Number of probes in probe-set) 2, This allows including probe-sets in which the average of probe-sets in a group is greater than the average expression of background probes of similar GC content as the probe-set probes as the center of background for the probe-set and enables one to derive the probe-set dispersion from the background probe-set variance.

In some embodiments of the present disclosure, probe-sets that exhibit no, or low variance may be excluded from further analysis. Low-variance probe-sets are excluded from the analysis via a Chi-Square test. A probe-set is considered to be low-variance if its transformed variance is to the left of the 99 percent confidence interval of the Chi-Squared distribution with (N−1) degrees of freedom. (N−1)*Probe-set Variance/(Gene Probe-set Variance). about.Chi-Sq(N−1) where N is the number of input CEL files, (N−1) is the degrees of freedom for the Chi-Squared distribution, and the "probe-set variance for the gene" is the average of probe-set variances across the gene. In some embodiments of the present invention, probe-sets for a given gene or transcript cluster may be excluded from further analysis if they contain less than a minimum number of probes that pass through the previously described filter steps for GC content, reliability, variance and the like. For example in some embodiments, probe-sets for a given gene or transcript cluster may be excluded from further analysis if they contain less than about 1, 2, 3, 4, 5, 6, 7, 8, 9, 10, 11, 12, 13, 14, 15, or less than about 20 probes.

Methods of data analysis of gene expression levels or of alternative splicing may further include the use of a feature selection method and/or process as provided herein. In some embodiments of the present invention, feature selection is provided by use of the LIMMA software package (Smyth, G. K. (2005). Limma: linear models for microarray data. In: Bioinformatics and Computational Biology Solutions using R and Bioconductor, R. Gentleman, V. Carey, S. Dudoit, R. Irizarry, W. Huber (eds.), Springer, New York, pages 397-420).

Methods of data analysis of gene expression levels and or of alternative splicing may further include the use of a pre-classifier method and/or process (e.g., implemented by a pre-classifier analysis module). For example, a method and/or process may use a cell-specific molecular fingerprint to pre-classify the samples according to their composition and then apply a correction/normalization factor. This data/information may then be fed in to a final classification method and/or process which would incorporate that information to aid in the final diagnosis.

In certain embodiments, the methods of the present invention include the use of a pre-classifier method and/or process (e.g., implemented by a pre-classifier analysis module) that uses a molecular fingerprint to pre-classify the samples as smoker or non-smoker prior to application of a UIP/non-UIP classifier of the present invention.

Methods of data analysis of gene expression levels and/or of alternative splicing may further include the use of a classifier method and/or process (e.g., implemented by a classifier analysis module) as provided herein. In some embodiments of the present invention a diagonal linear discriminant analysis, k-nearest neighbor classifier, support vector machine (SVM) classifier, linear support vector machine, random forest classifier, or a probabilistic model-based method or a combination thereof is provided for classification of microarray data. In some embodiments, identified markers that distinguish samples (e.g. first ILD from second ILD, normal vs. ILD) or distinguish subtypes (e.g. IPF vs. NSIP) are selected based on statistical significance of the difference in expression levels between classes of interest. In some cases, the statistical significance is adjusted by applying a Benjamin Hochberg or another correction for false discovery rate (FDR).

In some cases, the classifier may be supplemented with a meta-analysis approach such as that described by Fishel and Kaufman et al. 2007 Bioinformatics 23(13): 1599-606. In some cases, the classifier may be supplemented with a meta-analysis approach such as a repeatability analysis. In some cases, the repeatability analysis selects markers that appear in at least one predictive expression product marker set.

Methods for deriving and applying posterior probabilities to the analysis of microarray data are known in the art and have been described for example in Smyth, G. K. 2004 Stat. Appi. Genet. Mol. Biol. 3: Article 3. In some cases, the posterior probabilities may be used to rank the markers provided by the classifier. In some cases, markers may be ranked according to their posterior probabilities and those that pass a chosen threshold may be chosen as markers whose differential expression is indicative of or diagnostic for samples that are for example IPF or NSIP. Illustrative threshold values include prior probabilities of 0.7, 0.75, 0.8, 0.85, 0.9, 0.925, 0.95, 0.975, 0.98, 0.985, 0.99, 0.995 or higher.

A statistical evaluation of the results of the molecular profiling may provide, but is not limited to providing, a quantitative value or values indicative of one or more of the following: the likelihood of diagnostic accuracy; the likelihood of an ILD; the likelihood of a particular ILD; the likelihood of the success of a particular therapeutic intervention, the likelihood the subject is a smoker, and the likelihood the subject is a non-smoker. Thus a physician, who is not likely to be trained in genetics or molecular biology, need not understand the raw data. Rather, the data is presented directly to the physician in its most useful form to guide patient care. The results of the molecular profiling can be statistically evaluated using a number of methods known to the art including, but not limited to: the students T test, the two sided T test, pearson rank sum analysis, hidden markov model analysis, analysis of q-q plots, principal component analysis, one way ANOVA, two way ANOVA, LIMMA and the like.

In some embodiments of the present invention, the use of molecular profiling alone or in combination with cytological analysis may provide a classification, identification, or diagnosis that is between about 85% accurate and about 99% or about 100% accurate. In some cases, the molecular profiling process and/or cytology provide a classification, identification, diagnosis of an ILD that is about, or at least about 85%, 86%, 87%, 88%, 90%, 91%, 92%, 93%, 94%, 95%, 96%, 97%, 97.5%, 98%, 98.5%, 99%, 99.5%, 99.75%, 99.8%, 99.85%, or 99.9% accurate. In some embodiments, the molecular profiling process and/or cytology provide a classification, identification, or diagnosis of the presence of a particular ILD type (e.g. IPF; NSIP; HP) that is about, or at least about 85%, 86%, 87%, 88%, 90%, 91%, 92%, 93%, 94%, 95%, 96%, 97%, 97.5%, 98%, 98.5%, 99%, 99.5%, 99.75%, 99.8%, 99.85%, or 99.9% accurate.

In some cases, accuracy may be determined by tracking the subject over time to determine the accuracy of the original diagnosis. In other cases, accuracy may be established in a deterministic manner or using statistical methods. For example, receiver operator characteristic (ROC) analysis may be used to determine the optimal assay parameters to achieve a specific level of accuracy, specificity, positive predictive value, negative predictive value, and/or false discovery rate.

In some embodiments of the present disclosure, gene expression products and compositions of nucleotides encoding for such products which are determined to exhibit the greatest difference in expression level or the greatest difference in alternative splicing between a first ILD and a second ILD (e.g., between IPF and NSIP), between ILD and normal, and/or between smoker and non-smoker may be chosen for use as molecular profiling reagents of the present disclosure. Such gene expression products may be particularly useful by providing a wider dynamic range, greater signal to noise, improved diagnostic power, lower likelihood of false positives or false negative, or a greater statistical confidence level than other methods known or used in the art.

In other embodiments of the present invention, the use of molecular profiling alone or in combination with cytological analysis may reduce the number of samples scored as non-diagnostic by about, or at least about 100%, 99%, 95%, 90%, 80%, 75%, 70%, 65%, or about 60% when compared to the use of standard cytological techniques known to the art. In some cases, the methods of the present invention may reduce the number of samples scored as intermediate or suspicious by about, or at least about 100%, 99%, 98%, 97%, 95%, 90%, 85%, 80%, 75%, 70%, 65%, or about 60%, when compared to the standard cytological methods used in the art.

In some cases the results of the molecular profiling assays, are entered into a database for access by representatives or agents of a molecular profiling business, the individual, a medical provider, or insurance provider. In some cases assay results include sample classification, identification, or diagnosis by a representative, agent or consultant of the business, such as a medical professional. In other cases, a computer analysis of the data is provided automatically. In some cases the molecular profiling business may bill the individual, insurance provider, medical provider, researcher, or government entity for one or more of the following: molecular profiling assays performed, consulting services, data analysis, reporting of results, or database access.

In some embodiments of the present invention, the results of the molecular profiling are presented as a report on a computer screen or as a paper record. In some cases, the report may include, but is not limited to, such information as one or more of the following: the number of genes differentially expressed, the suitability of the original sample, the number of genes showing differential alternative splicing, a diagnosis, a statistical confidence for the diagnosis, the likelihood the subject is a smoker, the likelihood of an ILD, and indicated therapies.

(iv) Categorization of Samples Based on Molecular Profiling Results

The results of the molecular profiling may be classified into one of the following: smoker, non-smoker, ILD, a particular type of ILD, a non-ILD, or non-diagnostic (providing inadequate information concerning the presence or absence of an ILD). In some cases, the results of the molecular profiling may be classified into IPF versus NSIP categories. In particular cases, the results may be classified as UIP or non-UIP.

In some embodiments of the present invention, results are classified using a trained classifier. Trained classifiers of the present invention implement methods and/or processes that have been developed using a reference set of known ILD and normal samples, known smoker and non-smoker samples, or combinations of known ILD and normal samples from smokers and/or non-smokers including, but not limited to, samples with one or more histopathologies. In some embodiments, training (e.g., using a classifier training module) comprises comparison of gene expression product levels in a first set biomarkers from a first ILD to gene expression product levels in a second set of biomarkers from a second ILD, where the first set of biomarkers includes at least one biomarker that is not in the second set. In some embodiments, training (e.g., using a classifier training module) comprises comparison of gene expression product levels in a first set biomarkers from a first ILD that is non-UIP to gene expression product levels in a second set of biomarkers from a second ILD that is UIP, where the first set of biomarkers includes at least one biomarker that is not in the second set. In some embodiments, training (e.g., using a classifier training module) further comprises comparison of gene expression product levels in a first set biomarkers from a first subject that is a smoker to gene expression product levels in a second set of biomarkers from a second subject that is a non-smoker, where the first set of biomarkers includes at least one biomarker that is not in the second set. In some embodiments, either the entire classifier or portions of the classifier can be trained (e.g., using a classifier training module) using comparisons of expression levels of biomarker panels within a classification panel against all other biomarker panels (or all other biomarker signatures) used in the classifier.

Classifiers suitable for categorization of samples include but are not limited to k-nearest neighbor classifiers, support vector machines, linear discriminant analysis, diagonal linear discriminant analysis, updown, naive Bayesian classifiers, neural network classifiers, hidden Markov model classifiers, genetic classifiers, or any combination thereof.

In some cases, trained classifiers of the present invention may incorporate data other than gene expression or alternative splicing data such as but not limited to DNA polymorphism data, sequencing data, scoring or diagnosis by cytologists or pathologists of the present invention, information provided by the pre-classifier method and/or process of the present disclosure, or information about the medical history of the subject of the present disclosure.

When classifying a biological sample for diagnosis of ILD, there are typically two possible outcomes from a binary classifier. Similarly, when classifying a biological sample for diagnosis of smoker, there are typically two possible outcomes from a binary classifier. When a binary classifier is compared with actual true values (e.g., values from a biological sample), there are typically four possible outcomes. If the outcome from a prediction is p (where "p" is a positive classifier output, such as a particular ILD) and the actual value is also p, then it is called a true positive (TP); however if the actual value is n then it is said to be a false positive (FP). Conversely, a true negative has occurred when both the prediction outcome and the actual value are n (where "n" is a negative classifier output, such as no ILD, or absence of a particular disease tissue as described herein), and false negative is when the prediction outcome is n while the actual value is p. In one embodiment, consider a diagnostic test that seeks to determine whether a person has a certain disease. A false positive in this case occurs when the person tests positive, but actually does not have the disease. A false negative, on the other hand, occurs when the person tests negative, suggesting they are healthy, when they actually do have the disease. In some embodiments, a Receiver Operator Characteristic (ROC) curve assuming real-world prevalence of subtypes can be generated by re-sampling errors achieved on available samples in relevant proportions.

The positive predictive value (PPV), or precision rate, or post-test probability of disease, is the proportion of patients with positive test results who are correctly diagnosed. It is the most important measure of a diagnostic method as it reflects the probability that a positive test reflects the underlying condition being tested for. Its value does however depend on the prevalence of the disease, which may vary. In one example, FP (false positive); TN (true negative); TP (true positive); FN (false negative). False positive rate (α)=FP/(FP+TN)-specificity; False negative rate (β)=FN/(TP+FN)-sensitivity; Power=sensitivity=1-β; Likelihood-ratio positive=sensitivity/(1-specificity); Likelihood-ratio negative=(1-sensitivity)/specificity.

The negative predictive value is the proportion of patients with negative test results who are correctly diagnosed. PPV and NPV measurements can be derived using appropriate disease subtype prevalence estimates. An estimate of the pooled disease prevalence can be calculated from the pool of indeterminates which roughly classify into B vs M by surgery. For subtype specific estimates, in some embodiments, disease prevalence may sometimes be incalculable because there are not any available samples. In these cases, the subtype disease prevalence can be substituted by the pooled disease prevalence estimate.

In some embodiments, the level of expression products or alternative exon usage is indicative of one or the following: IPF, NSIP, or HP.

In some embodiments, the level of expression products or alternative exon usage is indicative that the subject is a smoker or a non-smoker.

In some embodiments, the results of the expression analysis of the subject methods provide a statistical confidence level that a given diagnosis is correct. In some embodiments, such statistical confidence level is at least about, or more than about 85%, 90%, 91%, 92%, 93%, 94%, 95%, 96%, 97%, 98%, 99% 99.5%, or more.

Reports

A subject method and/or system may include generating a report that provides an indication that a sample (a lung tissue sample) is an ILD sample (e.g., using a report module). A subject diagnostic method can include generating a report that provides an indication as to whether an individual being tested has an ILD. A subject diagnostic method can include generating a report that provides an indication as to whether an individual being tested is, or is not a smoker. A subject method (or report module) can include generating a report that provides an indication as to whether an individual being tested has IPF (and not, e.g., an ILD other than IPF; e.g., the report can indicate that the individual has IPF and not NSIP).

In some embodiments, a subject method of diagnosing an ILD involves generating a report (e.g., using a report module). Such a report can include information such as a likelihood that the patient has an ILD; a likelihood that the patient is a smoker; a recommendation regarding further evaluation; a recommendation regarding therapeutic drug and/or device intervention; and the like.

For example, the methods disclosed herein can further include a step of generating or outputting a report providing the results of a subject diagnostic method, which report can be provided in the form of an electronic medium (e.g., an electronic display on a computer monitor), or in the form of a tangible medium (e.g., a report printed on paper or other tangible medium). An assessment as to the results of a subject diagnostic method (e.g., a likelihood that an individual has an ILD; a likelihood that an individual has IPF; a likelihood that an individual is a smoker) can be referred to as a "report" or, simply, a "score." A person or entity that prepares a report ("report generator") may also perform steps such as sample gathering, sample processing, and the like. Alternatively, an entity other than the report generator can perform steps such as sample gathering, sample processing, and the like. A diagnostic assessment report can be provided to a user. A "user" can be a health professional (e.g., a clinician, a laboratory technician, a physician (e.g., a cardiologist), etc.).

A subject report can further include one or more of: 1) service provider information; 2) patient data; 3) data regarding the expression level of a given gene product or set of gene products, a score or classifier decision; 4) follow-up evaluation recommendations; 5) therapeutic intervention or recommendations; and 6) other features.

Further Evaluation

Based on the expression level of a given gene product or set of gene products, and/or based on a report (as described above), a physician or other qualified medical personnel can determine whether further evaluation of the test subject (the patient) is required. Further evaluation can include, e.g., spirometry.

Therapeutic Intervention

Based on the expression level of a given gene product or set of gene products, and/or based on a report (as described above), a physician or other qualified medical personnel can determine whether appropriate therapeutic intervention is advised.

Therapeutic intervention includes drug-based therapeutic intervention, device-based therapeutic intervention, and surgical intervention. Where a report indicates a likelihood that an individual has IPF, drug-based therapeutic intervention includes, e.g., administering to the individual an effective amount of pirfenidone, prednisone, azathioprine, or N-acetylcysteine. Surgical intervention includes, e.g., arterial bypass surgery.

Computer-Implemented Methods, Systems and Devices

Therapeutic Intervention

The methods of the present disclosure can be computer-implemented, such that method steps (e.g., assaying, comparing, calculating, and the like) are be automated in whole or in part.

Accordingly, the present disclosure provides methods, computer systems, devices and the like in connection with computer-implemented methods of facilitating a diagnosis of an interstitial lung disease (e.g., a diagnosis of IPF, NSIP, HP, etc.), including differential diagnosis.

The present disclosure further provides methods, computer systems, devices and the like in connection with computer-implemented methods of facilitating determination of smoker status (e.g., smoker vs. non-smoker).

The present disclosure further provides methods, computer systems, devices and the like in connection with computer-implemented methods of facilitating a diagnosis of an interstitial lung disease (e.g., a diagnosis of IPF, NSIP, HP, etc.), including differential diagnosis, wherein the methods further comprise determining a subjects smoker status (smoker vs. non-smoker) and incorporating smoker status into the determination of the subjects interstitial lung disease diagnosis. In some embodiments, (i) smoker status is incorporated into the interstitial lung disease diagnosis as a covariate in the model used during training (e.g., using a classifier training module). This approach boosts signal-to-noise ratio, particularly in data derived from smokers (were noise is higher) and allows data derived from smokers and non-smokers to be combined and used simultaneously. In some embodiments, (ii) smoker status is incorporated into the interstitial lung disease diagnosis by identifying one or more genes that are susceptible to smoker status bias and excluding such genes or weighing such genes differently than other genes that are not susceptible to smoker-status during interstitial lung disease diagnosis classifier training. In some embodiments, (iii) smoker status is incorporated into the interstitial lung disease diagnosis by constructing a tiered classification in which an initial classifier is trained to recognize the gene signatures that distinguish smokers from non-smokers (e.g., using a classifier training module). Once patient samples are pre-classified as "smoker" or "non-smoker" (e.g., using a pre-classifier analysis module), distinct classifiers that were each trained to distinguish UIP vs. Non UIP in smokers or non-smokers, respectively can be implemented to diagnose interstitial lung disease. In still further embodiments, such methods comprising the step of incorporating smoker status into the determination of the subjects interstitial lung disease diagnosis include a combination of one or more of the above mentioned means of such incorporation (i.e., a combination of two or more of embodiments (i) to (iii) in the instant paragraph.

For example, the method steps, including obtaining values for biomarker levels, comparing normalized biomarker (gene) expression levels to a control level, calculating the likelihood of an ILD (and optionally the likelihood a subject is a smoker), generating a report, and the like, can be completely or partially performed by a computer program product. Values obtained can be stored electronically, e.g., in a database, and can be subjected to a classifier executed by a programmed computer (e.g., using a classifier analysis module).

For example, the methods and/or systems of the present disclosure can involve inputting a biomarker level (e.g., a normalized expression level of a gene product) into a classifier analysis module to execute a method and/or process to perform the comparing and calculating step(s) described herein, and generate a report (e.g., using a report module) as described herein, e.g., by displaying or printing a report to an output device at a location local or remote to the computer. The output to the report can be a score (e.g., numerical score (representative of a numerical value) or a non-numerical score (e.g., non-numerical output (e.g., "IPF", "No evidence of IPF") representative of a numerical value or range of numerical values. In other aspects, the output may indicate "UIP" vs. "non-UIP." In other aspects, the output may indicate "Smoker" vs. "Non-smoker"

The present disclosure thus provides a computer program product including a computer readable storage medium having software and/or hardware modules stored on it. The software and/or hardware modules can, when executed by a processor, execute relevant calculations based on values obtained from analysis of one or more biological sample (e.g., lung tissue sample) from an individual. The computer program product has stored therein a computer program for performing the calculation(s).

The present disclosure provides systems for executing the program described above, which system generally includes: a) a central computing environment or processor executing software and/or hardware modules; b) an input device, operatively connected to the computing environment, to receive patient data, wherein the patient data can include, for example, biomarker level or other value obtained from an assay using a biological sample from the patient, as described above; c) an output device, connected to the computing environment, to provide information to a user (e.g., medical personnel); and d) a method and/or process executed by the central computing environment (e.g., a processor), where the method and/or process is executed based on the data received by the input device, and wherein the method and/or process calculates a value, which value is indicative of the likelihood the subject has an ILD, as described herein.

The present disclosure also provides systems for executing the program described above, which system generally includes: a) a central computing environment or processor executing software and/or hardware modules; b) an input device, operatively connected to the computing environment, to receive patient data, wherein the patient data can include, for example, biomarker level or other value obtained from an assay using a biological sample from the patient, as described above; c) an output device, connected to the computing environment, to provide information to a user (e.g., medical personnel); and d) a method and/or process executed by the central computing environment (e.g., a processor), where the method and/or process is executed based on the data received by the input device, wherein the method and/or process calculates a value, which value is indicative of the likelihood the subject has an ILD, as described herein, and wherein the method and/or process uses smoking status (smoker vs. non-smoker) as a covariate in the model used during training. In some embodiments, the method and/or process excludes or weighs one or more gene that is susceptible to smoker status bias differently during classifier training to enrich the feature space used for training with genes that are not confounded or affected by smoking status.

Figure 7A:
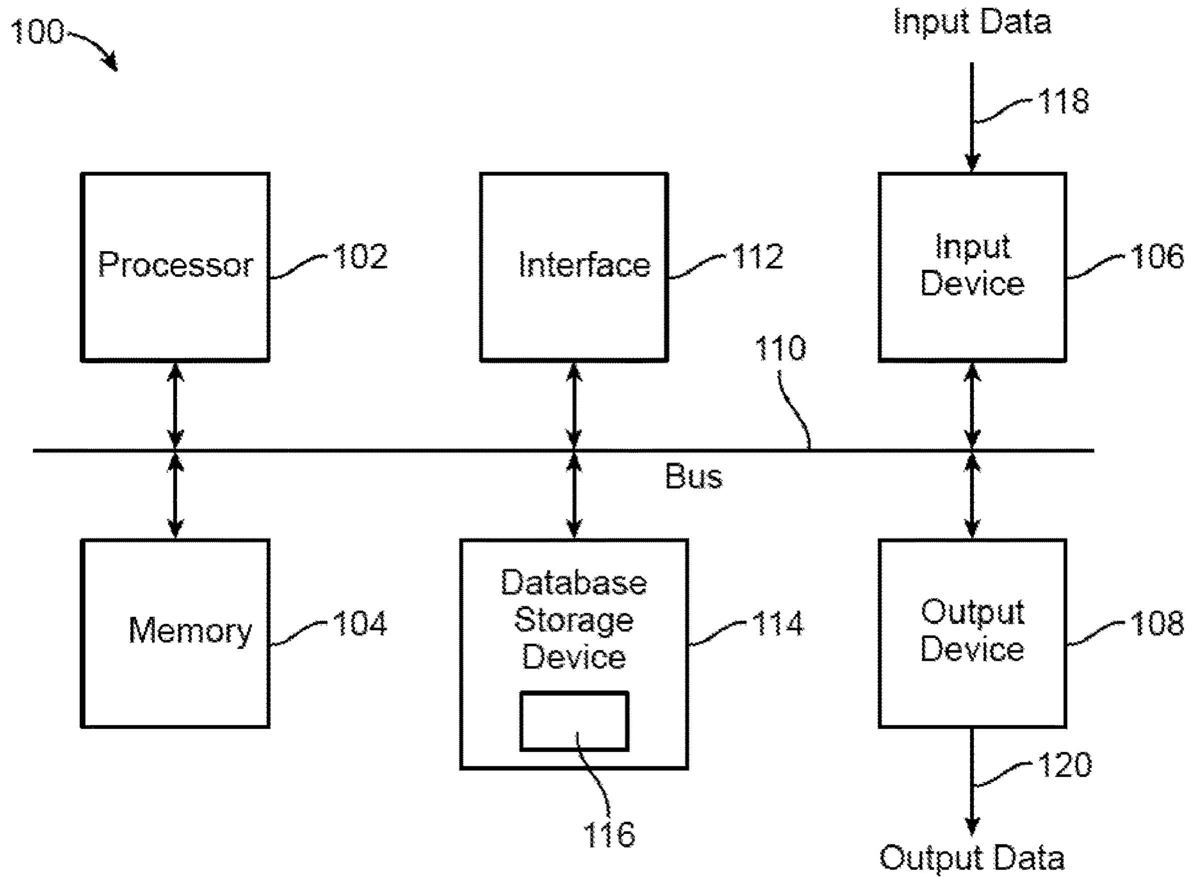
FIG. 7A. Illustration of a computer system usable for implementing aspects disclosed herein.

In still further embodiments, the present disclosure provides systems for executing the program described above, which system generally includes: a) a central computing environment or processor executing software and/or hardware modules; b) an input device, operatively connected to the computing environment, to receive patient data, wherein the patient data can include, for example, biomarker level or other value obtained from an assay using a biological sample from the patient, as described above; c) an output device, connected to the computing environment, to provide information to a user (e.g., medical personnel); and d) a first method and/or process executed by the central computing environment (e.g., a processor), where the first method and/or process is executed based on the data received by the input device, wherein the first method and/or process calculates a value, which value is indicative of the likelihood a subject is a smoker or a non-smoker, as described herein, wherein the subject's status as a smoker or non-smoker causes the first method and/or process to apply a second method and/or process specifically trained (e.g., using a classifier training module) to distinguish UIP vs. Non UIP in smokers or non-smokers, respectively and e) wherein the second method and/or process is executed by the central computing environment (e.g., a processor), where the second method and/or process is executed based on the data received by the input device, and wherein the second method and/or process calculates a value, which value is indicative of the likelihood the subject has an ILD, as described herein, Computer Systems FIG. 7A illustrates a processing system 100 including at least one processor 102, or processing unit or plurality of processors, memory 104, at least one input device 106 and at least one output device 108, coupled together via a bus or group of buses 110. Processing system can be implemented on any suitable device, such as, for example, a host device, a personal computer, a handheld or laptop device, a personal digital assistant, a multiprocessor system, a microprocessor-based system, a programmable consumer electronic device, a minicomputer, a server computer, a web server computer, a mainframe computer, and/or a distributed computing environment that includes any of the above systems or devices In certain embodiments, input device 106 and output device 108 can be the same device. An interface 112 can also be provided for coupling the processing system 100 to one or more peripheral devices, for example interface 112 can be a PCI card or PC card. At least one storage device 114 which houses at least one database 116 can also be provided.

The memory 104 can be any form of memory device, for example, volatile or nonvolatile memory, solid state storage devices, magnetic devices, etc. For example, in some embodiments, the memory 104 can be a random access memory (RAM), a memory buffer, a hard drive, a read-only memory (ROM), an erasable programmable read-only memory (EPROM), a database, and/or the like.

The processor 102 can include more than one distinct processing device, for example to handle different functions within the processing system 100. The processor 100 can be any suitable processing device configured to run or execute a set of instructions or code (e.g., stored in the memory) such as a general-purpose processor (GPP), a central processing unit (CPU), an accelerated processing unit (APU), a graphics processor unit (GPU), an Application Specific Integrated Circuit (ASIC), and/or the like. Such a processor 100 can run or execute a set of instructions or code stored in the memory associated with using a personal computer application, a mobile application, an internet web browser, a cellular and/or wireless communication (via a network), and/or the like. More specifically, the processor can execute a set of instructions or code stored in the memory 104 associated with analyzing and classifying data, as described herein.

Input device 106 receives input data 118 and can comprise, for example, a keyboard, a pointer device such as a pen-like device or a mouse, audio receiving device for voice controlled activation such as a microphone, data receiver or antenna such as a modem or wireless data adaptor, data acquisition card, etc. Input data 118 can come from different sources, for example keyboard instructions in conjunction with data received via a network.

Output device 108 produces or generates output data 120 and can comprise, for example, a display device or monitor in which case output data 120 is visual, a printer in which case output data 120 is printed, a port for example a USB port, a peripheral component adaptor, a data transmitter or antenna such as a modem or wireless network adaptor, etc. Output data 120 can be distinct and derived from different output devices, for example a visual display on a monitor in conjunction with data transmitted to a network. A user can view data output, or an interpretation of the data output, on, for example, a monitor or using a printer.

In some embodiments, the input device 106 and/or the output device 108 can be a communication interface configured to send and/or receive data via a network. More specifically, in such embodiments, the processing system 100 can act as a host device to one or more client devices (not shown in FIG. 7A). As such, the processing system 100 can send data to (e.g., output data 120) and receive data from (e.g., input data 118) the client devices. Such a communication interface can be any suitable module and/or device that can place the processing system 100 in communication with a client device such as one or more network interface cards or the like. Such a network interface card can include, for example, an Ethernet port, a WiFi® radio, a Bluetooth® radio, a near field communication (NFC) radio, and/or a cellular radio that can place the client device 150 in communication with the host device 110 via a network or the like.

The storage device 114 can be any form of data or information storage means, for example, volatile or nonvolatile memory, solid state storage devices, magnetic devices, etc. For example, in some embodiments, the storage device 114 can be a random access memory (RAM), a memory buffer, a hard drive, a read-only memory (ROM), an erasable programmable read-only memory (EPROM), a database, and/or the like.

In use, the processing system 100 is adapted to allow data or information to be stored in and/or retrieved from, via wired or wireless communication means, at least one database 116. The interface 112 may allow wired and/or wireless communication between the processing unit 102 and peripheral components that may serve a specialized purpose. In general, the processor 102 can receive instructions as input data 118 via input device 106 and can display processed results or other output to a user by utilizing output device 108. More than one input device 106 and/or output device 108 can be provided. The processing system 100 may be any suitable form of terminal, server, specialized hardware, or the like. The processing system 100 may be a part of a networked communications system.

Processing system 100 can connect to a network, for example, a local area network (LAN), a virtual network such as a virtual local area network (VLAN), a wide area network (WAN), a metropolitan area network (MAN), a worldwide interoperability for microwave access network (WiMAX), a cellular network, the Internet, and/or any other suitable network implemented as a wired and/or wireless network. For instance, when used in a LAN networking environment, the computing system environment 100 is connected to the LAN through a network interface or adapter. When used in a WAN networking environment, the computing system environment typically includes a modem or other means for establishing communications over the WAN, such as the Internet. The modem, which may be internal or external, may be connected to a system bus via a user input interface, or via another appropriate mechanism. In a networked environment, program modules depicted relative to the computing system environment 100, or portions thereof, may be stored in a remote memory storage device. It is to be appreciated that the illustrated network connections of FIG. 7 are examples and other means of establishing a communications link between multiple computers may be used.

Input data 118 and output data 120 can be communicated to other devices via the network. The transfer of information and/or data over the network can be achieved using wired communications means or wireless communications means. A server can facilitate the transfer of data between the network and one or more databases. A server and one or more databases provide an example of an information source.

Thus, the processing computing system environment 100 illustrated in FIG. 7A may operate in a networked environment using logical connections to one or more remote computers. The remote computer may be a personal computer, a server, a router, a network PC, a peer device, or other common network node, and typically includes many or all of the elements described above.

Figure 7B:
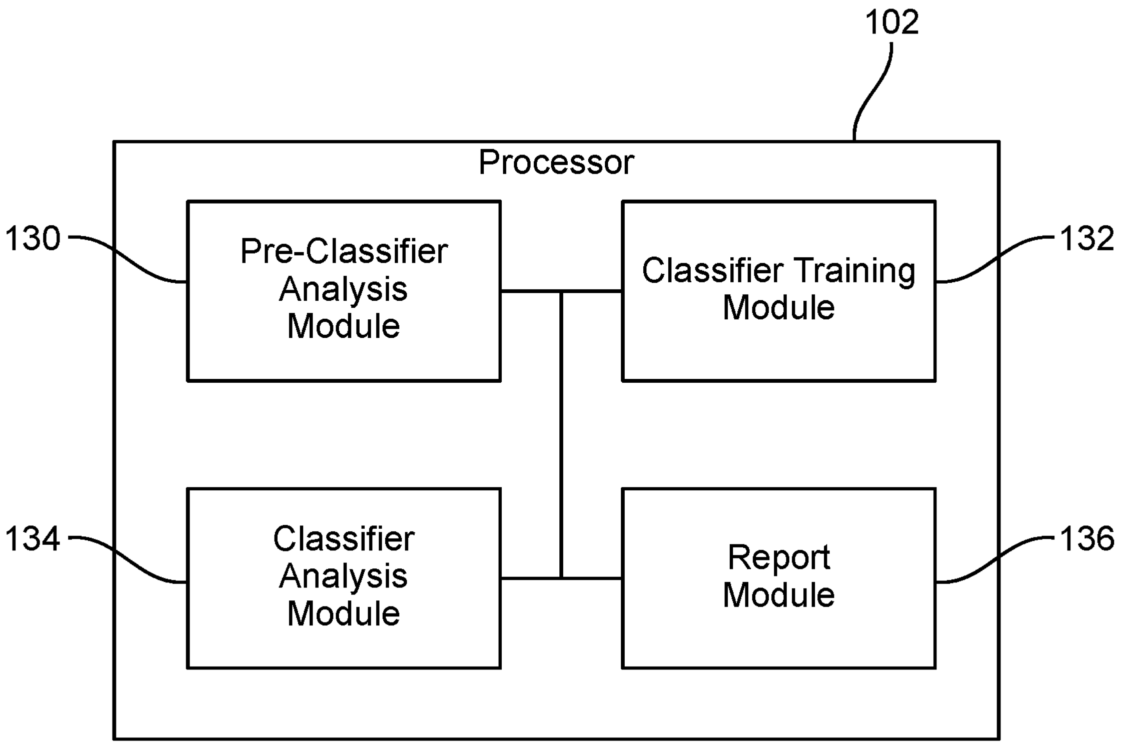
FIG. 7B. Detailed illustration of the processor of the computer system of FIG. 7A.

FIG. 7B illustrates the processor 102 of FIG. 7A in greater detail. The processor 102 can be configured to execute specific modules. The modules can be, for example, hardware modules, software modules stored in the memory 104 and/or executed in the processor 102, and/or any combination thereof. For example, as shown in FIG. 7B, the processor 102 includes and/or executes a pre-classifier analysis module 130, a classifier training module 132, a classifier analysis module 134 and a report module 136. As shown in FIG. 7B, the pre-classifier analysis module 130, the classifier training module 132, the classifier analysis module 134 and the report module 136 can be connected and/or electrically coupled. As such, signals can be sent between the pre-classifier analysis module 130, the classifier training module 132, the classifier analysis module 134 and the report module 136.

The classifier training module 132 can be configured to receive a corpora of data (e.g. gene expression data, sequencing data) and train a classifier. For example, clinical annotation data from samples previously identified as UIP and non-UIP (e.g., by an expert) can be received by the input device 106 and used by the classifier training module 132 to identify correlations between the samples previously identified as UIP and non-UIP. For example, expert TBB histopathology labels (i.e., UIP or Non UIP), expert HRCT labels, and/or expert patient-level clinical outcome labels can be obtained and used alone or in combination to train the classifier using microarray and/or sequencing data. The feature space used can include gene expression, variants, mutations, fusions, loss of heterozygoxity (LOH), biological pathway effect and/or any other dimension of the data that can be extracted as a feature for the purposes of training a machine-learning algorithm. In some embodiments, the feature space used for training a UIP vs. Non-UIP classifier, a smoker vs. Non-smoker classifier, or a UIP vs. Non-UIP and smoker vs. Non-smoker classifier includes gene expression, variants, mutations, fusions, loss of heterozygoxity (LOH), and biological pathway effect. In some embodiments, the feature space used for training a UIP vs. Non-UIP classifier, a smoker vs. Non-smoker classifier, or a UIP vs. Non-UIP and smoker vs. Non-smoker classifier includes gene expression and variant dimensions.

In some embodiments, the classifier training module 132 can train a smoker classifier and a non-smoker classifier based on an indication associated with whether a received sample is associated with a smoker or non-smoker. In other embodiments, the smoker/non-smoker can be used as an attribute (a model covariate) to train a single classifier. After the classifier is trained, it can be used to identify and/or classify newly received and unknown samples as described herein.

The pre-classifier analysis module 130 can identify whether a sample is associated with a smoker or a non-smoker. Specifically, the pre-classifier analysis module 130 can use any suitable method to identify and/or classify a sample as coming from an individual that smokes (or has a past history of heavy smoking) versus an individual that does not smoke (or has no smoking history). The classification can be done in any suitable manner such as, receiving an indication from a user, identification of genes that are susceptible to smoker-status bias, using a machine-learning classifier, and/or any other suitable method described herein.

The classifier analysis module 134 can input the sample into the classifier to identify and/or classify the received sample as associated with UIP and non-UIP. Specifically, the classifier analysis module 134 can use a trained classifier to identify whether the sample indicates UIP or non-UIP. In some embodiments, the classifier analysis module 134 can indicate a percentage or confidence score of the sample being associated with UIP or non-UIP. In some embodiments, the classifier analysis module 134 can execute two separate classifiers: one for smoker samples and the other for non-smoker samples (as determined by the pre-classifier analysis module 130). In other embodiments, a single classifier is executed for both smoker and non-smoker samples with an input for smoker status.

The report module 136 can be configured to generate any suitable report based on the outcome of the classifier analysis module 134 as described in further detail herein. In some cases, the report may include, but is not limited to, such information as one or more of the following: the number of genes differentially expressed, the suitability of the original sample, the number of genes showing differential alternative splicing, a diagnosis, a statistical confidence for the diagnosis, the likelihood the subject is a smoker, the likelihood of an ILD, and indicated therapies.

Figure 7C:
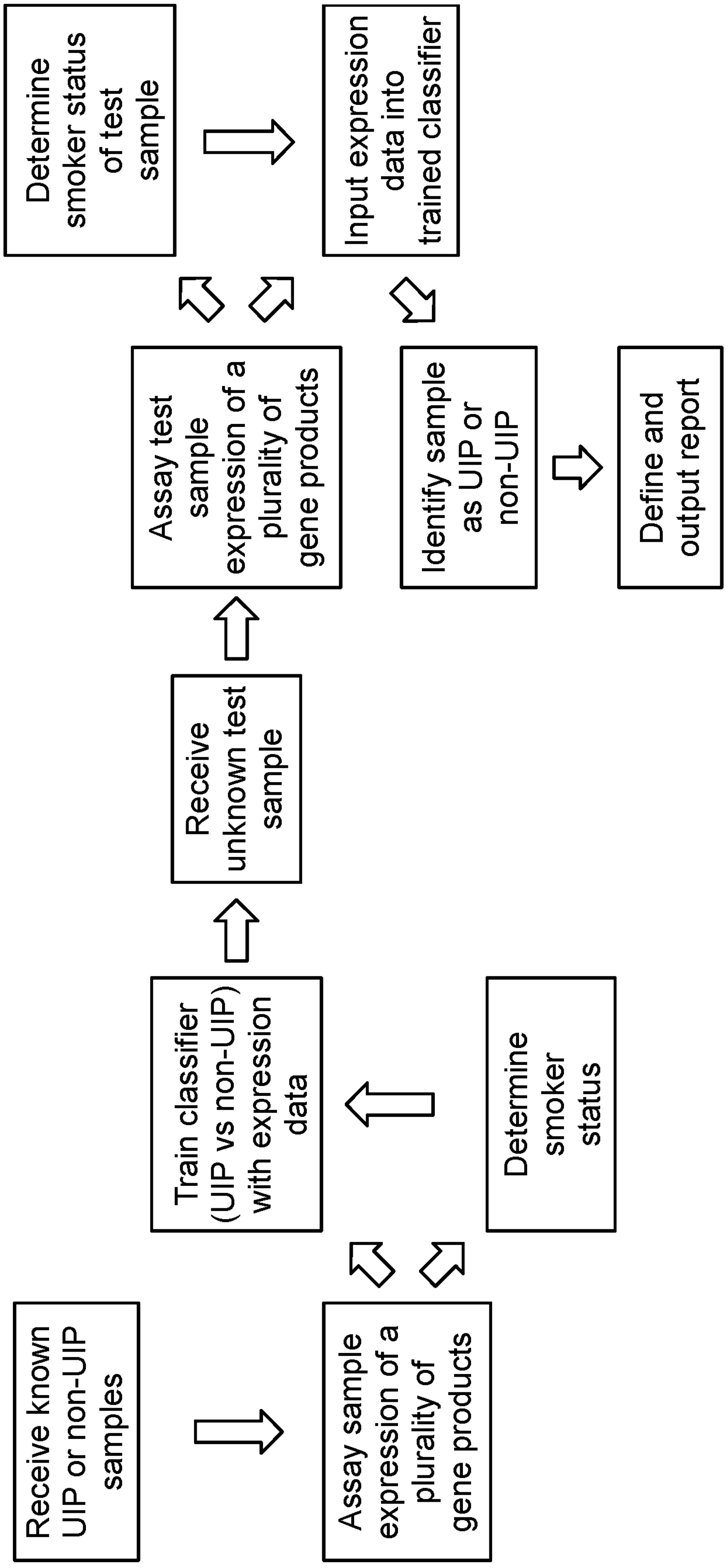
FIG. 7C. Detailed illustration of one non-limiting method of the present invention, wherein gene product expression data for known UIP and non-UIP samples are used to train a classifier (e.g., using a classifier training module) for differentiating UIP vs. non-UIP, wherein the classifier optionally considers smoker status as a covariant, and wherein gene product expression data from unknown samples are input into the trained classifier to identify the unknown samples as either UIP or non-UIP, and wherein the results of the classification via the classifier are defined and output via a report.

FIG. 7C illustrates a flow chart of one non-limiting embodiment of the present invention wherein gene product expression data for known UIP and non-UIP samples are used to train (e.g., using a classifier training module) a classifier for differentiating UIP vs. non-UIP, wherein the classifier optionally considers smoker status as a covariant, and wherein gene product expression data from unknown samples are input into the trained classifier to identify the unknown samples as either UIP or non-UIP, and wherein the results of the classification via the classifier are defined and output via a report.

Certain embodiments may be described with reference to acts and symbolic representations of operations that are performed by one or more computing devices, such as the computing system environment 100 of FIG. 7A. As such, it will be understood that such acts and operations, which are at times referred to as being computer-executed, include the manipulation by the processor of the computer of electrical signals representing data in a structured form. This manipulation transforms the data or maintains them at locations in the memory system of the computer, which reconfigures or otherwise alters the operation of the computer in a manner understood by those skilled in the art. The data structures in which data is maintained are physical locations of the memory that have particular properties defined by the format of the data. However, while an embodiment is being described in the foregoing context, it is not meant to be limiting as those of skill in the art will appreciate that the acts and operations described hereinafter may also be implemented in hardware.

Embodiments may be implemented with numerous other general-purpose or special-purpose computing devices and computing system environments or configurations. Examples of other computing systems, environments, and configurations that may be suitable for use with an embodiment include, but are not limited to, personal computers, handheld or laptop devices, personal digital assistants, multiprocessor systems, microprocessor-based systems, programmable consumer electronics, network, minicomputers, server computers, web server computers, mainframe computers, and distributed computing environments that include any of the above systems or devices.

Embodiments may be described in a general context of computer-executable instructions, such as hardware and/or software modules. An embodiment may also be practiced in a distributed computing environment where tasks are performed by remote processing devices that are linked through a communications network. In a distributed computing environment, program modules may be located in both local and remote computer storage media including memory storage devices.

Computer Program Products

The present disclosure provides computer program products that, when executed on a programmable computer such as that described above with reference to FIG. 7, can carry out the methods of the present disclosure. As discussed above, the subject matter described herein may be embodied in systems, apparatus, methods, and/or articles depending on the desired configuration. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g. video camera, microphone, joystick, keyboard, and/or mouse), and at least one output device (e.g. display monitor, printer, etc.).

Computer programs (also known as programs, software, software applications, applications, components, or code) include instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, etc.) used to provide machine instructions and/or data to a programmable processor, including a machine-readable medium that receives machine instructions as a machine-readable signal.

It will be apparent from this description that aspects of the present disclosure may be embodied, at least in part, in software, hardware, firmware, or any combination thereof. Thus, the techniques described herein are not limited to any specific combination of hardware circuitry and/or software, or to any particular source for the instructions executed by a computer or other data processing system. Rather, these techniques may be carried out in a computer system or other data processing system in response to one or more processors, such as a microprocessor, executing sequences of instructions stored in memory or other computer-readable medium including any type of ROM, RAM, cache memory, network memory, floppy disks, hard drive disk (HDD), solid-state devices (SSD), optical disk, CD-ROM, and magnetic-optical disk, EPROMs, EEPROMs, flash memory, or any other type of media suitable for storing instructions in electronic format.

In addition, the processor(s) may be, or may include, one or more programmable general-purpose or special-purpose microprocessors, digital signal processors (DSPs), programmable controllers, application specific integrated circuits (ASICs), programmable logic devices (PLDs), trusted platform modules (TPMs), or the like, or a combination of such devices. In alternative embodiments, special-purpose hardware such as logic circuits or other hardwired circuitry may be used in combination with software instructions to implement the techniques described herein.

Arrays and Kits

The present disclosure provides arrays and kits for use in carrying out a subject evaluating method or a subject diagnostic method.

Arrays

A subject array can comprise a plurality of nucleic acids, each of which hybridizes to a gene differentially expressed in a cell present in a tissue sample obtained from an individual being tested for an ILD.

A subject array can comprise a plurality of nucleic acids, each of which hybridizes to a gene differentially expressed in a cell present in a tissue sample obtained from an individual being tested for smoker status.

A subject array can comprise a plurality of nucleic acids, each of which hybridizes to a gene differentially expressed in a cell present in a tissue sample obtained from an individual being tested for both smoker status and an ILD.

A subject array can comprise a plurality of member nucleic acids, each of which member nucleic acids hybridizes to a different gene product. In some cases, two or more member nucleic acids hybridize to the same gene product; e.g., in some cases 2, 3, 4, 5, 6, 7, 8, 9, 10, or more member nucleic acids hybridize to the same gene product. A member nucleic acid can have a length of from about 5 nucleotides (nt) to about 100 nt, e.g., 5, 6, 7, 8, 9, 10, 11, 12, 13, 14, 15, 16, 17 18, 19, 20, 20-25, 25-30, 30-40, 40-50, 50-60, 60-70, 70-80, 80-90, or 90-100 nt. A nucleic acid can have one or more phosphate backbone modifications.

A subject array can include from about 10 to about $10^5$ unique member nucleic acids, or more than $10^5$ unique member nucleic acids. For example, a subject array can include from about 10 to about $10^2$, from about $10^2$ to about $10^3$, from about $10^3$ to about $10^4$, from about $10^4$ to about $10^5$, or more than $10^5$, unique member nucleic acids.

| Abbreviations | |
|---|---|
| adj.P.Value.edgeR: | False discovery rate adjusted p value of RNAseq gene expression data using edgeR analysis. |
| adj.P.Value.microarray | False discovery rate adjusted p value of RNAseq gene expression data using microarray analysis |
| adj.P.Value.npSeq: | False discovery rate adjusted p value of RNAseq gene expression data using npSeq analysis |
| BRONCH: | Broncholitis |
| CIF-NOC | Chronic Interstitial Fibrosis Not Otherwise Classified |
| edgeR: | an R package for the significance analysis of sequencing data |
| Ensembl ID: | Gene Identifier from Ensembl Genome Browser database |
| FDR: | False Discovery Rate, an adjusted p value that limits the possibility that the results are random due to the large number of genes simultaneously evaluated. |
| Gene Symbol: | Gene Identifier from HUGO Gene Nomenclature Committee |
| logFC.edgeR: | Log2 fold change of RNAseq gene expression data using edgeR analysis |
| logFC.microarray: | Log2 fold change of RNAseq gene expression data using LIMMA microarray analysis |
| logFC.npSeq: | Log2 fold change of RNAseq gene expression data using npSeq analysis |
| microarray: | Gene expression analysis using gene arrays such as from Affymetrix. |
| NML: | Normal Lung, usually obtained from human lung donor tissue that was ultimately never transplanted |
| npSeq: | an R package for the significance analysis of sequencing data |
| NSIP: | Non Specific Interstitial Pneumonia |
| OP: | Organizing Pneumonia |
| P.value.edgeR: | p value of RNAseq gene expression data using edgeR analysis |
| P.value.microarray: | p value of RNAseq gene expression data using LIMMA microarray analysis |

-continued

| Abbreviations | |
|---|---|
| P.value.npSeqp: | value of RNAseq gene expression data using npSeq analysis |
| RB: | Respiratory Broncholitis |
| REST: | A combination of all other ILDs except the subtype it is being compared to. Usually HP and NSIP, BRONCH, CIF-NOC, OP, RB and SARC. |
| SARC: | Sarcoidosis |
| SQC: | Squamous Cell Carcinoma |
| TCID: | "TCID" or "Transcript Cluster Identifier" refers to a gene level identifier used by all Affymetrix microarrays. Each TCID is associated with a fixed reference number that identifies a set of specific probes having sequences for a specific gene. Such specific probes are present on a given array commercially available from Affymetrix. TCID numbers thus refer to a gene product(s) of a specific gene, and can be found, e.g., at the following world wide web address: affymetrix.com/the sequences of which probes and gene products are hereby incorporation herein in their entirety. |
| UIP: | Usual Interstitial Pneumonia; the HRCT or histopathology pattern observed in IPF |
| LIMMA: | Linear Models for Microarray Data; an R package for the significance analysis of microarray data. |

"ENSEMBL ID" refers to a gene identifier number from the Ensembl Genome Browser database (see world wide web address: ensembl.org/index.html, incorporate herein). Each identifier begins with the letters ENSG to denote "Ensembl Gene". Each ENSEMBL ID number (i.e., each "gene" in the Ensembl database) refers to a gene defined by a specific start and stop position on a particular human chromosome, and therefore defines a specific locus of the human genome. As one of average skill in the art would fully appreciate, all of the gene symbols disclosed herein refer to gene sequences, which are readily available on publically available databases, e.g., UniGene database (Pontius J U, Wagner L, Schuler G D. UniGene: a unified view of the transcriptome. In: The NCBI Handbook. Bethesda (MD): National Center for Biotechnology Information; 2003, available at the world wide web address ncbi.nlm.nih.gov/unigene, incorporated herein), RefSeq (The NCBI handbook [Internet], Bethesda (MD): National Library of Medicine (US), National Center for Biotechnology Information; 2002 October Chapter 18, The Reference Sequence (RefSeq) Project, available at the world wide web address: ncbi.nlm.nih.gov/refseq/, incorporate herein), Ensembl (EMBL, available at the world wide web address: ensembl.org/index.html, incorporated herein), and the like. The sequences of the genes disclosed herein via their gene symbols, Ensembl IDs, and Entrez IDs are herein incorporated in their entirety.

All references, patents, and patent applications cited herein are incorporated in their entirety for all purposes.

EXAMPLES

Example 1

Sample Collection, Pathology Diagnosis, and Labeling

Video-assisted thoracoscopic surgery (VATS) specimens were prospectively collected as a part of an Institutional Review Board (IRB) approved ongoing multi-center clinical protocol, BRonchial sAmple collection for a noVel gEnomic test (BRAVE), sponsored by Veracyte, Inc. (South San Francisco, CA). Additional VATS and surgical lung biopsy specimens were obtained from banked sources.

Figure 5:
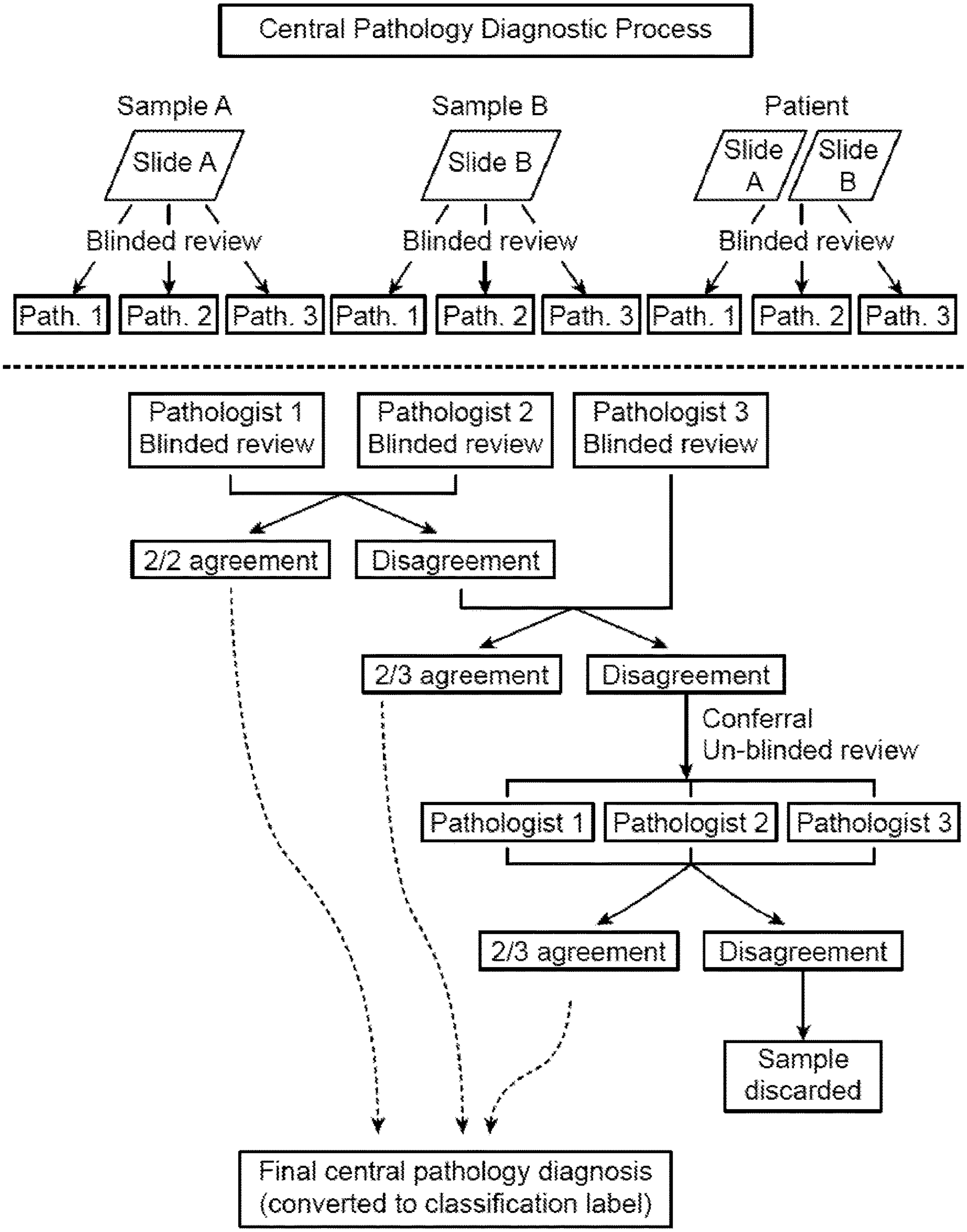
FIG. 5. Central pathology diagnostic process for a hypothetical patient with two samples (sample A and sample B). Three expert pathologists participate in the review process. For sample-level diagnosis, the glass slides for each sample are reviewed by each pathologist (Pathologist is abbreviated as Path). For patient-level diagnosis, glass slides from all samples (two in this exercise) are gathered and reviewed together by each pathologist. Both sample-level and patient-level diagnoses go through the same review process. A majority vote is used as the final diagnosis, unless expert pathologists disagree even after the conferral, in which case, the sample is omitted due to lack of confidence in the diagnosis. Only a single such case was observed among all banked tissues (n=128).

Following surgery, histology slides were collected, de-identified, and submitted to expert pathology review. Selected slides were scanned to construct a permanent digital file of microscopic images (Aperio, Vista, CA). Slides were evaluated according to the central pathology diagnostic process described in FIG. 5, resulting in both sample-level and patient-level pathology diagnoses. Pathology categories are summarized in Table 3. A patient can have more than one sample-level diagnosis (i.e. one per VATS sample per patient, most often one from each of the lower and upper lobes of the right lung), but can only have one patient-level diagnosis.

TABLE 3

List of all pathology diagnoses considered in our central pathology diagnostic process.

| Diagnosis | Abbreviation |
|---|---|
| Classic Usual Interstitial Pneumonia | Classic UIP |
| Difficult Usual Interstitial Pneumonia | Difficult UIP |
| Favor Usual Interstitial Pneumonia | Favor UIP |
| Cellular Non-specific Interstitial Pneumonia | Cellular NSIP |
| Fibrotic Non-specific Interstitial Pneumonia | Fibrotic NSIP |
| Both cellular and fibrotic Non-specific Interstitial Pneumonia | Both cellular and fibrotic NSIP |
| Favor Non-specific Interstitial Pneumonia | Favor NSIP |
| Hypersensitivity Pneumonitis | HP |
| Favor Hypersensitivity Pneumonitis | Favor HP |
| Chronic Interstitial Fibrosis, Not Otherwise Classified | CIF/NOC |
| Organizing Pneumonia | OP |
| Diffuse Alveolar Damage | DAD |
| Respiratory Bronchiolitis | RB |
| Smoking-Related Interstitial Fibrosis | SRIF |
| Emphysema | Emphysema |
| Bronchiolitis | Bronchiolitis |
| Sarcoidosis | Sarcoidosis |
| Lymphangioleiomyomatosis | LAM |
| Langerhans cell histiocytosis | LCH |
| Eosinophilic Pneumonia | EP |
| Non-diagnostic | ND |
| Other | Other |

Most diagnostic terminologies follow American Thoracic Society (ATS) 2011 or 2013 guidelines[5,6], but a few changes were made by the expert pathologist panel to better characterize features at the lobe level. In particular, 'Classic UIP' and 'Difficult UIP' were included instead of 'Definite UIP' and 'Probable UIP' as described in the ATS 2011 guidelines. Chronic Interstitial Fibrosis, Not Otherwise Classified (CIF/NOC) corresponds to unclassifiable fibrotic ILD. Three subcategories of CIF/NOC, 'Favor UIP', 'Favor NSIP', and 'Favor HP', were defined to specify cases of unclassifiable fibrosis which, in the judgment of the expert pathology panel, exhibit features suggestive of UIP, non-specific interstitial pneumonia (NSIP), or hypersensitivity pneumonitis (HP). A diagnosis of Smoking-Related Interstitial Fibrosis (SRIF) is also included[20].

For classification, sample-level pathology diagnoses were converted into binary class labels (UIP and non-UIP). Among the pathology diagnosis categories (Table 3), the 'UIP' class includes (1) UIP, (2) Classic UIP, (3) Difficult UIP, and (4) CIF/NOC, Favor UIP. All other pathology diagnoses except Non-diagnostic (ND) were assigned to the 'non-UIP' class.

Example 2

Sample Processing

Frozen tissue samples were mounted for sectioning using Tissue-Tek O.C.T. medium (Sakura Finetek U.S.A.) and 2×20 μm sections generated using a CM1800 cryostat (Leica Biosystems, Buffalo Grove, Illinois). Tissue curls were immediately immersed in RNAprotect (QIAGEN, Valencia, California), incubated overnight at 4° C. and stored at −80° C. until extraction. Whenever possible, adjacent 5 μm tissue curls were mounted onto glass slides and processed for hematoxylin and eosin (H&E) staining following standard procedures.

Nucleic acids were extracted using the AllPrep Micro Kit (QIAGEN) according to manufacturer's guidelines. Total RNA yield and quality was determined using Quant-it (Invitrogen) and Pico BioAnalyzer kits (Agilent). Fifteen nanograms of total RNA were amplified using Ovation FFPE WTA System (NuGEN, San Carlos, California), hybridized to GeneChip Gene ST 1.0 (Affymetrix, Santa Clara, California) microarrays, processed and scanned according to the manufacturer's protocols. Expression data was normalized by Robust Multi-array Average (RMA).

Example 3

Next-Generation RNA Sequencing

Whole transcriptome RNA sequencing was performed on select samples at a targeted minimum read depth of 80 million paired-end reads per sample. Briefly, 10 ng of total RNA was amplified using the Ovation RNASeq System v2 (NuGEN, San Carlos, California) and TruSeq (Illumina, San Diego, California) sequencing libraries were prepared and sequenced on an Illumina HiSeq according to manufacturer's instructions. Raw reads were aligned to the hg19 genome assembly using TopHat2. Gene counts were obtained using HTS eq and normalized in Bioconductor using the varianceStabilizingTransformation function in the DESeq2 package. Raw counts and normalized expression levels were obtained for 55,097 transcripts.

Example 4

Cohort Selection and Classifier Training

The study cohort initially included both banked (n=128) and prospectively collected BRAVE (n=38) tissues. Banked samples with poor cellularity on H&E staining (n=4 from a single patient) or normal lung tissue appearance (n=1) were excluded, as were samples diagnosed as 'unclassifiable fibrotic ILD' i.e. CIF/NOC (n=3) or samples that lacked pathology agreement by at least two pathologists (n=29). For BRAVE samples, CIF/NOC samples were not excluded. Only one BRAVE cohort sample was omitted, due to missing central pathology diagnosis. Processed RNA samples with residual genomic DNA contamination (n=2) or low RNA quality (RNA integrity number (RIN)<4) (n=1) were also excluded. After all exclusions, 125 samples from 86 patients remained for use in classification. The age, gender, smoking history and pathology diagnoses of included patients are summarized in Table 1.

TABLE 1

Cohort summary. Within each set of microarray data or RNASeq data, clinical factors such as age, gender and smoking history are summarized across patients. In addition, samples are summarized by sample-level pathology diagnosis (counts without parenthesis), and patients are summarized by patient-level pathology diagnosis (counts within parenthesis). Zeros in either case are due to discordance between sample-level and patient-level pathology; counts will therefore not be additive. Of the 36 samples in the RNASeq training set, 22 overlap with the microarray training set and 14 overlap with the microarray test set.

| | | | Microarray | | RNASeq |
|---|---|---|---|---|---|
| Category | Sub-category | All | Training | Test | Training |
| Size | Patient | 86 | 54 | 32 | 29 |
| Age | Mean (range) | 57.9 (25-83) | 58.9 (25-83) | 56.3 (32-76) | 60.5 (32-80) |
| Gender | Male | 32 (37.2%) | 22 (40.7%) | 10 (31.2%) | 16 (55.2%) |
| | Female | 54 (62.8%) | 32 (59.3%) | 22 (68.8%) | 13 (44.8%) |
| Smoking | Yes | 45 (52.3%) | 33 (61.1%) | 12 (37.5%) | 15 (51.7%) |
| | No | 38 (44.2%) | 19 (35.2%) | 19 (59.4%) | 14 (48.3%) |
| | Unknown | 3 (3.5%) | 2 (3.7%) | 1 (3.1%) | 0 |
| Pathology diagnosis | UIP | 45 (30) | 28 (18) | 17 (12) | 14 (14) |
| | Classic UIP | 8 (5) | 5 (4) | 3 (1) | 2 (0) |
| | Difficult UIP | 5 (2) | 3 (1) | 2 (1) | 1 (0) |
| | Favor UIP | 3 (1) | 3 (1) | 0 (0) | 0 (0) |
| | Fibrotic NSIP | 2 (0) | 0 (0) | 2 (0) | 0 (0) |
| | Cellular NSIP | 7 (0) | 5 (0) | 2 (0) | 2 (0) |
| | Both cellular and fibrotic NSIP | 14 (0) | 9 (0) | 5 (0) | 3 (0) |
| | NSIP | 0 (15) | 0 (10) | 0 (5) | 0 (5) |
| | Favor HP | 2 (1) | 0 (0) | 2 (1) | 0 (0) |
| | HP | 16 (14) | 11 (10) | 5 (4) | 3 (2) |
| | Unclassifiable fibrotic ILD | 4 (5) | 2 (3) | 2 (2) | 0 (0) |
| | Sarcoidosis | 4 (4) | 2 (2) | 2 (2) | 2 (2) |
| | RB | 4 (2) | 0 (1) | 4 (1) | 3 (1) |
| | OP | 2 (1) | 2 (1) | 0 (0) | 1 (1) |

TABLE 1-continued

Cohort summary. Within each set of microarray data or RNASeq data, clinical factors such as age, gender and smoking history are summarized across patients. In addition, samples are summarized by sample-level pathology diagnosis (counts without parenthesis), and patients are summarized by patient-level pathology diagnosis (counts within parenthesis). Zeros in either case are due to discordance between sample-level and patient-level pathology; counts will therefore not be additive. Of the 36 samples in the RNASeq training set, 22 overlap with the microarray training set and 14 overlap with the microarray test set.

| | | | Microarray | | RNASeq |
|---|---|---|---|---|---|
| Category | Sub-category | All | Training | Test | Training |
| | SRIF | 1 (1) | 0 (0) | 1 (1) | 1 (1) |
| | Bronchiolitis | 1 (1) | 1 (1) | 0 (0) | 1 (1) |
| | Emphysema | 2 (0) | 2 (0) | 0 (0) | 0 (0) |
| | DAD | 0 (1) | 0 (0) | 0 (1) | 0 (1) |
| | Other | 5 (3) | 4 (2) | 1 (1) | 3 (1) |
| | Total | 125 (86) | 77 (54) | 48 (32) | 36 (29) |

125 samples (86 patients) were available for microarray classification. The 86 patients were randomized into training and test sets while controlling for patient-level pathology subtype bias (Table 1). The microarray training set consists of 77 samples (39 UIP and 38 non-UIP) from 54 patients. The microarray test set consists of 48 samples (22 UIP vs. 26 non-UIP) from 32 patients.

RNASeq data was generated for a subset of 36 samples (17 UIP and 19 non-UIP) from 29 patients (Table 1), representing a spectrum of ILD subtypes. Among the 36 samples, 22 overlap with the microarray training set and 14 overlap with the microarray test set. Due to the small sample size of this dataset, classification performance was evaluated by cross-validation (CV) only.

Example 5

Training Models, Classification, Feature Selection

All statistical analyses were carried out using R version 3.0.1[21]. For the microarray classifier, genes differentially expressed between UIP and non-UIP classes were ranked by limma, then the top 200 genes with lowest false discovery rate (FDR) (<0.0003) were carried forward as candidate genes for model building. Several models were built using different methods, and the one with the lowest error was chosen. Feature selection and model estimation were performed by logistic regression with lasso penalty using glmnet. For the RNASeq classifier, genes were ranked by FDR resulting from a Wald-style test implemented in the DESeq2 package on the raw count data. The top features (N ranging from 10 to 200) were used to train a linear support vector machine (SVM) using the e1071 library on the normalized expression data.

Classifier performance was evaluated by CV and, when available, by an independent test set. To minimize over-fitting, a single patient was maintained as the smallest unit when defining the training/test set and the CV partition; i.e. all samples belonging to the same patient were held together as a group in the training/test set or in CV partitions. The CV methods used include leave-one-patient-out (LOPO) and 10-fold patient-level CV.

Performance was reported as the area under the curve (AUC), and specificity (1·0—false positive rate) and sensitivity (1·0—false negative rate) at a given score threshold. We set the score threshold to require at least >90% specificity. For each performance measurement, 95% confidence intervals were computed using 2000 stratified bootstrap replicates and the pROC package and reported as [CI lower-upper].

Example 6

Spatial Heterogeneity in Samplings From Explanted Lungs

Figure 6:
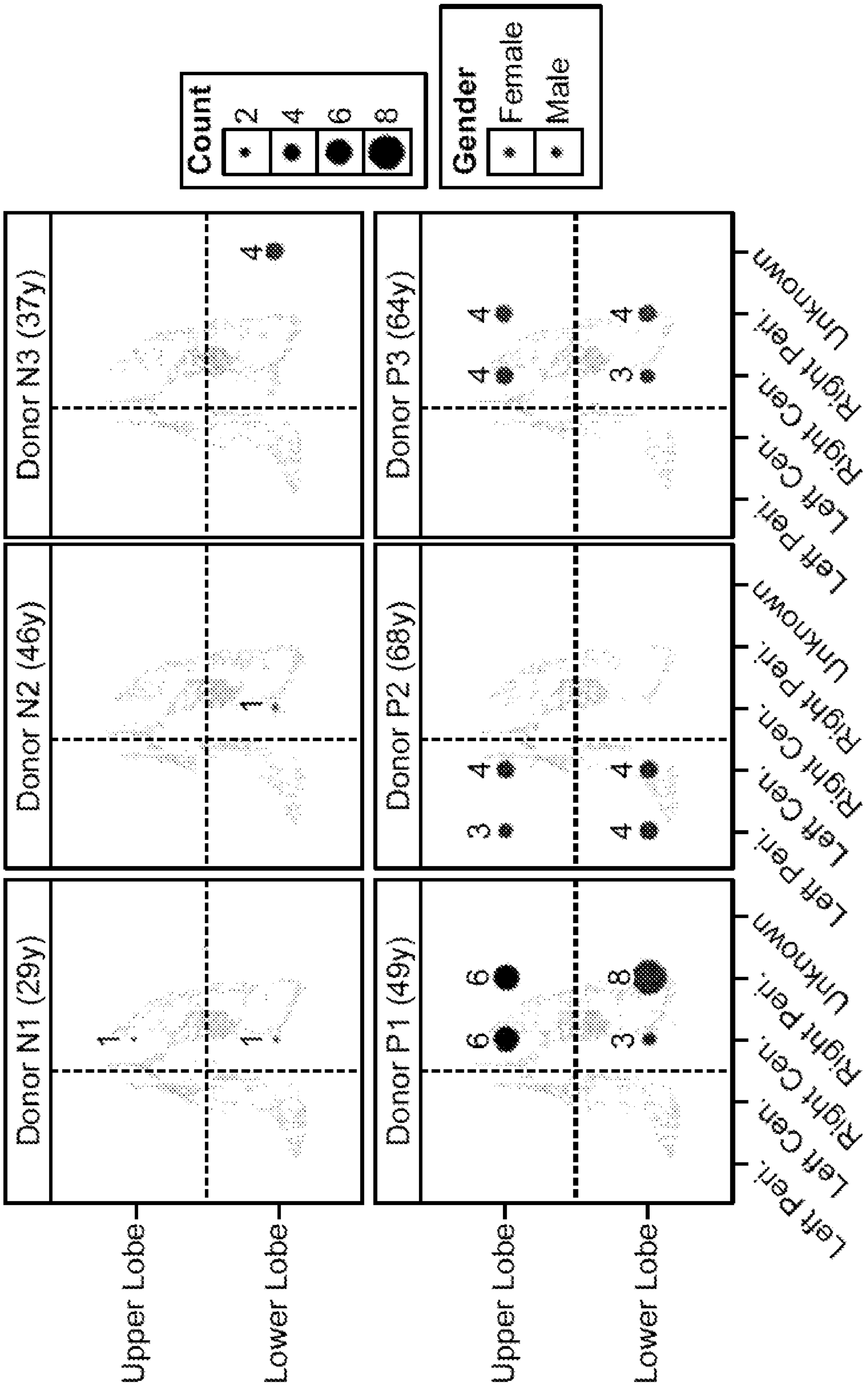
FIG. 6. Location of lung samplings from three normal organ donors (top) and three patients diagnosed with IPF (bottom). Donors N1-N3 and P3 were female. Donors P1 and P2 were male.

A total of 60 samplings from three normal lung donors (n=7) and three lungs from patients diagnosed with IPF (n=53) were analyzed using genome-wide microarray data. Intact normal and diseased lungs obtained during transplant procedures were collected following a protocol approved by the Institutional Review Board (IRB) of Inova Fairfax, Falls Church, Virginia. The upper and lower lobes of explanted lungs from three normal donors and three patients diagnosed with IPF were sampled centrally and peripherally. The location and number of the explant samples is illustrated in FIG. 6. Surgical pathology and final clinical diagnoses were provided by the originating institutions. Pathology over-reads by three expert pathologists unanimously confirmed UIP in all three IPF patient explant lungs.

Gene expression was evaluated in seven normal and 53 IPF explant lung samples. Genes differentially expressed between normal and IPF patient explant samples were identified and ranked by false discovery rate (FDR) using the R limma package (Smyth, G. K. (2005)). The top 200 genes differentially expressed between UIP and non-UIP classes in the microarray training set are shown in Table 12. Using the top 200 genes with the lowest FDR adjusted P-values (<1.45e-07), the Pearson correlation coefficient was calculated for all pairs of 53 UIP samples.

TABLE 12

Top 200 genes differentially expressed between UIP and non-UIP classes in the microarray training set, with indication of 22 genes used by the microarray classifier.

| TCID | GENE SYMBOL | logFC | MedExpr.UIP | MedExpr.NonUIP | FDR adjusted p-value | rank | Used by Classifier |
|---|---|---|---|---|---|---|---|
| 8117760 | HLA-F | −0.48 | 9.02 | 9.53 | 2.35E−09 | 1 | Used |
| 8177717 | HLA-F | −0.50 | 9.35 | 9.94 | 2.35E−09 | 2 | |
| 8179019 | HLA-F | −0.50 | 9.31 | 9.83 | 2.35E−09 | 3 | |
| 8101031 | CDKL2 | −0.95 | 7.31 | 8.16 | 1.29E−07 | 4 | Used |

TABLE 12-continued

Top 200 genes differentially expressed between UIP and non-UIP classes in the microarray training set, with indication of 22 genes used by the microarray classifier.

| TCID | GENE SYMBOL | logFC | MedExpr.UIP | MedExpr.NonUIP | FDR adjusted p-value | rank | Used by Classifier |
|---|---|---|---|---|---|---|---|
| 8106827 | GPR98 | −0.77 | 6.11 | 6.74 | 2.16E−07 | 5 | Used |
| 8100026 | ATP8A1 | −0.65 | 7.63 | 8.17 | 9.86E−07 | 6 | |
| 7931930 | PRKCQ | −0.64 | 6.78 | 7.40 | 1.81E−06 | 7 | Used |
| 8135661 | CFTR | −1.00 | 6.50 | 7.56 | 2.37E−06 | 8 | |
| 8177725 | HLA-G | −0.29 | 10.67 | 10.89 | 2.37E−06 | 9 | Used |
| 8179034 | HLA-G | −0.29 | 10.67 | 10.89 | 2.37E−06 | 10 | |
| 8123246 | SLC22A3 | −0.94 | 6.90 | 7.85 | 2.37E−06 | 11 | |
| 8118571 | PSMB9 | −0.53 | 10.04 | 10.68 | 2.37E−06 | 12 | |
| 8178211 | PSMB9 | −0.53 | 10.04 | 10.68 | 2.37E−06 | 13 | |
| 8179495 | PSMB9 | −0.53 | 10.04 | 10.68 | 2.37E−06 | 14 | |
| 8065719 | PXMP4 | −0.67 | 7.12 | 7.94 | 2.37E−06 | 15 | |
| 7926037 | PFKFB3 | −0.45 | 7.66 | 8.10 | 2.81E−06 | 16 | Used |
| 8037205 | CEACAM1 | −0.41 | 6.47 | 6.97 | 3.04E−06 | 17 | Used |
| 8178489 | HLA-C | −0.36 | 11.26 | 11.64 | 3.04E−06 | 18 | |
| 7917561 | GBP4 | −0.87 | 8.49 | 9.57 | 3.59E−06 | 19 | |
| 7968678 | FREM2 | −1.08 | 6.67 | 7.72 | 3.88E−06 | 20 | |
| 7907492 | RABGAP1L | −0.32 | 8.01 | 8.33 | 3.88E−06 | 21 | Used |
| 8124901 | HLA-C | −0.35 | 11.27 | 11.61 | 3.89E−06 | 22 | |
| 8096682 | ARHGEF38 | −0.78 | 6.52 | 7.21 | 3.89E−06 | 23 | |
| 8049187 | EFHD1 | 0.36 | 7.69 | 7.30 | 4.36E−06 | 24 | |
| 8117890 | HLA-B | −0.28 | 10.64 | 10.89 | 4.54E−06 | 25 | |
| 8179731 | HLA-B | −0.26 | 11.89 | 12.09 | 4.54E−06 | 26 | |
| 8154233 | CD274 | −0.84 | 6.35 | 7.14 | 4.54E−06 | 27 | Used |
| 8177788 | HLA-E | −0.29 | 10.68 | 10.94 | 4.54E−06 | 28 | |
| 8179103 | HLA-E | −0.29 | 10.68 | 10.94 | 4.54E−06 | 29 | |
| 8117777 | HLA-H | −0.24 | 9.99 | 10.21 | 4.89E−06 | 30 | |
| 7981290 | WARS | −0.55 | 9.39 | 9.97 | 5.08E−06 | 31 | |
| 8177732 | HLA-A | −0.27 | 11.72 | 12.01 | 5.30E−06 | 32 | |
| 7965565 | USP44 | −0.71 | 5.92 | 6.68 | 5.30E−06 | 33 | |
| 8125512 | TAP1 | −0.55 | 8.54 | 9.14 | 5.30E−06 | 34 | |
| 8178867 | TAP1 | −0.55 | 8.54 | 9.14 | 5.50E−06 | 35 | |
| 8180061 | TAP1 | −0.55 | 8.54 | 9.14 | 5.30E−06 | 36 | |
| 8022145 | L3MBTL4 | −0.37 | 6.74 | 7.07 | 5.37E−06 | 37 | |
| 8106098 | MAP1B | 0.68 | 8.77 | 8.00 | 5.37E−06 | 38 | |
| 7934719 | SFTPD | −0.71 | 9.02 | 9.63 | 5.75E−06 | 39 | |
| 7905929 | EFNA1 | −0.51 | 7.67 | 8.14 | 5.88E−06 | 40 | |
| 7917516 | GBP1 | −0.62 | 9.37 | 10.05 | 6.11E−06 | 41 | |
| 8161865 | PRUNE2 | 0.79 | 7.44 | 6.75 | 7.05E−06 | 42 | Used |
| 8044353 | ACOXL | −0.68 | 6.13 | 6.74 | 7.10E−06 | 43 | |
| 8057418 | ZNF385B | −0.71 | 6.95 | 7.71 | 7.15E−06 | 44 | |
| 8101131 | CXCL11 | −1.44 | 5.33 | 6.99 | 8.16E−06 | 45 | |
| 8058498 | FZD5 | −0.52 | 7.72 | 8.27 | 8.87E−06 | 46 | |
| 8082100 | PARP14 | −0.36 | 8.93 | 9.25 | 9.55E−06 | 47 | |
| 8001007 | PRSS8 | −0.51 | 7.39 | 7.89 | 9.85E−06 | 48 | |
| 8099760 | ARAP2 | −0.41 | 7.55 | 7.90 | 1.06E−05 | 49 | Used |
| 7914950 | CSF3R | −0.45 | 7.12 | 7.60 | 1.14E−05 | 50 | |
| 7972336 | DZIP1 | 0.33 | 7.72 | 7.47 | 1.16E−05 | 51 | Used |
| 8014591 | HNF1B | −0.53 | 6.88 | 7.33 | 1.20E−05 | 52 | |
| 8151423 | JPH1 | −0.52 | 6.68 | 7.17 | 1.21E−05 | 53 | |
| 8056217 | MXRA7 | 0.40 | 8.58 | 8.29 | 1.21E−05 | 54 | Used |
| 8117861 | HLA-L | −0.24 | 6.64 | 6.89 | 1.25E−05 | 55 | |
| 8179080 | HLA-L | −0.24 | 6.64 | 6.89 | 1.25E−05 | 56 | |
| 7976443 | IFI27 | −0.57 | 9.21 | 9.74 | 1.54E−05 | 57 | |
| 8022022 | LPIN2 | −0.30 | 8.06 | 8.37 | 1.55E−05 | 58 | |
| 7997593 | ATP2C2 | −0.46 | 6.73 | 7.13 | 1.62E−05 | 59 | |
| 8054846 | SCTR | −0.48 | 6.23 | 6.74 | 1.72E−05 | 60 | |
| 8178498 | HLA-B | −0.26 | 11.86 | 12.07 | 1.87E−05 | 61 | |
| 8140971 | SAMD9L | −0.48 | 8.09 | 8.52 | 2.12E−05 | 62 | |
| 7931728 | LARP4B | −0.28 | 8.76 | 9.07 | 2.15E−05 | 63 | |
| 8058857 | IGFBP5 | 0.62 | 10.41 | 9.73 | 2.15E−05 | 64 | |
| 7946504 | TMEM41B | −0.39 | 7.58 | 7.95 | 2.61E−05 | 65 | |
| 8057744 | STAT1 | −0.60 | 9.64 | 10.45 | 2.72E−05 | 66 | |
| 8107129 | SLCO4C1 | −1.08 | 7.96 | 8.93 | 2.72E−05 | 67 | |
| 8109938 | RANBP17 | −0.58 | 6.10 | 6.71 | 2.72E−05 | 68 | |
| 7934271 | PLA2G12B | −0.40 | 6.37 | 6.79 | 2.72E−05 | 69 | |
| 8126855 | PTCHD4 | 0.31 | 6.51 | 6.22 | 2.72E−05 | 70 | |
| 8097829 | FHDC1 | −0.54 | 6.39 | 6.91 | 2.80E−05 | 71 | |
| 8140478 | GSAP | −0.50 | 7.87 | 8.41 | 2.82E−05 | 72 | |
| 8079334 | LIMD1 | −0.34 | 7.37 | 7.66 | 2.83E−05 | 73 | |
| 7992828 | IL32 | −0.47 | 8.23 | 8.83 | 2.83E−05 | 74 | |
| 8103563 | DDX60 | −0.43 | 7.34 | 7.80 | 2.83E−05 | 75 | |
| 8082928 | CLDN18 | −1.10 | 8.77 | 9.84 | 2.83E−05 | 76 | |
| 7970716 | LNX2 | −0.46 | 8.40 | 8.79 | 3.01E−05 | 77 | |

TABLE 12-continued

Top 200 genes differentially expressed between UIP and non-UIP classes in the microarray training set, with indication of 22 genes used by the microarray classifier.

| TCID | GENE SYMBOL | logFC | MedExpr.UIP | MedExpr.NonUIP | FDR adjusted p-value | rank | Used by Classifier |
|---|---|---|---|---|---|---|---|
| 7944739 | CRTAM | −0.62 | 5.05 | 5.69 | 3.07E−05 | 78 | |
| 8089026 | STX19 | −0.49 | 5.91 | 6.36 | 3.18E−05 | 79 | |
| 8079377 | CXCR6 | −0.46 | 5.75 | 6.17 | 3.22E−05 | 80 | |
| 7956120 | ERBB3 | −0.65 | 7.37 | 7.96 | 3.67E−05 | 81 | |
| 7981514 | AHNAK2 | 0.54 | 7.30 | 6.80 | 3.84E−05 | 82 | |
| 8134036 | STEAP2 | 0.66 | 9.18 | 8.42 | 3.87E−05 | 83 | |
| 8109639 | PTTG1 | −0.67 | 7.91 | 8.53 | 3.89E−05 | 84 | |
| 8101118 | CXCL9 | −1.55 | 7.35 | 9.08 | 4.07E−05 | 85 | |
| 7919984 | SELENBP1 | −0.44 | 8.87 | 9.25 | 4.25E−05 | 86 | |
| 8108724 | PCDHB10 | 0.61 | 5.78 | 5.12 | 4.27E−05 | 87 | |
| 8126853 | PTCHD4 | 0.75 | 7.02 | 6.07 | 4.27E−05 | 88 | Used |
| 8134384 | DYNG1I1 | 0.23 | 5.71 | 5.43 | 4.52E−05 | 89 | |
| 7935535 | CRTAC1 | −0.68 | 6.04 | 6.73 | 4.73E−05 | 90 | |
| 8097080 | SYNPO2 | 0.89 | 9.20 | 8.26 | 4.73E−05 | 91 | |
| 8129410 | THEMIS | −0.85 | 6.35 | 7.33 | 4.73E−05 | 92 | |
| 7968035 | SPATA13 | −0.24 | 6.85 | 7.12 | 4.83E−05 | 93 | |
| 8104022 | PDLIM3 | 0.58 | 8.33 | 7.63 | 5.03E−05 | 94 | Used |
| 8125545 | HLA-DOA | −0.48 | 8.31 | 8.98 | 5.03E−05 | 95 | |
| 8115147 | CD74 | −0.20 | 12.35 | 12.54 | 5.03E−05 | 96 | |
| 8144758 | ZDHHC2 | −0.31 | 7.85 | 8.21 | 5.03E−05 | 97 | |
| 7910466 | CAPN9 | −0.71 | 5.34 | 6.15 | 5.03E−05 | 98 | |
| 8124911 | HLA-B | −0.25 | 11.87 | 12.05 | 5.12E−05 | 99 | |
| 7938834 | NAV2 | −0.36 | 7.79 | 8.04 | 5.18E−05 | 100 | |
| 8146092 | IDO1 | −1.21 | 6.59 | 8.00 | 5.43E−05 | 101 | |
| 8117800 | HLA-A | −0.25 | 11.70 | 11.94 | 5.43E−05 | 102 | |
| 8025918 | CNN1 | 0.86 | 8.39 | 7.52 | 5.43E−05 | 103 | Used |
| 8020847 | DTNA | 0.42 | 7.10 | 6.70 | 5.52E−05 | 104 | |
| 7934411 | USP54 | −0.43 | 7.89 | 8.31 | 5.61E−05 | 105 | |
| 8101126 | CXCL10 | −1.70 | 6.30 | 8.19 | 5.61E−05 | 106 | |
| 7993458 | C16orf45 | 0.39 | 7.38 | 7.02 | 5.62E−05 | 107 | |
| 8157027 | NIPSNAP3B | 0.29 | 5.25 | 4.98 | 5.62E−05 | 108 | Used |
| 8007931 | ITGB3 | 0.40 | 6.54 | 6.10 | 5.62E−05 | 109 | |
| 7947248 | KIF18A | −0.48 | 5.00 | 5.51 | 6.16E−05 | 110 | |
| 7978360 | GZMH | −0.58 | 6.95 | 7.54 | 6.51E−05 | 111 | |
| 8142997 | PLXNA4 | 0.44 | 6.55 | 6.07 | 6.64E−05 | 112 | |
| 8125993 | ETV7 | −0.28 | 5.78 | 6.03 | 6.97E−05 | 113 | |
| 8149725 | PEBP4 | −1.05 | 8.77 | 9.75 | 7.36E−05 | 114 | |
| 8178295 | UBD | −0.74 | 7.87 | 8.57 | 7.36E−05 | 115 | |
| 8122986 | SNX9 | 0.28 | 8.54 | 8.22 | 7.50E−05 | 116 | |
| 8154981 | UXC13B | −0.49 | 8.16 | 8.62 | 7.50E−05 | 117 | |
| 8175369 | MAP7D3 | 0.55 | 8.76 | 8.26 | 8.13E−05 | 118 | |
| 8091600 | PLCH1 | −0.62 | 6.84 | 7.31 | 8.13E−05 | 119 | |
| 8124650 | UBD | −0.75 | 7.99 | 8.74 | 8.22E−05 | 120 | |
| 8161044 | TPM2 | 0.60 | 10.51 | 9.89 | 8.37E−05 | 121 | |
| 8002218 | ESRP2 | −0.41 | 7.21 | 7.56 | 8.37E−05 | 122 | |
| 8180093 | HLA-DOA | −0.45 | 8.07 | 8.59 | 8.37E−05 | 123 | |
| 8136473 | TRIM24 | −0.28 | 8.33 | 8.58 | 8.41E−05 | 124 | |
| 7956856 | MSRB3 | 0.44 | 7.99 | 7.55 | 8.49E−05 | 125 | |
| 8035304 | BST2 | −0.50 | 8.02 | 8.52 | 8.49E−05 | 126 | |
| 8072710 | APOL6 | −0.37 | 8.35 | 8.84 | 8.51E−05 | 127 | |
| 8052882 | ADD2 | 0.28 | 5.63 | 5.38 | 8.58E−05 | 128 | |
| 7958019 | DRAM1 | −0.52 | 8.60 | 9.13 | 9.18E−05 | 129 | |
| 8069565 | BTG3 | −0.38 | 8.02 | 8.40 | 9.23E−05 | 130 | |
| 8114010 | IRF1 | −0.53 | 7.62 | 8.14 | 9.28E−05 | 131 | |
| 7986446 | ALDH1A3 | 0.49 | 8.01 | 7.51 | 9.28E−05 | 132 | |
| 8068583 | KCNJ15 | −0.76 | 8.89 | 9.53 | 9.68E−05 | 133 | |
| 7909586 | PPP2R5A | −0.37 | 7.92 | 8.32 | 1.05E−04 | 134 | |
| 8178220 | HLA-DPB1 | −0.54 | 9.76 | 10.34 | 1.06E−04 | 135 | |
| 8116932 | PHACTR1 | −0.38 | 7.38 | 7.81 | 1.15E−04 | 136 | |
| 8136095 | AHCYL2 | −0.57 | 8.98 | 9.39 | 1.23E−04 | 137 | |
| 8073088 | APOBEC3G | −0.53 | 7.17 | 7.77 | 1.31E−04 | 138 | |
| 8109462 | CNOT8 | −0.26 | 8.54 | 8.78 | 1.33E−04 | 139 | |
| 8006608 | CCL4L1 | −0.64 | 6.44 | 7.12 | 1.39E−04 | 140 | |
| 8083709 | SMC4 | −0.29 | 8.48 | 8.78 | 1.41E−04 | 141 | |
| 8138489 | CDCA7L | −0.44 | 7.79 | 8.21 | 1.45E−04 | 142 | |
| 7913858 | PAQR7 | 0.22 | 6.58 | 6.38 | 1.46E−04 | 143 | |
| 8148070 | COL14A1 | 0.71 | 9.87 | 9.29 | 1.48E−04 | 144 | |
| 8096314 | PKD2 | 0.32 | 8.43 | 8.07 | 1.50E−04 | 145 | |
| 8014349 | CCL15-CCL14 | 0.69 | 9.75 | 9.08 | 1.57E−04 | 146 | |
| 7919314 | FMO5 | −0.68 | 7.05 | 7.69 | 1.58E−04 | 147 | |
| 8006621 | CCL4L1 | −0.75 | 7.10 | 7.93 | 1.61E−04 | 148 | |
| 8019651 | CCL4L1 | −0.75 | 7.10 | 7.93 | 1.61E−04 | 149 | |
| 8089299 | CD47 | −0.25 | 10.44 | 10.72 | 1.61E−04 | 150 | |

TABLE 12-continued

Top 200 genes differentially expressed between UIP and non-UIP classes in the microarray training set, with indication of 22 genes used by the microarray classifier.

| TCID | GENE SYMBOL | logFC | MedExpr.UIP | MedExpr.NonUIP | FDR adjusted p-value | rank | Used by Classifier |
|---|---|---|---|---|---|---|---|
| 7904106 | MAGI3 | −0.42 | 7.60 | 7.99 | 1.71E−04 | 151 | |
| 8008321 | ACSF2 | −0.34 | 6.38 | 6.73 | 1.75E−04 | 152 | |
| 8005048 | MYOCD | 0.92 | 7.04 | 6.16 | 1.77E−04 | 153 | |
| 8042788 | ACTG2 | 0.98 | 10.11 | 9.21 | 1.79E−04 | 154 | Used |
| 7929466 | CYP2C18 | −0.35 | 5.09 | 5.39 | 1.84E−04 | 155 | |
| 8129888 | NHSL1 | −0.41 | 8.14 | 8.57 | 1.99E−04 | 156 | |
| 8173924 | NA | −0.95 | 5.22 | 6.25 | 2.03E−04 | 157 | Used |
| 7923958 | C1orf116 | −0.74 | 8.38 | 9.00 | 2.07E−04 | 158 | |
| 7979269 | GCH1 | −0.42 | 6.93 | 7.36 | 2.16E−04 | 159 | |
| 8020495 | CABLES1 | −0.37 | 7.82 | 8.21 | 2.17E−04 | 160 | |
| 7919645 | SV2A | 0.28 | 6.06 | 5.82 | 2.18E−04 | 161 | |
| 8077458 | EDEM1 | −0.33 | 7.97 | 8.32 | 2.18E−04 | 162 | |
| 8117476 | BTN3A3 | −0.40 | 8.58 | 9.00 | 2.24E−04 | 163 | |
| 8021376 | NEDD4L | −0.66 | 8.35 | 8.94 | 2.25E−04 | 164 | |
| 8056457 | SCN1A | −0.52 | 4.80 | 5.29 | 2.25E−04 | 165 | |
| 8150962 | TOX | −0.51 | 8.15 | 8.60 | 2.25E−04 | 166 | |
| 8058591 | ACADL | −1.01 | 6.63 | 7.62 | 2.26E−04 | 167 | |
| 8126653 | MRPL14 | −0.37 | 9.31 | 9.62 | 2.29E−04 | 168 | |
| 8098611 | TLR3 | −0.44 | 8.52 | 8.89 | 2.29E−04 | 169 | |
| 8066822 | SULF2 | 0.54 | 8.51 | 7.83 | 2.29E−04 | 170 | |
| 8109507 | ITK | −0.60 | 6.14 | 6.97 | 2.30E−04 | 171 | |
| 8099506 | TAPT1 | −0.32 | 7.42 | 7.70 | 2.32E−04 | 172 | |
| 7973564 | PSME1 | −0.19 | 9.85 | 10.07 | 2.34E−04 | 173 | |
| 7897044 | PRKCZ | −0.47 | 7.44 | 7.85 | 2.48E−04 | 174 | |
| 7974080 | MIA2 | −0.31 | 4.02 | 4.26 | 2.56E−04 | 175 | |
| 7917576 | GBP5 | −0.98 | 7.57 | 8.74 | 2.57E−04 | 176 | |
| 8085774 | ZNF385D | 0.99 | 7.66 | 6.39 | 2.58E−04 | 177 | |
| 7923386 | LMOD1 | 0.69 | 7.68 | 7.05 | 2.58E−04 | 178 | |
| 8073522 | SREBF2 | −0.28 | 8.20 | 8.44 | 2.59E−04 | 179 | |
| 7981460 | PPP1R13B | −0.25 | 7.83 | 8.04 | 2.62E−04 | 180 | |
| 8010454 | RNF213 | −0.36 | 8.63 | 9.01 | 2.63E−04 | 181 | |
| 8097903 | TLR2 | −0.37 | 7.77 | 8.26 | 2.68E−04 | 182 | |
| 8113369 | SLCO4C1 | −0.99 | 7.24 | 8.31 | 2.73E−04 | 183 | |
| 7950235 | STARD10 | −0.30 | 7.13 | 7.43 | 2.79E−04 | 184 | |
| 7910600 | KIAA1804 | −0.33 | 6.00 | 6.29 | 2.79E−04 | 185 | |
| 8117435 | BTN3A2 | −0.52 | 9.06 | 9.56 | 2.79E−04 | 186 | |
| 8143327 | PARP12 | −0.30 | 7.96 | 8.30 | 2.80E−04 | 187 | |
| 8087925 | TNNC1 | −0.90 | 8.53 | 9.30 | 2.82E−04 | 188 | |
| 8022045 | MYOM1 | 0.42 | 5.80 | 5.42 | 2.82E−04 | 189 | |
| 8096070 | BMP3 | −0.60 | 7.22 | 7.81 | 2.82E−04 | 190 | |
| 8075709 | APOL4 | −0.39 | 7.01 | 7.41 | 2.87E−04 | 191 | |
| 7915500 | C1orf210 | −0.32 | 7.17 | 7.59 | 2.91E−04 | 192 | |
| 7920297 | S100A14 | −0.56 | 8.42 | 8.87 | 2.94E−04 | 193 | |
| 7983630 | FGF7 | 0.67 | 7.64 | 6.98 | 2.94E−04 | 194 | |
| 8010287 | C1QTNF1 | 0.35 | 7.81 | 7.49 | 3.09E−04 | 195 | |
| 8018966 | TIMP2 | 0.18 | 10.53 | 10.34 | 3.09E−04 | 196 | Used |
| 7951593 | NA | −0.51 | 7.28 | 7.84 | 3.16E−04 | 197 | |
| 8048541 | DES | 0.71 | 8.81 | 8.19 | 3.20E−04 | 198 | Used |
| 7975361 | KIAA0247 | −0.22 | 8.17 | 8.37 | 3.20E−04 | 199 | |
| 8170428 | MTM1 | −0.31 | 7.23 | 7.52 | 3.22E−04 | 200 | |

Abbreviations: TCID = transcript-cluster identity; Symbol = gene symbol; logFC = log fold-change; MedExpr.UIP = median expression level across the UIP samples; MedExpr.NonUIP = median expression level across the UIP samples; FDR = false discovery rate; Used by classifier = indicator of whether the gene is used by the microarray classifier.

The number and location of the samplings (upper vs. lower and central vs. peripheral) are indicated in FIG. 6 and IPF patient clinical characteristics in Table 4. To identify genes useful in measuring spatial heterogeneity, we looked for differential expression in normal versus IPF samples. This comparison produced 5,000 significantly differentially expressed RNA transcripts with FDR <0.05 (data not shown). We selected the top 200 differentially expressed genes and measured pairwise correlation. The results for the three patients diagnosed with IPF are shown in FIG. 1. Although correlation across all IPF samples is high, three distinct patterns emerge in the correlation structure among IPF samples. One patient (P1) shows substantial differences in upper vs. lower lobe gene expression i.e. lower correlation in gene signals. One patient (P3) shows higher correlation between the upper and lower lobe samplings. The third patient (P2) shows an intermediate result between these two cases, with sometimes higher, and sometimes lower, correlation between samplings from the upper and lower lobes. These results, while on a small number of patients, suggest that samples with lobe-specific pathology may be more accurate during the training phase of classifier development. Based on this information we prepared a classifier using SLB tissues with truth labels assigned at the sample level, using lobe-derived pathology. Our results, which are presented in Example 7, demonstrate the presence of a molecular signature in SLB tissues that classifies UIP and non-UIP samples with high prospective accuracy.

TABLE 4

| Clinical characteristics of three IPF explant patients. | | | | |
|---|---|---|---|---|
| Patient | Gender | Age | Smoking Status | Clinical Remarks |
| P1 | M | 49 | non-smoker | Exertional dyspnea for ~2 years prior to initial evaluation. Pre-transplant SLB demonstrated clear UIP pattern, no granuloma or bronchiolocentricity. Diagnosis of IPF at transplant reported patchy subpleural and paraseptal interstitial fibrosis, dense scarring and honeycombing by surgical pathology. No evidence of granuloma or extensive inflammation. |
| P2 | M | 68 | 50 pack years | Initial evaluation occurred almost immediately after first presentation of exertional dyspnea; progressive worsening over ~2.5 years. Pathology at transplant demonstrated end-stage lung disease, diffuse fibrosis, temporal heterogeneity and fibroblastic foci suggestive of UIP. |
| P3 | F | 64 | 24 pack years | Exertional dyspnea for ~2 years prior to initial evaluation, worsening over the last year. Possible occupational exposure. Pre-transplant SLB demonstrated UIP pattern with fibroblastic foci consistent with IPF. Pathology at transplant showed interstitial fibrosis, giant cell reaction, reorganization, bronchiectasis and reactive lymph node. |

Example 7

Performance of Microarray Classifier on Surgical Lung Biopsies

Using sample-specific pathology labels on biopsies obtained during VATS, a microarray classifier was trained by logistic regression on the top 200 genes separating UIP and non-UIP samples (see Table 12). A final model was built with 22 genes (Table 5).

Expression data was normalized by Robust Multi-array Average (RMA). Feature selection and model estimation were performed by logistic regression with lasso penalty using glmnet3. Raw reads were aligned using TopHat. Gene counts were obtained using HTSeq and normalized using DESeq. The top features (N ranging from 10 to 200) were used to train a linear support vector machine (SVM) using the e1071 library. Confidence intervals were computed using the pROC package.

Figure 2A:
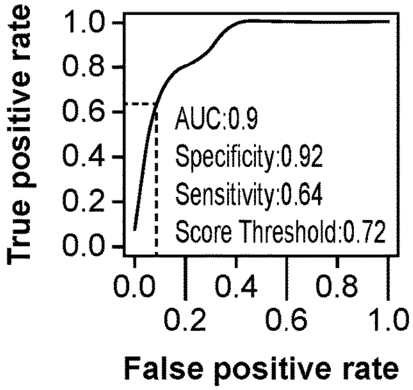
FIGS. 2A-2D. Performance of a classifier built using microarray data. ROC curves were used to characterize performance in the training set using leave-one-patient-out (LOPO) cross-validation (FIG. 2A) and in the independent test set by scoring the samples with a fixed model (FIG. 2C). Scores for individual samples are shown across patients in the training set (FIG. 2B), and across patients in an independent test set (FIG. 2D). Patient-level pathology diagnosis is shown on the x-axis. Samples with UIP pathology labels are indicated by closed circles, and non-UIP samples by pathology are shown in open triangles. A dotted horizontal line is drawn to indicate the threshold that corresponds to 92% specificity and 64% sensitivity (FIG. 2B) and 92% specificity and 82% sensitivity (FIG. 2D).
Figure 2B:
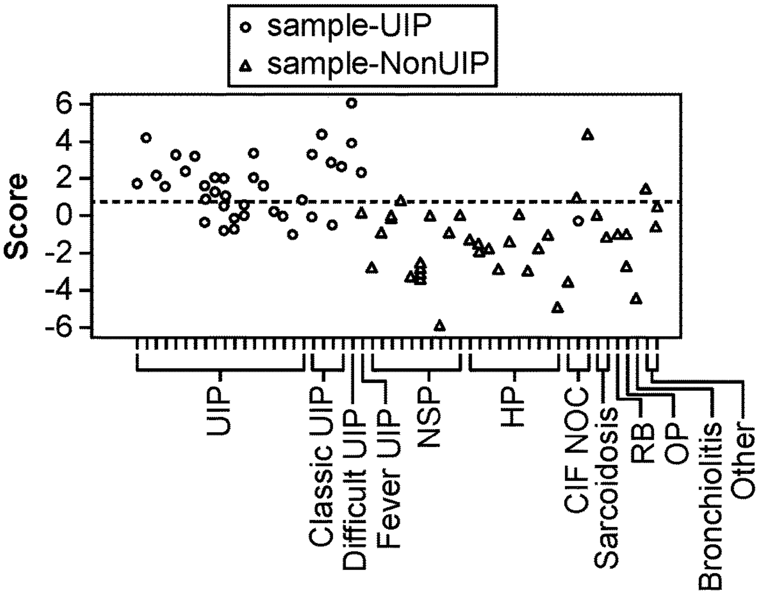

LOPO CV performance is summarized as a receiver operating characteristic (ROC) curve (FIG. 2A). The AUC is 0.9 [CI 0.82-0.96], with 92% [CI 84%400%] specificity and 64% [CI 49%-79%] sensitivity. Individual LOPO CV classification scores are shown for all patients (FIG. 2B). Among the three misclassified non-UIP samples, two have scores very close to the threshold (0.86 and 1.30), and one has a high score (421). The latter sample with the high score was diagnosed as an 'unclassifiable fibrotic ILD' at both the sample- and patient-level. Among the UIP samples, fifteen (36%) have a score below the threshold (false negatives) but none of those samples have a large negative score. Since LOPO CV in certain cases has the potential to overestimate performance, we also evaluated 10-fold patient-level CV (i.e., 10% of patients are left out in each loop) which gives very similar performance (the median AUC from five repeated 10-fold CVs is 0.88).

TABLE 5

| Twenty two genes included in a preferred array classifier. | | | | | |
|---|---|---|---|---|---|
| TCID | SYMBOL (SEQ ID NO.) | logFC | MedExpr.UIP | MedExpr.NonUIP | FDR |
| 8117760 | HLA-F (1) | −0.48 | 9.02 | 9.53 | 2.35E−09 |
| 8101031 | CDKL2 (2) | −0.95 | 7.31 | 8.16 | 1.29E−07 |
| 8106827 | GPR98 (3) | −0.77 | 6.11 | 6.74 | 2.16E−07 |
| 7931930 | PRKCQ (4) | −0.64 | 6.78 | 7.4 | 1.81E−06 |
| 8177725 | HLA-G (5) | −0.29 | 10.67 | 10.89 | 2.37E−06 |

TABLE 5-continued

Twenty two genes included in a preferred array classifier.

| TCID | SYMBOL (SEQ ID NO.) | logFC | MedExpr.UIP | MedExpr.NonUIP | FDR |
|---|---|---|---|---|---|
| 7926037 | PFKFB3 (6) | −0.45 | 7.66 | 8.1 | 2.81E−06 |
| 8037205 | CEACAM1 (7) | −0.41 | 6.47 | 6.97 | 3.04E−06 |
| 7907492 | RABGAP1L (8) | −0.32 | 8.01 | 8.33 | 3.88E−06 |
| 8154233 | CD274 (9) | −0.84 | 6.35 | 7.14 | 4.54E−06 |
| 8161865 | PRUNE2 (10) | 0.79 | 7.44 | 6.75 | 7.05E−06 |
| 8099760 | ARAP2 (11) | −0.41 | 7.55 | 7.9 | 1.06E−05 |
| 7972336 | DZIP1 (12) | 0.33 | 7.72 | 7.47 | 1.16E−05 |
| 8056217 | MXRA7 (13) | 0.4 | 8.58 | 8.29 | 1.21E−05 |
| 8126853 | PTCHD4 (14) | 0.75 | 7.02 | 6.07 | 4.27E−05 |
| 8104022 | PDLIM3 (15) | 0.58 | 8.33 | 7.63 | 5.03E−05 |
| 8025918 | CNN1 (16) | 0.86 | 8.39 | 7.52 | 5.43E−05 |
| 8157027 | NIPSNAP3B (17) | 0.29 | 5.25 | 4.98 | 5.62E−05 |
| 7913858 | PAQR7 (18) | 0.22 | 6.58 | 6.38 | 1.46E−04 |
| 8042788 | ACTG2 (19) | 0.98 | 10.11 | 9.21 | 1.79E−04 |
| 8173924 | NA (20) | −0.95 | 5.22 | 6.25 | 2.03E−04 |
| 8018966 | TIMP2 (21) | 0.18 | 10.53 | 10.34 | 3.09E−04 |
| 8048541 | DES (22) | 0.71 | 8.81 | 8.19 | 3.20E−04 |

Abbreviations:

TCID = transcript-cluster identify; Symbol = gene symbol; logFC = log fold-change; MedExpr.UIP = median expression level across the UIP samples; MedExpr.NonUIP = median expression level across the UIP samples; FDR = false discovery rate.

Figure 2C:
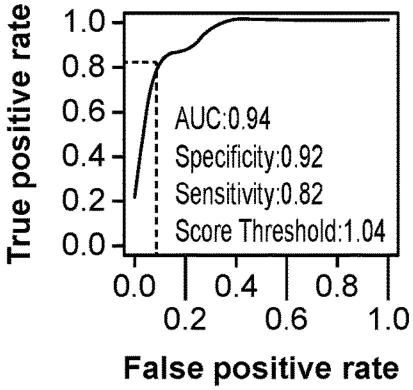
Figure 2D:
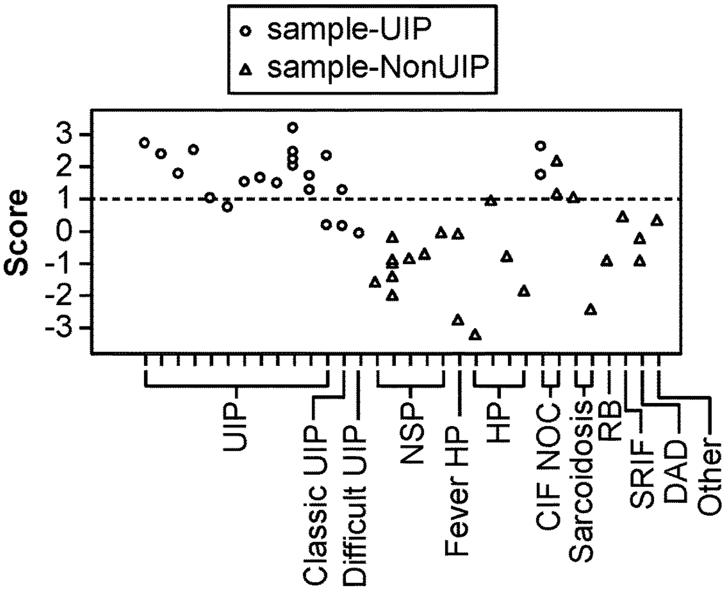

Independent test set performance is shown in FIG. 2C showing an AUC of 0.94 [CI 0.86-0.99], with 92% [CI 81%400%] specificity and 82% [CI 64%-95%] sensitivity. The individual classification score distribution shows good separation between UIP and non-UIP classes (FIG. 2D). The two misclassified non-UIP samples have both patient- and sample-level expert diagnoses of 'unclassifiable fibrotic ILD' indicating uncertainty in the diagnosis. The score range observed in the test set (FIG. 2D) is narrower than the range seen in LOPO CV scores (FIG. 2B), likely due to the larger variability inherent in applying a series of sub-classifiers within each CV loop, compared to scores obtained by applying a single model. Classification performance including 95% confidence intervals are summarized in Table 6.

TABLE 6

Classifier performance summary, including 95% confidence intervals (CI).

| | Array classifier (LOPO CV) | Array classifier (Testing) | RNASeq classifier (LOPO CV) | RNASeqSet-matched array classifier (LOPO CV) |
|---|---|---|---|---|
| AUC [95% CI] | 0.90 [0.82-0.96] | 0.94 [0.86-0.99] | 0.90 [0.77-1.00] | 0.86 [0.73-0.96] |
| Specificity [95% CI] | 92% [84%-100%] | 92% [81%-100%] | 95% [84%-100%] | 95% [84%-100%] |
| Sensitivity [95% CI] | 64% [49%-79%] | 82% [64%-95%] | 59% [35%-82%] | 47% [24%-71%] |
| Threshold | 0.72 | 1.04 | 0.64 | 1 |
| False positive count | 3 | 2 | 1 | 1 |
| True negative count | 35 | 24 | 18 | 18 |
| False negative count | 14 | 4 | 7 | 9 |

TABLE 6-continued

Classifier performance summary, including 95% confidence intervals (CI).

| | Array classifier (LOPO CV) | Array classifier (Testing) | RNASeq classifier (LOPO CV) | RNASeqSet-matched array classifier (LOPO CV) |
|---|---|---|---|---|
| True negative count | 25 | 18 | 10 | 8 |
| Total | 77 | 48 | 36 | 36 |

Our approach offers significant advantages. Earlier gene-expression profiling studies focused on comparing IPF versus a few non-IPF ILD subtypes such as HP or NSIP, or against subjects without ILD[18,19,23,25]. The non-UIP cohort reported here represents a broad spectrum of pathology subtypes including HP, NSIP, sarcoidosis, RB, bronchiolitis, organizing pneumonia (OP), and others, thus approximating the diversity of ILDs encountered in clinical practice. In addition, the classifier was trained and tested using a combination of banked and prospectively collected SLBs to ensure robustness against potential differences in sample handling and collection. Finally, many earlier studies focused on differential gene expression analyses alone, without building a classification engine. In contrast, our approach is a rigorous method for the development of molecular tests which, when properly trained and validated, generalized well to independent data sets.

Example 8

Performance of RNASeq Classifier on Surgical Lung Biopsies

Figure 3A:
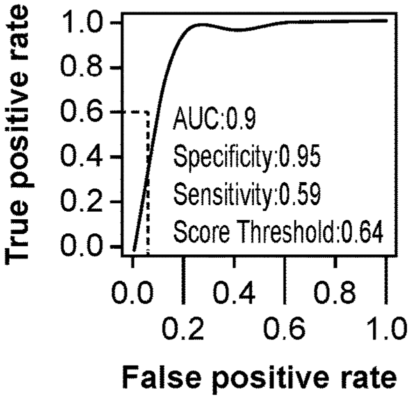
FIGS. 3A-3D. Performance of classifiers built using RNASeq (FIG. 3A and FIG. 3B) and microarray on the matched set (FIG. 3C and FIG. 3D). Leave-one-patient-out (LOPO) cross-validation was performed and receiver operator characteristic (ROC) curves were produced for RNASeq (FIG. 3A) and microarray (FIG. 3C) classifiers. Scores for individual samples in the training sets are shown for RNASeq (FIG. 3B), and microarray (FIG. 3D) classification. Patient-level pathology diagnosis is shown on the x-axis. Samples with UIP pathology labels are indicated by closed circles, and non-UIP samples by pathology are shown in open triangles. A score threshold corresponding to 95% specificity is indicated as a horizontal line in FIG. 3B and FIG. 3D.
Figure 3B:
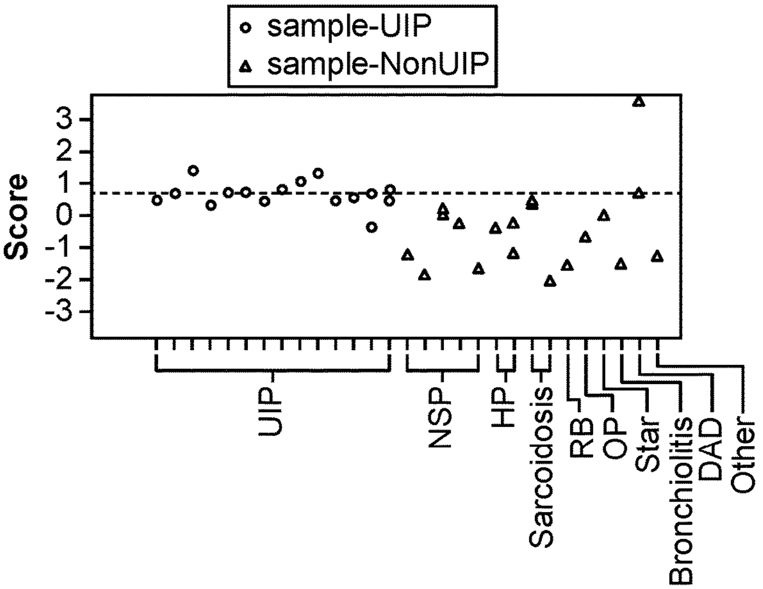
Figure 3C:
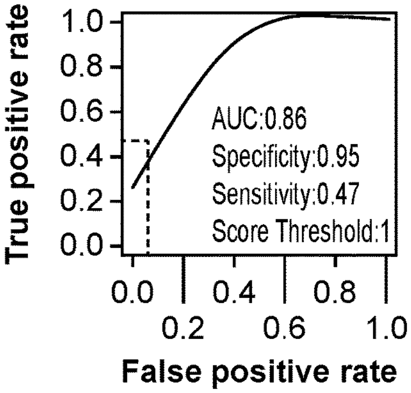
Figure 3D:
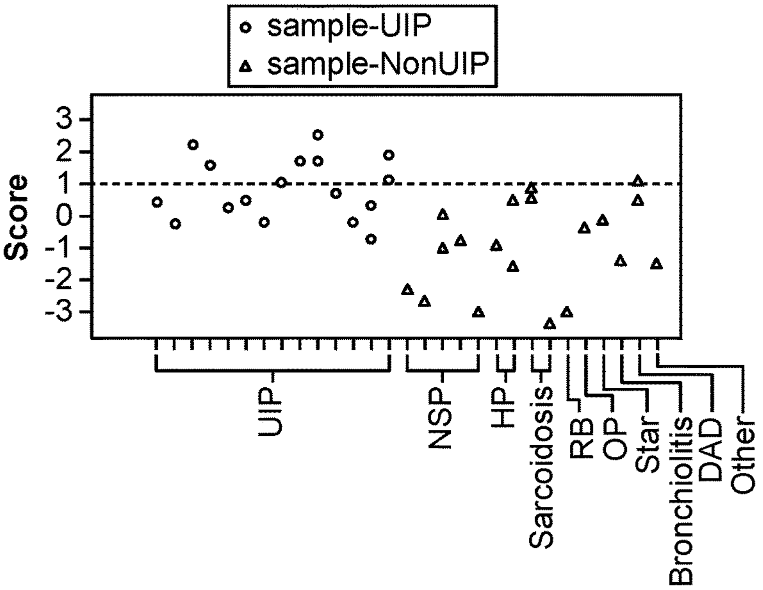

A subset of 36 samples with RNASeq data were used to train a linear SVM classifier and the performance evaluated by LOPO CV. AUCs are consistently above 0.80 for gene numbers spanning 10 to 200 (data not shown). We chose a model using 100 genes for further examination. The AUC is 0.9 [CI 0.77-1.00] (specificity=95% [CI 84%-100%], sensitivity=59% [CI 35%-82%]) (FIG. 3A). Only a single non-UIP sample is misclassified (FIG. 3B). The sample-level pathology for this sample is respiratory bronchiolitis (RB), and the patient-pathology is diffuse alveolar damage (DAD), two subtypes that may have been difficult to model because of their sparsity. We carried out a similar analysis using matching array data on the same set of samples; the array-based classifier achieves similar performance (AUC=0.86 [CI 0.73-0.96]) using 160 genes. Specificity is 95% [CI 84%400%] and sensitivity is 47% [CI 24%-71%] (FIG. 3C). Interestingly, the same non-UIP sample that was misclassified as a UIP by the RNASeq classifier is also misclassified by the microarray classifier (FIG. 3D). Overall, classification based on RNASeq achieves comparable performance to that of the array platform.

Example 9

Biological Pathways Associated with Genes Used by the Classifiers

To determine if there are common biological underpinnings across the genes selected by the machine learning process, we used over-representation analysis (ORA) to identify statistically significant participation of genes in selected pathways. Over/under-representation analyses (ORA) were performed using GeneTrail software (genetrail-.bioinf.uni-sb.de/) and the top 1,000 genes differentially expressed by limma between UIP and non-UIP samples (FDR <0.013) in the microarray testing set (n=77) as the ORA test sets. The ORA reference set included all human genes (n=44,829) and annotation in the KEGG pathways and gene ontology (GO) databases. Significance was evaluated via Fisher's exact test with a corrected FDR threshold of p<0.05.

In examining the top 1000 genes found in the UIP vs non-UIP comparison, distinct findings emerged (Table 2).

TABLE 2

Kyoto Encyclopedia of Genes and Genomes (KEGG) Pathways and Gene Ontologies (GO) over-represented in UIP and non-UIP samples. Categories in each sample cohort are ranked by FDR p value.

| Source | Category | No. expected | No. observed | ORA Proportion | FDR p value |
|---|---|---|---|---|---|
| | Over-represented in UIP | | | | |
| GO | Extracellular matrix | 5 | 31 | 6.2 | 1.46E−12 |
| GO | Muscle system process | 5 | 23 | 4.6 | 1.21E−07 |
| GO | Cell migration/motility | 9 | 27 | 3.0 | 7.31E−06 |
| KEGG | Focal adhesion | 6 | 21 | 3.5 | 1.20E−05 |
| GO | Contractile fiber | 2 | 12 | 6.0 | 1.73E−05 |
| KEGG | Calcium signaling, pathway | 5 | 18 | 3.6 | 5.38E−05 |
| KEGG | Dilated cardiomyopathy | 3 | 13 | 4.3 | 5.38E−05 |
| KEGG | ECM-receptor interaction | 2 | 12 | 6.0 | 5.95E−05 |
| KEGG | Vascular Muscle contraction | 3 | 14 | 4.7 | 5.95E−05 |
| KEGG | Hypertropic cardiomyopathy (HCM) | 2 | 11 | 5.5 | 2.90E−04 |
| KEGG | Arrhythmogenic right ventricular cardiomyopathy (ARVC) | 2 | 9 | 4.5 | 2.82E−03 |
| KEGG | Regulation of Actin cytoskeleton | 6 | 16 | 2.7 | 3.39E−03 |
| KEGG | Melanoma | 2 | 8 | 4.0 | 6.26E−03 |

TABLE 2-continued

Kyoto Encyclopedia of Genes and Genomes (KEGG) Pathways and Gene Ontologies (GO) over-represented in UIP and non-UIP samples. Categories in each sample cohort are ranked by FDR p value.

| Source | Category | No. expected | No. observed | ORA Proportion | FDR p value |
|---|---|---|---|---|---|
| KEGG | Cardiac muscle contraction | 2 | 7 | 3.5 | 4.53E−02 |
| KEGG | MAPK signaling pathway | 8 | 15 | 1.9 | 4.76E−02 |
| | Over-represented in non-UIP | | | | |
| KEGG | Allograft rejection | 1 | 15 | 15.0 | 9.25E−12 |
| KEGG | Cell adhesion molecules | 4 | 25 | 6.3 | 9.25E−12 |
| KEGG | Antigen processing and presentation | 2 | 19 | 9.5 | 3.40E−11 |
| KEGG | Type I diabetes mellitus | 1 | 14 | 14.0 | 5.95E−10 |
| GO | Immune response | 13 | 42 | 3.2 | 6.52E−09 |
| KEGG | Autoimmune thyroid disorder | 2 | 14 | 7.0 | 6.72E−09 |
| KEGG | Viral myocarditis | 2 | 16 | 8.0 | 6.72E−09 |
| KEGG | Phagosome | 5 | 20 | 4.0 | 7.01E−07 |
| GO | MHC class I receptor activity | 1 | 7 | 7.0 | 2.66E−05 |
| KEGG | Systemic lupus erythematosus | 4 | 16 | 4.0 | 6.11E−05 |
| KEGG | Leishmaniasis | 2 | 11 | 5.5 | 1.14E−04 |
| GO | Innate immune response | 3 | 14 | 4.7 | 2.34E−04 |
| KEGG | Asthma | 1 | 7 | 7.0 | 2.83E−04 |
| GO | Signal transducer activity | 24 | 48 | 2 | 3.44E−04 |
| GO | Antigen processing and presentation of endogenous antigen | 1 | 4 | 4 | 7.50E−04 |
| KEGG | Intestinal immune network for IgA production | 2 | 8 | 4.0 | 8.40E−04 |
| KEGG | Malaria | 2 | 8 | 4.0 | 1.04E−03 |
| GO | T cell activation | 3 | 12 | 4.0 | 1.58E−03 |
| KEGG | Natural killer cell mediated cytotoxicity | 4 | 13 | 3.3 | 1.91E−03 |
| KEGG | Endocytosis | 6 | 16 | 2.7 | 3.42E−03 |
| KEGG | Steroid biosynthesis | 1 | 4 | 4.0 | 8.78E−03 |
| KEGG | Tight junction | 4 | 11 | 2.8 | 1.50E−02 |
| KEGG | Proteasome | 1 | 6 | 6.0 | 1.71E−02 |
| KEGG | Primary immunodeficiency | 1 | 5 | 5.0 | 1.89E−02 |
| KEGG | Toll-like receptor signaling | 3 | 9 | 3.0 | 1.89E−02 |

Abbreviations:
FDR = false discovery rate; GO = Gene Ontology; KEGG = Kyoto Encyclopedia of Genes and Genomes; ORA = over-representation analysis.

In UIP, genes involved in cell adhesion, muscle disease, cell migration and motility predominate. These results are consistent with previous reports of pathways differentially regulated in IPF[18,19,22,23]. In contrast, other non-UIP subtypes overexpress genes involved in immune processes, including both the adaptive and innate systems. This enrichment could be due to the RB and HP subtypes present in the non-UIP cohort; diseases known to exhibit immune components'. Genes over-represented in KEGG pathways and Gene Ontology groups are summarized in Tables 7 and 8.

TABLE 7

Genes over-represented in KEGG pathways and Gene Ontology groups of UIP samples. OVER-REPRESENTED IN UIP

| Source | Category | No. observed | Genes Observed |
|---|---|---|---|
| GO | Extracellular matrix | 31 | ABI3BP, ADAMTS3, AEBP1, CLU, COL14A1, COL15A1, COL1A2, COL21A1, COL6A1, COL6A2, CPXM2, DST, FBLN1, FBN1, FGF10, FMOD, HTRA1, LAMA4, LAMB2, LAMC1, LTBP1, MGP, NID1, PLAT, POSTN, SERPINF1, SFRP2, SNCA, SPON1, TNC, VCAN |
| GO | Muscle system process | 23 | ACTA2, ACTG2, AGT, ATP1A2, BDKRB2, CALD1, CNN1, CRYAB, DES, DTNA, IGF1, LMOD1, MYH11, MYL9, MYLK, MYOCD, SLC6A8, SSPN, TNNI2, TNNT3, TPM1, TPM2, TPM4 |
| GO | Cell migration/motility | 27 | ADRA2A, AGT, ANGPT2, CCL24, CXCL12, ENPP2, F10, FGF10, FGF7, IGF1, IGFBP5, ITGB3, KRT2, LAMC1, NEXN, NR2F2, PDGFRB, PODN, PPAP2A, ROR2, S100A2, SCG2, SFRP2, SLIT3, THY1, TPM1, VCAN |

TABLE 7-continued

Genes over-represented in KEGG pathways and Gene Ontology groups of UIP samples. OVER-REPRESENTED IN UIP

| Source | Category | No. observed | Genes Observed |
|---|---|---|---|
| KEGG | Focal adhesion | 21 | ACTN1, COLIA2, COL6A1, COL6A2, FLNC, HGF, IGF1, ITGA7, ITGB3, ITGB4, LAMA4, LAMB2, LAMC1, MYL9, MYLK, PARVA, PDGFD, PDGFRB, SHC4, SPP1, TNC |
| GO | Contractile fiber | 12 | DES, MYH11, MYL9, MYOM1, NEXN, PGM5, SVIL, TNNI2, TNNT3, TPM1, TPM2, TPM4 |
| KEGG | Calcium signaling, pathway | 18 | ADCY3, AVPR1A, BDKRB2, CACNA1C, GNAL, GRIN2A, HRH1, HTR2A, MYLK, P2RX1, PDE1A, PDGFRB, PLCB1, PLN, PTGER3, RYR3, TACR1, TRPC1 |
| KEGG | Dilated cardiomyopathy | 13 | ADCY3, ADCY5, CACNA1C, CACNA2D1, DES, IGF1, ITGA7, ITGB3, ITGB4, PLN, TPM1, TPM2, TPM4 |
| KEGG | ECM-receptor interaction | 12 | COL1A2, COL6A1, COL6A2, ITGA7, ITGB3, ITGB4, LAMA4, LAMB2, LAMC1, SPP1, SV2A, TNC |
| KEGG | Vascular Muscle contraction | 14 | ACTA2, ACTG2, ADCY3, ADCY5, AVPR1A, CACNA1C, CALD1, KCNMB1, MRVI1, MYH11, MYL9, MYLK, PLA2G2A, PLCB1, |
| KEGG | Hypertropic cardiomyopathy (HCM) | 11 | CACNA1C, CACNA2D1, DES, IGF1, ITGA7, ITGB3, ITGB4, PRKAA2, TPM1, TPM2, TPM4 |
| KEGG | Arrhythmogenic right ventricular cardiomyopathy (ARVC) | 9 | ACTN1, CACNA1C, CACNA2D1, CDH2, DES, ITGA7, ITGB3, ITGB4, PKP2 |
| KEGG | Regulation of Actin cytoskeleton | 16 | ACTN1, BDKRB2, ENAH, FGF10, FGF14, FGF7, FGFR1, GNG12, ITGA7, ITGB3, ITGB4, MRAS, MYL9, MYLK, PDGFD, PDGFRB |
| KEGG | Melanoma | 8 | FGF10, FGF14, FGF7, FGFR1, HGF, IGF1, PDGFD, PDGFRB |
| KEGG | Cardiac muscle contraction | 7 | ATP1A2, ATP1B2, CACNA1C, CACNA2D1, TPM1, TPM2, TPM4 |
| KEGG | MAPK signaling pathway | 15 | CACNA1C, CACNA2D1, FGF10, FGF14, FGF7, FGFR1, FLNC, GNG12, HSPA2, MAP4K4, MRAS, NFATC4, PDGFRB, PLA2G2A, ZAK |

TABLE 8

Genes over-represented in KEGG pathways and Gene Ontology groups of non-UIP samples, OVER-REPRESENTED IN non-UIP

| Source | Category | No. observed | Genes Observed |
|---|---|---|---|
| KEGG | Allograft rejection | 15 | CD40, FASLG, HLA-A, HLA-B, HLA-C, HLA-DMA, HLA-DOA, HLA-DPA1, HLA-DPB1, HLA-DQA1, HLA-DRA, HLA-E, HLA-F, HLA-G, IFNG |
| KEGG | Cell adhesion molecules | 25 | CADM1, CD2, CD274, CD40, CD8A, CLDN18, CLDN4, F11R, HLA-A, HLA-B, HLA-C, HLA-, DMA, HLA-DOA, HLA-DPA1, HLA-DPB1, HLA-DQA1, HLA-DRA, HLA-E, HLA-F, HLA-G, ICAM1, ICOS, ITGAL, OCLN, SDC4 |
| KEGG | Antigen processing and presentation | 19 | CD74, CD8A, HLA-A, HLA-B, HLA-C, HLA-DMA, HLA-DOA, HLA-DPA1, HLA-DPB1, HLA-, DQA1, HLA-DRA, HLA-E, HLA-F, HLA-G, IFNG, PSME1, PSME2, TAP1, TAP2 |
| KEGG | Type I diabetes mellitus | 14 | FASLG, HLA-A, HLA-B, HLA-C, HLA-DMA, HLA-DOA, HLA-DPA1, HLA-DPB1, HLA-, DQA1, HLA-DRA, HLA-E, HLA-F, HLA-G, IFNG |
| GO | Immune response | 42 | APOBEC3G, AQP4, BST2, C2, CADM1, CCR5, CD274, CD74, CD8A, CRTAM, CTSC, CTSW, CXCL16, ERAP1, FCGR1A, FCGR1B, FCGR3A, GBP2, GCH1, GZMA, HLA-A, HLA-B, HLA-C, HLA-DPA1, HLA-DQA1, |

TABLE 8-continued

Genes over-represented in KEGG pathways and Gene Ontology groups of non-UIP samples, OVER-REPRESENTED IN non-UIP

| Source | Category | No. observed | Genes Observed |
|---|---|---|---|
| | | | HLA-DRA, HLA-H, ICAM1, ICOS, IL32, ITGAL, MICB, NUB1, PLA2G1B, PSMB10, S100A14, SFTPD, SKAP1, THEMIS, TLR2, TLR3, UBD |
| KEGG | Autoimmune thyroid disorder | 14 | CD40, FASLG, HLA-A, HLA-B, HLA-C, HLA-DMA, HLA-DOA, HLA-DPA1, HLA-DPB1, HLADQA1, HLA-DRA, HLA-E, HLA-F, HLA-G |
| KEGG | Viral myocarditis | 16 | CD40, HLA-A, HLA-B, HLA-C, HLA-DMA, HLA-DOA, HLA-DPA1, HLA-DPB1, HLA-DQA1, HLA-DRA, HLA-E, HLA-F, HLA-G, ICAM1, ITGAL, MYH14 |
| KEGG | Phagosome | 20 | ATP6V0D1, FCGR1A, FCGR3A, HLA-A, HLA-B, HLA-C, HLA-DMA, HLA-DOA, HLA-, DPA1, HLA-DPB1, HLA-DQA1, HLA-DRA, HLA-E, HLA-F, HLA-G, SFTPA1, SFTPD, TAP1, TAP2, TLR2 |
| GO | MHC class I receptor activity | 7 | HLA-A, HLA-B, HLA-C, HLA-E, HLA-F, HLA-G, HLA-H |
| KEGG | Systemic lupus erythematosus | 16 | C2, CD40, FCGR1A, FCGR3A, HIST1H2BJ, HIST1H3F, HIST1H4E, HIST2H2BE, HLA-, DMA, HLA-DOA, HLA-DPA1, HLA-DPB1, HLA-DQA1, HLA-DRA, IFNG, TRIM21 |
| KEGG | Leishmaniasis | 11 | FCGR1A, FCGR3A, HLA-DMA, HLA-DOA, HLA-DPA1, HLA-DPB1, HLA-DQA1, HLA-, DRA, IFNG, STAT1, TLR2 |
| GO | Innate immune response | 14 | APOBEC3G, AQP4, C2, CADM1, CRTAM, CXCL16, ERAP1, GCH1, NUB1, S100A14, SFTPD, TLR2, TLR3, UBD |
| KEGG | Asthma | 7 | CD40, HLA-DMA, HLA-DOA, HLA-DPA1, HLA-DPB1, HLA-DQA1, HLA-DRA |
| GO | Signal transducer activity | 48 | AGER, BST2, CCL4, CCL5, CCR5, CD2, CD40, CD47, CD74, CD8A, CLDN4, CXCL16, CXCR6, EBP, ERBB3, FCGR1A, FCGR1B, FGFR2, FLRT3, FZD5, GPR98, HLA-A, HLA-B, HLA-C, HLA-DOA, HLA-DPA1, HLA-DQA1, HLA-DRA, HLA-E, HLA-F, HLA-G, HLA-H, ICAM1, IL2RB, KLRB1, LDLR, MAP3K13, PTPRJ, SCTR, SDC4, SH2D1A, SKAP1, STAT1, TAPT1, TLR2, TLR3, TP53BP2, UNC13B |
| GO | Antigen processing and presentation of endogenous antigen | 4 | CD74, ERAP1, TAP1, TAP2 |
| KEGG | Intestinal immune network for IgA production | 8 | CD40, HLA-DMA, HLA-DOA, HLA-DPA1, HLA-DPB1, HLA-DQA1, HLA-DRA, ICOS |
| KEGG | Malaria | 8 | CD40, ICAM1, IFNG, ITGAL, KLRB1, KLRK1, SDC4, TLR2 |
| GO | T cell activation | 12 | CADM1, CD2, CD47, CD74, CD8A, CRTAM, ICAM1, ITGAL, KLRK1, MICB, SFTPD, THEMIS |
| KEGG | Natural killer cell mediated cytotoxicity | 13 | FASLG, FCGR3A, HLA-A, HLA-B, HLA-C, HLA-E, HLA-G, ICAM1, IFNG, ITGAL, KLRK1, MICB, SH2D1A |
| KEGG | Endocytosis | 16 | ARAP2, CCR5, DNM2, ERBB3, FGFR2, HLA-A, HLA-B, HLA-C, HLA-E, HLA-F, HLA-G, IL2RB, LDLR, NEDD4L, PARD6B, PRKCZ |
| KEGG | Steroid biosynthesis | 4 | DHCR24, EBP, FDFT1, SQLE |
| KEGG | Tight junction | 11 | CLDN18, CLDN4, F11R, INADL, LLGL2, MAGI3, MYH14, OCLN, PARD6B, PRKCQ, PRKCZ |
| KEGG | Proteasome | 6 | IFNG, PSMB10, PSMB8, PSMB9, PSME1, PSME2 |
| KEGG | Primary immunodeficiency | 5 | CD40, CD8A, ICOS, TAP1, TAP2 |
| KEGG | Toll-like receptor signaling | 9 | CCL4, CCL5, CD40, CXCL10, CXCL11, CXCL9, STAT1, TLR2, TLR3 |

Example 10

Mislabeling Simulation Study

A simulation study swapping binary classification labels (UIP or non-UIP) was performed on the microarray training set. Samples were selected at random for label permutation, at total proportions per simulation set ranging from 1% to 40%. The level of agreement in the blinded review of the three expert pathology diagnoses is 3/3 (n=44), 2/2 (n=8), 2/3 (n=24), and 1/3 (n=1). Sample labels were changed to the other class with a weight proportional to the probability accounting for the disagreement level in the blinded review of the three expert pathologists: 5% for 3/3 or 2/2 agreement, 50% for 2/3 agreement, and 90% for 1/3 agreement. Simulations were repeated 100 times at each proportion.

Figure 4:
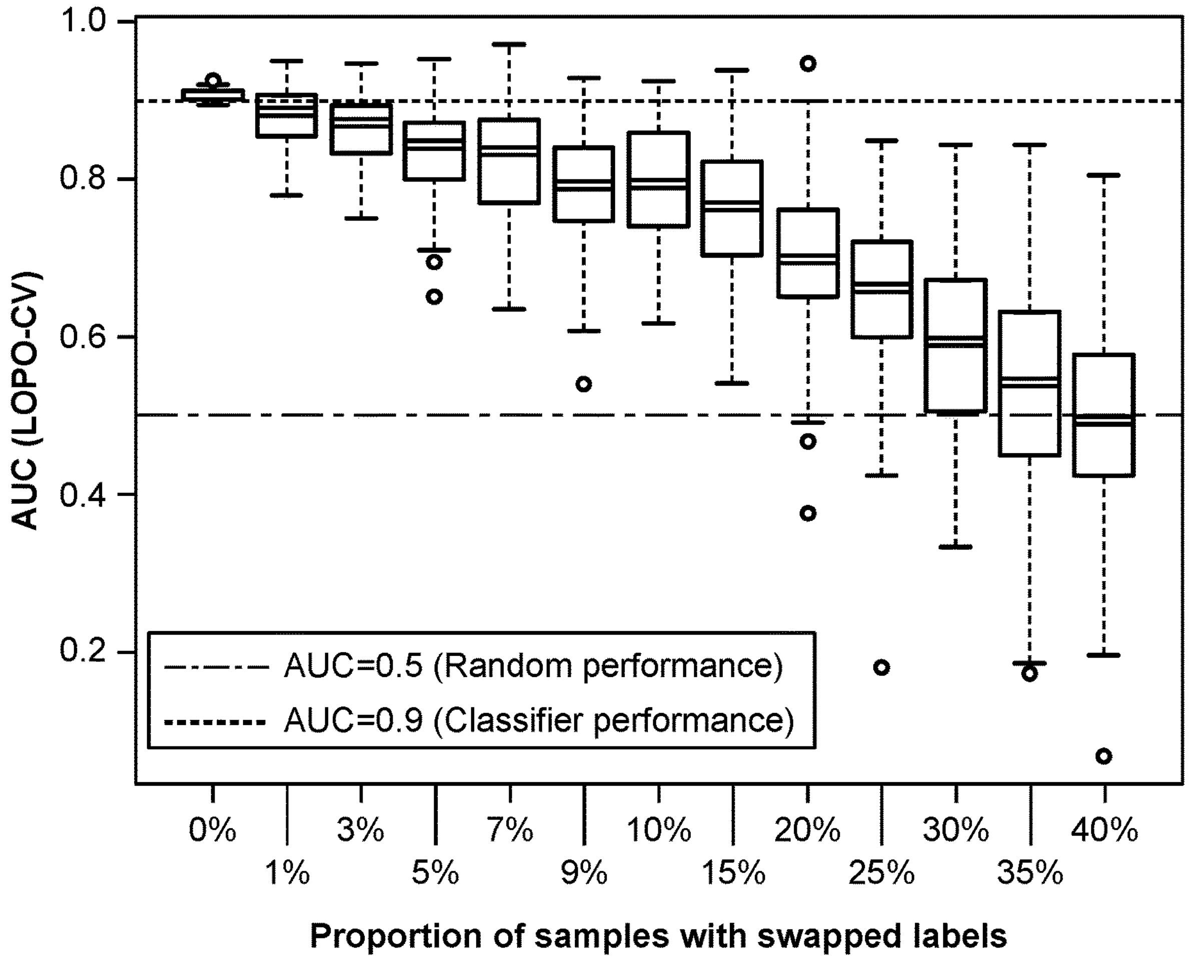
FIG. 4. Simulation study assessing the impact of mislabeling on the classification performance. The array training set (n=77) was used for this study. At a given proportion of swapped labels in the data set (x-axis), individual samples' classification labels were swapped to another class label with a weight accounting for the disagreement level of three expert pathology diagnoses. Each boxplot was drawn using LOPO CV performances (AUC) from 100 repeated simulations. The finer dotted horizontal line at AUC=0.5 represents random performance, i.e., no classification, and the coarser dotted line corresponds to the classifier performance shown in FIG. 2A.

The LOPO CV performance (AUC) was evaluated over 100 repeated simulations across a range of proportion of swapped labels (FIG. 4). When there is no label swap, the median performance is very close to the array classifier performance shown in FIG. 2A (AUC=0.9). (Using the same set of samples and labels, model estimation can have slight variability). As the swap rate increases, the performance decreases monotonically. When 40% of the labels are swapped, the median performance approaches 0.5, indicating classification is no better than random chance.

Example 11

Magnitude and direction of UIP/Non-UIP differential gene expression differs in smoker vs. non-smoker test subjects.

Interstitial lung diseases are more prevalent in persons that smoke, or have had a long history of smoking prior to quitting, than in persons who never smoked. We compared differential gene expression profiles of samples derived from smoker and non-smoker UIP or non-UIP subjects to determine if smoking status affects performance of UIP diagnostic classifiers.

Transbronchial biopsy samples were prepared [according to the methods described in Examples 1 and 2, and RNA sequencing analysis was performed according to the method described in Example 3]. RNASeq data was generated for a subset of 24 samples (9 UIP and 15 non-UIP), and differential gene expression was analyzed according to three binary comparisons: (i) UIP vs. non-UIP, n=9 and 15 samples, respectively; (ii) Non-smoker UIP vs. Non-smoker non-UIP, n=3 and 5 samples, respectively; and (iii) Smoker UIP vs. Smoker non-UIP, n=12 and 4 samples, respectively.

Figures 8, 9:
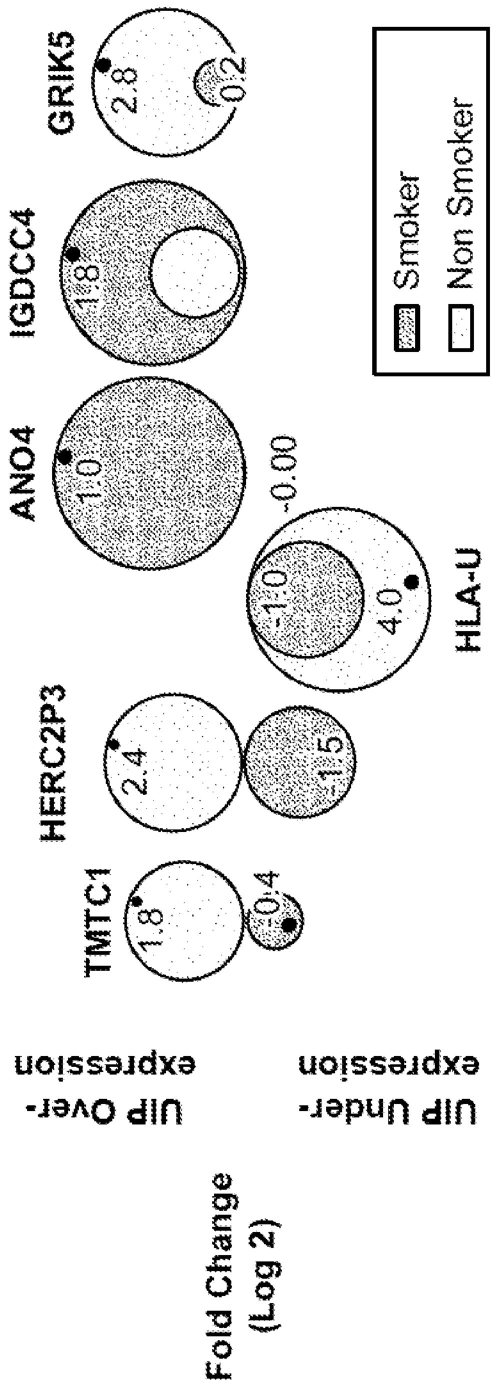
FIG. 8. Differential gene expression in UIP and Non-UIP samples between smokers and non-smokers. The number of genes differentially expressed between UIP and Non UIP samples differs drastically between smokers and non-smokers.
FIG. 9. Shows differential gene expression between UIP and Non-UIP samples is susceptible to smoker-status bias. Direction (i.e., over- vs. under-expression) and magnitude (circle size) of differential gene expression is confounded by smoking status.
Figure 10A:
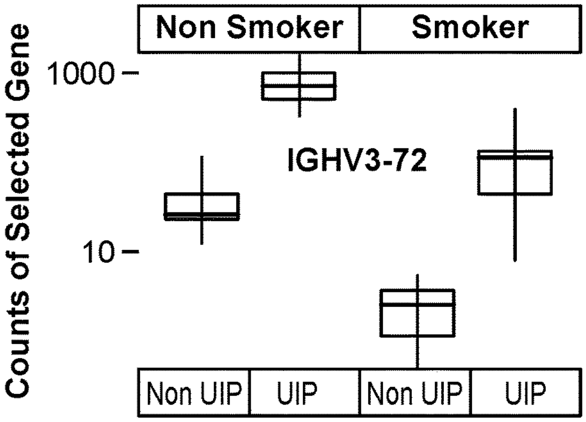
FIGS. 10A-10D. Examples of genes that are differentially expressed in UIP vs. Non-UIP and the effect of smoking status on expression levels.
Figure 10B:
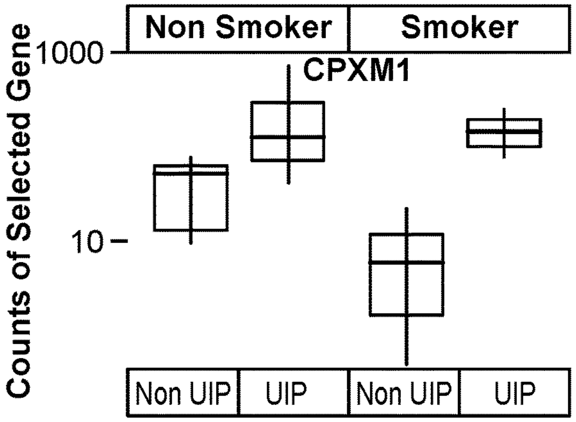
Figure 10C:
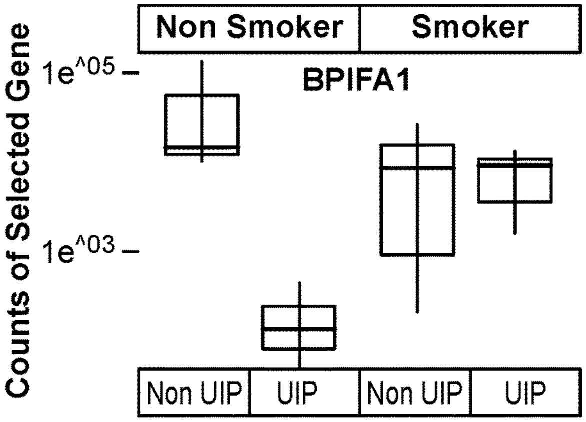
Figure 10D:
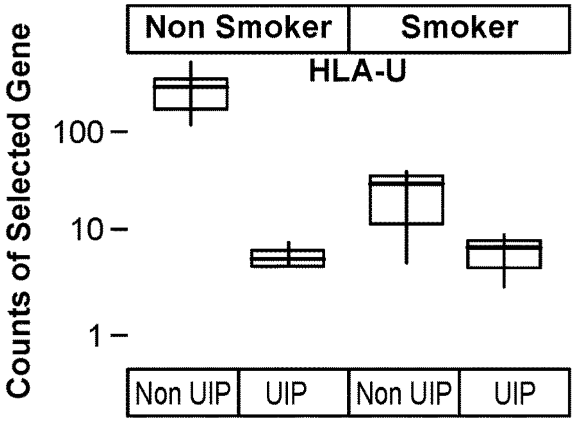

The results of the expression analysis for groups (i) to (iii) are shown in Tables 9 to 11, respectively, and are summarized in FIGS. 8-10. The number of genes differentially expressed between UIP and Non UIP samples differs drastically between smokers and non-smokers (64 differentially expressed in samples from smokers, 671 differentially expressed in samples from non-smokers) (FIG. 8). Moreover, certain genes that were differentially upregulated in non-smokers were downregulated on not differentially expressed in smokers (FIGS. 9 and 10). These data demonstrate that certain genes that are useful in UIP classification of samples from non-smokers are not informative, or can be contradictory in the diagnosis of the same disease, in smokers. Smoker-status differences in gene expression can reduce the performance of gene expression classifier predictions generated using traditional 2-class machine learning methods. We overcome this problem using three different techniques that are optionally combined or used individually in combination with the UIP vs. Non-UIP classifiers and methods of diagnosis UIP vs. Non-UIP via the diagnostic methods disclosed herein.

In a first approach, smoking status (smoker vs. non-smoker) is used as a covariate in the model during training. This simple approach boosts signal-to-noise ratio, particularly in data derived from smokers (were noise is higher) and allows data derived from smokers and non-smokers to be combined and used simultaneously.

In a second approach, genes that are susceptible to smoker-status bias are identified and excluded, or optionally weighted differently than genes that are not susceptible to such bias, during classifier training. This method enriches the feature space used for training with genes that are not confounded or affected by smoking status.

In a third approach, a tiered classification effort is utilized in which an initial classifier is trained to recognize gene signatures that distinguish smokers from non-smokers. Once patient samples are pre-classified as "smoker" or "non-smoker", distinct classifiers that were each trained to distinguish UIP vs. Non UIP in smokers or non-smokers, respectively, are implemented. Such smoker or non-smoker-specific classifiers provide improved diagnostic performance.

TABLE 9

Differentially expressed genes in UIP vs. Non-UIP samples, irrespective of smoker status.

| Table 9. All samples Ensembl ID | Entrez ID | Gene symbol | log2 Fold Change (UIP/NonUIP) | p value | FDR p value |
|---|---|---|---|---|---|
| ENSG00000204256 | 6046 | BRD2 | −0.30 | 4.03E−11 | 6.40E−07 |
| ENSG00000129204 | 9098 | USP6 | 1.88 | 2.57E−10 | 2.04E−06 |
| ENSG00000148357 | 256158 | HMCN2 | 1.71 | 1.62E−08 | 8.58E−05 |
| ENSG00000178031 | 92949 | ADAMTSL1 | 1.69 | 1.23E−07 | 4.83E−04 |
| ENSG00000112130 | 9025 | RNF8 | −0.40 | 1.52E−07 | 4.83E−04 |
| ENSG00000197705 | 57565 | KLHL14 | 1.58 | 1.97E−07 | 5.21E−04 |
| ENSG00000204632 | 3135 | HLA-G | −1.65 | 4.51E−07 | 1.02E−03 |
| ENSG00000157064 | 23057 | NMNAT2 | 1.47 | 6.62E−07 | 1.31E−03 |
| ENSG00000112245 | 7803 | PTP4A1 | −0.59 | 1.38E−06 | 2.43E−03 |
| ENSG00000114115 | 5947 | RBP1 | 0.95 | 1.69E−06 | 2.68E−03 |
| ENSG00000152413 | 9456 | HOMER1 | −0.48 | 2.30E−06 | 3.32E−03 |
| ENSG00000143603 | 3782 | KCNN3 | 0.81 | 2.85E−06 | 3.54E−03 |
| ENSG00000198074 | 57016 | AKR1B10 | −1.48 | 2.90E−06 | 3.54E−03 |
| ENSG00000160007 | 2909 | ARHGAP35 | −0.28 | 4.24E−06 | 4.49E−03 |
| ENSG00000076053 | 10179 | RBM7 | −0.30 | 4.23E−06 | 4.49E−03 |
| ENSG00000085563 | 5243 | ABCB1 | 1.40 | 5.90E−06 | 5.55E−03 |
| ENSG00000047365 | 116984 | ARAP2 | −0.60 | 5.95E−06 | 5.55E−03 |

TABLE 9-continued

Differentially expressed genes in UIP vs. Non-UIP samples, irrespective of smoker status.

| Table 9. All samples Ensembl ID | Entrez ID | Gene symbol | log2 Fold Change (UIP/NonUIP) | p value | FDR p value |
|---|---|---|---|---|---|
| ENSG00000130600 | 283120 | H19 | 1.45 | 7.10E−06 | 5.68E−03 |
| ENSG00000131355 | 84658 | ADGRE3 | 1.43 | 7.22E−06 | 5.68E−03 |
| ENSG00000135837 | 9857 | CEP350 | −0.23 | 6.63E−06 | 5.68E−03 |
| ENSG00000102221 | 9767 | JADE3 | −0.42 | 7.52E−06 | 5.68E−03 |
| ENSG00000105784 | 154661 | RUNDC3B | 1.31 | 1.02E−05 | 6.94E−03 |
| ENSG00000198734 | 2153 | F5 | 0.96 | 1.05E−05 | 6.94E−03 |
| ENSG00000124226 | 55905 | RNF114 | −0.39 | 1.04E−05 | 6.94E−03 |
| ENSG00000106852 | 26468 | LHX6 | 1.16 | 1.12E−05 | 7.10E−03 |
| ENSG00000183454 | 2903 | GRIN2A | 1.41 | 1.47E−05 | 8.93E−03 |
| ENSG00000170153 | 57484 | RNF150 | 1.04 | 1.54E−05 | 8.93E−03 |
| ENSG00000187527 | 344905 | ATP13A5 | −1.39 | 1.58E−05 | 8.93E−03 |
| ENSG00000244734 | 3043 | HBB | 1.40 | 1.71E−05 | 9.05E−03 |
| ENSG00000204936 | 57126 | CD177 | 1.40 | 1.67E−05 | 9.05E−03 |
| ENSG00000136560 | 10010 | TANK | −0.37 | 2.26E−05 | 1.16E−02 |
| ENSG00000196562 | 55959 | SULF2 | 0.98 | 2.87E−05 | 1.42E−02 |
| ENSG00000151789 | 79750 | ZNF385D | 1.36 | 3.17E−05 | 1.44E−02 |
| ENSG00000145808 | 171019 | ADAMTS19 | 1.07 | 3.14E−05 | 1.44E−02 |
| ENSG00000177666 | 57104 | PNPLA2 | −0.53 | 3.00E−05 | 1.44E−02 |
| ENSG00000007312 | 974 | CD79B | 1.31 | 3.51E−05 | 1.47E−02 |
| ENSG00000104213 | 5157 | PDGFRL | 1.24 | 3.53E−05 | 1.47E−02 |
| ENSG00000023171 | 57476 | GRAMD1B | −0.86 | 3.41E−05 | 1.47E−02 |
| ENSG00000117322 | 1380 | CR2 | 1.31 | 4.37E−05 | 1.78E−02 |
| ENSG00000171724 | 57687 | VAT1L | 1.33 | 4.51E−05 | 1.79E−02 |
| ENSG00000108852 | 4355 | MPP2 | 1.21 | 4.84E−05 | 1.87E−02 |
| ENSG00000136098 | 4752 | NEK3 | 0.51 | 5.00E−05 | 1.89E−02 |
| ENSG00000189056 | 5649 | RELN | 1.29 | 5.13E−05 | 1.89E−02 |
| ENSG00000054938 | 25884 | CHRDL2 | 1.30 | 6.70E−05 | 2.36E−02 |
| ENSG00000132704 | 79368 | FCRL2 | 1.30 | 6.62E−05 | 2.36E−02 |
| ENSG00000196628 | 6925 | TCF4 | 0.50 | 7.00E−05 | 2.41E−02 |
| ENSG00000142856 | 23421 | ITGB3BP | 0.55 | 7.32E−05 | 2.47E−02 |
| ENSG00000136153 | 4008 | LMO7 | −0.80 | 8.61E−05 | 2.85E−02 |
| ENSG00000203867 | 282996 | RBM20 | 1.20 | 9.01E−05 | 2.92E−02 |
| ENSG00000171049 | 2358 | FPR2 | 1.26 | 9.26E−05 | 2.94E−02 |
| ENSG00000152953 | 55351 | STK32B | 1.23 | 9.47E−05 | 2.95E−02 |
| ENSG00000099968 | 23786 | BCL2L13 | −0.37 | 9.73E−05 | 2.97E−02 |
| ENSG00000188536 | 3040 | HBA2 | 1.26 | 1.03E−04 | 3.00E−02 |
| ENSG00000198569 | 142680 | SLC34A3 | 0.94 | 1.04E−04 | 3.00E−02 |
| ENSG00000163701 | 132014 | IL17RE | −0.60 | 1.02E−04 | 3.00E−02 |
| ENSG00000197614 | 8076 | MFAP5 | 1.25 | 1.10E−04 | 3.12E−02 |
| ENSG00000146021 | 26249 | KLHL3 | 0.84 | 1.15E−04 | 3.19E−02 |
| ENSG00000156103 | 4325 | MMP16 | 1.25 | 1.21E−04 | 3.24E−02 |
| ENSG00000185022 | 23764 | MAFF | −1.05 | 1.20E−04 | 3.24E−02 |
| ENSG00000088882 | 56265 | CPXM1 | 1.22 | 1.32E−04 | 3.49E−02 |
| ENSG00000163032 | 7447 | VSNL1 | 0.78 | 1.38E−04 | 3.58E−02 |
| ENSG00000186184 | 51082 | POLR1D | −0.47 | 1.40E−04 | 3.58E−02 |
| ENSG00000177106 | 64787 | EPS8L2 | −0.52 | 1.42E−04 | 3.58E−02 |
| ENSG00000214711 | 440854 | CAPN14 | 1.23 | 1.44E−04 | 3.58E−02 |
| ENSG00000113212 | 56129 | PCDHB7 | 1.04 | 1.51E−04 | 3.64E−02 |
| ENSG00000001629 | 54467 | ANKIB1 | −0.22 | 1.52E−04 | 3.64E−02 |
| ENSG00000180871 | 3579 | CXCR2 | 1.20 | 1.79E−04 | 4.17E−02 |
| ENSG00000065618 | 1308 | COL17A1 | 1.04 | 1.79E−04 | 4.17E−02 |
| ENSG00000008394 | 4257 | MGST1 | −0.59 | 1.81E−04 | 4.17E−02 |
| ENSG00000185046 | 56899 | ANKS1B | 1.01 | 2.16E−04 | 4.82E−02 |
| ENSG00000165949 | 3429 | IFI27 | −1.05 | 2.14E−04 | 4.82E−02 |
| ENSG00000186847 | 3861 | KRT14 | 1.20 | 2.30E−04 | 5.04E−02 |
| ENSG00000136929 | 55363 | HEMGN | 1.19 | 2.35E−04 | 5.04E−02 |
| ENSG00000167107 | 80221 | ACSF2 | −0.55 | 2.35E−04 | 5.04E−02 |
| ENSG00000169129 | 84632 | AFAP1L2 | 0.87 | 2.45E−04 | 5.19E−02 |
| ENSG00000134762 | 1825 | DSC3 | 1.10 | 2.86E−04 | 5.88E−02 |
| ENSG00000212743 | NA | | 0.96 | 2.85E−04 | 5.88E−02 |
| ENSG00000149575 | 6327 | SCN2B | 1.13 | 3.00E−04 | 6.10E−02 |
| ENSG00000188257 | 5320 | PLA2G2A | 1.16 | 3.22E−04 | 6.15E−02 |
| ENSG00000102935 | 23090 | ZNF423 | 1.02 | 3.15E−04 | 6.15E−02 |
| ENSG00000143320 | 1382 | CRABP2 | 0.99 | 3.22E−04 | 6.15E−02 |
| ENSG00000138660 | 55435 | AP1AR | −0.49 | 3.07E−04 | 6.15E−02 |
| ENSG00000157601 | 4599 | MX1 | −0.88 | 3.15E−04 | 6.15E−02 |
| ENSG00000171847 | 55138 | FAM90A1 | 0.80 | 3.36E−04 | 6.22E−02 |
| ENSG00000115461 | 3488 | IGFBP5 | 0.71 | 3.37E−04 | 6.22E−02 |
| ENSG00000151632 | 1646 | AKR1C2 | −1.17 | 3.36E−04 | 6.22E−02 |
| ENSG00000189306 | 27341 | RRP7A | 0.44 | 3.42E−04 | 6.24E−02 |
| ENSG00000148541 | 220965 | FAM13C | 0.72 | 3.60E−04 | 6.49E−02 |
| ENSG00000111725 | 5564 | PRKAB1 | −0.49 | 3.65E−04 | 6.50E−02 |
| ENSG00000182885 | 222487 | ADGRG3 | 1.15 | 3.74E−04 | 6.54E−02 |
| ENSG00000206172 | 3039 | HBA1 | 1.15 | 3.80E−04 | 6.54E−02 |

TABLE 9-continued

Differentially expressed genes in UIP vs. Non-UIP samples, irrespective of smoker status.

| Table 9. All samples Ensembl ID | Entrez ID | Gene symbol | log2 Fold Change (UIP/NonUIP) | p value | FDR p value |
|---|---|---|---|---|---|
| ENSG00000157502 | 139221 | MUM1L1 | 1.09 | 3.77E−04 | 6.54E−02 |
| ENSG00000169891 | 9185 | REPS2 | −0.46 | 3.88E−04 | 6.54E−02 |
| ENSG00000129437 | 43847 | KLK14 | −1.09 | 3.85E−04 | 6.54E−02 |
| ENSG00000211956 | NA | IGHV4-34 | 1.15 | 3.93E−04 | 6.57E−02 |
| ENSG00000106483 | 6424 | SFRP4 | 1.15 | 4.19E−04 | 6.75E−02 |
| ENSG00000175879 | 3234 | HOXD8 | 1.13 | 4.36E−04 | 6.75E−02 |
| ENSG00000166947 | 2038 | EPB42 | 1.04 | 4.35E−04 | 6.75E−02 |
| ENSG00000028310 | 65980 | BRD9 | 0.17 | 4.15E−04 | 6.75E−02 |
| ENSG00000134046 | 8932 | MBD2 | −0.18 | 4.39E−04 | 6.75E−02 |
| ENSG00000011007 | 6924 | TCEB3 | −0.29 | 4.10E−04 | 6.75E−02 |
| ENSG00000198722 | 10497 | UNC13B | −0.46 | 4.24E−04 | 6.75E−02 |
| ENSG00000182795 | 79098 | C1orf116 | −0.80 | 4.33E−04 | 6.75E−02 |
| ENSG00000110042 | 23220 | DTX4 | −0.40 | 4.44E−04 | 6.78E−02 |
| ENSG00000169612 | 83640 | FAM103A1 | −0.67 | 4.56E−04 | 6.88E−02 |
| ENSG00000139517 | 222484 | LNX2 | −0.38 | 4.66E−04 | 6.98E−02 |
| ENSG00000165966 | 29951 | PDZRN4 | 1.14 | 4.80E−04 | 7.01E−02 |
| ENSG00000196109 | 163223 | ZNF676 | 1.12 | 4.81E−04 | 7.01E−02 |
| ENSG00000188517 | 84570 | COL25A1 | 1.12 | 4.86E−04 | 7.01E−02 |
| ENSG00000121898 | 119587 | CPXM2 | 1.07 | 4.83E−04 | 7.01E−02 |
| ENSG00000185739 | 6345 | SRL | 1.13 | 5.01E−04 | 7.10E−02 |
| ENSG00000166033 | 5654 | HTRA1 | 0.82 | 4.98E−04 | 7.10E−02 |
| ENSG00000179772 | 2307 | FOXS1 | 1.13 | 5.20E−04 | 7.17E−02 |
| ENSG00000172137 | 794 | CALB2 | 1.13 | 5.19E−04 | 7.17E−02 |
| ENSG00000086544 | 80271 | ITPKC | −0.42 | 5.15E−04 | 7.17E−02 |
| ENSG00000130513 | 9518 | GDF15 | −1.04 | 5.29E−04 | 7.17E−02 |
| ENSG00000129451 | 5655 | KLK10 | −1.05 | 5.26E−04 | 7.17E−02 |
| ENSG00000109472 | 1363 | CPE | 1.03 | 5.40E−04 | 7.20E−02 |
| ENSG00000171206 | 81603 | TRIM8 | −0.30 | 5.38E−04 | 7.20E−02 |
| ENSG00000128285 | 2847 | MCHR1 | 1.09 | 5.60E−04 | 7.40E−02 |
| ENSG00000197993 | 3792 | KEL | 1.08 | 5.68E−04 | 7.45E−02 |
| ENSG00000138642 | 55008 | HERC6 | −0.82 | 5.78E−04 | 7.51E−02 |
| ENSG00000162729 | 93185 | IGSF8 | 0.32 | 5.93E−04 | 7.65E−02 |
| ENSG00000105369 | 973 | CD79A | 1.11 | 6.54E−04 | 7.67E−02 |
| ENSG00000146374 | 84870 | RSPO3 | 1.11 | 6.56E−04 | 7.67E−02 |
| ENSG00000167483 | 199786 | FAM129C | 1.11 | 6.75E−04 | 7.67E−02 |
| ENSG00000205038 | 93035 | PKHD1L1 | 1.07 | 6.67E−04 | 7.67E−02 |
| ENSG00000158560 | 1780 | DYNC1I1 | 1.07 | 6.63E−04 | 7.67E−02 |
| ENSG00000101000 | 10544 | PROCR | 1.04 | 6.65E−04 | 7.67E−02 |
| ENSG00000197410 | 54798 | DCHS2 | 1.03 | 6.66E−04 | 7.67E−02 |
| ENSG00000137573 | 23213 | SULF1 | 1.02 | 6.74E−04 | 7.67E−02 |
| ENSG00000091972 | 4345 | CD200 | 1.01 | 6.81E−04 | 7.67E−02 |
| ENSG00000161381 | 57125 | PLXDC1 | 0.97 | 6.23E−04 | 7.67E−02 |
| ENSG00000067840 | 57595 | PDZD4 | 0.94 | 6.64E−04 | 7.67E−02 |
| ENSG00000244363 | NA | RPL7P23 | 0.77 | 6.71E−04 | 7.67E−02 |
| ENSG00000141698 | 115024 | NT5C3B | 0.41 | 6.51E−04 | 7.67E−02 |
| ENSG00000184056 | 26276 | VPS33B | 0.24 | 6.73E−04 | 7.67E−02 |
| ENSG00000226742 | 440498 | HSBP1L1 | −0.37 | 6.66E−04 | 7.67E−02 |
| ENSG00000064666 | 1265 | CNN2 | −0.38 | 6.73E−04 | 7.67E−02 |
| ENSG00000198142 | 65124 | SOWAHC | −0.53 | 6.36E−04 | 7.67E−02 |
| ENSG00000198183 | 51297 | BPIFA1 | −1.09 | 6.79E−04 | 7.67E−02 |
| ENSG00000185271 | 123103 | KLHL33 | 1.10 | 7.36E−04 | 7.96E−02 |
| ENSG00000143248 | 8490 | RGS5 | 1.10 | 7.26E−04 | 7.96E−02 |
| ENSG00000106018 | 7434 | VIPR2 | 1.10 | 7.45E−04 | 7.96E−02 |
| ENSG00000168542 | 1281 | COL3A1 | 1.10 | 7.33E−04 | 7.96E−02 |
| ENSG00000186105 | 100130733 | LRRC70 | 0.93 | 7.44E−04 | 7.96E−02 |
| ENSG00000265150 | NA | NA | 0.87 | 7.23E−04 | 7.96E−02 |
| ENSG00000172840 | 57546 | PDP2 | −0.34 | 7.47E−04 | 7.96E−02 |
| ENSG00000156675 | 80223 | RAB11FIP1 | −0.61 | 7.27E−04 | 7.96E−02 |
| ENSG00000108001 | 253738 | EBF3 | 1.10 | 7.84E−04 | 8.11E−02 |
| ENSG00000114948 | 8745 | ADAM23 | 1.08 | 7.82E−04 | 8.11E−02 |
| ENSG00000106404 | 24146 | CLDN15 | 1.08 | 7.73E−04 | 8.11E−02 |
| ENSG00000139910 | 4857 | NOVA1 | 1.07 | 7.92E−04 | 8.11E−02 |
| ENSG00000146802 | 64418 | TMEM168 | 0.33 | 7.92E−04 | 8.11E−02 |
| ENSG00000183486 | 4600 | MX2 | −0.91 | 7.89E−04 | 8.11E−02 |
| ENSG00000157766 | 176 | ACAN | 1.08 | 8.06E−04 | 8.16E−02 |
| ENSG00000214174 | 201283 | AMZ2P1 | −0.54 | 8.08E−04 | 8.16E−02 |
| ENSG00000185305 | 54622 | ARL15 | 0.67 | 8.21E−04 | 8.19E−02 |
| ENSG00000137709 | 25833 | POU2F3 | −0.67 | 8.17E−04 | 8.19E−02 |
| ENSG00000117707 | 5629 | PROX1 | 0.99 | 8.39E−04 | 8.31E−02 |
| ENSG00000144619 | 152330 | CNTN4 | 0.77 | 8.54E−04 | 8.41E−02 |
| ENSG00000158578 | 212 | ALAS2 | 1.08 | 8.94E−04 | 8.58E−02 |
| ENSG00000228570 | NA | NUTM2E | 1.08 | 9.23E−04 | 8.58E−02 |
| ENSG00000163735 | 6374 | CXCL5 | 1.08 | 9.30E−04 | 8.58E−02 |
| ENSG00000167476 | 126306 | JSRP1 | 1.07 | 9.11E−04 | 8.58E−02 |

TABLE 9-continued

Differentially expressed genes in UIP vs. Non-UIP samples, irrespective of smoker status.

| Table 9. All samples Ensembl ID | Entrez ID | Gene symbol | log2 Fold Change (UIP/NonUIP) | p value | FDR p value |
|---|---|---|---|---|---|
| ENSG00000116833 | 2494 | NR5A2 | 1.06 | 8.81E−04 | 8.58E−02 |
| ENSG00000120322 | 56128 | PCDHB8 | 1.05 | 9.31E−04 | 8.58E−02 |
| ENSG00000238741 | 677767 | SCARNA7 | 0.37 | 9.26E−04 | 8.58E−02 |
| ENSG00000169093 | 8623 | ASMTL | 0.23 | 9.12E−04 | 8.58E−02 |
| ENSG00000081026 | 260425 | MAGI3 | −0.61 | 9.06E−04 | 8.58E−02 |
| ENSG00000103528 | 51760 | SYT17 | −0.62 | 9.00E−04 | 8.58E−02 |
| ENSG00000100033 | 5625 | PRODH | −0.81 | 9.09E−04 | 8.58E−02 |
| ENSG00000165868 | 259217 | HSPA12A | 0.86 | 9.54E−04 | 8.75E−02 |
| ENSG00000163251 | 7855 | FZD5 | −0.74 | 9.87E−04 | 9.00E−02 |
| ENSG00000122140 | 51116 | MRPS2 | −0.38 | 9.93E−04 | 9.00E−02 |
| ENSG00000171792 | 83695 | RHNO1 | −0.48 | 1.00E−03 | 9.02E−02 |
| ENSG00000104369 | 56704 | JPH1 | −0.58 | 1.03E−03 | 9.20E−02 |
| ENSG00000168079 | 286133 | SCARA5 | 1.07 | 1.03E−03 | 9.21E−02 |
| ENSG00000092295 | 7051 | TGM1 | 1.00 | 1.04E−03 | 9.22E−02 |
| ENSG00000106809 | 4969 | OGN | 1.07 | 1.06E−03 | 9.35E−02 |
| ENSG00000163534 | 115350 | FCRL1 | 1.06 | 1.11E−03 | 9.44E−02 |
| ENSG00000091137 | 5172 | SLC26A4 | 1.00 | 1.10E−03 | 9.44E−02 |
| ENSG00000099958 | 91319 | DERL3 | 0.89 | 1.15E−03 | 9.44E−02 |
| ENSG00000153253 | 6328 | SCN3A | 0.82 | 1.16E−03 | 9.44E−02 |
| ENSG00000251402 | NA | FAM90A25P | 0.74 | 1.12E−03 | 9.44E−02 |
| ENSG00000120327 | 56122 | PCDHB14 | 0.72 | 1.09E−03 | 9.44E−02 |
| ENSG00000138795 | 51176 | LEF1 | 0.64 | 1.13E−03 | 9.44E−02 |
| ENSG00000144040 | 94097 | SFXN5 | 0.44 | 1.12E−03 | 9.44E−02 |
| ENSG00000155463 | 5018 | OXA1L | −0.20 | 1.15E−03 | 9.44E−02 |
| ENSG00000136830 | 64855 | FAM129B | −0.24 | 1.15E−03 | 9.44E−02 |
| ENSG00000141452 | 29919 | C18orf8 | −0.30 | 1.15E−03 | 9.44E−02 |
| ENSG00000148730 | 1979 | EIF4EBP2 | −0.33 | 1.12E−03 | 9.44E−02 |
| ENSG00000115415 | 6772 | STAT1 | −0.86 | 1.10E−03 | 9.44E−02 |
| ENSG00000126709 | 2537 | IFI6 | −1.03 | 1.15E−03 | 9.44E−02 |
| ENSG00000095951 | 3096 | HIVEP1 | −0.24 | 1.20E−03 | 9.76E−02 |
| ENSG00000187942 | 401944 | LDLRAD2 | 0.97 | 1.21E−03 | 9.80E−02 |
| ENSG00000105928 | 1687 | DFNA5 | 0.83 | 1.22E−03 | 9.81E−02 |
| ENSG00000224397 | NA | LINC01272 | 1.02 | 1.23E−03 | 9.83E−02 |
| ENSG00000170011 | 25924 | MYRIP | 0.86 | 1.32E−03 | 1.00E−01 |
| ENSG00000120784 | 22835 | ZFP30 | 0.37 | 1.30E−03 | 1.00E−01 |
| ENSG00000170185 | 84640 | USP38 | −0.26 | 1.31E−03 | 1.00E−01 |
| ENSG00000076513 | 88455 | ANKRD13A | −0.31 | 1.26E−03 | 1.00E−01 |
| ENSG00000135148 | 10906 | TRAFD1 | −0.32 | 1.28E−03 | 1.00E−01 |
| ENSG00000170085 | 375484 | SIMC1 | −0.43 | 1.32E−03 | 1.00E−01 |
| ENSG00000175324 | 27257 | LSM1 | −0.45 | 1.30E−03 | 1.00E−01 |
| ENSG00000141738 | 2886 | GRB7 | −0.54 | 1.28E−03 | 1.00E−01 |
| ENSG00000088002 | 6820 | SULT2B1 | −0.75 | 1.28E−03 | 1.00E−01 |
| ENSG00000010030 | 51513 | ETV7 | −0.86 | 1.29E−03 | 1.00E−01 |
| ENSG00000137959 | 10964 | IFI44L | −1.01 | 1.27E−03 | 1.00E−01 |

UIP (n = 9 samples); Non UIP (n = 15 samples). Positive log2 fold change value indicates over- expression in UIP relative to Non UIP; negative log2 value indicates under-expression in UIP relative to Non UIP. In this analysis the smoking history status of the patients involved was not evaluated, and the cohort harbored both smokers and non-smokers.

TABLE 10

Differentially expressed genes in non-smoker UIP vs. non-smoker Non-UIP samples.
Table 10. Non-smokers

| Ensembl ID | Entrez ID | Gene symbol | Log2 Fold Change (UIP/NonUIP) | P value | FDR P value |
|---|---|---|---|---|---|
| ENSG00000133687 | 83857 | TMTC1 | 1.72 | 4.52E−21 | 6.68E−17 |
| ENSG00000169129 | 84632 | AFAP1L2 | 1.63 | 1.62E−19 | 1.19E−15 |
| ENSG00000180229 | 283755 | HERC2P3 | 2.52 | 9.77E−15 | 4.81E−11 |
| ENSG00000107518 | 26033 | ATRNL1 | 3.00 | 2.49E−14 | 9.21E−11 |
| ENSG00000198380 | 2673 | GFPT1 | −0.62 | 9.55E−14 | 2.35E−10 |
| ENSG00000211976 | NA | IGHV3-73 | 2.21 | 9.47E−14 | 2.35E−10 |
| ENSG00000114902 | 28972 | SPCS1 | −0.64 | 1.99E−12 | 4.20E−09 |
| ENSG00000108001 | 253738 | EBF3 | 2.77 | 3.39E−12 | 6.27E−09 |
| ENSG00000154122 | 56172 | ANKH | 1.02 | 4.17E−12 | 6.85E−09 |
| ENSG00000012660 | 60481 | ELOVL5 | −0.66 | 6.94E−12 | 1.03E−08 |
| ENSG00000119888 | 4072 | EPCAM | −1.04 | 8.67E−12 | 1.16E−08 |
| ENSG00000147676 | 114569 | MAL2 | −1.08 | 1.83E−11 | 1.94E−08 |
| ENSG00000148357 | 256158 | HMCN2 | 1.99 | 1.62E−11 | 1.94E−08 |
| ENSG00000185499 | 4582 | MUC1 | −1.09 | 1.84E−11 | 1.94E−08 |

TABLE 10-continued

Differentially expressed genes in non-smoker UIP vs. non-smoker Non-UIP samples.
Table 10. Non-smokers

| Ensembl ID | Entrez ID | Gene symbol | Log2 Fold Change (UIP/NonUIP) | P value | FDR P value |
|---|---|---|---|---|---|
| ENSG00000157557 | 2114 | ETS2 | 0.73 | 8.18E−11 | 8.06E−08 |
| ENSG00000151789 | 79750 | ZNF385D | 2.73 | 1.04E−10 | 9.62E−08 |
| ENSG00000213088 | 2532 | ACKR1 | 2.18 | 3.53E−10 | 3.06E−07 |
| ENSG00000038210 | 55300 | PI4K2B | −0.77 | 4.14E−10 | 3.40E−07 |
| ENSG00000105426 | 5802 | PTPRS | 0.80 | 9.94E−10 | 7.73E−07 |
| ENSG00000100034 | 9647 | PPM1F | 1.27 | 1.17E−09 | 8.14E−07 |
| ENSG00000112562 | 64094 | SMOC2 | 1.70 | 1.21E−09 | 8.14E−07 |
| ENSG00000139211 | 347902 | AMIGO2 | 0.93 | 1.15E−09 | 8.14E−07 |
| ENSG00000130158 | 57572 | DOCK6 | 0.75 | 1.42E−09 | 9.10E−07 |
| ENSG00000124145 | 6385 | SDC4 | −0.67 | 2.44E−09 | 1.44E−06 |
| ENSG00000129255 | 9526 | MPDU1 | −0.54 | 2.44E−09 | 1.44E−06 |
| ENSG00000100219 | 7494 | XBP1 | −1.02 | 2.76E−09 | 1.48E−06 |
| ENSG00000120318 | 64411 | ARAP3 | 0.93 | 2.80E−09 | 1.48E−06 |
| ENSG00000144136 | 6574 | SLC20A1 | −0.65 | 2.63E−09 | 1.48E−06 |
| ENSG00000140873 | 170692 | ADAMTS18 | 2.27 | 3.32E−09 | 1.69E−06 |
| ENSG00000120693 | 4093 | SMAD9 | 1.43 | 4.04E−09 | 1.99E−06 |
| ENSG00000080007 | 55510 | DDX43 | −2.11 | 6.55E−09 | 3.12E−06 |
| ENSG00000105737 | 2901 | GRIK5 | 2.34 | 8.09E−09 | 3.54E−06 |
| ENSG00000157064 | 23057 | NMNAT2 | 2.14 | 8.14E−09 | 3.54E−06 |
| ENSG00000161381 | 57125 | PLXDC1 | 1.21 | 7.73E−09 | 3.54E−06 |
| ENSG00000154736 | 11096 | ADAMTS5 | 1.92 | 1.01E−08 | 4.13E−06 |
| ENSG00000185046 | 56899 | ANKS1B | 1.51 | 9.78E−09 | 4.13E−06 |
| ENSG00000104213 | 5157 | PDGFRL | 2.09 | 1.19E−08 | 4.52E−06 |
| ENSG00000166398 | 9710 | KIAA0355 | 0.82 | 1.19E−08 | 4.52E−06 |
| ENSG00000189058 | 347 | APOD | 1.55 | 1.14E−08 | 4.52E−06 |
| ENSG00000102935 | 23090 | ZNF423 | 1.47 | 1.34E−08 | 4.86E−06 |
| ENSG00000111145 | 2004 | ELK3 | 0.89 | 1.35E−08 | 4.86E−06 |
| ENSG00000138160 | 3832 | KIF11 | −1.35 | 1.44E−08 | 5.06E−06 |
| ENSG00000197147 | 23507 | LRRC8B | −0.89 | 1.80E−08 | 6.19E−06 |
| ENSG00000131386 | 117248 | GALNT15 | 2.41 | 1.95E−08 | 6.39E−06 |
| ENSG00000177839 | 56127 | PCDHB9 | 1.87 | 1.91E−08 | 6.39E−06 |
| ENSG00000114446 | 55081 | IFT57 | −0.65 | 2.20E−08 | 7.06E−06 |
| ENSG00000198932 | 9737 | GPRASP1 | 0.90 | 2.34E−08 | 7.36E−06 |
| ENSG00000178031 | 92949 | ADAMTSL1 | 2.30 | 2.50E−08 | 7.70E−06 |
| ENSG00000230989 | 3281 | HSBP1 | −0.74 | 2.59E−08 | 7.80E−06 |
| ENSG00000100065 | 29775 | CARD10 | 1.69 | 2.91E−08 | 8.60E−06 |
| ENSG00000142798 | 3339 | HSPG2 | 1.20 | 3.13E−08 | 9.06E−06 |
| ENSG00000134533 | 85004 | RERG | 1.68 | 3.70E−08 | 1.05E−05 |
| ENSG00000105784 | 154661 | RUNDC3B | 2.28 | 3.87E−08 | 1.08E−05 |
| ENSG00000039068 | 999 | CDH1 | −0.87 | 6.14E−08 | 1.55E−05 |
| ENSG00000104549 | 6713 | SQLE | −1.38 | 6.10E−08 | 1.55E−05 |
| ENSG00000105996 | 3199 | HOXA2 | 1.60 | 5.72E−08 | 1.55E−05 |
| ENSG00000130234 | 59272 | ACE2 | −1.52 | 6.19E−08 | 1.55E−05 |
| ENSG00000162881 | 165140 | OXER1 | 1.30 | 5.81E−08 | 1.55E−05 |
| ENSG00000177098 | 6330 | SCN4B | 1.12 | 6.10E−08 | 1.55E−05 |
| ENSG00000007312 | 974 | CD79B | 2.13 | 6.62E−08 | 1.58E−05 |
| ENSG00000163898 | 200879 | LIPH | −0.91 | 6.52E−08 | 1.58E−05 |
| ENSG00000189377 | 284340 | CXCL17 | −1.17 | 6.53E−08 | 1.58E−05 |
| ENSG00000198814 | 2710 | GK | −0.83 | 6.79E−08 | 1.59E−05 |
| ENSG00000076944 | 6813 | STXBP2 | −0.56 | 7.52E−08 | 1.71E−05 |
| ENSG00000153902 | 163175 | LGI4 | 1.74 | 7.53E−08 | 1.71E−05 |
| ENSG00000117448 | 10327 | AKR1A1 | −0.63 | 7.74E−08 | 1.73E−05 |
| ENSG00000164530 | 221476 | PI16 | 2.17 | 8.33E−08 | 1.84E−05 |
| ENSG00000233297 | NA | RASA4DP | 2.29 | 9.09E−08 | 1.97E−05 |
| ENSG00000182718 | 302 | ANXA2 | −0.62 | 9.95E−08 | 2.13E−05 |
| ENSG00000110455 | 84680 | ACCS | 0.98 | 1.03E−07 | 2.17E−05 |
| ENSG00000197253 | 64499 | TPSB2 | 2.07 | 1.10E−07 | 2.29E−05 |
| ENSG00000125999 | 92747 | BPIFB1 | −1.76 | 1.15E−07 | 2.37E−05 |
| ENSG00000211936 | NA | NA | 2.23 | 1.22E−07 | 2.47E−05 |
| ENSG00000108852 | 4355 | MPP2 | 1.68 | 1.28E−07 | 2.55E−05 |
| ENSG00000119514 | 79695 | GALNT12 | −0.60 | 1.64E−07 | 3.18E−05 |
| ENSG00000146021 | 26249 | KLHL3 | 1.36 | 1.63E−07 | 3.18E−05 |
| ENSG00000173702 | 56667 | MUC13 | −2.33 | 1.78E−07 | 3.41E−05 |
| ENSG00000116748 | 270 | AMPD1 | 1.80 | 1.85E−07 | 3.50E−05 |
| ENSG00000196411 | 2050 | EPHB4 | 0.86 | 2.09E−07 | 3.91E−05 |
| ENSG00000086061 | 3301 | DNAJA1 | −0.73 | 2.20E−07 | 4.07E−05 |
| ENSG00000074181 | 4854 | NOTCH3 | 0.92 | 2.24E−07 | 4.07E−05 |
| ENSG00000181234 | 92293 | TMEM132C | 2.08 | 2.26E−07 | 4.07E−05 |
| ENSG00000074590 | 9891 | NUAK1 | 1.27 | 2.47E−07 | 4.39E−05 |
| ENSG00000154263 | 10349 | ABCA10 | 1.44 | 2.92E−07 | 5.14E−05 |
| ENSG00000186322 | NA | NA | 1.99 | 3.30E−07 | 5.74E−05 |
| ENSG00000130164 | 3949 | LDLR | −1.00 | 3.36E−07 | 5.77E−05 |
| ENSG00000133935 | 11161 | C14orf1 | −0.76 | 3.54E−07 | 5.99E−05 |

TABLE 10-continued

Differentially expressed genes in non-smoker UIP vs. non-smoker Non-UIP samples.
Table 10. Non-smokers

| Ensembl ID | Entrez ID | Gene symbol | Log2 Fold Change (UIP/NonUIP) | P value | FDR P value |
|---|---|---|---|---|---|
| ENSG00000151892 | 2674 | GFRA1 | 1.96 | 3.57E−07 | 5.99E−05 |
| ENSG00000196628 | 6925 | TCF4 | 0.93 | 3.65E−07 | 6.06E−05 |
| ENSG00000106070 | 2887 | GRB10 | 1.22 | 3.94E−07 | 6.46E−05 |
| ENSG00000076555 | 32 | ACACB | 1.06 | 4.48E−07 | 7.27E−05 |
| ENSG00000173947 | 128344 | PIFO | −1.26 | 4.74E−07 | 7.61E−05 |
| ENSG00000004468 | 952 | CD38 | −1.40 | 5.09E−07 | 8.08E−05 |
| ENSG00000154330 | 5239 | PGM5 | 1.72 | 5.62E−07 | 8.83E−05 |
| ENSG00000085185 | 63035 | BCORL1 | 0.61 | 5.71E−07 | 8.88E−05 |
| ENSG00000157933 | 6497 | SKI | 0.57 | 5.77E−07 | 8.89E−05 |
| ENSG00000080854 | 22997 | IGSF9B | 1.56 | 6.01E−07 | 9.16E−05 |
| ENSG00000244734 | 3043 | HBB | 2.28 | 6.25E−07 | 9.42E−05 |
| ENSG00000080572 | 139212 | PIH1D3 | −1.44 | 6.80E−07 | 1.02E−04 |
| ENSG00000154529 | 728577 | CNTNAP3B | 1.83 | 7.23E−07 | 1.07E−04 |
| ENSG00000142731 | 10733 | PLK4 | −1.30 | 9.19E−07 | 1.34E−04 |
| ENSG00000146425 | 6993 | DYNLT1 | −1.05 | 9.34E−07 | 1.35E−04 |
| ENSG00000109861 | 1075 | CTSC | −0.92 | 9.89E−07 | 1.42E−04 |
| ENSG00000118640 | 8673 | VAMP8 | −0.83 | 1.00E−06 | 1.43E−04 |
| ENSG00000091262 | 368 | ABCC6 | −0.97 | 1.05E−06 | 1.48E−04 |
| ENSG00000012124 | 933 | CD22 | 1.94 | 1.08E−06 | 1.48E−04 |
| ENSG00000079337 | 10411 | RAPGEF3 | 1.63 | 1.09E−06 | 1.48E−04 |
| ENSG00000113161 | 3156 | HMGCR | −1.13 | 1.09E−06 | 1.48E−04 |
| ENSG00000183346 | 219621 | C10orf107 | −1.22 | 1.07E−06 | 1.48E−04 |
| ENSG00000197705 | 57565 | KLHL14 | 2.01 | 1.11E−06 | 1.49E−04 |
| ENSG00000215217 | 134121 | C5orf49 | −1.20 | 1.14E−06 | 1.52E−04 |
| ENSG00000070190 | 27071 | DAPP1 | −1.19 | 1.19E−06 | 1.55E−04 |
| ENSG00000165434 | 283209 | PGM2L1 | −0.92 | 1.18E−06 | 1.55E−04 |
| ENSG00000102738 | 10240 | MRPS31 | −0.97 | 1.22E−06 | 1.56E−04 |
| ENSG00000132698 | 57111 | RAB25 | −0.79 | 1.22E−06 | 1.56E−04 |
| ENSG00000186105 | 100130733 | LRRC70 | 1.77 | 1.24E−06 | 1.58E−04 |
| ENSG00000123983 | 2181 | ACSL3 | −0.87 | 1.38E−06 | 1.72E−04 |
| ENSG00000188010 | 729967 | MORN2 | −1.27 | 1.37E−06 | 1.72E−04 |
| ENSG00000138670 | 153020 | RASGEF1B | −0.83 | 1.56E−06 | 1.94E−04 |
| ENSG00000152104 | 5784 | PTPN14 | 0.94 | 1.62E−06 | 1.98E−04 |
| ENSG00000165995 | 783 | CACNB2 | 1.24 | 1.62E−06 | 1.98E−04 |
| ENSG00000109586 | 51809 | GALNT7 | −0.94 | 1.73E−06 | 2.10E−04 |
| ENSG00000129946 | 25759 | SHC2 | 1.66 | 1.82E−06 | 2.18E−04 |
| ENSG00000139910 | 4857 | NOVA1 | 2.15 | 1.99E−06 | 2.37E−04 |
| ENSG00000188175 | 253012 | HEPACAM2 | −1.75 | 2.01E−06 | 2.37E−04 |
| ENSG00000174405 | 3981 | LIG4 | −0.58 | 2.04E−06 | 2.37E−04 |
| ENSG00000181885 | 1366 | CLDN7 | −1.13 | 2.03E−06 | 2.37E−04 |
| ENSG00000187134 | 1645 | AKR1C1 | −0.86 | 2.07E−06 | 2.39E−04 |
| ENSG00000253731 | 56109 | PCDHGA6 | 1.19 | 2.09E−06 | 2.39E−04 |
| ENSG00000090006 | 8425 | LTBP4 | 1.38 | 2.13E−06 | 2.42E−04 |
| ENSG00000176438 | 161176 | SYNE3 | 0.98 | 2.18E−06 | 2.44E−04 |
| ENSG00000188536 | 3040 | HBA2 | 2.17 | 2.17E−06 | 2.44E−04 |
| ENSG00000141198 | 10040 | TOM1L1 | −0.57 | 2.27E−06 | 2.50E−04 |
| ENSG00000164124 | 55314 | TMEM144 | −0.88 | 2.26E−06 | 2.50E−04 |
| ENSG00000068912 | 27248 | ERLEC1 | −0.48 | 2.33E−06 | 2.55E−04 |
| ENSG00000167779 | 3489 | IGFBP6 | 1.85 | 2.44E−06 | 2.65E−04 |
| ENSG00000159212 | 54102 | CLIC6 | −0.90 | 2.50E−06 | 2.70E−04 |
| ENSG00000116833 | 2494 | NR5A2 | 1.94 | 2.54E−06 | 2.72E−04 |
| ENSG00000197614 | 8076 | MFAP5 | 2.15 | 2.70E−06 | 2.87E−04 |
| ENSG00000152518 | 678 | ZFP36L2 | 0.79 | 2.81E−06 | 2.96E−04 |
| ENSG00000177156 | 6888 | TALDO1 | −0.45 | 2.83E−06 | 2.96E−04 |
| ENSG00000144619 | 152330 | CNTN4 | 0.79 | 2.89E−06 | 3.01E−04 |
| ENSG00000124772 | 57699 | CPNE5 | 1.80 | 2.99E−06 | 3.04E−04 |
| ENSG00000166908 | 79837 | PIP4K2C | −0.49 | 2.99E−06 | 3.04E−04 |
| ENSG00000168765 | 2948 | GSTM4 | 0.72 | 2.95E−06 | 3.04E−04 |
| ENSG00000105928 | 1687 | DFNA5 | 1.47 | 3.02E−06 | 3.05E−04 |
| ENSG00000186471 | 158798 | AKAP14 | −1.21 | 3.04E−06 | 3.05E−04 |
| ENSG00000183604 | NA | SMG1P5 | 1.68 | 3.12E−06 | 3.11E−04 |
| ENSG00000182272 | 338707 | B4GALNT4 | 1.65 | 3.32E−06 | 3.29E−04 |
| ENSG00000170017 | 214 | ALCAM | −1.08 | 3.37E−06 | 3.32E−04 |
| ENSG00000163191 | 6282 | S100A11 | −0.92 | 3.77E−06 | 3.69E−04 |
| ENSG00000100243 | 1727 | CYB5R3 | 0.31 | 3.83E−06 | 3.70E−04 |
| ENSG00000119616 | 51077 | FCF1 | −0.57 | 3.81E−06 | 3.70E−04 |
| ENSG00000106852 | 26468 | LHX6 | 1.71 | 3.86E−06 | 3.70E−04 |
| ENSG00000164056 | 10252 | SPRY1 | 1.10 | 4.26E−06 | 4.06E−04 |
| ENSG00000256870 | 160728 | SLC5A8 | −1.68 | 4.31E−06 | 4.08E−04 |
| ENSG00000112110 | 29074 | MRPL18 | −0.74 | 4.36E−06 | 4.10E−04 |
| ENSG00000243716 | 440345 | NPIPB5 | 0.46 | 4.42E−06 | 4.13E−04 |
| ENSG00000182093 | 7485 | WRB | −0.58 | 4.63E−06 | 4.30E−04 |
| ENSG00000213398 | 3931 | LCAT | 0.87 | 4.66E−06 | 4.31E−04 |

TABLE 10-continued

Differentially expressed genes in non-smoker UIP vs. non-smoker Non-UIP samples.
Table 10. Non-smokers

| Ensembl ID | Entrez ID | Gene symbol | Log2 Fold Change (UIP/NonUIP) | P value | FDR P value |
|---|---|---|---|---|---|
| ENSG00000079459 | 2222 | FDFT1 | −0.89 | 4.75E−06 | 4.36E−04 |
| ENSG00000163082 | 130367 | SGPP2 | −0.75 | 4.82E−06 | 4.40E−04 |
| ENSG00000181722 | 26137 | ZBTB20 | 0.71 | 4.96E−06 | 4.50E−04 |
| ENSG00000152953 | 55351 | STK32B | 2.03 | 5.05E−06 | 4.55E−04 |
| ENSG00000070193 | 2255 | FGF10 | 1.89 | 5.24E−06 | 4.67E−04 |
| ENSG00000106404 | 24146 | CLDN15 | 2.03 | 5.27E−06 | 4.67E−04 |
| ENSG00000107281 | 56654 | NPDC1 | 1.21 | 5.22E−06 | 4.67E−04 |
| ENSG00000107949 | 56647 | BCCIP | −0.61 | 5.32E−06 | 4.68E−04 |
| ENSG00000161055 | 92304 | SCGB3A1 | −1.74 | 6.01E−06 | 5.25E−04 |
| ENSG00000087916 | NA | NA | −1.75 | 6.14E−06 | 5.34E−04 |
| ENSG00000119139 | 9414 | TJP2 | −0.47 | 6.21E−06 | 5.36E−04 |
| ENSG00000151468 | 83643 | CCDC3 | 1.74 | 6.27E−06 | 5.39E−04 |
| ENSG00000205809 | 3822 | KLRC2 | −1.67 | 6.68E−06 | 5.70E−04 |
| ENSG00000131374 | 9779 | TBC1D5 | 0.35 | 6.76E−06 | 5.71E−04 |
| ENSG00000178741 | 9377 | COX5A | −0.63 | 6.73E−06 | 5.71E−04 |
| ENSG00000075142 | 6717 | SRI | −0.78 | 6.86E−06 | 5.73E−04 |
| ENSG00000141720 | NA | NA | 0.40 | 6.87E−06 | 5.73E−04 |
| ENSG00000159167 | 6781 | STC1 | 1.91 | 6.99E−06 | 5.80E−04 |
| ENSG00000081818 | 56131 | PCDHB4 | 1.46 | 7.29E−06 | 5.95E−04 |
| ENSG00000135773 | 10753 | CAPN9 | −0.90 | 7.27E−06 | 5.95E−04 |
| ENSG00000165300 | 26050 | SLITRK5 | 1.88 | 7.26E−06 | 5.95E−04 |
| ENSG00000133321 | 5920 | RARRES3 | −1.58 | 7.92E−06 | 6.43E−04 |
| ENSG00000160447 | 29941 | PKN3 | 1.30 | 8.24E−06 | 6.66E−04 |
| ENSG00000136859 | 23452 | ANGPTL2 | 1.38 | 8.33E−06 | 6.69E−04 |
| ENSG00000222009 | 149478 | BTBD19 | 1.14 | 8.54E−06 | 6.82E−04 |
| ENSG00000185250 | 285755 | PPIL6 | −1.17 | 8.59E−06 | 6.83E−04 |
| ENSG00000164330 | 1879 | EBF1 | 1.73 | 8.71E−06 | 6.86E−04 |
| ENSG00000182771 | 2894 | GRID1 | 1.81 | 8.73E−06 | 6.86E−04 |
| ENSG00000137842 | 80021 | TMEM62 | −0.91 | 8.80E−06 | 6.88E−04 |
| ENSG00000088538 | 1795 | DOCK3 | 1.25 | 8.88E−06 | 6.91E−04 |
| ENSG00000178966 | 80010 | RMI1 | −0.93 | 9.01E−06 | 6.97E−04 |
| ENSG00000133665 | 84332 | DYDC2 | −1.18 | 9.18E−06 | 7.06E−04 |
| ENSG00000117322 | 1380 | CR2 | 2.00 | 9.44E−06 | 7.23E−04 |
| ENSG00000100170 | 6523 | SLC5A1 | −1.54 | 1.00E−05 | 7.61E−04 |
| ENSG00000101384 | 182 | JAG1 | 0.73 | 1.00E−05 | 7.61E−04 |
| ENSG00000120756 | 5357 | PLS1 | −1.01 | 1.10E−05 | 8.29E−04 |
| ENSG00000102098 | 10389 | SCML2 | 1.41 | 1.12E−05 | 8.41E−04 |
| ENSG00000114200 | 590 | BCHE | 1.93 | 1.13E−05 | 8.41E−04 |
| ENSG00000013275 | 5704 | PSMC4 | −0.67 | 1.15E−05 | 8.50E−04 |
| ENSG00000108953 | 7531 | YWHAE | −0.48 | 1.15E−05 | 8.50E−04 |
| ENSG00000140181 | NA | NA | 1.02 | 1.17E−05 | 8.53E−04 |
| ENSG00000152939 | 153562 | MARVELD2 | −0.86 | 1.16E−05 | 8.53E−04 |
| ENSG00000162882 | 23498 | HAAO | 1.22 | 1.28E−05 | 9.29E−04 |
| ENSG00000088448 | 55608 | ANKRD10 | 0.59 | 1.31E−05 | 9.49E−04 |
| ENSG00000272636 | 8447 | DOC2B | 1.36 | 1.34E−05 | 9.64E−04 |
| ENSG00000052802 | 6307 | MSMO1 | −1.29 | 1.36E−05 | 9.70E−04 |
| ENSG00000077063 | 83992 | CTTNBP2 | 1.25 | 1.37E−05 | 9.70E−04 |
| ENSG00000112972 | 3157 | HMGCS1 | −1.11 | 1.36E−05 | 9.70E−04 |
| ENSG00000133019 | 1131 | CHRM3 | 1.44 | 1.37E−05 | 9.70E−04 |
| ENSG00000069329 | 55737 | VPS35 | −0.48 | 1.40E−05 | 9.88E−04 |
| ENSG00000166265 | 116159 | CYYR1 | 1.63 | 1.42E−05 | 9.94E−04 |
| ENSG00000159399 | 3099 | HK2 | −1.04 | 1.44E−05 | 1.00E−03 |
| ENSG00000257057 | NA | C11orf97 | −1.40 | 1.47E−05 | 1.02E−03 |
| ENSG00000065618 | 1308 | COL17A1 | 1.62 | 1.52E−05 | 1.05E−03 |
| ENSG00000163624 | 1040 | CDS1 | −1.01 | 1.67E−05 | 1.14E−03 |
| ENSG00000164764 | 157869 | SBSPON | 1.82 | 1.67E−05 | 1.14E−03 |
| ENSG00000171444 | 4163 | MCC | 0.99 | 1.67E−05 | 1.14E−03 |
| ENSG00000183323 | 202243 | CCDC125 | −1.05 | 1.66E−05 | 1.14E−03 |
| ENSG00000152332 | 127933 | UHMK1 | −0.55 | 1.71E−05 | 1.16E−03 |
| ENSG00000205277 | 10071 | MUC12 | 1.47 | 1.75E−05 | 1.18E−03 |
| ENSG00000091592 | 22861 | NLRP1 | 0.94 | 1.77E−05 | 1.18E−03 |
| ENSG00000101230 | 140862 | ISM1 | 1.31 | 1.77E−05 | 1.18E−03 |
| ENSG00000112981 | 8382 | NME5 | −1.10 | 1.79E−05 | 1.18E−03 |
| ENSG00000196263 | 57573 | ZNF471 | 0.81 | 1.79E−05 | 1.18E−03 |
| ENSG00000149809 | 7108 | TM7SF2 | −0.74 | 1.81E−05 | 1.19E−03 |
| ENSG00000139644 | 7009 | TMBIM6 | −0.60 | 1.83E−05 | 1.20E−03 |
| ENSG00000116138 | 23341 | DNAJC16 | −0.51 | 1.88E−05 | 1.21E−03 |
| ENSG00000143248 | 8490 | RGS5 | 1.70 | 1.88E−05 | 1.21E−03 |
| ENSG00000183644 | 399949 | C11orf88 | −1.23 | 1.88E−05 | 1.21E−03 |
| ENSG00000109814 | 7358 | UGDH | −0.76 | 1.89E−05 | 1.22E−03 |
| ENSG00000131475 | 84313 | VPS25 | −0.57 | 1.94E−05 | 1.24E−03 |
| ENSG00000183454 | 2903 | GRIN2A | 1.94 | 1.98E−05 | 1.26E−03 |
| ENSG00000057252 | 6646 | SOAT1 | −0.77 | 2.07E−05 | 1.31E−03 |

TABLE 10-continued

Differentially expressed genes in non-smoker UIP vs. non-smoker Non-UIP samples.
Table 10. Non-smokers

| Ensembl ID | Entrez ID | Gene symbol | Log2 Fold Change (UIP/NonUIP) | P value | FDR P value |
|---|---|---|---|---|---|
| ENSG00000106123 | 2051 | EPHB6 | 1.12 | 2.11E−05 | 1.31E−03 |
| ENSG00000133067 | 59352 | LGR6 | 1.51 | 2.11E−05 | 1.31E−03 |
| ENSG00000138356 | 316 | AOX1 | 1.79 | 2.09E−05 | 1.31E−03 |
| ENSG00000173269 | 79812 | MMRN2 | 1.69 | 2.09E−05 | 1.31E−03 |
| ENSG00000186642 | 5138 | PDE2A | 1.94 | 2.12E−05 | 1.31E−03 |
| ENSG00000178053 | 4291 | MLF1 | −1.06 | 2.15E−05 | 1.33E−03 |
| ENSG00000087995 | 339175 | METTL2A | −0.57 | 2.18E−05 | 1.34E−03 |
| ENSG00000130600 | 283120 | H19 | 1.87 | 2.18E−05 | 1.34E−03 |
| ENSG00000114573 | 523 | ATP6V1A | −0.62 | 2.24E−05 | 1.35E−03 |
| ENSG00000131203 | 3620 | IDO1 | −1.91 | 2.23E−05 | 1.35E−03 |
| ENSG00000143036 | 126969 | SLC44A3 | −0.74 | 2.21E−05 | 1.35E−03 |
| ENSG00000262209 | 56102 | PCDHGB3 | 1.37 | 2.22E−05 | 1.35E−03 |
| ENSG00000168079 | 286133 | SCARA5 | 1.77 | 2.29E−05 | 1.37E−03 |
| ENSG00000163534 | 115350 | FCRL1 | 1.93 | 2.35E−05 | 1.40E−03 |
| ENSG00000165304 | 9833 | MELK | −1.58 | 2.36E−05 | 1.40E−03 |
| ENSG00000101421 | 128866 | CHMP4B | −0.48 | 2.37E−05 | 1.41E−03 |
| ENSG00000162961 | 84661 | DPY30 | −0.75 | 2.53E−05 | 1.49E−03 |
| ENSG00000188931 | 257177 | CFAP126 | −1.15 | 2.53E−05 | 1.49E−03 |
| ENSG00000129467 | 196883 | ADCY4 | 1.60 | 2.55E−05 | 1.49E−03 |
| ENSG00000173530 | 8793 | TNFRSF10D | 0.83 | 2.54E−05 | 1.49E−03 |
| ENSG00000158683 | 168507 | PKD1L1 | 1.68 | 2.68E−05 | 1.56E−03 |
| ENSG00000000003 | 7105 | TSPAN6 | −1.01 | 2.70E−05 | 1.56E−03 |
| ENSG00000135679 | 4193 | MDM2 | −0.59 | 2.70E−05 | 1.56E−03 |
| ENSG00000241244 | NA | IGKV1D-16 | 1.79 | 2.76E−05 | 1.58E−03 |
| ENSG00000086548 | 4680 | CEACAM6 | −1.11 | 2.86E−05 | 1.64E−03 |
| ENSG00000005108 | 221981 | THSD7A | 1.06 | 2.87E−05 | 1.64E−03 |
| ENSG00000163001 | 112942 | CFAP36 | −0.57 | 2.91E−05 | 1.65E−03 |
| ENSG00000178445 | 2731 | GLDC | 1.32 | 2.92E−05 | 1.65E−03 |
| ENSG00000196586 | 4646 | MYO6 | −0.56 | 2.94E−05 | 1.66E−03 |
| ENSG00000130300 | 83483 | PLVAP | 1.89 | 2.97E−05 | 1.66E−03 |
| ENSG00000173068 | 54796 | BNC2 | 1.44 | 2.98E−05 | 1.66E−03 |
| ENSG00000211972 | NA | IGHV3-66 | 1.82 | 2.98E−05 | 1.66E−03 |
| ENSG00000163531 | 23114 | NFASC | 0.75 | 3.10E−05 | 1.72E−03 |
| ENSG00000145287 | 51316 | PLAC8 | −1.30 | 3.13E−05 | 1.72E−03 |
| ENSG00000157764 | 673 | BRAF | 0.36 | 3.14E−05 | 1.72E−03 |
| ENSG00000197959 | 26052 | DNM3 | 1.09 | 3.12E−05 | 1.72E−03 |
| ENSG00000119138 | 687 | KLF9 | 1.20 | 3.18E−05 | 1.74E−03 |
| ENSG00000185760 | 56479 | KCNQ5 | 1.62 | 3.26E−05 | 1.78E−03 |
| ENSG00000066382 | 744 | MPPED2 | 1.28 | 3.35E−05 | 1.80E−03 |
| ENSG00000088986 | 8655 | DYNLL1 | −0.77 | 3.32E−05 | 1.80E−03 |
| ENSG00000104413 | 54845 | ESRP1 | −0.77 | 3.35E−05 | 1.80E−03 |
| ENSG00000116906 | 8443 | GNPAT | −0.33 | 3.32E−05 | 1.80E−03 |
| ENSG00000165716 | 138311 | FAM69B | 1.58 | 3.34E−05 | 1.80E−03 |
| ENSG00000163263 | 388701 | C1orf189 | −1.27 | 3.44E−05 | 1.83E−03 |
| ENSG00000163993 | 6286 | S100P | −1.73 | 3.46E−05 | 1.84E−03 |
| ENSG00000102287 | 2564 | GABRE | 1.02 | 3.59E−05 | 1.90E−03 |
| ENSG00000011523 | 23177 | CEP68 | 0.74 | 3.67E−05 | 1.94E−03 |
| ENSG00000149212 | 143686 | SESN3 | 0.83 | 3.74E−05 | 1.96E−03 |
| ENSG00000174059 | 947 | CD34 | 1.78 | 3.73E−05 | 1.96E−03 |
| ENSG00000178125 | 286187 | PPP1R42 | −1.05 | 3.74E−05 | 1.96E−03 |
| ENSG00000145494 | 4726 | NDUFS6 | −0.39 | 3.84E−05 | 2.00E−03 |
| ENSG00000166562 | 90701 | SEC11C | −0.65 | 3.97E−05 | 2.06E−03 |
| ENSG00000261934 | 56107 | PCDHGA9 | 0.90 | 3.99E−05 | 2.06E−03 |
| ENSG00000126895 | 554 | AVPR2 | 1.24 | 4.01E−05 | 2.06E−03 |
| ENSG00000131844 | 64087 | MCCC2 | −0.44 | 4.04E−05 | 2.07E−03 |
| ENSG00000166813 | 374654 | KIF7 | 1.34 | 4.12E−05 | 2.11E−03 |
| ENSG00000185245 | 2811 | GP1BA | 1.18 | 4.22E−05 | 2.15E−03 |
| ENSG00000057704 | 57458 | TMCC3 | 1.54 | 4.29E−05 | 2.18E−03 |
| ENSG00000148541 | 220965 | FAM13C | 1.17 | 4.38E−05 | 2.21E−03 |
| ENSG00000224114 | NA | | −1.66 | 4.44E−05 | 2.24E−03 |
| ENSG00000068796 | 3796 | KIF2A | −0.75 | 4.51E−05 | 2.26E−03 |
| ENSG00000254986 | 10072 | DPP3 | −0.57 | 4.52E−05 | 2.26E−03 |
| ENSG00000266714 | NA | MYO15B | 0.93 | 4.52E−05 | 2.26E−03 |
| ENSG00000145824 | 9547 | CXCL14 | 1.80 | 4.67E−05 | 2.32E−03 |
| ENSG00000262576 | 56111 | PCDHGA4 | 1.35 | 4.70E−05 | 2.33E−03 |
| ENSG00000204604 | 90333 | ZNF468 | −0.74 | 4.96E−05 | 2.45E−03 |
| ENSG00000111834 | 345895 | RSPH4A | −1.07 | 5.07E−05 | 2.46E−03 |
| ENSG00000134202 | 2947 | GSTM3 | 1.58 | 4.99E−05 | 2.46E−03 |
| ENSG00000139193 | 939 | CD27 | 1.61 | 5.06E−05 | 2.46E−03 |
| ENSG00000142687 | 79932 | KIAA0319L | −0.66 | 5.07E−05 | 2.46E−03 |
| ENSG00000143653 | 51097 | SCCPDH | −0.61 | 5.05E−05 | 2.46E−03 |
| ENSG00000187244 | 4059 | BCAM | 0.98 | 5.00E−05 | 2.46E−03 |
| ENSG00000225698 | NA | IGHV3-72 | 1.84 | 5.26E−05 | 2.54E−03 |

TABLE 10-continued

Differentially expressed genes in non-smoker UIP vs. non-smoker Non-UIP samples.
Table 10. Non-smokers

| Ensembl ID | Entrez ID | Gene symbol | Log2 Fold Change (UIP/NonUIP) | P value | FDR P value |
|---|---|---|---|---|---|
| ENSG00000162896 | 5284 | PIGR | −1.10 | 5.29E−05 | 2.54E−03 |
| ENSG00000253485 | 56110 | PCDHGA5 | 1.40 | 5.32E−05 | 2.55E−03 |
| ENSG00000103184 | 9717 | SEC14L5 | −1.57 | 5.39E−05 | 2.57E−03 |
| ENSG00000117399 | 991 | CDC20 | −1.23 | 5.38E−05 | 2.57E−03 |
| ENSG00000128591 | 2318 | FLNC | 1.71 | 5.43E−05 | 2.57E−03 |
| ENSG00000153291 | 9481 | SLC25A27 | 0.80 | 5.42E−05 | 2.57E−03 |
| ENSG00000143153 | 481 | ATP1B1 | −0.71 | 5.54E−05 | 2.62E−03 |
| ENSG00000161798 | 362 | AQP5 | −1.15 | 5.59E−05 | 2.63E−03 |
| ENSG00000138413 | 3417 | IDH1 | −0.56 | 5.62E−05 | 2.64E−03 |
| ENSG00000070182 | 6710 | SPTB | 1.24 | 5.67E−05 | 2.65E−03 |
| ENSG00000165325 | 159989 | CCDC67 | −1.20 | 5.68E−05 | 2.65E−03 |
| ENSG00000073060 | 949 | SCARB1 | 1.42 | 5.92E−05 | 2.75E−03 |
| ENSG00000120437 | 39 | ACAT2 | −1.08 | 5.99E−05 | 2.77E−03 |
| ENSG00000181789 | 22820 | COPG1 | −0.45 | 6.01E−05 | 2.77E−03 |
| ENSG00000265150 | NA | NA | 1.14 | 6.00E−05 | 2.77E−03 |
| ENSG00000211934 | NA | IGHV1-2 | 1.76 | 6.10E−05 | 2.80E−03 |
| ENSG00000143772 | 3707 | ITPKB | 0.62 | 6.17E−05 | 2.82E−03 |
| ENSG00000109846 | 1410 | CRYAB | 1.44 | 6.45E−05 | 2.93E−03 |
| ENSG00000138031 | 109 | ADCY3 | 1.04 | 6.49E−05 | 2.93E−03 |
| ENSG00000148180 | 2934 | GSN | 0.67 | 6.48E−05 | 2.93E−03 |
| ENSG00000253910 | 56103 | PCDHGB2 | 1.36 | 6.45E−05 | 2.93E−03 |
| ENSG00000156966 | 93010 | B3GNT7 | −0.86 | 6.54E−05 | 2.94E−03 |
| ENSG00000130770 | 93974 | ATPIF1 | −0.63 | 6.74E−05 | 3.02E−03 |
| ENSG00000170312 | 983 | CDK1 | −1.01 | 6.74E−05 | 3.02E−03 |
| ENSG00000140263 | 6652 | SORD | −1.46 | 6.79E−05 | 3.03E−03 |
| ENSG00000139625 | 7786 | MAP3K12 | 0.86 | 7.13E−05 | 3.17E−03 |
| ENSG00000089356 | 5349 | FXYD3 | −1.11 | 7.18E−05 | 3.19E−03 |
| ENSG00000172349 | 3603 | IL16 | 0.87 | 7.60E−05 | 3.36E−03 |
| ENSG00000103534 | 79838 | TMC5 | −1.14 | 7.68E−05 | 3.39E−03 |
| ENSG00000138175 | 403 | ARL3 | −0.75 | 7.75E−05 | 3.40E−03 |
| ENSG00000204632 | 3135 | HLA-G | −1.80 | 7.73E−05 | 3.40E−03 |
| ENSG00000156675 | 80223 | RAB11FIP1 | −0.72 | 7.88E−05 | 3.44E−03 |
| ENSG00000081870 | 51668 | HSPB11 | −0.85 | 7.95E−05 | 3.45E−03 |
| ENSG00000133056 | 5287 | PIK3C2B | 0.47 | 7.94E−05 | 3.45E−03 |
| ENSG00000133313 | 55748 | CNDP2 | −0.77 | 7.98E−05 | 3.46E−03 |
| ENSG00000184903 | 83943 | IMMP2L | 0.82 | 8.32E−05 | 3.60E−03 |
| ENSG00000068976 | 5837 | PYGM | 1.50 | 8.37E−05 | 3.60E−03 |
| ENSG00000037042 | 27175 | TUBG2 | 0.71 | 8.40E−05 | 3.61E−03 |
| ENSG00000168056 | 4054 | LTBP3 | 0.85 | 8.45E−05 | 3.61E−03 |
| ENSG00000168067 | 5871 | MAP4K2 | 0.60 | 8.44E−05 | 3.61E−03 |
| ENSG00000119630 | 5228 | PGF | 1.77 | 8.51E−05 | 3.62E−03 |
| ENSG00000116678 | 3953 | LEPR | 1.54 | 8.58E−05 | 3.64E−03 |
| ENSG00000166226 | 10576 | CCT2 | −0.59 | 8.78E−05 | 3.72E−03 |
| ENSG00000167088 | 6632 | SNRPD1 | −0.54 | 8.80E−05 | 3.72E−03 |
| ENSG00000105696 | 25789 | TMEM59L | 1.67 | 8.95E−05 | 3.73E−03 |
| ENSG00000105711 | 6324 | SCN1B | 1.26 | 8.96E−05 | 3.73E−03 |
| ENSG00000134339 | 6289 | SAA2 | −1.78 | 8.97E−05 | 3.73E−03 |
| ENSG00000139631 | 51380 | CSAD | 0.90 | 8.88E−05 | 3.73E−03 |
| ENSG00000162928 | 5194 | PEX13 | −0.59 | 8.91E−05 | 3.73E−03 |
| ENSG00000005189 | 81691 | | −0.88 | 9.05E−05 | 3.74E−03 |
| ENSG00000137947 | 2959 | GTF2B | −0.53 | 9.01E−05 | 3.74E−03 |
| ENSG00000166793 | 219539 | YPEL4 | 1.34 | 9.06E−05 | 3.74E−03 |
| ENSG00000156299 | 7074 | TIAM1 | 0.90 | 9.12E−05 | 3.75E−03 |
| ENSG00000138385 | 6741 | SSB | −0.66 | 9.17E−05 | 3.77E−03 |
| ENSG00000231259 | NA | | 0.99 | 9.22E−05 | 3.77E−03 |
| ENSG00000150773 | 120379 | PIH1D2 | −1.07 | 9.31E−05 | 3.80E−03 |
| ENSG00000172586 | 118487 | CHCHD1 | −0.80 | 9.32E−05 | 3.80E−03 |
| ENSG00000134058 | 1022 | CDK7 | −0.78 | 9.49E−05 | 3.84E−03 |
| ENSG00000196636 | 57001 | SDHAF3 | −0.92 | 9.47E−05 | 3.84E−03 |
| ENSG00000116288 | 11315 | PARK7 | −0.33 | 9.92E−05 | 4.00E−03 |
| ENSG00000078596 | 9452 | ITM2A | 1.13 | 1.01E−04 | 4.05E−03 |
| ENSG00000092096 | 51310 | SLC22A17 | 1.07 | 1.01E−04 | 4.05E−03 |
| ENSG00000233974 | NA | | 1.28 | 1.01E−04 | 4.05E−03 |
| ENSG00000104419 | 10397 | NDRG1 | 1.20 | 1.02E−04 | 4.07E−03 |
| ENSG00000197993 | 3792 | KEL | 1.38 | 1.02E−04 | 4.08E−03 |
| ENSG00000000419 | 8813 | DPM1 | −0.56 | 1.03E−04 | 4.08E−03 |
| ENSG00000075089 | 64431 | ACTR6 | −0.66 | 1.04E−04 | 4.08E−03 |
| ENSG00000101443 | 10406 | WFDC2 | −1.35 | 1.04E−04 | 4.08E−03 |
| ENSG00000140526 | 11057 | ABHD2 | −0.77 | 1.03E−04 | 4.08E−03 |
| ENSG00000198087 | 23607 | CD2AP | −0.57 | 1.04E−04 | 4.08E−03 |
| ENSG00000149150 | 8501 | SLC43A1 | 0.96 | 1.05E−04 | 4.11E−03 |
| ENSG00000251039 | NA | IGKV2D-40 | 1.53 | 1.05E−04 | 4.11E−03 |
| ENSG00000172935 | 116535 | MRGPRF | 1.56 | 1.06E−04 | 4.13E−03 |

TABLE 10-continued

Differentially expressed genes in non-smoker UIP vs. non-smoker Non-UIP samples.
Table 10. Non-smokers

| Ensembl ID | Entrez ID | Gene symbol | Log2 Fold Change (UIP/NonUIP) | P value | FDR P value |
|---|---|---|---|---|---|
| ENSG00000221716 | 677799 | SNORA11 | 1.44 | 1.06E−04 | 4.14E−03 |
| ENSG00000148400 | 4851 | NOTCH1 | 0.61 | 1.08E−04 | 4.16E−03 |
| ENSG00000224411 | NA | HSP90AA2P | −0.80 | 1.07E−04 | 4.16E−03 |
| ENSG00000103168 | 9013 | TAF1C | 0.98 | 1.11E−04 | 4.28E−03 |
| ENSG00000032742 | 8100 | IFT88 | −0.68 | 1.13E−04 | 4.34E−03 |
| ENSG00000112297 | 202 | AIM1 | −0.48 | 1.15E−04 | 4.42E−03 |
| ENSG00000172037 | 3913 | LAMB2 | 0.72 | 1.15E−04 | 4.42E−03 |
| ENSG00000119328 | 54942 | FAM206A | −0.63 | 1.17E−04 | 4.45E−03 |
| ENSG00000164114 | 79884 | MAP9 | −0.78 | 1.17E−04 | 4.45E−03 |
| ENSG00000100591 | 10598 | AHSA1 | −0.74 | 1.22E−04 | 4.62E−03 |
| ENSG00000127884 | 1892 | ECHS1 | −0.42 | 1.24E−04 | 4.62E−03 |
| ENSG00000134709 | 51361 | HOOK1 | −0.81 | 1.23E−04 | 4.62E−03 |
| ENSG00000153904 | 23576 | DDAH1 | −0.53 | 1.22E−04 | 4.62E−03 |
| ENSG00000165929 | 123036 | TC2N | −0.81 | 1.24E−04 | 4.62E−03 |
| ENSG00000169550 | 143662 | MUC15 | −1.09 | 1.23E−04 | 4.62E−03 |
| ENSG00000214776 | NA | | 1.28 | 1.23E−04 | 4.62E−03 |
| ENSG00000163406 | 6565 | SLC15A2 | −0.97 | 1.24E−04 | 4.63E−03 |
| ENSG00000177054 | 54503 | ZDHHC13 | −0.84 | 1.24E−04 | 4.63E−03 |
| ENSG00000100626 | 57452 | GALNT16 | 1.34 | 1.27E−04 | 4.70E−03 |
| ENSG00000129055 | 25847 | ANAPC13 | −0.81 | 1.27E−04 | 4.70E−03 |
| ENSG00000080824 | 3320 | HSP90AA1 | −0.67 | 1.28E−04 | 4.72E−03 |
| ENSG00000119912 | 3416 | IDE | −0.54 | 1.31E−04 | 4.81E−03 |
| ENSG00000148346 | 3934 | LCN2 | −1.55 | 1.31E−04 | 4.82E−03 |
| ENSG00000211459 | NA | MT-RNR1 | 0.83 | 1.32E−04 | 4.85E−03 |
| ENSG00000175309 | 85007 | PHYKPL | 0.77 | 1.33E−04 | 4.87E−03 |
| ENSG00000178460 | 157777 | MCMDC2 | −1.36 | 1.33E−04 | 4.87E−03 |
| ENSG00000159079 | 56683 | C21orf59 | −1.02 | 1.37E−04 | 4.99E−03 |
| ENSG00000137691 | 85016 | C11orf70 | −1.02 | 1.38E−04 | 5.02E−03 |
| ENSG00000185585 | 169611 | OLFML2A | 1.02 | 1.39E−04 | 5.02E−03 |
| ENSG00000127838 | 25953 | PNKD | −0.49 | 1.40E−04 | 5.06E−03 |
| ENSG00000143387 | 1513 | CTSK | 1.44 | 1.40E−04 | 5.06E−03 |
| ENSG00000142733 | 9064 | MAP3K6 | 0.60 | 1.42E−04 | 5.11E−03 |
| ENSG00000147862 | 4781 | NFIB | 0.61 | 1.46E−04 | 5.22E−03 |
| ENSG00000115339 | 2591 | GALNT3 | −0.90 | 1.46E−04 | 5.23E−03 |
| ENSG00000073969 | 4905 | NSF | −0.51 | 1.48E−04 | 5.28E−03 |
| ENSG00000109971 | 3312 | HSPA8 | −0.53 | 1.49E−04 | 5.29E−03 |
| ENSG00000116299 | 57535 | KIAA1324 | −0.76 | 1.51E−04 | 5.35E−03 |
| ENSG00000092421 | 57556 | SEMA6A | 1.00 | 1.52E−04 | 5.36E−03 |
| ENSG00000129493 | 25938 | HEATR5A | −0.39 | 1.52E−04 | 5.36E−03 |
| ENSG00000197279 | 7718 | ZNF165 | −0.98 | 1.51E−04 | 5.36E−03 |
| ENSG00000161544 | 114757 | CYGB | 0.93 | 1.54E−04 | 5.41E−03 |
| ENSG00000211890 | NA | IGHA2 | 1.70 | 1.54E−04 | 5.42E−03 |
| ENSG00000133063 | 1118 | CHIT1 | 1.69 | 1.57E−04 | 5.50E−03 |
| ENSG00000160469 | 84446 | BRSK1 | 1.36 | 1.62E−04 | 5.63E−03 |
| ENSG00000185681 | 254956 | MORN5 | −1.16 | 1.61E−04 | 5.63E−03 |
| ENSG00000122420 | 5737 | PTGFR | −1.33 | 1.63E−04 | 5.66E−03 |
| ENSG00000130066 | 6303 | SAT1 | −0.63 | 1.63E−04 | 5.66E−03 |
| ENSG00000179222 | 9500 | MAGED1 | −0.58 | 1.65E−04 | 5.72E−03 |
| ENSG00000095380 | 54187 | NANS | −0.75 | 1.68E−04 | 5.79E−03 |
| ENSG00000089127 | 4938 | OAS1 | −1.31 | 1.69E−04 | 5.83E−03 |
| ENSG00000066185 | 84217 | ZMYND12 | −1.04 | 1.70E−04 | 5.83E−03 |
| ENSG00000234745 | 3106 | HLA-B | −0.84 | 1.71E−04 | 5.85E−03 |
| ENSG00000175792 | 8607 | RUVBL1 | −0.80 | 1.72E−04 | 5.88E−03 |
| ENSG00000101846 | 412 | STS | −0.54 | 1.75E−04 | 5.97E−03 |
| ENSG00000206149 | 440248 | HERC2P9 | 0.90 | 1.78E−04 | 6.06E−03 |
| ENSG00000076685 | 22978 | NT5C2 | −0.42 | 1.79E−04 | 6.09E−03 |
| ENSG00000069702 | 7049 | TGFBR3 | 0.94 | 1.80E−04 | 6.10E−03 |
| ENSG00000153292 | 266977 | ADGRF1 | −1.45 | 1.81E−04 | 6.11E−03 |
| ENSG00000059145 | 64718 | UNKL | 0.91 | 1.83E−04 | 6.14E−03 |
| ENSG00000113212 | 56129 | PCDHB7 | 1.36 | 1.83E−04 | 6.14E−03 |
| ENSG00000177455 | 930 | CD19 | 1.71 | 1.82E−04 | 6.14E−03 |
| ENSG00000106483 | 6424 | SFRP4 | 1.62 | 1.83E−04 | 6.14E−03 |
| ENSG00000013016 | 30845 | EHD3 | 1.11 | 1.85E−04 | 6.18E−03 |
| ENSG00000168961 | 3965 | LGALS9 | −0.70 | 1.85E−04 | 6.18E−03 |
| ENSG00000163131 | 1520 | CTSS | −0.77 | 1.87E−04 | 6.24E−03 |
| ENSG00000147041 | 94122 | SYTL5 | −1.12 | 1.89E−04 | 6.25E−03 |
| ENSG00000214517 | 51400 | PPME1 | −0.60 | 1.89E−04 | 6.25E−03 |
| ENSG00000211956 | NA | IGHV4-34 | 1.68 | 1.89E−04 | 6.26E−03 |
| ENSG00000110675 | 55531 | ELMOD1 | 1.58 | 1.91E−04 | 6.29E−03 |
| ENSG00000128039 | 79644 | SRD5A3 | −0.97 | 1.93E−04 | 6.35E−03 |
| ENSG00000185813 | 5833 | PCYT2 | −0.92 | 1.95E−04 | 6.40E−03 |
| ENSG00000184254 | 220 | ALDH1A3 | −0.68 | 2.01E−04 | 6.58E−03 |
| ENSG00000084207 | 2950 | GSTP1 | −0.85 | 2.03E−04 | 6.59E−03 |

TABLE 10-continued

Differentially expressed genes in non-smoker UIP vs. non-smoker Non-UIP samples.
Table 10. Non-smokers

| Ensembl ID | Entrez ID | Gene symbol | Log2 Fold Change (UIP/NonUIP) | P value | FDR P value |
|---|---|---|---|---|---|
| ENSG00000123243 | 80760 | ITIH5 | 1.40 | 2.03E−04 | 6.59E−03 |
| ENSG00000143106 | 5686 | PSMA5 | −0.56 | 2.02E−04 | 6.59E−03 |
| ENSG00000167775 | 51293 | CD320 | 0.85 | 2.03E−04 | 6.59E−03 |
| ENSG00000187391 | 9863 | MAGI2 | 0.92 | 2.03E−04 | 6.59E−03 |
| ENSG00000168477 | 7148 | TNXB | 1.50 | 2.08E−04 | 6.74E−03 |
| ENSG00000241755 | NA | IGKV1-9 | 1.66 | 2.11E−04 | 6.81E−03 |
| ENSG00000136810 | 7295 | TXN | −0.77 | 2.13E−04 | 6.87E−03 |
| ENSG00000104332 | 6422 | SFRP1 | 1.68 | 2.14E−04 | 6.87E−03 |
| ENSG00000184076 | 29796 | UQCR10 | −0.78 | 2.14E−04 | 6.87E−03 |
| ENSG00000106537 | 27075 | TSPAN13 | −0.82 | 2.15E−04 | 6.88E−03 |
| ENSG00000127362 | 50831 | TAS2R3 | 1.02 | 2.16E−04 | 6.91E−03 |
| ENSG00000160213 | 1476 | CSTB | −0.51 | 2.17E−04 | 6.91E−03 |
| ENSG00000067064 | 3422 | IDI1 | −0.95 | 2.19E−04 | 6.95E−03 |
| ENSG00000143196 | 1805 | DPT | 1.57 | 2.21E−04 | 7.00E−03 |
| ENSG00000105929 | 50617 | ATP6V0A4 | −1.54 | 2.24E−04 | 7.09E−03 |
| ENSG00000145391 | 80854 | SETD7 | 0.69 | 2.27E−04 | 7.16E−03 |
| ENSG00000066735 | 26153 | KIF26A | 1.55 | 2.28E−04 | 7.19E−03 |
| ENSG00000108179 | 10105 | PPIF | −0.65 | 2.30E−04 | 7.22E−03 |
| ENSG00000124107 | 6590 | SLPI | −1.05 | 2.30E−04 | 7.22E−03 |
| ENSG00000163902 | 6184 | RPN1 | −0.42 | 2.31E−04 | 7.22E−03 |
| ENSG00000198919 | 9666 | DZIP3 | −0.79 | 2.31E−04 | 7.22E−03 |
| ENSG00000134363 | 10468 | FST | 1.30 | 2.32E−04 | 7.24E−03 |
| ENSG00000133328 | 54979 | HRASLS2 | −1.41 | 2.35E−04 | 7.32E−03 |
| ENSG00000100968 | 4776 | NFATC4 | 1.14 | 2.36E−04 | 7.33E−03 |
| ENSG00000097007 | 25 | ABL1 | 0.38 | 2.41E−04 | 7.46E−03 |
| ENSG00000147155 | 10682 | EBP | −0.75 | 2.41E−04 | 7.46E−03 |
| ENSG00000184432 | 9276 | COPB2 | −0.48 | 2.43E−04 | 7.50E−03 |
| ENSG00000135387 | 4076 | CAPRIN1 | −0.38 | 2.44E−04 | 7.52E−03 |
| ENSG00000177169 | 8408 | ULK1 | 0.49 | 2.47E−04 | 7.58E−03 |
| ENSG00000086232 | 27102 | EIF2AK1 | −0.46 | 2.49E−04 | 7.63E−03 |
| ENSG00000132141 | 10693 | CCT6B | −0.92 | 2.50E−04 | 7.66E−03 |
| ENSG00000102900 | 9688 | NUP93 | −0.43 | 2.51E−04 | 7.66E−03 |
| ENSG00000117528 | 5825 | ABCD3 | −0.57 | 2.52E−04 | 7.67E−03 |
| ENSG00000167523 | 124045 | SPATA33 | −0.90 | 2.54E−04 | 7.74E−03 |
| ENSG00000203734 | 345930 | ECT2L | −0.91 | 2.60E−04 | 7.88E−03 |
| ENSG00000044115 | 1495 | CTNNA1 | −0.40 | 2.65E−04 | 8.04E−03 |
| ENSG00000065361 | 2065 | ERBB3 | −0.86 | 2.67E−04 | 8.06E−03 |
| ENSG00000138294 | NA | NA | −1.54 | 2.67E−04 | 8.06E−03 |
| ENSG00000197697 | NA | NA | −0.77 | 2.68E−04 | 8.07E−03 |
| ENSG00000184983 | 4700 | NDUFA6 | −0.52 | 2.69E−04 | 8.07E−03 |
| ENSG00000155254 | 83742 | MARVELD1 | 1.25 | 2.73E−04 | 8.17E−03 |
| ENSG00000081760 | 65985 | AACS | −0.64 | 2.74E−04 | 8.17E−03 |
| ENSG00000132746 | 222 | ALDH3B2 | −1.46 | 2.74E−04 | 8.17E−03 |
| ENSG00000151364 | 65987 | KCTD14 | −1.25 | 2.73E−04 | 8.17E−03 |
| ENSG00000164347 | 84340 | GFM2 | −0.86 | 2.75E−04 | 8.17E−03 |
| ENSG00000105875 | 29062 | WDR91 | 0.65 | 2.77E−04 | 8.21E−03 |
| ENSG00000136153 | 4008 | LMO7 | −0.80 | 2.81E−04 | 8.31E−03 |
| ENSG00000116133 | 1718 | DHCR24 | −0.76 | 2.83E−04 | 8.35E−03 |
| ENSG00000124201 | 57169 | ZNFX1 | −0.52 | 2.84E−04 | 8.37E−03 |
| ENSG00000158234 | 55179 | FAIM | −0.82 | 2.85E−04 | 8.38E−03 |
| ENSG00000144834 | 29114 | TAGLN3 | −1.37 | 2.86E−04 | 8.41E−03 |
| ENSG00000099290 | 387680 | FAM21A | −1.43 | 2.87E−04 | 8.42E−03 |
| ENSG00000149021 | 7356 | SCGB1A1 | −1.45 | 2.90E−04 | 8.49E−03 |
| ENSG00000135378 | 79056 | PRRG4 | −0.92 | 2.92E−04 | 8.54E−03 |
| ENSG00000134744 | 23318 | ZCCHC11 | 0.50 | 2.99E−04 | 8.71E−03 |
| ENSG00000005175 | 79657 | RPAP3 | −0.38 | 3.01E−04 | 8.77E−03 |
| ENSG00000173467 | 155465 | AGR3 | −0.78 | 3.04E−04 | 8.81E−03 |
| ENSG00000164251 | 2150 | F2RL1 | −0.87 | 3.12E−04 | 9.03E−03 |
| ENSG00000253250 | 100127983 | C8orf88 | 1.46 | 3.14E−04 | 9.09E−03 |
| ENSG00000090061 | 8812 | CCNK | −0.34 | 3.23E−04 | 9.32E−03 |
| ENSG00000101204 | 1137 | CHRNA4 | 1.64 | 3.23E−04 | 9.32E−03 |
| ENSG00000143127 | 8515 | ITGA10 | 1.00 | 3.26E−04 | 9.36E−03 |
| ENSG00000187800 | 375033 | PEAR1 | 1.54 | 3.29E−04 | 9.45E−03 |
| ENSG00000162909 | 824 | CAPN2 | −0.49 | 3.32E−04 | 9.51E−03 |
| ENSG00000103316 | 1428 | CRYM | −1.06 | 3.34E−04 | 9.55E−03 |
| ENSG00000069869 | 4734 | NEDD4 | 0.92 | 3.37E−04 | 9.58E−03 |
| ENSG00000162407 | 8613 | PPAP2B | 1.12 | 3.37E−04 | 9.58E−03 |
| ENSG00000143933 | 805 | CALM2 | −0.58 | 3.40E−04 | 9.66E−03 |
| ENSG00000125827 | 56255 | TMX4 | 0.60 | 3.41E−04 | 9.67E−03 |
| ENSG00000185055 | NA | EFCAB10 | −1.13 | 3.47E−04 | 9.82E−03 |
| ENSG00000029993 | 3149 | HMGB3 | −0.96 | 3.54E−04 | 9.94E−03 |
| ENSG00000135424 | 3679 | ITGA7 | 1.29 | 3.53E−04 | 9.94E−03 |
| ENSG00000158373 | 3017 | HIST1H2BD | −0.54 | 3.52E−04 | 9.94E−03 |

TABLE 10-continued

Differentially expressed genes in non-smoker UIP vs. non-smoker Non-UIP samples.
Table 10. Non-smokers

| Ensembl ID | Entrez ID | Gene symbol | Log2 Fold Change (UIP/NonUIP) | P value | FDR P value |
|---|---|---|---|---|---|
| ENSG00000165097 | 221656 | KDM1B | −0.71 | 3.53E−04 | 9.94E−03 |
| ENSG00000173432 | 6288 | SAA1 | −1.61 | 3.55E−04 | 9.95E−03 |

UIP (n = 3 samples); Non-UIP (n = 5 samples). Positive log2 fold change value indicates over-expression in UIP relative to Non UIP; negative log2 value indicates under-expression in UIP relative to Non UIP. In this analysis only patients without any smoking history were evaluated, hence this subset harbored only non-smokers.

TABLE 11

Differentially expressed genes in UIP samples from smokers vs. Non-UIP samples from smokers.
Table 11. Smokers

| Ensembl ID | Entrez ID | Gene symbol | Log2 Fold Change (UIP/NonUIP) | p value | FDR P value |
|---|---|---|---|---|---|
| ENSG00000137968 | 204962 | SLC44A5 | 3.58 | 2.38E−20 | 3.68E−16 |
| ENSG00000099968 | 23786 | BCL2L13 | −0.68 | 3.12E−18 | 2.41E−14 |
| ENSG00000168329 | 1524 | CX3CR1 | 2.27 | 8.45E−14 | 4.35E−10 |
| ENSG00000088882 | 56265 | CPXM1 | 2.72 | 1.16E−11 | 4.49E−08 |
| ENSG00000152672 | 165530 | CLEC4F | 2.63 | 1.78E−11 | 5.49E−08 |
| ENSG00000129204 | 9098 | USP6 | 2.74 | 5.40E−11 | 1.39E−07 |
| ENSG00000132823 | 51526 | OSER1 | −0.56 | 3.27E−10 | 7.21E−07 |
| ENSG00000177666 | 57104 | PNPLA2 | −0.84 | 9.60E−10 | 1.85E−06 |
| ENSG00000125730 | 718 | C3 | 1.60 | 1.11E−09 | 1.90E−06 |
| ENSG00000198074 | 57016 | AKR1B10 | −2.89 | 1.97E−09 | 3.04E−06 |
| ENSG00000198142 | 65124 | SOWAHC | −1.00 | 3.09E−09 | 4.34E−06 |
| ENSG00000112130 | 9025 | RNF8 | −0.56 | 4.53E−09 | 5.83E−06 |
| ENSG00000255112 | 57132 | CHMP1B | −0.86 | 1.94E−08 | 2.31E−05 |
| ENSG00000145888 | 2741 | GLRA1 | 2.19 | 2.15E−08 | 2.37E−05 |
| ENSG00000151632 | 1646 | AKR1C2 | −2.37 | 2.60E−08 | 2.68E−05 |
| ENSG00000238741 | 677767 | SCARNA7 | 0.58 | 2.90E−08 | 2.80E−05 |
| ENSG00000148948 | 57689 | LRRC4C | 2.14 | 3.13E−08 | 2.84E−05 |
| ENSG00000179344 | 3119 | HLA-DQB1 | 2.30 | 2.89E−07 | 2.35E−04 |
| ENSG00000211789 | NA | TRAV12-2 | 2.44 | 2.75E−07 | 2.35E−04 |
| ENSG00000106565 | 28959 | TMEM176B | 1.55 | 3.23E−07 | 2.44E−04 |
| ENSG00000204338 | NA | CYP21A1P | 2.23 | 3.32E−07 | 2.44E−04 |
| ENSG00000010932 | 2326 | FMO1 | 2.17 | 4.30E−07 | 3.01E−04 |
| ENSG00000103742 | 57722 | IGDCC4 | 2.37 | 4.82E−07 | 3.24E−04 |
| ENSG00000162692 | 7412 | VCAM1 | 2.12 | 5.91E−07 | 3.80E−04 |
| ENSG00000158481 | 911 | CD1C | 1.96 | 6.26E−07 | 3.87E−04 |
| ENSG00000136098 | 4752 | NEK3 | 0.67 | 6.66E−07 | 3.95E−04 |
| ENSG00000134375 | 10440 | TIMM17A | −0.48 | 7.00E−07 | 4.00E−04 |
| ENSG00000127951 | 10875 | FGL2 | 1.23 | 1.18E−06 | 6.49E−04 |
| ENSG00000185022 | 23764 | MAFF | −1.68 | 1.22E−06 | 6.49E−04 |
| ENSG00000100079 | 3957 | LGALS2 | 1.93 | 1.51E−06 | 7.56E−04 |
| ENSG00000151572 | 121601 | ANO4 | 2.28 | 1.57E−06 | 7.56E−04 |
| ENSG00000238460 | NA | | 1.65 | 1.52E−06 | 7.56E−04 |
| ENSG00000187527 | 344905 | ATP13A5 | −2.18 | 1.99E−06 | 9.29E−04 |
| ENSG00000176153 | 2877 | GPX2 | −2.11 | 2.29E−06 | 1.04E−03 |
| ENSG00000105559 | 57664 | PLEKHA4 | 1.30 | 2.99E−06 | 1.32E−03 |
| ENSG00000178115 | NA | GOLGA8Q | 2.05 | 3.27E−06 | 1.40E−03 |
| ENSG00000137033 | 90865 | IL33 | 1.41 | 4.10E−06 | 1.68E−03 |
| ENSG00000196735 | 3117 | HLA-DQA1 | 2.10 | 4.14E−06 | 1.68E−03 |
| ENSG00000007944 | 29116 | MYLIP | −0.46 | 4.53E−06 | 1.79E−03 |
| ENSG00000130695 | 64793 | CEP85 | −0.76 | 4.86E−06 | 1.88E−03 |
| ENSG00000262539 | NA | | −2.01 | 5.01E−06 | 1.89E−03 |
| ENSG00000174194 | NA | NA | 1.27 | 5.42E−06 | 1.99E−03 |
| ENSG00000178187 | 285676 | ZNF454 | 1.08 | 6.40E−06 | 2.25E−03 |
| ENSG00000204256 | 6046 | BRD2 | −0.33 | 6.28E−06 | 2.25E−03 |
| ENSG00000002933 | 55365 | TMEM176A | 1.30 | 6.91E−06 | 2.36E−03 |
| ENSG00000196139 | 8644 | AKR1C3 | −1.45 | 7.02E−06 | 2.36E−03 |
| ENSG00000186529 | 4051 | CYP4F3 | −1.80 | 8.32E−06 | 2.66E−03 |
| ENSG00000227097 | NA | RPS28P7 | 1.59 | 8.45E−06 | 2.66E−03 |
| ENSG00000244486 | 91179 | SCARF2 | 1.00 | 8.18E−06 | 2.66E−03 |
| ENSG00000172985 | 344558 | SH3RF3 | 0.84 | 9.51E−06 | 2.94E−03 |
| ENSG00000023171 | 57476 | GRAMD1B | −1.22 | 1.13E−05 | 3.21E−03 |
| ENSG00000065613 | 9748 | SLK | −0.49 | 1.09E−05 | 3.21E−03 |
| ENSG00000143603 | 3782 | KCNN3 | 1.09 | 1.07E−05 | 3.21E−03 |
| ENSG00000154096 | 7070 | THY1 | 2.05 | 1.14E−05 | 3.21E−03 |
| ENSG00000178562 | 940 | CD28 | 2.08 | 1.11E−05 | 3.21E−03 |

TABLE 11-continued

Differentially expressed genes in UIP samples from smokers vs. Non-UIP samples from smokers. Table 11. Smokers

| Ensembl ID | Entrez ID | Gene symbol | Log2 Fold Change (UIP/NonUIP) | p value | FDR P value |
|---|---|---|---|---|---|
| ENSG00000196839 | 100 | ADA | 1.10 | 1.16E−05 | 3.21E−03 |
| ENSG00000159618 | 221188 | ADGRG5 | 1.59 | 1.21E−05 | 3.27E−03 |
| ENSG00000128309 | 4357 | MPST | −0.73 | 1.36E−05 | 3.61E−03 |
| ENSG00000168229 | 5729 | PTGDR | 1.61 | 1.39E−05 | 3.62E−03 |
| ENSG00000125510 | 4987 | OPRL1 | 1.56 | 1.45E−05 | 3.73E−03 |
| ENSG00000017427 | 3479 | IGF1 | 1.86 | 1.54E−05 | 3.83E−03 |
| ENSG00000159228 | 873 | CBR1 | −1.00 | 1.53E−05 | 3.83E−03 |
| ENSG00000136490 | 80774 | LIMD2 | 1.68 | 1.76E−05 | 4.19E−03 |
| ENSG00000177156 | 6888 | TALDO1 | −0.78 | 1.76E−05 | 4.19E−03 |
| ENSG00000225614 | 84627 | ZNF469 | 0.98 | 1.72E−05 | 4.19E−03 |
| ENSG00000218336 | 55714 | TENM3 | 1.69 | 1.88E−05 | 4.40E−03 |
| ENSG00000151693 | 8853 | ASAP2 | −0.60 | 1.97E−05 | 4.54E−03 |
| ENSG00000211941 | NA | IGHV3-11 | 2.04 | 2.00E−05 | 4.54E−03 |
| ENSG00000140961 | 29948 | OSGIN1 | −1.25 | 2.11E−05 | 4.73E−03 |
| ENSG00000124782 | 6239 | RREB1 | −0.41 | 2.30E−05 | 5.08E−03 |
| ENSG00000103222 | 4363 | ABCC1 | −0.81 | 2.55E−05 | 5.47E−03 |
| ENSG00000196664 | 51284 | TLR7 | 1.53 | 2.54E−05 | 5.47E−03 |
| ENSG00000148357 | 256158 | HMCN2 | 1.92 | 2.61E−05 | 5.53E−03 |
| ENSG00000124151 | 8202 | NCOA3 | −0.39 | 2.87E−05 | 6.00E−03 |
| ENSG00000211653 | NA | IGLV1-40 | 1.99 | 2.98E−05 | 6.06E−03 |
| ENSG00000230006 | 645784 | ANKRD36BP2 | 1.82 | 2.97E−05 | 6.06E−03 |
| ENSG00000106809 | 4969 | OGN | 1.85 | 3.11E−05 | 6.23E−03 |
| ENSG00000162877 | 148811 | PM20D1 | 1.70 | 3.17E−05 | 6.28E−03 |
| ENSG00000128016 | 7538 | ZFP36 | −1.41 | 3.51E−05 | 6.77E−03 |
| ENSG00000196345 | 55888 | ZKSCAN7 | 0.83 | 3.49E−05 | 6.77E−03 |
| ENSG00000108821 | 1277 | COL1A1 | 1.88 | 3.56E−05 | 6.78E−03 |
| ENSG00000137573 | 23213 | SULF1 | 1.63 | 3.68E−05 | 6.93E−03 |
| ENSG00000197993 | 3792 | KEL | 1.86 | 3.93E−05 | 7.32E−03 |
| ENSG00000170153 | 57484 | RNF150 | 1.44 | 4.36E−05 | 8.00E−03 |
| ENSG00000130513 | 9518 | GDF15 | −1.73 | 4.55E−05 | 8.20E−03 |
| ENSG00000174123 | 81793 | TLR10 | 1.81 | 4.57E−05 | 8.20E−03 |
| ENSG00000110076 | 9379 | NRXN2 | 1.95 | 4.68E−05 | 8.30E−03 |
| ENSG00000182551 | 55256 | ADI1 | −0.52 | 5.20E−05 | 9.08E−03 |
| ENSG00000182557 | 201305 | SPNS3 | 1.65 | 5.23E−05 | 9.08E−03 |
| ENSG00000117215 | 26279 | PLA2G2D | 1.94 | 5.54E−05 | 9.50E−03 |
| ENSG00000128285 | 2847 | MCHR1 | 1.85 | 5.80E−05 | 9.83E−03 |
| ENSG00000183813 | 1233 | CCR4 | 1.90 | 6.00E−05 | 1.01E−02 |
| ENSG00000007312 | 974 | CD79B | 1.81 | 6.30E−05 | 1.04E−02 |
| ENSG00000163817 | 54716 | SLC6A20 | 1.85 | 6.43E−05 | 1.06E−02 |
| ENSG00000102802 | 84935 | MEDAG | 1.85 | 6.69E−05 | 1.09E−02 |
| ENSG00000101134 | 55816 | DOK5 | 1.90 | 7.00E−05 | 1.10E−02 |
| ENSG00000102362 | 94121 | SYTL4 | −0.80 | 6.89E−05 | 1.10E−02 |
| ENSG00000128000 | 163131 | ZNF780B | 0.66 | 7.03E−05 | 1.10E−02 |
| ENSG00000256229 | 90649 | ZNF486 | 1.00 | 7.04E−05 | 1.10E−02 |
| ENSG00000086102 | 4799 | NFX1 | −0.36 | 7.46E−05 | 1.14E−02 |
| ENSG00000099875 | 2872 | MKNK2 | −0.58 | 7.58E−05 | 1.14E−02 |
| ENSG00000171502 | 255631 | COL24A1 | 1.24 | 7.69E−05 | 1.14E−02 |
| ENSG00000211637 | NA | IGLV4-69 | 1.91 | 7.66E−05 | 1.14E−02 |
| ENSG00000244731 | 720 | C4A | 1.50 | 7.70E−05 | 1.14E−02 |
| ENSG00000082641 | 4779 | NFE2L1 | −0.32 | 7.79E−05 | 1.14E−02 |
| ENSG00000136802 | 56262 | LRRC8A | −0.91 | 8.12E−05 | 1.18E−02 |
| ENSG00000225784 | NA | NA | 1.81 | 8.26E−05 | 1.19E−02 |
| ENSG00000181631 | 53829 | P2RY13 | 1.57 | 8.40E−05 | 1.20E−02 |
| ENSG00000116031 | 50489 | CD207 | 1.47 | 8.80E−05 | 1.25E−02 |
| ENSG00000108106 | 27338 | UBE2S | −0.71 | 9.40E−05 | 1.32E−02 |
| ENSG00000105639 | 3718 | JAK3 | 1.60 | 1.06E−04 | 1.43E−02 |
| ENSG00000125804 | 284800 | FAM182A | 1.82 | 1.07E−04 | 1.43E−02 |
| ENSG00000139722 | 79720 | VPS37B | −0.67 | 1.07E−04 | 1.43E−02 |
| ENSG00000157557 | 2114 | ETS2 | −0.85 | 1.03E−04 | 1.43E−02 |
| ENSG00000165841 | 1557 | CYP2C19 | −1.37 | 1.07E−04 | 1.43E−02 |
| ENSG00000182487 | 654816 | NCF1B | 1.59 | 1.05E−04 | 1.43E−02 |
| ENSG00000171847 | 55138 | FAM90A1 | 1.18 | 1.08E−04 | 1.43E−02 |
| ENSG00000162804 | 25992 | SNED1 | 0.71 | 1.09E−04 | 1.43E−02 |
| ENSG00000186184 | 51082 | POLR1D | −0.67 | 1.11E−04 | 1.43E−02 |
| ENSG00000172493 | 4299 | AFF1 | −0.34 | 1.14E−04 | 1.47E−02 |
| ENSG00000179954 | 284297 | SSC5D | 1.43 | 1.15E−04 | 1.47E−02 |
| ENSG00000244682 | NA | FCGR2C | 1.54 | 1.17E−04 | 1.48E−02 |
| ENSG00000081148 | 50939 | IMPG2 | 0.85 | 1.23E−04 | 1.54E−02 |
| ENSG00000126353 | 1236 | CCR7 | 1.51 | 1.26E−04 | 1.57E−02 |
| ENSG00000197705 | 57565 | KLHL14 | 1.75 | 1.27E−04 | 1.57E−02 |
| ENSG00000232268 | 390037 | OR52I1 | 1.53 | 1.30E−04 | 1.59E−02 |
| ENSG00000099204 | 3983 | ABLIM1 | −0.69 | 1.32E−04 | 1.61E−02 |

TABLE 11-continued

Differentially expressed genes in UIP samples from smokers vs. Non-UIP samples from smokers. Table 11. Smokers

| Ensembl ID | Entrez ID | Gene symbol | Log2 Fold Change (UIP/NonUIP) | p value | FDR P value |
|---|---|---|---|---|---|
| ENSG00000158477 | 909 | CD1A | 1.84 | 1.39E−04 | 1.68E−02 |
| ENSG00000172336 | 10248 | POP7 | −0.45 | 1.40E−04 | 1.68E−02 |
| ENSG00000138109 | 1559 | CYP2C9 | −1.47 | 1.44E−04 | 1.71E−02 |
| ENSG00000124766 | 6659 | SOX4 | −0.89 | 1.50E−04 | 1.77E−02 |
| ENSG00000114115 | 5947 | RBP1 | 0.96 | 1.57E−04 | 1.84E−02 |
| ENSG00000156463 | 153769 | SH3RF2 | −1.28 | 1.62E−04 | 1.88E−02 |
| ENSG00000038358 | 23644 | EDC4 | −0.26 | 1.64E−04 | 1.88E−02 |
| ENSG00000211899 | NA | IGHM | 1.79 | 1.64E−04 | 1.88E−02 |
| ENSG00000263503 | NA | | −1.70 | 1.66E−04 | 1.88E−02 |
| ENSG00000005955 | NA | NA | −0.32 | 1.71E−04 | 1.91E−02 |
| ENSG00000144040 | 94097 | SFXN5 | 0.69 | 1.71E−04 | 1.91E−02 |
| ENSG00000105058 | 26017 | FAM32A | −0.37 | 1.90E−04 | 2.11E−02 |
| ENSG00000135837 | 9857 | CEP350 | −0.29 | 1.92E−04 | 2.12E−02 |
| ENSG00000205148 | NA | NA | 1.63 | 1.93E−04 | 2.12E−02 |
| ENSG00000028277 | 5452 | POU2F2 | 1.61 | 1.97E−04 | 2.15E−02 |
| ENSG00000211747 | NA | TRBV20-1 | 1.78 | 2.04E−04 | 2.20E−02 |
| ENSG00000148730 | 1979 | EIF4EBP2 | −0.51 | 2.25E−04 | 2.40E−02 |
| ENSG00000181036 | 343413 | FCRL6 | 1.52 | 2.26E−04 | 2.40E−02 |
| ENSG00000138660 | 55435 | AP1AR | −0.61 | 2.29E−04 | 2.41E−02 |
| ENSG00000144619 | 152330 | CNTN4 | 1.25 | 2.28E−04 | 2.41E−02 |
| ENSG00000000971 | 3075 | CFH | 0.81 | 2.42E−04 | 2.46E−02 |
| ENSG00000099251 | 158160 | HSD17B7P2 | 0.95 | 2.44E−04 | 2.46E−02 |
| ENSG00000156140 | 9508 | ADAMTS3 | 1.24 | 2.42E−04 | 2.46E−02 |
| ENSG00000163113 | NA | NA | −0.63 | 2.41E−04 | 2.46E−02 |
| ENSG00000181458 | 55076 | TMEM45A | 1.40 | 2.37E−04 | 2.46E−02 |
| ENSG00000251287 | 644974 | ALG1L2 | 1.42 | 2.44E−04 | 2.46E−02 |
| ENSG00000086544 | 80271 | ITPKC | −0.57 | 2.52E−04 | 2.52E−02 |
| ENSG00000167984 | 197358 | NLRC3 | 1.07 | 2.55E−04 | 2.54E−02 |
| ENSG00000149633 | 85449 | KIAA1755 | 1.69 | 2.59E−04 | 2.56E−02 |
| ENSG00000102271 | 56062 | KLHL4 | 1.75 | 2.62E−04 | 2.58E−02 |
| ENSG00000137815 | 23168 | RTF1 | −0.36 | 2.81E−04 | 2.72E−02 |
| ENSG00000141682 | 5366 | PMAIP1 | −1.36 | 2.81E−04 | 2.72E−02 |
| ENSG00000179909 | 7710 | ZNF154 | 1.14 | 2.80E−04 | 2.72E−02 |
| ENSG00000110427 | 25758 | KIAA1549L | 1.52 | 2.89E−04 | 2.77E−02 |
| ENSG00000144567 | 79137 | FAM134A | −0.43 | 2.97E−04 | 2.83E−02 |
| ENSG00000206561 | 8292 | COLQ | 0.81 | 3.01E−04 | 2.85E−02 |
| ENSG00000100304 | 23170 | TTLL12 | −0.92 | 3.11E−04 | 2.86E−02 |
| ENSG00000108852 | 4355 | MPP2 | 1.61 | 3.07E−04 | 2.86E−02 |
| ENSG00000181350 | 388341 | LRRC75A | 1.56 | 3.11E−04 | 2.86E−02 |
| ENSG00000186350 | 6256 | RXRA | −0.53 | 3.08E−04 | 2.86E−02 |
| ENSG00000253816 | NA | | 0.93 | 3.05E−04 | 2.86E−02 |
| ENSG00000026751 | 57823 | SLAMF7 | 1.36 | 3.13E−04 | 2.86E−02 |
| ENSG00000142178 | 150094 | SIK1 | −1.46 | 3.17E−04 | 2.86E−02 |
| ENSG00000148848 | 8038 | ADAM12 | 1.19 | 3.16E−04 | 2.86E−02 |
| ENSG00000148339 | 114789 | SLC25A25 | −0.71 | 3.20E−04 | 2.88E−02 |
| ENSG00000137747 | 84000 | TMPRSS13 | −0.89 | 3.23E−04 | 2.88E−02 |
| ENSG00000164061 | 8927 | BSN | 1.16 | 3.29E−04 | 2.92E−02 |
| ENSG00000102221 | 9767 | JADE3 | −0.48 | 3.34E−04 | 2.95E−02 |
| ENSG00000134291 | 79022 | TMEM106C | −0.84 | 3.67E−04 | 3.20E−02 |
| ENSG00000160007 | 2909 | ARHGAP35 | −0.32 | 3.69E−04 | 3.20E−02 |
| ENSG00000198060 | 54708 | MARCH5 | −0.39 | 3.67E−04 | 3.20E−02 |
| ENSG00000111725 | 5564 | PRKAB1 | −0.72 | 3.71E−04 | 3.20E−02 |
| ENSG00000211598 | NA | IGKV4-1 | 1.72 | 3.76E−04 | 3.23E−02 |
| ENSG00000101096 | 4773 | NFATC2 | 0.89 | 3.82E−04 | 3.25E−02 |
| ENSG00000215156 | 646652 | | 1.07 | 3.83E−04 | 3.25E−02 |
| ENSG00000117090 | 6504 | SLAMF1 | 1.64 | 3.89E−04 | 3.26E−02 |
| ENSG00000211892 | NA | IGHG4 | 1.71 | 3.88E−04 | 3.26E−02 |
| ENSG00000129245 | 9513 | FXR2 | −0.35 | 4.00E−04 | 3.33E−02 |
| ENSG00000211685 | NA | IGLC7 | 1.71 | 4.06E−04 | 3.37E−02 |
| ENSG00000085265 | 2219 | FCN1 | 1.67 | 4.11E−04 | 3.38E−02 |
| ENSG00000108691 | 6347 | CCL2 | 1.64 | 4.16E−04 | 3.38E−02 |
| ENSG00000109787 | 51274 | KLF3 | −0.67 | 4.15E−04 | 3.38E−02 |
| ENSG00000243264 | NA | IGKV2D-29 | 1.71 | 4.13E−04 | 3.38E−02 |
| ENSG00000178199 | 340152 | ZC3H12D | 1.65 | 4.19E−04 | 3.38E−02 |
| ENSG00000152413 | 9456 | HOMER1 | −0.58 | 4.24E−04 | 3.39E−02 |
| ENSG00000211893 | NA | IGHG2 | 1.70 | 4.25E−04 | 3.39E−02 |
| ENSG00000241755 | NA | IGKV1-9 | 1.70 | 4.21E−04 | 3.39E−02 |
| ENSG00000017797 | 10928 | RALBP1 | −0.39 | 4.36E−04 | 3.44E−02 |
| ENSG00000136826 | 9314 | KLF4 | −1.16 | 4.37E−04 | 3.44E−02 |
| ENSG00000102245 | 959 | CD40LG | 1.65 | 4.53E−04 | 3.49E−02 |
| ENSG00000144792 | 285349 | ZNF660 | 0.91 | 4.51E−04 | 3.49E−02 |
| ENSG00000151012 | 23657 | SLC7A11 | −1.55 | 4.45E−04 | 3.49E−02 |

TABLE 11-continued

Differentially expressed genes in UIP samples from smokers vs. Non-UIP samples from smokers. Table 11. Smokers

| Ensembl ID | Entrez ID | Gene symbol | Log2 Fold Change (UIP/NonUIP) | p value | FDR P value |
|---|---|---|---|---|---|
| ENSG00000182218 | 84439 | HHIPL1 | 1.55 | 4.48E−04 | 3.49E−02 |
| ENSG00000204961 | 9752 | PCDHA9 | 1.11 | 4.54E−04 | 3.49E−02 |
| ENSG00000160229 | NA | ZNF66 | 0.77 | 4.59E−04 | 3.51E−02 |
| ENSG00000087842 | 8544 | PIR | −0.94 | 4.67E−04 | 3.55E−02 |
| ENSG00000108344 | 5709 | PSMD3 | −0.35 | 4.76E−04 | 3.60E−02 |
| ENSG00000167077 | 150365 | MEI1 | 1.53 | 4.87E−04 | 3.67E−02 |
| ENSG00000211625 | NA | IGKV3D-20 | 1.68 | 4.91E−04 | 3.68E−02 |
| ENSG00000087152 | 56970 | ATXN7L3 | −0.27 | 5.09E−04 | 3.80E−02 |
| ENSG00000138166 | 1847 | DUSP5 | −1.57 | 5.15E−04 | 3.82E−02 |
| ENSG00000187987 | 222696 | ZSCAN23 | 1.19 | 5.20E−04 | 3.84E−02 |
| ENSG00000166676 | 780776 | TVP23A | 1.60 | 5.24E−04 | 3.85E−02 |
| ENSG00000107736 | 64072 | CDH23 | 1.28 | 5.27E−04 | 3.86E−02 |
| ENSG00000109685 | 7468 | WHSC1 | −0.43 | 5.41E−04 | 3.93E−02 |
| ENSG00000240382 | NA | IGKV1-17 | 1.67 | 5.43E−04 | 3.93E−02 |
| ENSG00000196724 | 147686 | ZNF418 | 0.90 | 5.47E−04 | 3.95E−02 |
| ENSG00000178031 | 92949 | ADAMTSL1 | 1.64 | 5.54E−04 | 3.98E−02 |
| ENSG00000109854 | 10553 | HTATIP2 | −0.72 | 5.69E−04 | 4.03E−02 |
| ENSG00000128606 | 10234 | LRRC17 | 1.37 | 5.69E−04 | 4.03E−02 |
| ENSG00000211974 | NA | | 1.66 | 5.69E−04 | 4.03E−02 |
| ENSG00000145002 | 653333 | FAM86B2 | 1.42 | 5.90E−04 | 4.14E−02 |
| ENSG00000185271 | 123103 | KLHL33 | 1.66 | 5.88E−04 | 4.14E−02 |
| ENSG00000147394 | 7739 | ZNF185 | −0.95 | 6.04E−04 | 4.22E−02 |
| ENSG00000105369 | 973 | CD79A | 1.65 | 6.09E−04 | 4.23E−02 |
| ENSG00000205403 | 3426 | CFI | 0.87 | 6.11E−04 | 4.23E−02 |
| ENSG00000242732 | 340526 | RGAG4 | 0.69 | 6.16E−04 | 4.24E−02 |
| ENSG00000074410 | 771 | CA12 | −1.59 | 6.25E−04 | 4.29E−02 |
| ENSG00000107020 | 55848 | PLGRKT | 0.66 | 6.34E−04 | 4.31E−02 |
| ENSG00000145555 | 4651 | MYO10 | −0.45 | 6.31E−04 | 4.31E−02 |
| ENSG00000183486 | 4600 | MX2 | −1.26 | 6.46E−04 | 4.37E−02 |
| ENSG00000066827 | 57623 | ZFAT | 0.33 | 6.62E−04 | 4.46E−02 |
| ENSG00000225217 | NA | HSPA7 | 1.46 | 6.65E−04 | 4.46E−02 |
| ENSG00000143851 | 5778 | PTPN7 | 1.35 | 6.77E−04 | 4.50E−02 |
| ENSG00000161381 | 57125 | PLXDC1 | 1.44 | 6.76E−04 | 4.50E−02 |
| ENSG00000134775 | 80206 | FHOD3 | 1.24 | 6.89E−04 | 4.55E−02 |
| ENSG00000154040 | 26256 | CABYR | −1.18 | 6.89E−04 | 4.55E−02 |
| ENSG00000239951 | NA | IGKV3-20 | 1.64 | 6.97E−04 | 4.58E−02 |
| ENSG00000137709 | 25833 | POU2F3 | −0.82 | 7.04E−04 | 4.60E−02 |
| ENSG00000123159 | 10755 | GIPC1 | −0.48 | 7.11E−04 | 4.61E−02 |
| ENSG00000211939 | NA | NA | 1.63 | 7.10E−04 | 4.61E−02 |
| ENSG00000211666 | NA | IGLV2-14 | 1.63 | 7.17E−04 | 4.63E−02 |
| ENSG00000227507 | 4050 | LTB | 1.60 | 7.24E−04 | 4.66E−02 |
| ENSG00000171714 | 203859 | ANO5 | 1.12 | 7.41E−04 | 4.75E−02 |
| ENSG00000078589 | 27334 | P2RY10 | 1.38 | 7.53E−04 | 4.76E−02 |
| ENSG00000108381 | 443 | ASPA | 1.44 | 7.50E−04 | 4.76E−02 |
| ENSG00000186310 | 4675 | NAP1L3 | 1.58 | 7.47E−04 | 4.76E−02 |
| ENSG00000164398 | 23305 | ACSL6 | 1.19 | 7.61E−04 | 4.80E−02 |
| ENSG00000117122 | 4237 | MFAP2 | 1.28 | 7.65E−04 | 4.80E−02 |
| ENSG00000145536 | 170690 | ADAMTS16 | 1.62 | 7.71E−04 | 4.80E−02 |
| ENSG00000251402 | NA | FAM90A25P | 1.02 | 7.70E−04 | 4.80E−02 |
| ENSG00000161681 | 50944 | SHANK1 | 1.62 | 7.95E−04 | 4.93E−02 |
| ENSG00000130584 | 140685 | ZBTB46 | 0.99 | 8.00E−04 | 4.93E−02 |
| ENSG00000204839 | 642475 | MROH6 | −1.17 | 8.02E−04 | 4.93E−02 |
| ENSG00000204544 | 394263 | MUC21 | −1.52 | 8.06E−04 | 4.94E−02 |
| ENSG00000112245 | 7803 | PTP4A1 | −0.59 | 8.14E−04 | 4.97E−02 |
| ENSG00000137265 | 3662 | IRF4 | 1.61 | 8.28E−04 | 5.04E−02 |
| ENSG00000105364 | 51073 | MRPL4 | −0.56 | 8.39E−04 | 5.06E−02 |
| ENSG00000178922 | 81888 | HYI | 0.84 | 8.36E−04 | 5.06E−02 |
| ENSG00000118849 | 5918 | RARRES1 | 1.24 | 8.47E−04 | 5.09E−02 |
| ENSG00000212743 | NA | | 1.23 | 8.58E−04 | 5.13E−02 |
| ENSG00000135074 | 8728 | ADAM19 | 1.42 | 8.76E−04 | 5.16E−02 |
| ENSG00000152689 | 25780 | RASGRP3 | 1.42 | 8.72E−04 | 5.16E−02 |
| ENSG00000154640 | 10950 | BTG3 | −0.77 | 8.74E−04 | 5.16E−02 |
| ENSG00000196581 | 55966 | AJAP1 | −1.59 | 8.74E−04 | 5.16E−02 |
| ENSG00000211950 | NA | IGHV1-24 | 1.60 | 9.04E−04 | 5.30E−02 |
| ENSG00000188171 | 199777 | ZNF626 | 0.72 | 9.17E−04 | 5.36E−02 |
| ENSG00000134490 | 85019 | TMEM241 | 0.50 | 9.27E−04 | 5.40E−02 |
| ENSG00000186854 | 129293 | TRABD2A | 1.13 | 9.34E−04 | 5.42E−02 |
| ENSG00000173198 | 10800 | CYSLTR1 | 1.16 | 9.39E−04 | 5.43E−02 |
| ENSG00000132669 | 54453 | RIN2 | −0.47 | 9.54E−04 | 5.48E−02 |
| ENSG00000211640 | NA | IGLV6-57 | 1.59 | 9.52E−04 | 5.48E−02 |
| ENSG00000159450 | 7062 | TCHH | −1.34 | 9.59E−04 | 5.48E−02 |
| ENSG00000143515 | 57198 | ATP8B2 | 0.79 | 9.73E−04 | 5.54E−02 |

TABLE 11-continued

Differentially expressed genes in UIP samples from smokers vs. Non-UIP samples from smokers.
Table 11. Smokers

| Ensembl ID | Entrez ID | Gene symbol | Log2 Fold Change (UIP/NonUIP) | p value | FDR P value |
|---|---|---|---|---|---|
| ENSG00000198734 | 2153 | F5 | 1.10 | 9.90E−04 | 5.62E−02 |
| ENSG00000229645 | NA | NA | 1.32 | 9.99E−04 | 5.65E−02 |
| ENSG00000106333 | 5118 | PCOLCE | 1.21 | 1.02E−03 | 5.66E−02 |
| ENSG00000166869 | 63928 | CHP2 | 1.49 | 1.01E−03 | 5.66E−02 |
| ENSG00000243238 | NA | IGKV2-30 | 1.59 | 1.02E−03 | 5.66E−02 |
| ENSG00000259236 | NA | GOLGA8VP | 1.52 | 1.01E−03 | 5.66E−02 |
| ENSG00000240864 | NA | IGKV1-16 | 1.59 | 1.02E−03 | 5.67E−02 |
| ENSG00000170509 | 345275 | HSD17B13 | 1.49 | 1.03E−03 | 5.68E−02 |
| ENSG00000235602 | 642559 | POU5F1P3 | 1.51 | 1.06E−03 | 5.84E−02 |
| ENSG00000125813 | 5075 | PAX1 | 1.57 | 1.10E−03 | 6.04E−02 |
| ENSG00000138413 | 3417 | IDH1 | −0.69 | 1.11E−03 | 6.04E−02 |
| ENSG00000161896 | 117283 | IP6K3 | −1.20 | 1.11E−03 | 6.04E−02 |
| ENSG00000183624 | 56941 | HMCES | −0.49 | 1.11E−03 | 6.04E−02 |
| ENSG00000196834 | 653269 | POTEI | 1.56 | 1.11E−03 | 6.04E−02 |
| ENSG00000110777 | 5450 | POU2AF1 | 1.42 | 1.14E−03 | 6.10E−02 |
| ENSG00000183773 | 150209 | AIFM3 | 1.17 | 1.14E−03 | 6.10E−02 |
| ENSG00000225698 | NA | IGHV3-72 | 1.57 | 1.13E−03 | 6.10E−02 |
| ENSG00000023445 | 330 | BIRC3 | 0.84 | 1.18E−03 | 6.27E−02 |
| ENSG00000100078 | 50487 | PLA2G3 | 1.42 | 1.18E−03 | 6.27E−02 |
| ENSG00000116690 | 10216 | PRG4 | 1.56 | 1.19E−03 | 6.27E−02 |
| ENSG00000136011 | 55576 | STAB2 | 1.54 | 1.19E−03 | 6.27E−02 |
| ENSG00000172986 | 727936 | GXYLT2 | 0.82 | 1.19E−03 | 6.27E−02 |
| ENSG00000196344 | 131 | ADH7 | −1.54 | 1.19E−03 | 6.27E−02 |
| ENSG00000197006 | 51108 | METTL9 | −0.35 | 1.21E−03 | 6.33E−02 |
| ENSG00000087303 | 22795 | NID2 | 1.37 | 1.22E−03 | 6.34E−02 |
| ENSG00000211947 | NA | IGHV3-21 | 1.56 | 1.23E−03 | 6.38E−02 |
| ENSG00000170471 | 57148 | RALGAPB | −0.27 | 1.23E−03 | 6.39E−02 |
| ENSG00000146374 | 84870 | RSPO3 | 1.55 | 1.25E−03 | 6.45E−02 |
| ENSG00000221970 | 346528 | OR2A1 | 1.49 | 1.26E−03 | 6.48E−02 |
| ENSG00000163354 | 127579 | DCST2 | 1.15 | 1.27E−03 | 6.50E−02 |
| ENSG00000008277 | 53616 | ADAM22 | 0.80 | 1.28E−03 | 6.51E−02 |
| ENSG00000198829 | 56670 | SUCNR1 | 1.51 | 1.27E−03 | 6.51E−02 |
| ENSG00000145808 | 171019 | ADAMTS19 | 1.13 | 1.29E−03 | 6.51E−02 |
| ENSG00000197102 | 1778 | DYNC1H1 | −0.25 | 1.29E−03 | 6.51E−02 |
| ENSG00000198821 | 919 | CD247 | 1.40 | 1.30E−03 | 6.58E−02 |
| ENSG00000221914 | 5520 | PPP2R2A | −0.36 | 1.32E−03 | 6.64E−02 |
| ENSG00000078898 | 80341 | BPIFB2 | −1.47 | 1.36E−03 | 6.69E−02 |
| ENSG00000122140 | 51116 | MRPS2 | −0.56 | 1.35E−03 | 6.69E−02 |
| ENSG00000123595 | 9367 | RAB9A | −0.50 | 1.35E−03 | 6.69E−02 |
| ENSG00000145782 | 9140 | ATG12 | 0.46 | 1.35E−03 | 6.69E−02 |
| ENSG00000163297 | 118429 | ANTXR2 | 0.84 | 1.35E−03 | 6.69E−02 |
| ENSG00000180479 | 51276 | ZNF571 | 0.65 | 1.36E−03 | 6.69E−02 |
| ENSG00000182578 | 1436 | CSF1R | 1.23 | 1.35E−03 | 6.69E−02 |
| ENSG00000185518 | 9899 | SV2B | 1.22 | 1.37E−03 | 6.71E−02 |
| ENSG00000056586 | 54542 | RC3H2 | −0.24 | 1.38E−03 | 6.74E−02 |
| ENSG00000021574 | 6683 | SPAST | −0.28 | 1.39E−03 | 6.76E−02 |
| ENSG00000008394 | 4257 | MGST1 | −0.73 | 1.40E−03 | 6.77E−02 |
| ENSG00000112715 | 7422 | VEGFA | −1.09 | 1.40E−03 | 6.77E−02 |
| ENSG00000171724 | 57687 | VAT1L | 1.54 | 1.41E−03 | 6.81E−02 |
| ENSG00000124226 | 55905 | RNF114 | −0.35 | 1.43E−03 | 6.87E−02 |
| ENSG00000147459 | 80005 | DOCK5 | −0.44 | 1.45E−03 | 6.93E−02 |
| ENSG00000147140 | 4841 | NONO | −0.27 | 1.46E−03 | 6.99E−02 |
| ENSG00000118922 | 11278 | KLF12 | 0.79 | 1.49E−03 | 7.08E−02 |
| ENSG00000142731 | 10733 | PLK4 | −1.30 | 1.50E−03 | 7.12E−02 |
| ENSG00000159388 | 7832 | BTG2 | −1.23 | 1.50E−03 | 7.12E−02 |
| ENSG00000168904 | 123355 | LRRC28 | −0.39 | 1.53E−03 | 7.20E−02 |
| ENSG00000234231 | NA | | 1.34 | 1.53E−03 | 7.20E−02 |
| ENSG00000187446 | 11261 | CHP1 | −0.52 | 1.54E−03 | 7.22E−02 |
| ENSG00000180251 | 389015 | SLC9A4 | −1.51 | 1.55E−03 | 7.25E−02 |
| ENSG00000165912 | 29763 | PACSIN3 | −0.86 | 1.55E−03 | 7.25E−02 |
| ENSG00000165178 | 654817 | NCF1C | 1.35 | 1.56E−03 | 7.25E−02 |
| ENSG00000128383 | 200315 | APOBEC3A | 1.48 | 1.59E−03 | 7.39E−02 |
| ENSG00000155158 | 158219 | TTC39B | −0.49 | 1.60E−03 | 7.40E−02 |
| ENSG00000224041 | NA | IGKV3D-15 | 1.51 | 1.62E−03 | 7.45E−02 |
| ENSG00000101782 | 8780 | RIOK3 | −0.40 | 1.65E−03 | 7.55E−02 |
| ENSG00000108671 | 5717 | PSMD11 | −0.30 | 1.65E−03 | 7.55E−02 |
| ENSG00000135821 | 2752 | GLUL | −0.54 | 1.65E−03 | 7.55E−02 |
| ENSG00000076053 | 10179 | RBM7 | −0.35 | 1.68E−03 | 7.62E−02 |
| ENSG00000122966 | 11113 | CIT | −1.03 | 1.68E−03 | 7.62E−02 |
| ENSG00000253755 | NA | IGHGP | 1.52 | 1.68E−03 | 7.62E−02 |
| ENSG00000120129 | 1843 | DUSP1 | −1.38 | 1.73E−03 | 7.64E−02 |
| ENSG00000121807 | 729230 | CCR2 | 1.29 | 1.72E−03 | 7.64E−02 |

TABLE 11-continued

Differentially expressed genes in UIP samples from smokers vs. Non-UIP samples from smokers. Table 11. Smokers

| Ensembl ID | Entrez ID | Gene symbol | Log2 Fold Change (UIP/NonUIP) | p value | FDR P value |
|---|---|---|---|---|---|
| ENSG00000134046 | 8932 | MBD2 | −0.24 | 1.73E−03 | 7.64E−02 |
| ENSG00000135773 | 10753 | CAPN9 | −1.11 | 1.73E−03 | 7.64E−02 |
| ENSG00000136830 | 64855 | FAM129B | −0.31 | 1.72E−03 | 7.64E−02 |
| ENSG00000157601 | 4599 | MX1 | −1.06 | 1.72E−03 | 7.64E−02 |
| ENSG00000162949 | 92291 | CAPN13 | 0.99 | 1.69E−03 | 7.64E−02 |
| ENSG00000173653 | 9986 | RCE1 | −0.43 | 1.73E−03 | 7.64E−02 |
| ENSG00000177106 | 64787 | EPS8L2 | −0.65 | 1.73E−03 | 7.64E−02 |
| ENSG00000115590 | 7850 | IL1R2 | −1.50 | 1.74E−03 | 7.65E−02 |
| ENSG00000136816 | 27348 | TOR1B | −0.45 | 1.75E−03 | 7.68E−02 |
| ENSG00000091831 | 2099 | ESR1 | 1.43 | 1.78E−03 | 7.76E−02 |
| ENSG00000101544 | 22850 | ADNP2 | −0.34 | 1.78E−03 | 7.76E−02 |
| ENSG00000086548 | 4680 | CEACAM6 | −1.10 | 1.79E−03 | 7.78E−02 |
| ENSG00000141738 | 2886 | GRB7 | −0.76 | 1.79E−03 | 7.78E−02 |
| ENSG00000224078 | NA | SNHG14 | 0.61 | 1.80E−03 | 7.78E−02 |
| ENSG00000131408 | 7376 | NR1H2 | −0.42 | 1.81E−03 | 7.80E−02 |
| ENSG00000111412 | 79794 | C12orf49 | −0.81 | 1.82E−03 | 7.84E−02 |
| ENSG00000124356 | 10617 | STAMBP | −0.33 | 1.85E−03 | 7.95E−02 |
| ENSG00000232216 | NA | IGHV3-43 | 1.49 | 1.86E−03 | 7.96E−02 |
| ENSG00000115963 | 390 | RND3 | −0.89 | 1.90E−03 | 8.05E−02 |
| ENSG00000120647 | 84318 | CCDC77 | −0.46 | 1.90E−03 | 8.05E−02 |
| ENSG00000141540 | 94015 | TTYH2 | 1.04 | 1.90E−03 | 8.05E−02 |
| ENSG00000147234 | 84443 | FRMPD3 | 1.24 | 1.90E−03 | 8.05E−02 |
| ENSG00000189221 | 4128 | MAOA | −1.08 | 1.91E−03 | 8.08E−02 |
| ENSG00000125430 | 9953 | HS3ST3B1 | −0.95 | 1.94E−03 | 8.15E−02 |
| ENSG00000144191 | 1261 | CNGA3 | 1.43 | 1.94E−03 | 8.15E−02 |
| ENSG00000132405 | 57533 | TBC1D14 | −0.40 | 1.95E−03 | 8.16E−02 |
| ENSG00000179840 | 644997 | PIK3CD-AS1 | 1.50 | 1.96E−03 | 8.16E−02 |
| ENSG00000259261 | NA | IGHV4OR15-8 | 1.49 | 1.96E−03 | 8.16E−02 |
| ENSG00000147168 | 3561 | IL2RG | 1.31 | 1.98E−03 | 8.21E−02 |
| ENSG00000164692 | 1278 | COL1A2 | 1.46 | 2.03E−03 | 8.40E−02 |
| ENSG00000013563 | 1774 | DNASE1L1 | −0.82 | 2.04E−03 | 8.42E−02 |
| ENSG00000103522 | 50615 | IL21R | 1.46 | 2.04E−03 | 8.42E−02 |
| ENSG00000108091 | 8030 | CCDC6 | −0.30 | 2.11E−03 | 8.64E−02 |
| ENSG00000157954 | 26100 | WIPI2 | −0.40 | 2.11E−03 | 8.64E−02 |
| ENSG00000070214 | 23446 | SLC44A1 | −0.42 | 2.13E−03 | 8.70E−02 |
| ENSG00000156671 | 142891 | SAMD8 | −0.39 | 2.17E−03 | 8.80E−02 |
| ENSG00000174807 | 57124 | CD248 | 1.46 | 2.17E−03 | 8.80E−02 |
| ENSG00000154277 | 7345 | UCHL1 | −1.35 | 2.19E−03 | 8.82E−02 |
| ENSG00000157766 | 176 | ACAN | 1.48 | 2.18E−03 | 8.82E−02 |
| ENSG00000171475 | 147179 | WIPF2 | −0.44 | 2.19E−03 | 8.82E−02 |
| ENSG00000211945 | NA | IGHV1-18 | 1.48 | 2.19E−03 | 8.82E−02 |
| ENSG00000186407 | 342510 | CD300E | 1.46 | 2.21E−03 | 8.86E−02 |
| ENSG00000211659 | NA | IGLV3-25 | 1.48 | 2.21E−03 | 8.86E−02 |
| ENSG00000167797 | 10263 | CDK2AP2 | −0.53 | 2.24E−03 | 8.92E−02 |
| ENSG00000132465 | 3512 | JCHAIN | 1.47 | 2.25E−03 | 8.95E−02 |
| ENSG00000201643 | 677801 | SNORA14A | 0.93 | 2.25E−03 | 8.95E−02 |
| ENSG00000036530 | 10858 | CYP46A1 | 1.15 | 2.26E−03 | 8.96E−02 |
| ENSG00000162782 | 163589 | TDRD5 | 1.42 | 2.27E−03 | 8.96E−02 |
| ENSG00000224373 | NA | IGHV4-59 | 1.47 | 2.28E−03 | 8.96E−02 |
| ENSG00000132938 | 23281 | MTUS2 | 1.44 | 2.28E−03 | 8.96E−02 |
| ENSG00000112299 | 8876 | VNN1 | 1.37 | 2.35E−03 | 9.19E−02 |
| ENSG00000164100 | 9348 | NDST3 | 1.12 | 2.36E−03 | 9.22E−02 |
| ENSG00000165949 | 3429 | IFI27 | −1.30 | 2.36E−03 | 9.22E−02 |
| ENSG00000107643 | 5599 | MAPK8 | −0.33 | 2.39E−03 | 9.29E−02 |
| ENSG00000184481 | 4303 | FOXO4 | −0.55 | 2.40E−03 | 9.29E−02 |
| ENSG00000105122 | 64926 | RASAL3 | 1.32 | 2.43E−03 | 9.40E−02 |
| ENSG00000167100 | 201191 | SAMD14 | 1.44 | 2.44E−03 | 9.42E−02 |
| ENSG00000198848 | 1066 | CES1 | −1.10 | 2.51E−03 | 9.63E−02 |
| ENSG00000211964 | NA | IGHV3-48 | 1.45 | 2.50E−03 | 9.63E−02 |
| ENSG00000099958 | 91319 | DERL3 | 0.90 | 2.51E−03 | 9.63E−02 |
| ENSG00000010017 | 10048 | RANBP9 | −0.43 | 2.54E−03 | 9.69E−02 |
| ENSG00000189056 | 5649 | RELN | 1.38 | 2.54E−03 | 9.69E−02 |
| ENSG00000213988 | 7643 | ZNF90 | 0.83 | 2.57E−03 | 9.74E−02 |
| ENSG00000232810 | 7124 | TNF | 1.30 | 2.57E−03 | 9.74E−02 |
| ENSG00000011295 | 54902 | TTC19 | −0.30 | 2.58E−03 | 9.75E−02 |
| ENSG00000126062 | 11070 | TMEM115 | −0.34 | 2.61E−03 | 9.82E−02 |
| ENSG00000211933 | NA | IGHV6-1 | 1.44 | 2.61E−03 | 9.82E−02 |
| ENSG00000181588 | 399664 | MEX3D | −0.62 | 2.62E−03 | 9.84E−02 |
| ENSG00000122188 | 54900 | LAX1 | 1.37 | 2.64E−03 | 9.89E−02 |

TABLE 11-continued

Differentially expressed genes in UIP samples from smokers vs. Non-UIP samples from smokers.
Table 11. Smokers

| Ensembl ID | Entrez ID | Gene symbol | Log2 Fold Change (UIP/NonUIP) | p value | FDR P value |
|---|---|---|---|---|---|
| ENSG00000162772 | 467 | ATF3 | −1.35 | 2.65E−03 | 9.90E−02 |
| ENSG00000157064 | 23057 | NMNAT2 | 1.33 | 2.67E−03 | 9.95E−02 |

UIP (n = 12 samples); Non UIP (n = 4 samples). Positive log2 fold change value indicates over-expression in UIP relative to Non UIP; negative log2 value indicates under-expression in UIP relative to Non UIP. In this analysis only patients with a smoking history were evaluated, hence this subset harbored only smokers.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™, Ruby, Visual Basic™, R, and/or other object-oriented, procedural, statistical, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (e.g., Haskell, Erlang, etc.), logical programming languages (e.g., Prolog), object-oriented programming languages (e.g., Java, C++, etc.), statistical programming languages and/or environments (e.g., R, etc.; or other suitable programming languages and/or development tools. Additional examples of computer code include, but are not limited to, control signals, encrypted code, and compressed code.

REFERENCES

All of the following references are incorporated herein in their entirety.

1. du Bois R M. Strategies for treating idiopathic pulmonary fibrosis. Nature reviews Drug discovery 2010; 9(2): 129-40.
2. Hodnett P A, Naidich D P. Fibrosing Interstitial Lung Disease: A Practical HRCT Based Approach to Diagnosis and Management and Review of the Literature. American Journal of Respiratory Critical Care Medicine 2013.
3. American Thoracic Society. Idiopathic pulmonary fibrosis: diagnosis and treatment. International consensus statement. American Thoracic Society (ATS), and the European Respiratory Society (ERS). American journal of respiratory and critical care medicine 2000; 161(2 Pt 1): 646-64.
4. King T E, Jr., Pardo A, Selman M. Idiopathic pulmonary fibrosis. Lancet 2011; 378(9807): 1949-61.
5. Raghu G, Collard H R, Egan J J, et al. An official ATS/ERS/JRS/ALAT statement: idiopathic pulmonary fibrosis: evidence-based guidelines for diagnosis and management. American journal of respiratory and critical care medicine 2011; 183(6): 788-824.
6. Wells A U. The revised ATS/ERS/JRS/ALAT diagnostic criteria for idiopathic pulmonary fibrosis (IPF)—practical implications. Respiratory research 2013; 14 Suppl 1: S2.
7. Fernandez Perez E R, Daniels C E, Schroeder D R, et al. Incidence, prevalence, and clinical course of idiopathic pulmonary fibrosis: a population-based study. Chest 2010; 137(1): 129-37.
8. du Bois R M, Weycker D, Albera C, et al. Ascertainment of individual risk of mortality for patients with idiopathic pulmonary fibrosis. American journal of respiratory and critical care medicine 2011; 184(4): 459-66.

9. King T E, Jr., Bradford W Z, Castro-Bemardini S, et al. A phase 3 trial of pirfenidone in patients with idiopathic pulmonary fibrosis. N Engl J Med 2014; 370(22): 2083-92.
10. Richeldi L, du Bois R M, Raghu G, et al. Efficacy and safety of nintedanib in idiopathic pulmonary fibrosis. N Engl J Med 2014; 370(22): 2071-82.
11. Woodcock H V, Maher T M. The treatment of idiopathic pulmonary fibrosis. F1000prime reports 2014; 6: 16.
12. Coffin V, Richeldi L. Neglected evidence in idiopathic pulmonary fibrosis and the importance of early diagnosis and treatment. European respiratory review: an official journal of the European Respiratory Society 2014; 23(131): 106-10.
13. Sumikawa H, Johkoh T, Colby T V, et al. Computed tomography findings in pathological usual interstitial pneumonia: relationship to survival. American journal of respiratory and critical care medicine 2008; 177(4): 433-9.
14. Wells A U. Managing diagnostic procedures in idiopathic pulmonary fibrosis. European respiratory review: an official journal of the European Respiratory Society 2013; 22(128): 158-62.
15. Collard H R, King T E, Jr., Bartelson B B, Vourlekis J S, Schwarz M I, Brown K K. Changes in clinical and physiologic variables predict survival in idiopathic pulmonary fibrosis. American journal of respiratory and critical care medicine 2003; 168(5): 538-42.
16. Nicholson A G, Addis B J, Bharucha H, et al. Inter-observer variation between pathologists in diffuse parenchymal lung disease. Thorax 2004; 59(6): 500-5.
17. Flaherty K R, King T E, Jr., Raghu G, et al. Idiopathic interstitial pneumonia: what is the effect of a multidisciplinary approach to diagnosis? American journal of respiratory and critical care medicine 2004; 170(8): 904-10.
18. Selman M, Pardo A, Barrera L, et al. Gene expression profiles distinguish idiopathic pulmonary fibrosis from hypersensitivity pneumonitis. American journal of respiratory and critical care medicine 2006; 173(2): 188-98.
19. Lockstone H E, Sanderson S, Kulakova N, et al. Gene set analysis of lung samples provides insight into pathogenesis of progressive, fibrotic pulmonary sarcoidosis. American journal of respiratory and critical care medicine 2010; 181(12): 1367-75.
20. Katzenstein A L. Smoking-related interstitial fibrosis (SRIF), pathogenesis and treatment of usual interstitial pneumonia (UIP), and transbronchial biopsy in UIP. Modern pathology: an official journal of the United States and Canadian Academy of Pathology, Inc 2012; 25 Suppl 1: S68-78.
21. Team R C. R: A language and environment for statistical computing. R Foundation for Statistical Computing, Vienna, Austria wwwR-projectorg/2014.
22. Pardo A, Gibson K, Cisneros J, et al. Up-regulation and profibrotic role of osteopontin in human idiopathic pulmonary fibrosis. PLoS medicine 2005; 2(9): e251.
23. DePianto D J, Chandriani S, Abbas A R, et al. Heterogeneous gene expression signatures correspond to distinct lung pathologies and biomarkers of disease severity in idiopathic pulmonary fibrosis. Thorax 2014.
24. Selman M, Pardo A, King T E, Jr. Hypersensitivity pneumonitis: insights in diagnosis and pathobiology. American journal of respiratory and critical care medicine 2012; 186(4): 314-24.
25. Yang I V, Coldren C D, Leach S M, et al. Expression of cilium-associated genes defines novel molecular subtypes of idiopathic pulmonary fibrosis. Thorax 2013.
26. Garcia-Alvarez J, Ramirez R, Checa M, et al. Tissue inhibitor of metalloproteinase-3 is up-regulated by transforming growth factor-betal in vitro and expressed in fibroblastic foci in vivo in idiopathic pulmonary fibrosis. Experimental lung research 2006; 32(5): 201-14.
27. Piotrowski W J, Gorski P, Pietras T, Fendler W, Szemraj J. The selected genetic polymorphisms of metalloproteinases MMP2, 7, 9 and MMP inhibitor TIMP2 in sarcoidosis. Medical science monitor: international medical journal of experimental and clinical research 2011; 17(10): CR598-607.
28. Chaudhuri R, McSharry C, Brady J, et al. Low sputum MMP-9/TIMP ratio is associated with airway narrowing in smokers with asthma. The European respiratory journal: official journal of the European Society for Clinical Respiratory Physiology 2014; 44(4): 895-904.
29. Hviid T V, Milman N, Hylenius S, Jakobsen K, Jensen M S, Larsen L G. HLA-G polymorphisms and HLA-G expression in sarcoidosis. Sarcoidosis, vasculitis, and diffuse lung diseases: official journal of WASOG/World Association of Sarcoidosis and Other Granulomatous Disorders 2006; 23(1): 30-7.
30. Li G Y, Kim M, Kim J H, Lee M O, Chung J H, Lee B H. Gene expression profiling in human lung fibroblast following cadmium exposure. Food and chemical toxicology: an international journal published for the British Industrial Biological Research Association 2008; 46(3): 1131-7.
31. Ozsolak F, Milos P M. RNA sequencing: advances, challenges and opportunities. Nature reviews Genetics 2011; 12(2): 87-98.
32. Mutz K O, Heilkenbrinker A, Lonne M, Walter J G, Stahl F. Transcriptome analysis using next-generation sequencing. Current opinion in biotechnology 2013; 24(1): 22-30.

What is claimed is:

1. A method for generating a classification of a biological sample as being positive for usual interstitial pneumonia (UIP) or non-UIP, comprising:

(a) performing an imaging test, a pulmonary function test, or a lung tissue analysis on a subject to produce a test result, wherein said test result indicates that said subject is suspected of having interstitial lung disease;

(b) responsive to said test result produced in (a), obtaining a biological sample from said subject, wherein said biological sample comprises a transbronchial biopsy sample or a bronchoalveolar lavage sample;

(c) assaying nucleic acid molecules derived from said biological sample to determine a level of expression of a plurality of genes; and (d) processing with a classifier said level of expression of said plurality of genes to generate a classification of said biological sample as being positive for UIP or non-UIP, wherein said classifier differentiates between said UIP and a plurality of non-UIP subtypes, wherein said plurality of non-UIP subtypes comprises hypersensitivity pneumonitis (HP), non-specific interstitial pneumonia (NSIP), sarcoidosis, respiratory bronchiolitis (RB), bronchiolitis, diffuse alveolar damage (DAD), and organizing pneumonia (OP).

2. The method of claim 1, wherein said assaying further comprises sequencing.

3. The method of claim 2, wherein said sequencing further comprises whole transcriptome shotgun sequencing.

4. The method of claim 1, wherein said assaying further comprises reverse transcription polymerase chain reaction (RT-PCR) or deoxyribonucleic acid (DNA) microarray hybridization.

5. The method of claim 1, wherein said nucleic acid molecules comprise ribonucleic acid (RNA) molecules, and wherein said assaying comprises generating complementary DNA (cDNA) molecules from said RNA molecules.

6. The method of claim 5, wherein said assaying further comprises amplifying said cDNA molecules.

7. The method of claim 1, wherein said assaying further comprises determining a level of expression of at least one control nucleic acid molecule in said biological sample.

8. The method of claim 1, wherein said classifier comprises a machine learning algorithm that is trained to differentiate between said UIP and said plurality of non-UIP subtypes.

9. The method of claim 8, wherein said machine learning algorithm is trained with a training set that is independent of said biological sample.

10. The method of claim 8, wherein said machine learning algorithm is trained using features comprising gene expression variants, gene fusions, loss of heterozygosity, or biological pathway effect.

11. The method of claim 1, wherein said classifier further comprises a machine learning algorithm that is trained to recognize gene signatures that distinguish non-smokers from smokers.

12. The method of claim 1, wherein said biological sample is fresh-frozen or fixed.

13. The method of claim 1, wherein said subject is suspected of having said interstitial lung disease based at least in part on one or more clinical signs or one or more symptoms.

14. The method of claim 13, wherein said one or more symptoms comprises shortness of breath or dry cough.

15. The method of claim 1, wherein said biological sample is derived from a subject that is a smoker or has a past history of smoking.

16. The method of claim 1, wherein (d) further comprises generating a classification of said biological sample as being positive for UIP, and wherein said method further comprises administering a therapeutic intervention capable of treating UIP to said subject, based on said classification of said biological sample as being positive for UIP.

17. The method of claim 16, wherein said therapeutic intervention comprises pirfenidone, prednisone, azathioprine, N-acetylcysteine, or surgery.

18. The method of claim 1, wherein (a) further comprises performing said imaging test.

19. The method of claim 18, wherein said imaging test comprises a chest X-ray or computerized tomography.

20. The method of claim 1, wherein (a) further comprises performing said pulmonary function test.

21. The method of claim 20, wherein said pulmonary function test comprises spirometry, oximetry, or an exercise stress test.

22. The method of claim 1, wherein (a) further comprises performing said lung tissue analysis.

23. The method of claim 22, wherein said lung tissue analysis comprises histological or cytological analysis of a lung tissue sample of said subject.

24. The method of claim 1, wherein said biological sample comprises said transbronchial biopsy sample.

25. The method of claim 1, wherein said biological sample comprises said bronchoalveolar lavage sample.

* * * * *

SEQUENCE LISTING

```
Sequence total quantity: 22
SEQ ID NO: 1            moltype = DNA  length = 1041
FEATURE                 Location/Qualifiers
source                  1..1041
                        mol_type = unassigned DNA
                        organism = Homo sapiens
SEQUENCE: 1
atggcgcccc gaagcctcct cctgctgctc tcaggggccc tggccctgac cgatacttgg  60
gcaggctccc actccttgag gtatttcagc accgctgtgt cgcggcccgg ccgcggggag  120
ccccgctaca tcgccgtgga gtacgtagac gacacgcaat tcctgcggtt cgacagcgac  180
gccgcgattc cgaggatgga gccgcgggag ccgtgggtgg agcaagaggg gccgcagtat  240
tgggagtgga ccacagggta cgccaaggcc aacgcacaga ctgaccgagt ggccctgagg  300
aacctgctcc gccgctacaa ccagagcgag gctgggtctc acaccctcca gggaatgaat  360
ggctgcgaca tggggcccga cggacgcctc ctccgcgggt atcaccagca cgcgtacgac  420
```

ggcaaggatt acatctccct gaacgaggac ctgcgctcct ggaccgcggc ggacaccgtg 480
gctcagatca cccagcgctt ctatgaggca gaggaatatg cagaggagtt caggacctac 540
ctggagggcg agtgcctgga gttgctccgc agatacttgg agaatgggaa ggagacgcta 600
cagcgcgcag atcctccaaa ggcacacgtt gcccaccacc ccatctctga ccatgaggcc 660
accctgaggt gctgggccct gggcttctac cctgcggaga tcacgctgac ctggcagcgg 720
gatggggagg aacagaccca ggacacagag cttgtggaga ccaggcctgc aggggatgga 780
accttccaga agtgggccgc tgtggtggtg ccttctggag aggaacagag atacacatgc 840
catgtgcagc acgaggggct gccccagccc ctcatcctga gatgggagca gtctccccag 900
cccaccatcc ccatcgtggg catcgttgct ggccttgttg tccttggagc tgtggtcact 960
ggagctgtgg tcgctgctgt gatgtggagg aagaagagct cagatagaaa cagagggagc 1020
tactctcagg ctgcagtgtg a 1041

SEQ ID NO: 2 moltype = DNA length = 1993
FEATURE Location/Qualifiers
source 1..1993
mol_type = unassigned DNA
organism = Homo sapiens
SEQUENCE: 2
caggtgttgg tgcctgccgt gaacgcattc tgacctgggc cgtatctgtc tcccaagact 60
ttgtgcctat ggttggggac agagtgaggt cgttgccttg acgacgacag catgcggccc 120
gtggtcctcc taagtgtgag cttgcggcgg accgaggccc acctgcctcc ctgcctgctt 180
cgccctggac tcgtgactgc gtccgcagaa gaaatcacaa cagcgctgga attgctagtt 240
tgctaggcag catcttttgg acctgcgaac catatgcatt tcacctcaaa tttgtttcca 300
agttgaaaac ctttgggtct ttctatgcga acggattgaa gaaacgcaaa aagtttctac 360
ggactttaaa ttaaaatgga aaaatatgaa aacctgggtt tggttggaga agggagttat 420
ggaatggtga tgaagtgtag gaataaagat actggaagaa ttgtggccat aaagaagttc 480
ttagaaagtg acgatgacaa aatggttaaa aagattgcaa tgcgagaaat caagttacta 540
aagcaactta ggcatgaaaa cttggtgaat ctcttggaag tgtgtaagaa aaaaaaacga 600
tggtacctag tctttgaatt tgttgaccac acaattcttg atgacttgga gctctttcca 660
aatggactag actaccaagt agttcaaaag tatttgtttc agattattaa tggaattgga 720
ttttgtcaca gtcacaatat catacacaga gatataaagc cagagaatat attagtctcc 780
cagtctggcg ttgtcaagct atgcgatttt ggatttgcgc gaacattggc agctcctggg 840
gaggtttata ctgattatgt ggcaacccga tggtacagag ctccagaact attggttggt 900
gatgtcaagt atggcaaggc tgttgatgtg tgggccattg gttgtctggt aactgaaatg 960
ttcatggggg aacccctatt tcctggagat tctgatattg atcagctata tcatattatg 1020
atgtgtttag gtaatctaat tccaaggcat caggagcttt ttaataaaaa tcctgtgttt 1080
gctggagtaa ggttgcctga aatcaaggaa agagaacctc ttgaaagacg ctatcctaag 1140
ctctctgaag tggtgataga tttagcaaag aaatgcttac atattgaccc cgacaaaaga 1200
cccttctgtg ctgagctcct acaccatgat ttctttcaaa tggatggatt tgctgagagg 1260
ttttcccaag aactacagtt aaaagtacag aaagatgcca gaaatgtttc tttatctaaa 1320
aaatcccaaa acagaaagaa ggaaaaagaa aaagatgatt ccttagttga agaaagaaaa 1380
acacttgtgg tacaggatac caatgctgat cccaaaatta aggattataa actatttaaa 1440
ataaaaggct caaaaattga tggagaaaaa gctgaaaaag gcaatagagc ttcaaatgcc 1500
agctgtctcc atgacagtag gacaagccac aacaaaatag tgccttcaac aagcctcaaa 1560
gactgcagca atgtcagcgt ggaccacaca aggaatccaa gcgtggcaat tcccccactt 1620
acacacaatc tttctgcagt tgctcccagc attaattctg gaatggggac tgagactata 1680
ccaattcagg gttacagagt ggatgagaaa actaagaagt gttctattcc atttgttaaa 1740
ccgaacagac attccccatc aggcatttat aacattaatg tgaccacatt agtatcagga 1800
cctcccctgt cagatgattc agggggctgat ttgcctcaaa tggaacacca gcactgagaa 1860
ccattttggt tctgaactgg atgatgctct tgcacttgag atgacatctt cttgcagcaa 1920
gaaaaaaaaa aaaaaaaaaa aaaaaaaaac aaaaaaaaaa aaaaaaaaaa aaaaaaaaaa 1980
aaaaaaaaaa aaa 1993

SEQ ID NO: 3 moltype = DNA length = 3918
FEATURE Location/Qualifiers
source 1..3918
mol_type = unassigned DNA
organism = Homo sapiens
SEQUENCE: 3
gttaattgga gcccacgcct gaatctagat ttcagtgttg cagtgattac aatattggat 60
aatgatgacc tggcaggaat ggatatttcc ttccccgaga caactgtggc tgtagcagtt 120
gacacaactc tcattcctgt agaaactgaa tccaccacat acctcagcac aagcaagacg 180
actaccattc tgcagccaac caacgtggtt gccattgtta ctgaggcaac tggtgtatct 240
gccatccctg agaaacttgt cacccttcat ggcacacctg ctgtgtctga aaagcctgat 300
gtggccactg taactgccaa tgtttccatt catggaacat tcagccttgg gccatccatt 360
gtttatattg aagaggagat gaagaatggc acattcaaca ctgcagaagt tcttatccga 420
agaactggtg ggtttactgg caatgtcagc ataacagtta aaactttcgg tgaaagatgt 480
gctcagatgg aaccaaatgc attgcccttt cgtggtatct atgggatttc caacctaaca 540
tgggcagttg aagaagaaga ctttgaagaa caaactctta cccttatatt cctagatgga 600
gaaagagaac gtaaagtatc agttcaaatt ttggatgatg atgagcctga ggggcaggaa 660
ttcttctacg tgtttctcac aaaccctcaa gggggagcac agattgtgga ggggaaggat 720
gatactggat ttgcagcttt tgccatggtt attattacag ggagtgacct tcacaatggc 780
atcataggat tcagtgagga gtcccagagt ggactagaac tcagggaagg agctgttatg 840
agaagattgc accttattgt cacaagacag ccaaacaggg cctttgaaga tgtcaaggtc 900
ttttggcgag tcacacttaa caaaacagtc gtcgtgctcc agaaggatgg ggtaaacctg 960
atggaggaac ttcagtctgt gtcagggacc acaacctgta caatgggtca aacaaaatgc 1020
tttatcagca ttgaactcaa accagaaaag gtaccacagg ttgaagtgta ttttttgtg 1080
gaactatatg aagctactgc tggagcagca ataaacaaca gtgccagatt cgcacagatt 1140
aaaatcttag aaagtgatga atctcaaagc cttgtgtatt tttctgtggg ttctcggctg 1200

```
gcagtggctc acaagaaggc cactttaatc agtctgcagg tggccagaga ttctgggaca  1260
ggactaatga tgtctgttaa ctttagtacc caggagttga ggagtgctga aacaattggt  1320
cgtaccatca tatctccagc tatttctgga aaggattttg tgataactga aggcacattg  1380
gtctttgaac ctggccagag aagcactgta ttggatgtca tcctaacgcc agagacagga  1440
tctttaaatt catttcctaa acgcttccag attgtccttt ttgacccaaa aggtggtgcc  1500
agaattgata aagtgtatgg gactgccaac atcactcttg tctcagatgc agattcgcag  1560
gccatttggg ggcttgcaga tcagctacat cagcctgtga atgatgatat tctcaacaga  1620
gtgctccata ccatcagcat gaaagtggcc acagaaaaca cagatgaaca actcagtgcc  1680
atgatgcatt taatagaaaa gataactact gaaggaaaaa ttcaagcttt cagtgttgcc  1740
agccgaactc ttttctatga gattctttgt tctcttatta acccaaagcg caaggacact  1800
aggggattca gtcactttgc tgaagtgact gagaattttg ccttttctct gctgactaat  1860
gttacttgcg gctctcctgg tgaaaaaagc aaaaccatcc ttgatagttg cccatatttg  1920
tcaatattgg ctcttcactg gtatcctcag caaatcaatg gacacaagtt tgaaggaaag  1980
gaaggagatt acattcgaat tccagagagg ctactggatg tccaggatgc agaaataatg  2040
gctgggaaaa gtacatgtaa attagtccag tttacagagt atagcagcca acagtggttt  2100
ataagtggaa acaatcttcc taccctaaaa aataaggtat tatctttgag tgtgaaaggt  2160
cagagttcac aactcctgac taatgacaat gaggttctct acaggattta tgctgctgag  2220
cctagaatta ttcctcagac atctctgtgt ctcctttgga atcaggctgc tgcaagctgg  2280
ttgtctgaca gtcagttttg caaagtgatt gaggaaactg cagactatgt ggaatgtgcc  2340
tgttcacaca tgtctgtgta tgctgtctat gctcggactg acaacttgtc ttcatacaat  2400
gaagccttct tcacttctgg atttatatgt atctcaggtc tttgcttggc tgttctttcc  2460
catatcttct gtgccaggta ctccatgttt gcagctaaac ttctgactca catgatggca  2520
gccagcttag gtacacagat tctgtttctg gcgtctgcat acgcaagtcc ccaactcgct  2580
gaggagagct gttcagctat ggctgctgtc acacattacc tgtatctttg ccagtttagc  2640
tggatgctca ttcagtctgt gaatttctgg tacgtgctgg tgatgaatga tgagcacaca  2700
gagaggcgat atctgctgtt tttccttctg agttggggac taccagcttt tgtggtgatt  2760
ctcctcatag ttattttgaa aggaatctat catcagagca tgtcacagat ctatggactc  2820
attcatggtg acctgtgttt tattccaaac gtctatgctg ctttgttcac tgcagctctt  2880
gttcctttga cgtgcctcgt ggtggtgttc gtggtgttca tccatgccta ccaggtgaag  2940
ccacagtgga aagcatatga tgatgtcttc agaggaagga caaatgctgc agaaattcca  3000
ctgattttat atctctttgc tctgatttcc gtgacatggc tttggggagg actacacatg  3060
gcctacagac acttctggat gttggttctc tttgtcattt tcaacagtct gcagggactt  3120
tatgttttca tggtttattt cattttacac aaccaaatgt gttgccctat gaaggccagt  3180
tacactgtgg aaatgaatgg gcatcctgga cccagcacag ccttttttcac gcccgggagt  3240
ggaatgcctc ctgctggagg ggaaatcagc aagtccaccc agaatctcat cggtgctatg  3300
gaggaggtgc cacctgactg ggagagagca tccttccaac agggcagtca ggccagccct  3360
gatttaaagc caagtccaca aaatggagcc acgttcccgt cctctggagg atatggccag  3420
gggtcactga tagccgatga ggagtcccag gagtttgatg atttaatatt tgcattaaaa  3480
actggtgctg gtctcagtgt cagtgataat gaatctggtc aaggcagcca ggagggggggc  3540
accttgactg actcccagat cgtggagctc aggaggatac ccatcgccga cactcacctg  3600
tagcacctca ctaaccattc gactgagcac actttcatat ttgtatcagc ttttgtgcta  3660
aaactctcta agtacatcca cctgtgtaat aggaacctgt gaattgtact ggatgattaa  3720
tacaaacgtg attgttgtat ttggagtata aattactgat tgtatgtgac ctgaaaattc  3780
actgctataa gaaaggtgga gtcagtttgt atcagttaat aggatgttca tattccaagg  3840
atattagttg ttttttttaat catcctatat ggctaacatt gtttaatgaa agtaataatc  3900
aataaagcaa tagaatct                                                3918
```

```
SEQ ID NO: 4            moltype = DNA  length = 2705
FEATURE                 Location/Qualifiers
source                  1..2705
                        mol_type = unassigned DNA
                        organism = Homo sapiens
SEQUENCE: 4
tgctcgctcc agggcgcaac catgtcgcca tttcttcgga ttggcttgtc caactttgac  60
tgcgggtcct gccagtcttg tcagggcgag gctgttaacc cttactgtgc tgtgctcgtc  120
aaagagtatg tcgaatcaga gaacgggcag atgtatatcc agaaaaagcc taccatgtac  180
ccaccctggg acagcacttt tgatgcccat atcaacaagg gaagagtcat gcagatcatt  240
gtgaaaggca aaaacgtgga cctcatctct gaaaccaccg tggagctcta ctcgctggct  300
gagaggtgca ggaagaacaa cgggaagaca gaaatatggt tagagctgaa acctcaaggc  360
cgaatgctaa tgaatgcaag atactttctg gaaatgagtg acacaaagga catgaatgaa  420
tttgagacgg aaggcttctt tgctttgcat cagcgccggg gtgccatcaa gcaggcaaag  480
gtccaccacg tcaagtgcca cgagttcact gccaccttct tcccacagcc cacattttgc  540
tctgtctgcc acgagtttgt ctggggcctg aacaaacagg gctaccagtg ccgacaatgc  600
aatgcagcaa ttcacaagaa gtgtattgat aaagttatag caaagtgcac aggatcagct  660
atcaatagcc gagaaaccat gttccacaag gagagattca aaattgacat gccacacaga  720
tttaaagtct acaattacaa gagcccgacc ttctgtgaac actgtgggac cctgctgtgg  780
ggactggcac ggcaaggact caagtgtgat gcatgtggca tgaatgtgca tcatagatgc  840
cagacaaagg tggccaacct ttgtggcata aaccagaagc taatggctga agcgctggcc  900
atgattgaga gcactcaaca ggctcgctgc ttaagagata ctgaacagat cttcagagaa  960
ggtccggttg aaattggtct cccatgctcc atcaaaaatg aagcaaggcc gccatgttta  1020
ccgacaccgg gaaaaagaga gcctcagggc atttcctggg agtctccgtt ggatgaggtg  1080
gataaaatgt gccatcttcc agaacctgaa ctgaacaaag aaagaccatc tctgcagatt  1140
aaactaaaaa ttgaggattt tatcttgcac aaaatgttgg ggaaaggaag ttttggcaag  1200
gtcttcctgg cagaattcaa gaaaaccaat caatttttcg caataaaggc cttaaagaaa  1260
gatgtggtct tgatggacga tgatgttgag tgcacgatgg tagagaagag agttctttcc  1320
ttggcctggg agcatccgtt tctgacgcac atgttttgta cattccagac caaggaaaac  1380
ctcttttttg tgatggagta cctcaacgga ggggacttaa tgtaccacat ccaaagctgc  1440
cacaagttcg acctttccag agcgacgttt tatgctgctg aaatcattct tggtctgcag  1500
ttccttcatt ccaaaggaat agtctacagg gacctgaagc tagataacat cctgttagac  1560
```

```
aaagatggac atatcaagat cgcggatttt ggaatgtgca aggagaacat gttaggagat  1620
gccaagacga ataccttctg tgggacacct gactacatcg ccccagagat cttgctgggt  1680
cagaaataca accactctgt ggactggtgg tccttcgggg ttctccttta tgaaatgctg  1740
attggtcagt cgcctttcca cgggcaggat gaggaggagc tcttccactc catccgcatg  1800
gacaatccct tttacccacg gtggctggag aaggaagcaa aggaccttct ggtgaagctc  1860
ttcgtgcgag aacctgagaa gaggctgggc gtgaggggag acatccgcca gcaccctttg  1920
tttcgggaga tcaactggga ggaacttgaa cggaaggaga ttgacccacc gttccggccg  1980
aaagtgaaat caccatttga ctgcagcaat ttcgacaaag aattcttaaa cgagaagccc  2040
cggctgtcat ttgccgacag agcactgatc aacagcatgg accagaatat gttcaggaac  2100
ttttccttca tgaaccccgg gatggagcgg ctgatatcct gaatcttgcc cctccagaga  2160
caggaaagaa tttgccttct ccctgggaac tggttcaaga gacactgctt gggttccttt  2220
ttcaacttgg aaaaagaaag aaacactcaa caataaagac tgagacccgt tcgcccccat  2280
gtgactttat ctgtagcaga aaccaagtct acttcactaa tgacgatgcc gtgtgtctcg  2340
tctcctgaca tgtctcacag acgctcctga agttaggtca ttactaacca tagttattta  2400
cttgaaagat gggtctccgc acttggaaag gtttcaagac ttgatactgc aataaattat  2460
ggctcttcac ctgggcgcca actgctgatc aacgaaatgc ttgttgaatc aggggcaaac  2520
ggagtacaga cgtctcaaga ctgaaacggc cccattgcct ggtctagtag cggatctcac  2580
tcagccgcag acaagtaatc actaacccgt tttattctat cctatctgtg gatgtataaa  2640
tgctgggggc cagccctgga taggttttta tgggaattct ttacaataaa catagcttgt  2700
acttg                                                              2705

SEQ ID NO: 5           moltype = DNA  length = 1578
FEATURE                Location/Qualifiers
source                 1..1578
                       mol_type = unassigned DNA
                       organism = Homo sapiens
SEQUENCE: 5
agtgtggtac tttgtcttga ggagatgtcc tggactcaca cggaaactta gggctacgga  60
atgaagttct cactcccatt aggtgacagg tttttagaga agccaatcag cgtcgccgcg  120
gtcctggttc taaagtcctc gctcacccac ccggactcat tctccccaga cgccaaggat  180
ggtggtcatg gcgccccgaa ccctcttcct gctgctctcg gggcccctga ccctgaccga  240
gacctgggcg ggctcccact ccatgaggta tttcagcgcc gccgtgtccc ggcccggccg  300
cggggagccc cgcttcatcg ccatgggcta cgtggacgac acgcagttcg tgcggttcga  360
cagcgactcg gcgtgtccga ggatggagcc gcgggcgccg tgggtggagc aggaggggcc  420
ggagtattgg gaagaggaga cacggaacac caaggcccac gcacagactg acagaatgaa  480
cctgcagacc ctgcgcggct actacaacca gagcgaggcc agttctcaca ccctccagtg  540
gatgattggc tgcgacctgg ggtccgacgg acgcctcctc cgcgggtatg aacagtatgc  600
ctacgatggc aaggattacc tcgccctgaa cgaggacctg cgctcctgga ccgcagcgga  660
cactgcggct cagatctcca agcgcaagtg tgaggcggcc aatgtggctg aacaaaggag  720
agcctacctg gagggcacgt gcgtggagtg gctccacaga tacctggaga acgggaagga  780
gatgctgcag cgcgcggacc cccccaagac acacgtgacc caccaccctg tctttgacta  840
tgaggccacc ctgaggtgct gggccctggg cttctaccct gcggagatca tactgacctg  900
gcagcgggat ggggaggacc agacccagga cgtggagctc gtggagacca ggcctgcagg  960
ggatggaacc ttccagaagt gggcagctgt ggtggtgcct tctggagagg agcagagata  1020
cacgtgccat gtgcagcatg aggggctgcc ggagcccctc atgctgagat ggaagcagtc  1080
ttccctgccc accatcccca tcatgggtat cgttgctggc ctggttgtcc ttgcagctgt  1140
agtcactgga gctgcggtcg ctgctgtgct gtggagaaag aagagctcag attgaaaagg  1200
agggagctac tctcaggctg caatgtgaaa cagctgccct gtgtgggact gagtggcaag  1260
tccctttgtg acttcaagaa ccctgactcc tctttgtgca gagaccagcc cacccctgtg  1320
cccaccatga ccctcttcct catgctgaac tgcattcctt ccccaatcac ctttcctgtt  1380
ccagaaaagg ggctgggatg tctccgtctc tgtctcaaat ttgtggtcca ctgagctata  1440
acttacttct gtattaaaat tagaatctga gtataaattt actttttcaa attatttcca  1500
agagagattg atgggttaat taaaggagaa gattcctgaa atttgagaga caaaataaat  1560
ggaagacatg agaacttt                                                1578

SEQ ID NO: 6           moltype = DNA  length = 4553
FEATURE                Location/Qualifiers
source                 1..4553
                       mol_type = unassigned DNA
                       organism = Homo sapiens
SEQUENCE: 6
acgcgtctgc ggccagcccg gactctttaa aagccggcgg tgcgcggggc atcccagcca  60
agccggagag gaggcgagca gcagggcctg gtggcgagag cgcggctgtc actgcgcccg  120
agcatcccag agctttccga gcggacgagc cggccgtgcc gggcatcccc agcctcgcta  180
ccctcgcagc acacgtcgag ccccgcacag gcgagggtcc ggaacttagc ccaaagcacg  240
tttcccctgg cagcgcagga aacgcccggc cgcgcgccgg cgcacgcccc cctctcctcc  300
tttgttccgg gggtcggcgg ccgctctcct gccagcgtcg ggatctcggc cccgggaggc  360
gggccgtcgg gcgcagccgc gaagatgccg ttggaactga cgcagagccg agtgcagaag  420
atctgggtgc ccgtggacca caggccctcg ttgcccagat cctgtgggcc aaagctgacc  480
aactccccca ccgtcatcgt catggtgggc ctccccgccc ggggcaagac ctacatctcc  540
aagaagctga ctcgctacct caactggatt ggcgtcccca caaaagtgtt caacgtcggg  600
gagtatcgcc gggaggctgt gaagcagtac agctcctaca acttcttccg ccccgacaat  660
gaggaagcca tgaaagtccg gaagcaatgt gccttagctg ccttgagaga tgtcaaaagc  720
tacctggcga aagaaggggg acaaattgcg gttttcgatg ccaccaatac tactagagag  780
aggagacaca tgatccttca ttttgccaaa gaaaatgact ttaaggcgtt tttcatcgag  840
tcggtgtgcg acgaccctac agttgtggcc tccaatatca tggaagttaa aatctccagc  900
ccggattaca aagactgcaa ctcggcagaa gccatggacg acttcatgaa gaggatcagt  960
tgctatgaag ccagctacca gcccctcgac cccgacaaat gcgacaggga cttgtcgctg  1020
atcaaggtga ttgacgtggg ccggaggttc ctggtgaacc gggtgcagga ccacatccag  1080
```

```
agccgcatcg tgtactacct gatgaacatc cacgtgcagc cgcgtaccat ctacctgtgc  1140
cggcacggcg agaacgagca caacctccag ggccgcatcg gggcgactc aggcctgtcc  1200
agccggggca agaagtttgc cagtgctctg agcaagttcg tggaggagca gaacctgaag  1260
gacctgcgcg tgtggaccag ccagctgaag agcaccatcc agacggccga ggcgctgcgg  1320
ctgccctacg agcagtggaa ggcgctcaat gagatcgacg cgggcgtctg tgaggagctg  1380
acctacgagg agatcaggga cacctaccct gaggagtatg cgctgcggga gcaggacaag  1440
tactattacc gctaccccac cggggagtcc taccaggacc tggtccagcg cttggagcca  1500
gtgatcatgg agctggagcg gcaggagaat gtgctggtca tctgccacca ggccgtcctg  1560
cgctgcctgc ttgcctactt cctggataag agtgcagagg agatgcccta cctgaaatgc  1620
cctcttcaca ccgtcctgaa actgacgcct gtcgcttatg gctgccgtgt ggaatccatc  1680
tacctgaacg tggagtccgt ctgcacacac cgggagaggt cagaggatgc aaagaaggga  1740
cctaacccgc tcatgagacg caatagtgtc accccgctag ccagccccga acccaccaaa  1800
aagcctcgca tcaacagctt tgaggagcat gtggcctcca cctcggccgc cctgcccagc  1860
tgcctgcccc cggaggtgcc cacgcagctg cctggacaaa acatgaaagg ctcccggagc  1920
agcgctgact cctccaggaa acactgaggc agacgtgtcg gttccattcc atttccattt  1980
ctgcagctta gcttgtgtcc tgccctccgc ccgaggcaaa acgtatcctg aggacttctt  2040
ccggagaggg tggggtggag cagcggggga gccttggccg aagagaacca tgcttggcac  2100
cgtctgtgtc ccctcggccg ctggacacca gaaagccacg tgggtccctg gcgccctgcc  2160
tttagccgtg gggcccccac ctccactctc tgggtttcct aggaatgtcc agcctcggag  2220
accttcacaa agccttggga gggtgatgag tgctggtcct gacaggaggc cgctggggac  2280
actgtgctgt tttgtttcgt ttctgtgatc tcccggcacg tttggagctg ggaagaccac  2340
actggtggca gaatcctaaa attaaaggag gcaggctcct agttgctgaa agttaaggaa  2400
tgtgtaaaac ctccacgtga ctgtttggtg catcttgacc tgggaagacg cctcatggga  2460
acgaacttgg acaggtgttg ggttgaggcc tcttctgcag gaagtccctg agctgagacg  2520
caagttggct gggtggtccg caccctggct ctcctgcagg tccacacacc ttccaggcct  2580
gtggcctgcc tccaaagatg tgcaagggca ggctggctgc acggggagag ggaagtattt  2640
tgccgaaata tgagaactgg ggcctcctgc tcccagggag ctccagggcc cctctctcct  2700
cccacctgga cttgggggga actgagaaac actttcctgg agctgctggc ttttgcactt  2760
ttttgatggc agaagtgtga cctgagagtc ccaccttctc ttcaggaacg tagatgttgg  2820
ggtgtcttgc cctggggggc ttggaacctc tgaaggtggg gagcggaaca cctggcatcc  2880
ttccccagca cttgcattac cgtccctgct cttcccaggt ggggacagtg gcccaagcaa  2940
ggcctcactc gcagccactt cttcaagagc tgcctgcaca ctgtcttgga gcatctgcct  3000
tgtgcctggc actctgccgg tgccttggga aggtcggaag agtggacttt gtcctggcct  3060
tcccttcatg gcgtctatga cacttttgtg gtgatggaaa gcatgggacc tgtcgtctca  3120
gcctgttggt ttctcctcat tgcctcaaac cctggggtag gtgggacggg gggtctcgtg  3180
cccagatgaa accatttgga aactcggcag cagagtttgt ccaaatgacc cttttcagga  3240
tgtctcaaag cttgtgccaa aggtcacttt tctttcctgc cttctgctgt gagccctgag  3300
atcctcctcc cagctcaagg gacaggtcct gggtgagggt gggagattta gacacctgaa  3360
actgggcgtg gagagaagag ccgttgctgt ttgtttttttg ggaagagctt ttaaagaatg  3420
catgtttttt tcctggttgg aattgagtag gaactgaggc tgtgcttcag gtatggtaca  3480
atcaagtggg ggattttcat gctgaaccat tcaagccctc cccgcccgtt gcacccactt  3540
tggctggcgt ctgctggaga ggatgtctct gtccgcattc ccgtgcagct ccaggctcgc  3600
gcagttttct ctctctccct ggatgttgag tctcatcaga atatgtgggt agggggtgga  3660
cgtgcacggg tgcatgattg tgcttaactt ggttgtattt ttcgatttga catggaaggc  3720
ctgttgcttt gctcttgaga atagtttctc gtgtccccct cgcaggcctc attctttgaa  3780
catcgactct gaagtttgat acagataggg gcttgatagc tgtggtcccc tctcccctct  3840
gactacctaa aatcaatacc taaatacaga agccttggtc taacacggga cttttagttt  3900
gcgaagggcc tagataggga gagaggtaac atgaatctgg acagggaggg agatactata  3960
gaaaggagaa cactgcctac tttgcaagcc agtgacctgc cttttgaggg gacattggac  4020
gggggccggg ggcgggggtt gggtttgagc tacagtcatg aacttttggc gtctactgat  4080
tcctccaact ctccacccca caaaataacg gggaccaata tttttaactt tgcctatttg  4140
tttttgggtg agtttccccc ctccttattc tgtcctgaga ccacgggcaa agctcttcat  4200
tttgagagag aagaaaaact gtttggaacc acaccaatga tatttttctt tgtaatactt  4260
gaaatttatt tttttattat tttgatagca gatgtgctat ttatttattt aatatgtata  4320
aggagcctaa acaatagaaa gctgtagaga ttgggtttca ttgttaattg gtttgggagc  4380
ctcctatgtg tgacttatga cttctctgtg ttctgtgtat ttgtctgaat taatgacctg  4440
ggatataaag ctatgctagc tttcaaacag gagatgcctt tcagaaattt gtatattttg  4500
cagttgccag accaataaaa tacctggttg aaatacatgg acgaagtaaa aaa         4553

SEQ ID NO: 7           moltype = DNA  length = 1773
FEATURE                Location/Qualifiers
source                 1..1773
                       mol_type = unassigned DNA
                       organism = Homo sapiens
SEQUENCE: 7
ggaaaacagc agaggtgaca gagcagccgt gctcgaagcg ttcctggagc ccaagctctc  60
ctccacaggt gaagacaggg ccagcaggag acaccatggg gcacctctca gccccacttc  120
acagagtgcg tgtaccctgg caggggcttc tgctcacagc ctcacttcta accttctgga  180
acccgcccac cactgcccag ctcactactg aatccatgcc attcaatgtt gcagagggga  240
aggaggttct tctccttgtc cacaatctgc cccagcaact ttttggctac agctggtaca  300
aaggggaaag agtggatggc aaccgtcaaa ttgtaggata tgcaatagga actcaacaag  360
ctaccccagg gcccgcaaac agcggtcgag agacaatata ccccaatgca tccctgctga  420
tccagaacgt cacccagaat gacacaggat tctacaccct acaagtcata aagtcagatc  480
ttgtgaatga agaagcaact ggacagttcc atgtataccc ggagctgccc aagccctcca  540
tctccagcaa caactccaac cctgtggagg acaaggatgc tgtggccttc acctgtgaac  600
ctgagactca ggacacaacc tacctgtggt ggataaacaa tcagagcctc ccggtcagtc  660
ccaggctgca gctgtccaat ggcaacagga ccctcactct actcagtgtc acaaggaatg  720
acacaggacc ctatgagtgt gaaatacaga acccagtgag tgcgaaccgc agtgacccag  780
tcaccttgaa tgtcacctat ggcccggaca cccccaccat ttccccttca gacacctatt  840
```

```
accgtccagg ggcaaacctc agcctctcct gctatgcagc ctctaaccca cctgcacagt  900
actcctggct tatcaatgga acattccagc aaagcacaca agagctcttt atccctaaca  960
tcactgtgaa taatagtgga tcctatacct gccacgccaa taactcagtc actggctgca  1020
acaggaccac agtcaagacg atcatagtca ctgagctaag tccagtagta gcaaagcccc  1080
aaatcaaagc cagcaagacc acagtcacag gagataagga ctctgtgaac ctgacctgct  1140
ccacaaatga cactggaatc tccatccgtt ggttcttcaa aaaccagagt ctcccgtcct  1200
cggagaggat gaagctgtcc cagggcaaca ccaccctcag cataaaccct gtcaagaggg  1260
aggatgctgg gacgtattgg tgtgaggtct tcaacccaat cagtaagaac caaagcgacc  1320
ccatcatgct gaacgtaaac tgtaagtgac tcctcacccc ttcctatatg tccctctagg  1380
attactctgt caatggtgtg caaaatggat aaaactcaca ggaggcagaa tatcaatgaa  1440
gagaccatta tagcaaacag aattgcaaag tggttaagag ctcagctcag gccgggcaca  1500
gtggctcacg cctgtgatcc cagcagtttg ggaggccaag gcgggcggat cacgagggca  1560
ggagatcgag gccatcctgg ctaatatggt gaaaccccgt gtctactaga aatacaaaaa  1620
aaaattagcc gggcatggtg gcgggcgcct gtggtcccag ctactcggga ggctgaggcg  1680
ggagaatggc gtgaacctgg gaggcggagc tttcagtgag ccgagatggt gccactgcac  1740
tccagtctgg gcaacagggc aagactctgt ctc                              1773

SEQ ID NO: 8           moltype = DNA  length = 1956
FEATURE                Location/Qualifiers
source                 1..1956
                       mol_type = unassigned DNA
                       organism = Homo sapiens
SEQUENCE: 8
gtgatgtgtt taccttcagt gtctccttgg aggtaaaaga agacgatgga aaaggaaact  60
ttagccctgt gcctaggata gagataaatt ttatttcaaa ttaaagcaag gaatagagaa  120
gaaggttgtg attacagtgc agcaactttc taacaaagaa ttagctattg aaagatgttt  180
tggaatgtta ttaagcccag gtcgaaacgt gaagaacagt gacatgcatt tactggatat  240
ggaatccatg ggaaagagct atgatgggag agcttatgtc atcactggca tgtggaaccc  300
caatgcacca gtatttctgg cacttaacga ggaaacccca aaagataagc aagtatacat  360
gactgtggca gtggatatgg tagtcacaga ggtggtggag cctgttcgct ttctcctgga  420
gacagtagtc cgtgtgtacc ctgcaaatga gcgattttgg tatttcagca gaaagacttt  480
cacagagact ttcttcatga gattgaaaca gtctgaggga aaaggccata ccaatgctgg  540
agatgcaata tatgaggtgg tgagtctaca gcgagagtct gacaaggagg aaccagtcac  600
tcctactagt ggaggggtc caatgtcacc ccaggatgat gaagcagaag aggagagtga  660
taatgaactc tcaagtggaa caggtgatgt gtctaaggat tgtcctgaga agatcctgta  720
ttcttgggga gagttgctag gaaaatggca cagtaacctt ggtgcacgac cgaaagggct  780
gtctactctg gtgaagagtg gtgtccctga agcattgagg gcagaggtat ggcagttatt  840
ggcaggctgc catgacaacc aggcaatgct ggatagatac cgaattctta tcacaaaggt  900
ctgttggagt ttgctggagg tccactccag accctgtttg cctgggtatc accagtggaa  960
gctgcagaac agcaaatatt gcagaatggc aaatgttgct gcctgatcct tcctctggaa  1020
gcttcatctc agaagggcac ctggctgtat gaggtgtcgg ttggcccctc ctgggaggtg  1080
tctcccaatt agactactca ggtgtcaggg acccacttga ggaggcagtc tgtccattct  1140
caggtcccaa actacatgct gggagaacca ctactctctt caaagctgtc agacagggac  1200
atttaagtct gcagaagttt ctgctgccgt ttgttcaact atgccctgcc cccagtactg  1260
gagtccagga aggcaggcag gcctccttga gctttggtgg gctccaccca gttcagtctt  1320
cccggctgct ttgtttacct actcaagctt cagcaatggc ggatgcccct ccctcagcct  1380
tgctgacact tgcggcttga tctcagactg ctgtgttagc agtgagtgag gctccgtggg  1440
tgtgggactc tccgagccag gtgcgggata taatctcctg gtgttccgtt tgctaagacc  1500
attggaaaag cgcagtatta gggtgggagg gtcccgattt tccaggtact atctgtcatg  1560
gcttcccttg gctaggaaag ggaattcccc aacccttgc acttcccagg tgaggcaatg  1620
ccccacgctg ctccttgggc tgcacccact gtgtgacaag ccccagtgag atgaacccgg  1680
tacctctgtt ggaaatgcag aaatcacctg tcttctgcgt cgctcacgct gggagctgta  1740
gactggagct gttccttttt ggccatcttg gaacctcggt tcaaacctga gttgtaatac  1800
tcactcttcc tgttgctgcc tatgtaattt tgtagaagtt acctaattgc ttccaagctt  1860
ctgttggatt ttttgagaac tgaatgacat agtacatttt gagtgcttaa tgtattgctt  1920
tgtgcatggt attatttaat aaatattagc tttggt                           1956

SEQ ID NO: 9           moltype = DNA  length = 873
FEATURE                Location/Qualifiers
source                 1..873
                       mol_type = unassigned DNA
                       organism = Homo sapiens
SEQUENCE: 9
atgaggatat ttgctgtctt tatattcatg acctactggc atttgctgaa cgcatttact  60
gtcacggttc ccaaggacct atatgtggta gagtatggta gcaatatgac aattgaatgc  120
aaattcccag tagaaaaaca attagacctg gctgcactaa ttgtctattg ggaaatggag  180
gataagaaca ttattcaatt tgtgcatgga gaggaagacc tgaaggttca gcatagtagc  240
tacagacaga gggcccggct gttgaaggac cagctctccc tgggaaatgc tgcacttcag  300
atcacagatg tgaaattgca ggatgcaggg gtgtaccgct gcatgatcag ctatggtggt  360
gccgactaca agcgaattac tgtgaaagtc aatgccccat acaacaaaat caaccaaaga  420
attttggttg tggatccagt cacctctgaa catgaactga catgtcaggc tgagggctac  480
cccaaggccg aagtcatctg gacaagcagt gaccatcaag tcctgagtgg taagaccacc  540
accaccaatt ccaagagaga ggagaagctt ttcaatgtga ccagcacact gagaatcaac  600
acaacaacta atgagatttt ctactgcact tttaggagat tagatcctga ggaaaaccat  660
acagctgaat tggtcatccc agaactacct ctggcacatc ctccaaatga aaggactcac  720
ttggtaattc tgggagccat cttattatgc cttggtgtag cactgacatt catcttccgt  780
ttaagaaaag ggagaatgat ggatgtgaaa aatgtggca tccaagatac aaactcaaag  840
aagcaaagtg atacacattt ggaggagacg taa                              873
```

```
SEQ ID NO: 10          moltype = DNA  length = 1264
FEATURE                Location/Qualifiers
source                 1..1264
                       mol_type = unassigned DNA
                       organism = Homo sapiens
SEQUENCE: 10
ggagggagca gtcggtcgct gcgccccggc gggccacttt cccgggaccc cgctcgtctt  60
ccttgggccg agattttcca ctgcgcccct ccgagtaccc gggttccaaa cccctagcca  120
cgacatggaa gaattttgc aacgcgccaa atctaaactg aatcgaagca aacgcttgga  180
gaaggtccat gtggttattg ggcctaaatc gtgtgacttg gattctctca tttctacctt  240
cacatatgct tactttctag acaaggtcag tccaccaggg gttctgtgtt taccagtgct  300
gaacatacca agaactgaat tcaactactt caccgagacg aggtttattt tagaagagct  360
aaatatttcc gaatcattcc acatattccg ggatgaaatt aacctgcatc agctaaatga  420
tgaagggaag ttatcgataa cacttgttgg cagcagtgtg ctggcgagtg aagacaaaac  480
tttagaatca gcagttgtca aagtcattaa tccggttgag cagagcgatg ccaacgttga  540
gttccgagag tcttcctctt ctctcgtgct aaaggagatt ctccaagagg ctcctgagct  600
catcaccgag caactggctc atcgcctcag aggtagcatt cttttcaagt ggatgaccat  660
ggaatcagag aagatctcag agaagcagga ggaaattctt tctatcctgg aagaaaaatt  720
tcctaacttg cctccaagag aggacatcat caacgtccta caggagaccc agttcagtgc  780
tcagggttta agtattgaac agacaatgtt gaaagatcta aaggagctgt cagatggaga  840
aataaaagtg gccattagta ctgtgagcat gaaccttgag gtaagggtgg gaatgctttt  900
ttagcattga ttgatttccc acaattgcag tctgagcaac tggaatgtaa ctctctccat  960
tggataagtc catgatagtc ctttgcttct ttgtgataca tttgacttgg aatatagtgg  1020
caggttatta tttgggtgaa aacactatgc taagtcaatg aaaaatgcca aacctggatt  1080
ctcaagatga atgctctttc attcatctca gtaaaacaaa gcctaaaaca aacactcaga  1140
tgtgggtgta tatttaacct gtttaatagc aattatgata tgtgtgatta ggttcacttc  1200
catattttct gtgtaccacc ctgtattgtt catagaactt ttcttaaaaa aaaaaaaaaa  1260
aaaa                                                               1264

SEQ ID NO: 11          moltype = DNA  length = 2592
FEATURE                Location/Qualifiers
source                 1..2592
                       mol_type = unassigned DNA
                       organism = Homo sapiens
SEQUENCE: 11
atggatgcta gcatttggag caatgaactc atcgagcttt ttattgtcat tggaaacaaa  60
agagcaaatg acttttgggc tggtaatctt caaaaggatg aagaattaca tatggactca  120
ccagtagaaa agagaaaaaa ctttattact cagaaatata aagaaggaaa attcagaaaa  180
actcttttgg catctctcac caaagaagaa ttaaataagg ctctatgtgc tgctgtagtg  240
aaaccggatg ttctagaaac aatggctttg ctgttcagtg gagcagatgt catgtgtgcc  300
accggagacc ccgtgcatag cacccccctat ctgctagcca agaaagctgg gcaaagtctg  360
caaatggaat ttctctacca taacaaattc tcagatttcc ctcaacatga tattcattcc  420
gagggtgtat taagtcaaga gtcttcccag tccacattcc tctgtgactt tttatatcaa  480
gctccttctg ctgcttctaa actctcttca gagaaaaaac tgcttgaaga gacaaataaa  540
aaatggtgtg ttttggaagg aggcttcttg agttactatg aaaatgataa gtctaccaca  600
cctaatggca ccattaatat caatgaagtt atctgcctgg ctatacacaa agaggacttc  660
tatttaaata ctgggcccat ctttatcttt gagatctact taccctccga acgtgtgttt  720
ttatttggag ctgaaacatc tcaagctcaa agaaaatgga cagaggcaat agccaagcat  780
tttgttccct tatttgctga aaacttaaca gaagctgact atgatttgat tggtcaactc  840
ttctacaaag actgccatgc cctggatcag tggagaaaag gctggtttgc tatggacaaa  900
tccagcttgc atttttgcct tcaaatgcaa gaagttcagg gagatagaat gcacttaaga  960
agactgcaag agctaacaat cagcacaatg gttcaaaatg ggggaaaaact ggatgtttta  1020
ctcttggtag aaaaagggag aacattatac atccatgggc ataccaagtt ggatttcaca  1080
gtctggcata ctgcaattga aaaagcagca ggtacagatg gtaatgcttt acaagatcag  1140
cagctcagca aaaatgacgt tcccattata gtgaacagct gtatagcatt tgttacacag  1200
tatggtttag gatgcaaata tatctatcaa aagaatggtg atcctttgca tataagtgaa  1260
ctcctggaga gtttcaaaaa ggatgcaaga agctttaaat tgagggctgg aaaacatcag  1320
cttgaagatg tgacggctgt gttgaaaagt tttctctctg acattgatga tgcactgctt  1380
actaaggagc tctacccata ttggatctct gctttagata cgcaagatga caaggaaaga  1440
attaaaaaat atggagcatt tatacgttct cttccagggg tcaaccgagc aacactagca  1500
gctatcattg aacacctgta tagggttcag aaatgctcag aaatcaatca catgaatgcc  1560
cataatttgg ccttggtctt ttcatcctgt ttgtttcaaa cgaagggaca aactagtgaa  1620
gaagtgaatg taattgagga cctaattaat aattatgtag aaatatttga ggttaaagaa  1680
gatcaagtca aacaaatgga catagaaaat agctttatta ccaagtggaa agacacccaa  1740
gtttcccagg ctggagattt gttaattgaa gtatatgtag aaaggaagga acccgactgt  1800
agtattataa ttcggatatc tcctgtgatg gaagcagaag aattaactaa tgatatatta  1860
gcgataaaaa atattattcc tacaaaaggt gatatttggg ccacatttga agtcattgaa  1920
aatgaagagc tagagcgtcc tcttcactac aaggaaaatg tactggagca ggtgcttcgg  1980
tggagttcat tagctgaacc tggctctgct tacctggtgg tgaagagatt cttaaccgct  2040
gacacaatta aacactgcag tgaccggagt acactgggaa gcatcaaaga aggaatcttg  2100
aaaatcaaag aagaaccatc caaaatacta tctggaaata agtttcaaga ccggtatttt  2160
gttttacgag atgggtttct ctttctttac aaggatgtga agagtagtaa acatgacaag  2220
atgttttctc tcagttccat gaagttttat cgtggagtga aaaagaaaat gaagcctcca  2280
acaagctggg gattgaccgc atattctgag aaacatcact ggcacctgtg ttgtgatagt  2340
tcacgaactc agacggagtg gatgaccagt atctttattg cccagcatga atatgatata  2400
tggccaccag ctggaaagga acgaaaacgt tcaataacca aaaatcccaa aattggaggt  2460
ttgcctctga ttcctataca gcatgagggg aatgcaacct tggcccggaa aatattgaga  2520
gtgcaagagc agaacttgaa aggctgcggc tcagtgaaaa gtgtgataaa gagtccgtgg  2580
actctagctt aa                                                      2592
```

```
SEQ ID NO: 12           moltype = DNA  length = 4502
FEATURE                 Location/Qualifiers
source                  1..4502
                        mol_type = unassigned DNA
                        organism = Homo sapiens
SEQUENCE: 12
cgagggaaga ggccggaggg agatcgcgga ggggaggggg cgggaggggg gtggggtatc  60
ctgagtcgtc cgtggtccgg agtctggaag gccctagagc ggcgccagtc gacccgcctc  120
gccacaactt gcccagacca gacacgtttc atcctgcgcc ctgcaagaag gagccggcct  180
gcctctctcc gctttgctgc tcctcggcct ccgcgggccc ggcccgcgtc agcagcgacc  240
ctggggtctg ggtcccctgt gtcgcccccg cccgcctgca gcgcccggca cccgcccagg  300
agcgcgcagc tggggttcta gggacgtata cttgagcaag agagaccaca gctcttgttc  360
ccgctgatcc tgcagcccag tggatggagt ccagaatcta cagacctgcc aggaaagaaa  420
aaaaattcct gatgtctggt ccaagcagga attccccggt ggattgggga atgtctggct  480
tttcctcagc ttattgatct ctgtggtaac cactggaggc cccagaaga cccatagaaa  540
tgagaggcct gaggtctaca agtcgctgct agaaatattt tagcctctcc aaagcccaga  600
atgcagcccc gacccaagtt tgtaagggtt ctgggtgcac gctgaccctg cgcgggcaga  660
cgcgcccttt gctccaggtc cggacctggg cgctgctata gcaacgtcct ggacgcccag  720
accttaggcc gccgccgccg cggaagcgag gaacccggcc ttctcccgct cctgagggct  780
gtggcggcgg cggcccggga ggcggcccag gctgggtaaa gaccgcccgg ctcctcctat  840
gcaagctgag gcagcggatt ggttttcaag catgcccttc cagaagcatg tctactaccc  900
gctcgccagc ggcccagagg ggcccgacgt cgctgtggcc gccgccgccg cgggtgcggc  960
ctccatggcc tgtgcgcccc ccagcgcggc ttcggggccc ctgcccttct tccagttcag  1020
gccgcggctg gagagtgtgg actggcggcg gctgagcgcc atcgacgtgg acaaggtggc  1080
gggggctgtg gacgtgctga cgctgcagga gaacatcatg aacatcacct tctgcaagct  1140
ggaagacgag aagtgcccac actgccagtc gggggtggac ccggtgctgc tgaagctcat  1200
ccgtctggcg cagttcacca tcgagtactt gctgcactca caagagttcc tcacctcgca  1260
gctgcacacc ctggaggagc ggctgcgcct gagccactgc gacggcgagc agagcaagaa  1320
gctgctcacc aagcaggcgg gggagatcaa gacgctcaag gaagagtgca aacgccggaa  1380
gaagatgatc tccacccagc agctgatgat cgaggccaaa gccaactatt accagtgcca  1440
tttttgtgac aaggccttta tgaaccaagc ttttctacaa agtcacattc aacgccgcca  1500
cactgaagaa aattctcatt ttgagtatca gaaaaatgca cagattgaga agctccggag  1560
tgagatcgtc gtattgaagg aagagctgca gctcaccagg tctgagctag aggctgcaca  1620
ccatgccagt gcagtcagat tctccaagga atatgaaatg cagaaaacaa aagaggaaga  1680
ctttttgaag ttatttgaca ggtggaaaga agaagaaaag gagaaactag ttgatgaaat  1740
ggaaaaagtc aaggagatgt ttatgaagga atttaaagaa ttaacttcga agaattcagc  1800
attagaatat caactgtcag aaatccagaa gtccaatatg cagatcaagt ccaacatagg  1860
cacattaaaa gatgcacacg agtttaaaga agaccgttct ccatatcccc aggatttcca  1920
taatgtcatg cagcttcttg atagtcagga aagcaaatgg acagctcgag ttcaagctat  1980
tcatcaagaa cacaagaaag agaagggtcg gctcctgtca catatagaga aacttcgaac  2040
ctcaatgata gatgatctaa atgcaagcaa tgttttctat aagaaaagga tagaagagct  2100
agggcagaga ctccaggagc agaatgagct gattataact cagagacagc agattaaaga  2160
ctttacctgt aatccattaa acagtatcag tgaacccaaa gtgaatgccc cagccctgca  2220
cactttggaa actaaatcaa gtctgccaat ggtgcatgaa caggcattct cgtcgcacat  2280
actggaacca atagaagaac tttcagagga agaaaaagga agggaaaatg aacagaaatt  2340
aaataacaac aaaatgcatt taaggaaagc tttgaagagt aactcctccc tcactaaggg  2400
actaagaaca atggtggagc agaacttgat ggagaaactg gaaaccttgg ggattaatgc  2460
agatatacgt ggcatttcaa gtgatcagtt gcatagagta ctaaaaagtg tggaatcaga  2520
aagacataag caagaaagag aaatacctaa ctttcatcaa attcgagaat tccttgaaca  2580
tcaagtcagc tgtaaaattg aggagaaagc actactctct tcagatcagt gcagtgtttc  2640
tcaaatggat accctttcaa ctggagaagt acccaaaatg atacaacttc cttccaaaaa  2700
cagacaactg attagacaaa aagctgtttc tactgatagg acatctgttc caaaaattaa  2760
gaaaaatgtc atggaagatc cttttcccag aaagtcttca actattacga cccctccttt  2820
tagttcagag gaggagcagg aggacgacga cctcatccgg gcatacgcat ccccaggccc  2880
acttcctgtg ccgccaccac aaaacaaggg cagcttcggg aagaacacag tgaaaagtga  2940
cgcggacggg accgagggaa gcgaaatcga ggacactgat gattctccca agcccgcagg  3000
agtcgccgtt aaaacaccta ctgaaaaagt tgaaaagatg tttccacatc gcaaaaatgt  3060
gaacaaacca gtcggtggaa ctaatgtccc tgagatgttt atcaaaaaag aagaattaca  3120
agaactaaag tgtgcggatg tggaggatga agactgggac atatcatccc tagaggaaga  3180
gatatctttg ggaaaaaaat ctgggaaaga acagaaggaa cctccacctg cgaaaaatga  3240
accacatttt gctcatgtgc taaatgcctg gggcgcattt aatcctaagg ggccaaaggg  3300
agaaggactt caagaaaatg aatcaagcac attaaaaagc agcttagtaa ctgtgactga  3360
ttggagcgac acttcagatg tctaattcca catgtcagaa gattattcca gaagccagca  3420
gtatttcagt atcacagtgt ttcagtaatt tgcctccatg attctagtgc ttctgcctta  3480
ccgtgtttcc cacagcaaca cagagactga ttcaaagaac aatggtctct ttaatggcac  3540
ccaatacagt attgaaaatc agatcatcaa cagtatttcg aagcatgtaa aggtgtttaa  3600
gacttccgct gctgcttaaa aataacatgt cattgaagtc ataaaaagtt ttttcttcag  3660
aaaggtactc tagtgttaag tgtatttttt tcaactaatt ttttagtgaa tttttttaa  3720
acttacagca tgttttggtt tgaattacta aaactttaaa aaatattttt cttatgtatg  3780
ctgtcgtatc gtaggcgttt atattataaa attctgttag tagtcttaaa attgaattgg  3840
tggaaccact aatccttaaa agttagtctg gttatttttc atatagaagt aagtttaatc  3900
cgagtgtggt ggtgttcacc tttaatccca gctacttggg aggctgaggt gggaggataa  3960
cttgagcaca ggagttcaag accagcgtgg gcaatatagc aagactccac ccctccacac  4020
cccaaaaaag taagtttagg attagaatat agctaggtcc aatgttaaat acattttcct  4080
ggagtacatt tgtcacattc agctttgagc cactgtaagc atgttactat taaatggttg  4140
gttattttat atagcatatt ctttatcttg gatattttat gaataaagta tagttatttt  4200
aagtgccaat taatttatca gactaaatag aaaatatttg agccattact gaattcacat  4260
atgtatgttt ttttttacta tttaaaatac ccaacatgta ttatgaaata cctcaaaagt  4320
```

```
aatttagtta cattcttaaa caatgacatt gtcgaaagaa agttcttata agctgttttt  4380
tgcattttta taacttggtt atactatatt ctgtttccaa gtaacctttt aactaaaaga  4440
tttgttgggt tttagatctc ttttcatttg tcaacctttt cagtaaagcc ctctgttaca  4500
tc                                                                 4502

SEQ ID NO: 13          moltype = DNA  length = 1887
FEATURE                Location/Qualifiers
source                 1..1887
                       mol_type = unassigned DNA
                       organism = Homo sapiens
SEQUENCE: 13
cggggcgcgg cgggctccct cggggtccca gctggccggc actcggcggc cgcggcgcga  60
tggaggcgcc ggccgagcta ctggccgcgc tgcctgcgct ggccaccgcg ctggcccttc  120
tgctcgcctg gctactggtg cggcgtgggg cggccgcgag cccggagcct gcccgcgcgc  180
ccccggaacc cgcgcccccg gccgaggcca ccggggcccc ggcgccgtcc cgcccctgcg  240
cccccgagcc ggcggcctcg cccgcggggc cggaggagcc tggagagccc gcggggctgg  300
gggagctcgg ggagcctgcg ggaccggggg agcccgaagg gccaggggat cccgcggcgg  360
cgccagcgga ggcggaggag caggcggtgg aggcgaggca ggaagaggag caggacttgg  420
atggtgagaa ggggccatca tcggaagggc ctgaggagga ggacggagaa ggcttctcct  480
tcaaatacag ccccgggaag ctgaggggaa accagtacaa gaagatgatg accaaagagg  540
agctggagga ggagcagaga actgaagaat aacgaagtta tccttagcgt cctcctaaag  600
gcttttcctt ttggcatctt aaaagcttga gagataaaac ggaaacccca gagaggagtc  660
tgggcaggct cccagggtgc atgctgcctc cataaatctg ctgagctcta gaccctcaat  720
caggacttgt ccccttggcta gcaggatcct gggaacacct ttggccctgc cctgtgtaga  780
gatgttcatg tctgttcctg tgggtcactt tgttaagctg aagagtttta agaggtagag  840
ctcagaccct ggactgggat ttttcttacc actcaaactt gctatccaca caccctgcac  900
accttagata aaaagaacat tttaaaagca gagttcactt tcactccagt ctcccctctt  960
ttgccctcac tgaagccaaa ccacagaaga ctttgaggaa tgagagacaa atgaggtaga  1020
gctcacctgt gctcaccagc tccgtcaggg tggtcagccg acccctttcc ctgggaaccc  1080
cacttctctc tgtggctggc ttggttgtcg gggtgagat gccatattga ttacagggca  1140
gcaaagaacc agtaccagga atttacttga ccattcccct tatttttcat ctagaggaat  1200
ctcggattca gccctttcat tgctaagaca ccttttcact gaggttctta ccagctcagc  1260
caaatctcca ctctgctata gcagaagcaa taatgtttgc tttaaaaaga tttcttgacc  1320
tatgcctttt cttagaaagt ttgatagatt agttagaact tcagatcatc agatcagtct  1380
caaatgggtt tcttggaatt ttatatttga caatatttat actataccaa actcatttgc  1440
agttcttagg tttgttggtt aaaacatttt tttaaagcag taagtttata gaaaatgttt  1500
tcatttaatg gaaggctggg gaatgtccag catcaacccc tatggcatgc attcccagtg  1560
gccttctcat ctgggcctgg aacctttggt tcagggctta ggggagaaca ggccacatgg  1620
caacagccac acagtcattg ccttcaacac agagccacgt gtccccaaac agcaatagtc  1680
atgcccttgt ccaggctggg atctaattga tacaataggt cgttgactcc ctcctagtag  1740
agctatctag gtttgtctgg aaagtttccg accctggctt ataggcacca cacctcatgt  1800
actcctcatg gcttggatct ctgtattcag cctttgttca gtccaataaa ctttgagtag  1860
atgatctcaa aaaaaaaaaa aaaaaaa                                      1887

SEQ ID NO: 14          moltype = DNA  length = 2850
FEATURE                Location/Qualifiers
source                 1..2850
                       mol_type = unassigned DNA
                       organism = Homo sapiens
SEQUENCE: 14
gagaacgggg tagcccggcg cttacacatg tcacatgtgc tttttaagac ggccgggagc  60
gcctgcgagc tggatctggt ggaggatgct gcggcaggtg cttcgcagag ggctccagtc  120
gttctgccac aggctgggtt tgtgcgtgag ccggcacccg gtctttttcc tcaccgtgcc  180
cgcagtcctg acaatcacct tcggcctcag cgcgctcaac cgcttccagc ccgagggcga  240
cctggagcgc ctggtcgctc ccagccacag cctggccaag atcgagcgca gcctggccag  300
cagccttttc cccctggacc agtccaaaag ccagctctat tcggacttac acacccctgg  360
gaggtatggc agggtgatcc tcctctcccc aaccggggac aatattttgc tccaggctga  420
ggggatcctg cagacccacc gagccgtgct ggaaatgaag gatgggagga acagttttat  480
tggacaccaa ctgggcgggg tagtggaagt gccaaacagc aaagatcagc gggtcaagtc  540
agccagagcc attcaaatca cctactacct ccagacctat ggctctgcca cccaagacct  600
catagggggag aagtgggaga atgagttctg taagcttata aggaagctcc aggaggagca  660
tcaagaactc cagctctact ctttagcatc ctttagcctc tggagggact ttcataagac  720
cagcatcctg gccagaagca aggtcctggt gagcctcgtg ctgatcctga ccacagccac  780
cctctccagc tccatgaagg actgcttgcg cagtaagccc ttcctgggcc tcctgggggt  840
gctcacagta tgcatctcca tcatcacagc agcagggatc ttcttcatca ccgatggaaa  900
gtacaactcc accctgctgg gaatcccgtt cttcgccatg ggtcatggaa ctaaaggagt  960
gtttgagctt ctgtccggat ggcggagaac caaagagaac ttgcccttca aagacaggat  1020
agcagatgcc tattctgatg tgatggtcac ctataccatg accagctccc tgtacttcat  1080
cacttttggc atgggtgcca gcccattcac aaacatagag gctgtgaagg tcttctgtca  1140
aaacatgtgt gtctctattc tgttgaacta cttctacatt ttctccttct ttggctcctg  1200
tctggtcttt gctggccaac tagagcaaaa ccgctaccac agcatctttt gctgtaagat  1260
cccttctgca gaatacctgg atcgcaaacc tgtgtggttc cagacagtga tgagtgatgg  1320
gcatcaacag acgtcccatc atgagacgaa cccctaccag caccacttca ttcagcactt  1380
cctccgtgaa cattataatg aatggattac caatatatat gtgaagccat ttgttgtcat  1440
cctctatctc atttatgcct ccttctcctt catggggtgc ttacagatca gtgacggagc  1500
caacatcatc aatctactag ccagtgattc gccaagtgtt tcctatgcca tggttcagca  1560
gaaatatttc agcaactata gccctgtgat aggattctac gtctatgagc ccctagagta  1620
ctggaacagc agcgtccagg atgacctaag aagactctgt agtggattca ctgcagtgtc  1680
ctgggtggag cagtactacc agttcctgaa agtcagcaac gtcagtgcca ataacaaaag  1740
```

-continued

```
tgacttcatc agtgtcctgc aaagctcatt tttaaaaaag ccagaattcc agcattttcg  1800
aaatgatatc atcttctcca aggcagggga tgaaagcaat atcattgctt ctcgcttgta  1860
tctggtggcc aggactagca gagacaagca gaaagaaatc acagaagtgt tggaaaagct  1920
gaggccccta tccctctcaa agagcatccg attcatcgtg ttcaacccct cctttgtctt  1980
catggaccat tacagcttgt ctgtcacagt gcctgttctg attgcaggct ttggtgttct  2040
cctggtgtta atcctgactt ttttcctagt gatccaccct ctgggaaact tctggctaat  2100
tcttagcgtc acctcaattg agctgggcgt tctgggctta atgacattat ggaacgtcga  2160
catggattgc atttctatct tgtgccttat ctacaccttg aatttcgcca ttgaccactg  2220
tgcaccactg cttttcacat ttgtattagc aactgagcac acccgaacac aatgtataaa  2280
aagctccttg caagaccatg ggacagccat tttgcaaaat gttacttctt ttcttattgg  2340
gttagtcccc cttctatttg tgccttcgaa cctgaccttc acactgttca aatgcttgct  2400
gctcactggg ggttgcacac ttctgcactg ttttgttatt ttacctgtgt tcctaacgtt  2460
tttccccccct tccaaaaagc accacaagaa aaagaaacgt gccaagcgaa aggagagaga  2520
ggaaattgaa tgcatagaaa ttcaagagaa cccggatcac gtcaccacag tatgaggggt  2580
atagaccagt ggattatttt tcttttccag tattgcacaa tgatgcaggg caagtaaagc  2640
tcagacctca gctgcttggg ctggccaggg gtaacaaggc aagtcagatc aagagtgcat  2700
tattcatgac acttcaaggt gcctgcttct tgggggggaag agggaataaa aaaagaggaa  2760
aaagttattt gcaaccttgt tctcctctaa aaacaagttt ctggatgtaa tctgagagct  2820
cttccaagga atggatgaat caatggagtg                                  2850

SEQ ID NO: 15          moltype = DNA  length = 1491
FEATURE                Location/Qualifiers
source                 1..1491
                       mol_type = unassigned DNA
                       organism = Homo sapiens
SEQUENCE: 15
gccctgcgcg gggacactca gagcccggtg gggggaggaa ggcggcatgc cccagacggt  60
gatcctcccg ggccctgcgg cctggggctt caggctctca gggggcatag acttcaacca  120
gcctttggtc atcaccagga ttacaccagg aagcaaggcg gcaggtgcca acctgtgtcc  180
tggagatgtc atcctggcta ttgacggctt tgggacagag tccatgactc atgctgatgc  240
gcaggacagg attaaagcag cagctcacca gctgtgtctc aaaattgaca ggggagaaac  300
tcacttatgg tctccacaag tatctgaaga tgggaaagcc catcctttca aaatcaactt  360
agaatcagaa ccacaggacg ggaactactt tgaacacaag cataatattc ggcccaaacc  420
tttcgtgatc ccgggccgaa gcagtggatg cagcactccc tccgggattg actgtggcag  480
tggacgcagc accccttctt ctgtcagtac tgttagtacc atttgcccag gtgacttgaa  540
agttgcggct aagctggccc ctaacattcc tttggaaatg gaacttcctg gtgtgaagat  600
tgtacatgct cagtttaata cacctatgca gttgtactca gatgacaata ttatggaaac  660
actccagggt caggtttcaa cagccctagg ggaaatacct ttgatgagcg agcccacagc  720
ctcggtgccc cccgagtcgg acgtgtaccg gatgctccac gacaatcgga atgagcccac  780
acagcctcgc cagtcgggct ccttcagagt gctccaggga atggtggacg atggctctga  840
tgaccgtccg gctggaacgc ggagtgtgag agctccggtg acgaaagtcc atggcggttc  900
aggcggggca cagaggatgc cgctctgtga caaatgtggc agtggcatag tcggtgctgt  960
ggtgaaggcg cgggataagt accggcaccc tgagtgcttc gtgtgtgccg actgcaacct  1020
caacctcaag caaaagggct acttcttcat agaaggggag ctgtactgcg aaacccacgc  1080
aagagcccgc acaaaacccc caagaggcta tgacacggtc actctgtatc ccaaagctta  1140
agtctctgca ggcgtggcac acgcacgcac ccacccacgc gcacttacac gagaagacat  1200
tcatggcttt gggcagaagg attgtgcaga ttgtcaactc caaatctaaa gtcaaggctt  1260
tagaccttta tcctattgtt tattgaggaa aaggaatggg aggcaaatgc ctgctatgtg  1320
aaaaaaacat acacttagct atgttttgca actctttttg ggctagcaa taatgatatt  1380
taaagcaata atttttgta tgtcatactc cacaatttac atgtatatta cagccatcaa  1440
acacataaac atcaagatat ttgaaggact ctaattgtct ttccttgaca a          1491

SEQ ID NO: 16          moltype = DNA  length = 1504
FEATURE                Location/Qualifiers
source                 1..1504
                       mol_type = unassigned DNA
                       organism = Homo sapiens
SEQUENCE: 16
tgcagacgga acttcagccg ctgcctctgt tctcagcgtc agtgccgcca ctgcccccgc  60
cagagcccac cggccagcat gtcctctgct cacttcaacc gaggccctgc ctacgggctg  120
tcagccgagg ttaagaacaa gctggcccag aagtatgacc accagcggga gcaggagctg  180
agagagtgga tcgagggggt gacaggccgt cgcatcggca acaacttcat ggacggcctc  240
aaagatggca tcattctttg cgaattcatc aataagctgc agccaggctc cgtgaagaag  300
atcaatgagt caacccaaaa ttggcaccag ctggagaaca tcggcaactt catcaaggcc  360
atcaccaagt atggggtgaa gccccacgac atttttgagg ccaacgacct gtttgagaac  420
accaaccata cacaggtgca gtccaccctc ctggctttgg ccagcatggc gaagacgaaa  480
ggaaacaagg tgaacgtggg agtgaagtac gcagagaagc aggagcggaa attcgagccg  540
gggaagctaa gagaagggcg gaacatcatt gggcttcaga tgggcagcaa caagtttgcc  600
agccagcagg gcatgacggc ctatggcacc cggcgccacc tctacgaccc caagctgggc  660
acagaccagc ctctggacca ggcgaccatc agcctgcaga tgggcaccaa caaaggagcc  720
agccaggctg gcatgactgc gccagggacc aagcggcaga tcttcgagcc ggggctgggc  780
atggagcact gcgacacgct caatgtcagc ctgcagatgg gcagcaacaa gggcgcctcg  840
cagcggggca tgacggtgta tgggctgcca cgccaggtct acgaccccaa gtactgtctg  900
actcccgagt acccagagct gggtgagccc gcccacaacc accacgcaca caactactac  960
aattccgcct aggtccacaa ggccttcact gttttccccc caagggaggc tgctgctgct  1020
cttggctgga gccagccagg gccagccgac cccctctccc tgcatggcat cctccagccc  1080
ctgtagaact caacctctac agggttagag tttggagaga gcagactggc gggggcccca  1140
ttggggggaa ggggaccctc cgctctgtag tgctacaggg tccaacatag aacagggtgt  1200
ccccaacagc gcccaaagga cgcactgagc aacgctattc cagctgtccc cccactccct  1260
```

```
cacaagtggg tacccccagg accagaagct cccccagcaa agcccccaga gcccaggctc  1320
ggcctgcccc caccccattc ccgcagtggg agcaaactgc atgcccagag acccagcgga  1380
cacacgcggt ttggtttgca gcgactggca tactatgtgg atgtgacagt ggcgtttgta  1440
atgagagcac tttctttttt ttctatttca ctggagcaca ataaatggct gtaaaatcta  1500
cacg                                                               1504

SEQ ID NO: 17          moltype = DNA  length = 1781
FEATURE                Location/Qualifiers
source                 1..1781
                       mol_type = unassigned DNA
                       organism = Homo sapiens
SEQUENCE: 17
actcgggaag acttcagaga agtctcacaa aggactcggc tggctgcttt tctcagtgcc  60
gaagccgcgc catgctcgtt ctcagaagcg gcctgaccaa ggcgcttgcc tcacggacgc  120
tcgcgcctca ggtgtgttca tcttttgcta cgggccctag acaatacgat ggaacgttct  180
atgaatttcg tacttattac cttaaacctt caaatatgaa tgcgttcatg gaaaatctta  240
agaaaaacat tcatcttcgg acctcttact ctgaattggt tggattctgg agtgtagaat  300
ttggaggcag aacgaataaa gtgtttcata tttggaagta tgataatttt gctcatcgag  360
ctgaagttcg gaaagcctta gccaactgta aggaatggca agaacaatct atcattccaa  420
atttggctcg cattgataaa caagagacgg aaattactta cctgatacca tggtccaaat  480
tagaaaagcc tccaaaagaa ggagtctatg aactagctgt ttttcagatg aaacctggtg  540
ggccagctct gtggggtgat gcatttgaaa gagcaattaa tgcccatgtc aatttaggct  600
acacaaaagt agttggtgtt ttccacacag aatatggaga actcaacaga gttcatgttc  660
tttggtggaa tgagagtgca gatagtcgtg cagctgggag acataagtcc catgaggatc  720
ccagagttgt ggcggctgtt cgggaaagtg tcaactacct agtttctcag cagaatatgc  780
ttctgattcc tgcatcattt tcaccattga aatagtttc tactgaaata caaaacattt  840
cattaactgc tctaagatgt gtctgctaat ggtgcttaaa ttctcccaag aggttctcgc  900
ttttatttga aggaggtggt aagttaatta gttaatttgc tgtgcttctt gcatttttga  960
aagttacata ttctccactg ctttaagaaa taattcagtt cactttcacc ttggcatttc  1020
agtatctgtt acacattaga agtagttgtc actatttcat catcttggtt tttcatttgt  1080
tttagaatac ctcttctgta ttttgataac tcattgcttt atagcatttt cttttactca  1140
aataaggatt ttacatttcc ttgcctgaca gtatttttga attatttata taaaatatct  1200
atcttttcat catgtctata gttcctgaga ttttaaaaaa atttgcttag taaaggttat  1260
tttgtgatat aaaatgggat ttataaaaat attagattgt ttatttcttt actgtggaaa  1320
agtagaatgt catctgtatt aattattgct tttacattca ttgattatta gtcattctaa  1380
cttggaaaat aatgcaattg ggtcacagtg ttaaaaatct agaaaagact tgttggttta  1440
tatgctgaaa ttgttcattt ataattaatt ttactaattt ctccttagtt tggatcacta  1500
acagagatct tgggacattt atttgtttta aagaaatatt tatggttatg gaaacgcttg  1560
ccctaataaa aatcctgcat attcattgtt tttttaaatt cacattttat acttatatga  1620
tctctaaagc tcttgctatg ttgctataag acagtaatat agtgataatt taccaacttt  1680
attgaaaatg ttgttacatc aataaaatag catgctggga acctgagaag gaaggtttct  1740
ttagtactgc caaaaaaaaa aaaaaaaaaa aaaaaaaaaa a                      1781

SEQ ID NO: 18          moltype = DNA  length = 3023
FEATURE                Location/Qualifiers
source                 1..3023
                       mol_type = unassigned DNA
                       organism = Homo sapiens
SEQUENCE: 18
tgaattcaaa acagttactc tgaatggtct ttgctaagaa caatttaatg attaagtaag  60
gtcagtgtcc ttggaagtcc aaactctagc cagatttccc tggtctacac ccctagggat  120
aaggtaaatg tttaagcaca cagtgaactt cctgaggccc ccaaatctaa tggaactagc  180
tattgagggc taaaagagga tggttttttt agaaaactcg aagcaaatct ctcaggctgg  240
ggatatttca aagactacta ctattattat taataacaat tgcaatattt gttgagtccc  300
taaatgaagc taaaactttg ttctaataaa tttaatcttt acagcaacct atgaggtaga  360
taatattgtc attcccatga gggagctaag gatcagagaa ggtaagtcac ttgtctaagg  420
tcacatagct agcatgttat gcaatcagga gtcaaacctg gtttgtctga atctgaagtc  480
catctgctct gtgcactttt ataccgtctg ctttttcctt tattcctaac cttcttccat  540
tctgattccc actgagtagt ggacaggaac cactgaagtt tgcctgacac catcaaccag  600
gccctagtca cctggctttg cctttgccct gctgtgtgat cttagctccc tgcccaggcc  660
cacagccatg gccatggccc agaaactcag ccacctcctg ccgagtctgc ggcaggtcat  720
ccaggagcct cagctatctc tgcagccaga gcctgtcttc acggtggatc gagctgaggt  780
gccgccgctc ttctggaagc cgtacatcta tgcgggctac cggccgctgc atcagacctg  840
gcgcttctat ttccgcacgc tgttccagca gcacaacgag gccgtgaatg tctggaccca  900
cctgctggcg gccctggtac tgctgctgcg gctggccctc tttgtggaga ccgtggactt  960
ctggggagac ccacacgccc tgcccctctt catcattgtc cttgcctctt tcacctacct  1020
ctccttcagt gccttggctc acctcctgca ggccaagtct gagttctggc attacagctt  1080
cttcttcctg gactatgtgg gggtggccgt gtaccagttt ggcagtgcct tggcacactt  1140
ctactatgct atcgagcccg cctggcatgc ccaggtgcag gctgttttc tgcccatggc  1200
tgcctttctc gcctggcttt cctgcattgg ctcctgctat aacaagtaca tccagaaacc  1260
aggcctgctg ggccgcacat gccaggaggt gccctccgtc ctggcctacg cactggacat  1320
tagtcctgtg gtgcatcgta tcttcgtgtc ctccgacccc accacggatg atccagctct  1380
tctctaccac aagtgccagg tggtcttctt tctgctggct gctgccttct tctctacctt  1440
catgcccgag cgctggttcc ctggcagctg ccatgtcttc gggcagggcc accaactttt  1500
ccacatcttc ttggtgctgt gcacgctggc tcagctggag gctgtggcac tggactatga  1560
ggcccgacgg cccatctatg agcctctgca cacgcactgg cctcacaact tttctggcct  1620
cttcctgctc acggtgggca gcagcatcct cactgcattc ctcctgagcc agctggtaca  1680
gcgcaaactt gatcagaaga ccaagtgaag gggatggca tctggtaggg agggaggtat  1740
agttggggga caggggtctg ggtttggctc caggtgggaa caaggcctgg taaagttgtt  1800
```

```
tgtgtctggc ccacagtgac tctctgtgca cgactcaact gccaagggca tcactggcca  1860
attcttggat ttagggattg gctaggagtt gctggggtcc actcctgggc ctgccccagc  1920
tccttgccca gggagaggga aagagttaac ggtgtgggcc actccagctt gcccttccac  1980
tgccactcac tggggtgagg ctgggggtca gcttggtgag gattggggct tctagattgt  2040
ctaggcagga ggtgaaactt aggccagagt cagatttgag ctgagccagg ggaggccttg  2100
gcaacctact tctactcaga tttcattgct ggatgcggaa ggggtaggcc caaaatatat  2160
acaggatctt actgtccctt gaagcccagc cacaagtgtt ggagctgcag agagacccca  2220
aaggtagtag attgtgccag atacaaatgg gtcccatcca gtgcttcata ctccttcagt  2280
cactatccca gacagtgagc cccagatctc ctagctctgg cttctgtgtc ccacacggcc  2340
tgttcccagc ttctctcctg gttcccttgt tacggattca tttatccatt cagtgtttcc  2400
tgggcctctg ctcagaggca ggtcaccact gggccctgtg gatcaatgca agatgacaaa  2460
ggcttttttt tttttttttt tttttttttt ttttgaggag tttcgctctt gttggctagg  2520
ctggagtaaa atggtgcgat ctcggctcac tgcacctccg cctcccaggt tcaagcgatt  2580
ttcctgcctc agcctcccga gtagctgggg ttacaggcat gcaccaccat gcctggctaa  2640
ttttctgtat ttttagtaga gacggggttt ctccatgttg gtcaggctgg tcttgaactc  2700
ctgacctcag gtgatctgcc cgtctcggcc tcccaaagtg ctgggattac cggcatgagc  2760
cactgcgcct ggccgacaaa ggctttgata tcagaatgaa ctgtcaaggg aggtgctgga  2820
gagggattaa cctgtgctgc ctgggaccct cagggtctta ggttggggag tgtgaatagg  2880
agtttgcaga tggagaatag gaagggcatt ccaggcagag ggaaacctgt gcagagacca  2940
agaggtgtgg aaggaaaagt ggggttgggg ctgggtggtc tggattatgg cctggatgca  3000
ataaagtact gtgacagtag cca                                          3023

SEQ ID NO: 19          moltype = DNA  length = 1345
FEATURE                Location/Qualifiers
source                 1..1345
                       mol_type = unassigned DNA
                       organism = Homo sapiens
SEQUENCE: 19
gcctctgggg ttttatattg ctctggtatt catgccaaag acacaccagc cctcagtcac  60
tgggagaaga acctctcata ccctcggtgc tccagtcccc agctcactca gccacacaca  120
ccatgtgtga agaggagacc accgcgctcg tgtgtgacaa tggctctggc ctgtgcaagg  180
caggcttcgc aggagatgat gccccccggg ctgtcttccc ctccattgtg ggccgccctc  240
gccaccaggg tgtgatggtg ggaatgggcc agaaagacag ctatgtgggg gatgaggctc  300
agagcaagcg agggatccta actctcaaat accccattga acacggcatc atcaccaact  360
gggatgacat ggagaagatc tggcaccact ccttctacaa tgagctgcgt gtagcacctg  420
aagagcaccc caccctgctc acagaggctc ccctaaatcc caaggccaac agggaaaaga  480
tgacccagat catgtttgaa accttcaatg tccctgccat gtacgtcgcc attcaagctg  540
tgctctccct ctatgcctct ggccgcacga caggcatcgt cctggattca ggtgatggcg  600
tcacccacaa tgtccccatc tatgaaggct atgccctgcc ccatgccatc atgcgcctgg  660
acttggctgg ccgtgacctc acggactacc tcatgaagat cctcacagag agaggctatt  720
cctttgtgac cacagctgag agagaaattg tgcgagacat caaggagaag ctgtgctatg  780
tggccctgga ttttgagaat gagatggcca cagcagcttc ctcttcctcc ctggagaaga  840
gctatgagct gccagatggg caggttatca ccattggcaa tgagcgcttc cgctgccctg  900
agaccctctt ccagccttcc tttattggca tggagtccgc tggaattcat gagacaacct  960
acaattccat catgaagtgt gacattgaca tccgtaagga cttatatgcc aacaatgtcc  1020
tctctggggg caccaccatg taccctggca ttgctgacag gatgcagaag gagatcacag  1080
ccctggcccc cagcaccatg aagatcaaga ttattgctcc cccagagcgg aagtactcag  1140
tctggatcgg gggctctatc ctggcctctc tctccacctt ccagcagatg tggatcagca  1200
agcctgagta tgatgaggca gggccctcca ttgtccacag gaagtgcttc taaagtcaga  1260
acaggttctc caaggatccc ctcgagacta ctctgttacc agtcatgaaa cattaaaacc  1320
tacaagcctt aaaaaaaaaa aaaaa                                        1345

SEQ ID NO: 20          moltype = DNA  length = 109
FEATURE                Location/Qualifiers
source                 1..109
                       mol_type = unassigned DNA
                       organism = Homo sapiens
SEQUENCE: 20
gaaagggtgg cattataggg ttccacaacc atgtctaaca ccttggacaa gagcagcaca  60
ctgaatgggt ttatgatcct atgtgggcac ttctcctgga tattgttga              109

SEQ ID NO: 21          moltype = DNA  length = 3670
FEATURE                Location/Qualifiers
source                 1..3670
                       mol_type = unassigned DNA
                       organism = Homo sapiens
SEQUENCE: 21
cgcagcaaac acatccgtag aaggcagcgc ggccgccgag aaccgcagcg ccgctcgccc  60
gccgcccccc accccgccgc cccgcccggc gaattgcgcc ccgcgcccct cccctcgcgc  120
ccccgagaca aagaggagag aaagtttgcg cggccgagcg gggcaggtga ggagggtgag  180
ccgcgcggga ggggcccgcc tcggccccgg ctcagccccc gcccgcgccc ccagcccgcc  240
gccgcgagca gcgcccggac cccccagcgg cggcccccgc ccgcccagcc ccccggcccg  300
ccatgggcgc cgcggcccgc accctgcggc tggcgctcgg cctcctgctg ctggcgacgc  360
tgcttcgccc ggccgacgcc tgcagctgct ccccggtgca cccgcaacag gcgttttgca  420
atgcagatgt agtgatcagg gccaaagcgg tcagtgagaa ggaagtggac tctggaaacg  480
acatttatgg caaccctatc aagaggatcc agtatgagat caagcagata aagatgttca  540
aagggcctga gaaggatata gagtttatct acacggcccc ctcctcggca gtgtgtgggg  600
tctcgctgga cgttggagga aagaaggaat atctcattgc aggaaaggcc gagggggacg  660
gcaagatgca catcaccctc tgtgacttca tcgtgccctg ggacaccctg agcaccaccc  720
```

```
agaagaagag cctgaaccac aggtaccaga tgggctgcga gtgcaagatc acgcgctgcc  780
ccatgatccc gtgctacatc tcctccccgg acgagtgcct ctggatggac tgggtcacag  840
agaagaacat caacgggcac caggccaagt tcttcgcctg catcaagaga agtgacggct  900
cctgtgcgtg gtaccgcggc gcggcgcccc ccaagcagga gtttctcgac atcgaggacc  960
cataagcagg cctccaacgc ccctgtggcc aactgcaaaa aaagcctcca agggtttcga  1020
ctggtccagc tctgacatcc cttcctggaa acagcatgaa taaaacactc atcccatggg  1080
tccaaattaa tatgattctg ctccccctt ctccttttag acatggttgt gggtctggag  1140
ggagacgtgg gtccaaggtc ctcatcccat cctccctctg ccaggcacta tgtgtctggg  1200
gcttcgatcc ttgggtgcag gcagggctgg gacacgcggc ttccctccca gtccctgcct  1260
tggcaccgtc acagatgcca agcaggcagc acttagggat ctcccagctg ggttagggca  1320
gggcctggaa atgtgcattt tgcagaaact tttgagggtc gttgcaagac tgtgtagcag  1380
gcctaccagg tccctttcat cttgagaggg acatggccct tgttttctgc agcttccacg  1440
cctctgcact ccctgcccct ggcaagtgct cccatcgccc cggtgcccac catgagctcc  1500
cagcacctga ctccccccac atccaagggc agcctggaac cagtggctag ttcttgaagg  1560
agccccatca atcctattaa tcctcagaat tccagtggga gcctccctct gagccttgta  1620
gaaatgggag cgagaaaccc cagctgagct gcgttccagc ctcagctgag tctttttggt  1680
ctgcacccac ccccccaccc cccccccccc gcccacatgc tccccagctt gcaggaggaa  1740
tcggtgaggt cctgtcctga ggctgctgtc cggggccggt ggctgccctc aaggtccctt  1800
ccctagctgc tgcggttgcc attgcttctt gcctgttctg gcatcaggca cctggattga  1860
gttgcacagc tttgctttat ccgggcttgt gtgcagggcc cggctgggct ccccatctgc  1920
acatcctgag gacagaaaaa gctgggtctt gctgtgccct cccaggctta gtgttccctc  1980
cctcaaagac tgacagccat cgttctgcac ggggctttct gcatgtgacg ccagctaagc  2040
atagtaagaa gtccagccta ggaagggaag gattttggag gtaggtggct ttggtgacac  2100
actcacttct ttctcagcct ccaggacact atggcctgtt ttaagagaca tcttattttt  2160
ctaaaggtga attctcagat gataggtgaa cctgagttgc agatatacca acttctgctt  2220
gtatttctta aatgacaaag attacctagc taagaaactt cctagggaac tagggaacct  2280
atgtgttccc tcagtgtggt ttcctgaagc cagtgatatg gggttagga taggaagaac  2340
tttctcggta atgataagga gaatctcttg tttcctccca cctgtgttgt aaagataaac  2400
tgacgatata caggcacatt atgtaaacat acacacgcaa tgaaaccgaa gcttggcggc  2460
ctgggcgtgg tcttgcaaaa tgcttccaaa gccaccttag cctgttctat tcagcggcaa  2520
ccccaaagca cctgttaaga ctcctgaccc ccaagtggca tgcagccccc atgcccaccg  2580
ggacctggtc agcacagatc ttgatgactt ccctttctag ggcagactgg gagggtatcc  2640
aggaatcggc ccctgcccca cgggcgtttt catgctgtac agtgacctaa agttggtaag  2700
atgtcataat ggaccagtcc atgtgatttc agtatataca actccaccag acccctccaa  2760
cccatataac accccacccc tgttcgcttc ctgtatggtg atatcatatg taacatttac  2820
tcctgtttct gctgattgtt tttttaatgt tttggtttgt ttttgacatc agctgtaatc  2880
attcctgtgc tgtgtttttt attacccttg gtaggtatta gacttgcact tttttaaaaa  2940
aaggtttctg catcgtggaa gcatttgacc cagagtggaa cgcgtggcct atgcaggtgg  3000
attccttcag gtctttcctt tggttctttg agcatctttg ctttcattcg tctcccgtct  3060
ttggttctcc agttcaaatt attgcaaagt aaaggatctt tgagtaggtt cggtctgaaa  3120
ggtgtggcct ttatatttga tccacacacg ttggtctttt aaccgtgctg agcagaaaac  3180
aaaacaggtt aagaagagcc gggtggcagc tgacagagga agccgctcaa ataccttcac  3240
aataaatagt ggcaatatat atatagttta agaaggctct ccatttggca tcgtttaatt  3300
tatatgttat gttctaagca cagctctctt ctcctatttt catcctgcaa gcaactcaaa  3360
atatttaaaa taaagtttac attgtagtta ttttcaaatc tttgcttgat aagtattaag  3420
aaatattgga cttgctgccg taatttaaag ctctgttgat tttgtttccg tttggatttt  3480
tgggggaggg gagcactgtg tttatgctgg aatatgaagt ctgagacctt ccggtgctgg  3540
gaacacacaa gagttgttga aagttgacaa gcagactgcg catgtctctg atgctttgta  3600
tcattcttga gcaatcgctc ggtccgtgga caataaacag tattatcaaa gagaaaaaaa  3660
aaaaaaaaaa                                                        3670

SEQ ID NO: 22          moltype = DNA  length = 1426
FEATURE                Location/Qualifiers
source                 1..1426
                       mol_type = unassigned DNA
                       organism = Homo sapiens
SEQUENCE: 22
atgagccagg cctactcgtc cagccagcgc gtgtcctcct accgccgcac cttcggcggg  60
gccccgggct tcccgctcgg ctccccgccg agctcgcccg tgttcccgcg ggcgggtttc  120
ggctctaagg gctcctccag ctcggtgacg tcccgcgtgt accaggtgtc gcgcacgtcg  180
ggcggggccg ggggcctggg gtcgctgcgg gccagccggc tggggaccac ccgcacgccc  240
tcctcctacg gcgcaggcga gctgctggac ttctcactgg ccgacgcggt gaaccaggag  300
tttctgacca cgcgcaccaa cgagaaggtg gagctgcagg agctcaatga ccgcttcgcc  360
aactacatcg agaaggtgcg cttcctggag cagcagaacg cggcgctcgc cgccgaagtg  420
aaccggctca agggccgcga gccgacgcga gtggccgagc tctacgagga ggagctgcgg  480
gagctgcggc gccaggtgga ggtgctcact aaccagcgcg cgcgcgtcga cgtcgagcgc  540
gacaacctgc tcgacgacct gcagcggctc aaggccaagc tgcaggagga gattcagttg  600
aaggaagaag cagagaacaa tttggctgcc ttccgagcgg acgtggatgc agctactcta  660
gctcgcattg acctggagcg cagaattgaa tctctcaacg aggagatcgc gttccttaag  720
aaagtgcatg aagaggagat ccgtgagttg caggctcagc ttcaggaaca gcaggtccag  780
gtggagatgg acatgtctaa gccagacctc actgccgccc tcagggacat ccgggctcag  840
tatgagacca tcgcggctaa gaacatttct gaagctgagg agtggtacaa gtcgaaggtg  900
tcagacctga cccaggcagc caacaagaac aacgacgccc tgcgccaggc caagcaggag  960
atgatggaat accgacacca gatccagtcc tacacctgcg agattgacgc cctgaagggc  1020
actaacgatt ccctgatgag gcagatgcgg gaattggagg accgatttgc cagtgaggcc  1080
agtggctacc aggacattgc gcgcctggag gaggaaatcc ggcacctcaa ggatgagatg  1140
gcccgccatc tgcgcgagta ccaggacctg ctcaacgtga agatggccct ggatgtggag  1200
attgccacct accggaagct gctggaggga gaggagagcc ggatcaatct ccccatccag  1260
acctactctg ccctcaactt ccgagaaacc agccctgagc aaaggggttc tgaggtccat  1320
```

-continued

```
accaagaaga cggtgatgat caagaccatc gagacacggg atggggaggt cgtcagtgag  1380
gccacacagc agcagcatga agtgctctaa agacgagaga ccctct                 1426
```